United States Patent
Cui et al.

(10) Patent No.: US 11,542,240 B2
(45) Date of Patent: Jan. 3, 2023

(54) STK19 INHIBITORS FOR TREATMENT OF CANCER

(71) Applicants: TRUSTEES OF BOSTON UNIVERSITY, Boston, MA (US); XIAMEN UNIVERSITY, Fujian (CN)

(72) Inventors: Rutao Cui, Belmont, MA (US); Chengqian Yin, Cambridge, MA (US); Xianming Deng, Xiamen (CN); Ting Zhang, Xiamen (CN)

(73) Assignees: TRUSTEES OF BOSTON UNIVERSITY, Boston, MA (US); XIAMEN UNIVERSITY, Xiamen (CN)

( * ) Notice: Subject to any disclaimer, the term of this patent is extended or adjusted under 35 U.S.C. 154(b) by 0 days.

(21) Appl. No.: 16/722,224

(22) Filed: Dec. 20, 2019

(65) Prior Publication Data

US 2020/0199081 A1  Jun. 25, 2020

Related U.S. Application Data

(60) Provisional application No. 62/782,820, filed on Dec. 20, 2018.

(51) Int. Cl.
| | |
|---|---|
| *C07D 239/84* | (2006.01) |
| *C07D 401/12* | (2006.01) |
| *C07D 401/14* | (2006.01) |
| *C07D 403/04* | (2006.01) |
| *C07D 239/82* | (2006.01) |
| *C07D 405/14* | (2006.01) |
| *A61P 35/00* | (2006.01) |
| *C07D 413/14* | (2006.01) |
| *C07K 16/28* | (2006.01) |

(52) U.S. Cl.
CPC ............ *C07D 239/84* (2013.01); *A61P 35/00* (2018.01); *C07D 239/82* (2013.01); *C07D 401/12* (2013.01); *C07D 401/14* (2013.01); *C07D 403/04* (2013.01); *C07D 405/14* (2013.01); *C07D 413/14* (2013.01); *C07K 16/2818* (2013.01)

(58) Field of Classification Search
CPC .. C07D 239/82; C07D 239/84; C07D 401/12; C07D 401/14
See application file for complete search history.

(56) References Cited

U.S. PATENT DOCUMENTS

| | | | | |
|---|---|---|---|---|
| 3,511,836 A | * | 5/1970 | Hess | C07D 403/04 544/291 |
| 3,980,650 A | * | 9/1976 | Nauta | C07D 239/95 544/284 |
| 7,442,507 B2 | | 10/2008 | Polsky et al. | |
| 9,630,947 B2 | | 4/2017 | Suzuki et al. | |
| 2008/0207614 A1 | | 8/2008 | Lee et al. | |
| 2010/0317607 A1 | * | 12/2010 | Wynne | C07D 471/04 514/40 |
| 2011/0008289 A1 | | 1/2011 | Blatt et al. | |

FOREIGN PATENT DOCUMENTS

| | | | |
|---|---|---|---|
| WO | 2005110455 A2 | | 11/2005 |
| WO | 2008141275 A1 | | 11/2008 |
| WO | 2009073513 A1 | | 6/2009 |
| WO | WO 2018/005799 | * | 1/2018 |
| WO | WO 2018/005799 A1 | * | 1/2018 |

OTHER PUBLICATIONS

Sundriyal et al., Histone lysine methyltransferase structure activity relationships that allow for segregation of G9a inhibition and anti-Plasmodium activity, MedChemComm, 8, pp. 1069-1092 (2017).*
Xiong et al., Discovery of Potent and Selective Inhibitors for G9a-Like Protein (GLP) Lysine Methyltransferase, Journal of Medicinal Chemistry, 60, pp. 1876-1891 (2017).*
Yin et al., Pharmacological Targeting of STK19 Inhibits Oncogenic NRAS-Driven Melanomagenesis, Cell, 176, pp. 1113-1127, Feb. 21, 2019.*
STN Registry RN 2393598-20-2 (Supplier: FCH Group), Dec. 18, 2019.*
PubChem CID 53315441, 9 pages (Aug. 19, 2011).*
Liu et al., Discovery of an in vivo Chemical Probe of the Lysine Methyltransferases G9a and GLP, Journal of Medicinal Chemistry, 56 (21), pp. 8931-8942 (2013).*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Acute Leukemia, Merck Manual (Online Edition) 6 pages, pp. 1-6 (2013).*

(Continued)

*Primary Examiner* — Deepak R Rao
(74) *Attorney, Agent, or Firm* — Nixon Peabody LLP; Ronald I. Eisenstein; Ravinderjit S. Braich

(57) ABSTRACT

Provided herein are compositions and methods for the treatment and prevention of cancer, including melanoma.

24 Claims, 40 Drawing Sheets

Specification includes a Sequence Listing.

(56) References Cited

OTHER PUBLICATIONS

Ackermann et al. "Metastasizing melanoma formation caused by expression of activated N-RasQ61K on an INK4a-deficient background." Cancer Research 65(10): 4005-4011 (2005).
Ahearn et al. "Regulating the regulator: post-translational modification of RAS." Nature Reviews Molecular Cell Biology 13(1): 39-51 (2012).
Akbani et al. "Genomic classification of cutaneous melanoma." Cell 161(7): 1681-1696 (2015).
American Cancer Society®, Cancer Facts & FIGs., 2019; available on the world wide web at https://www.cancer.org/content/dam/cancer-org/research/cancer-facts-and-statistics/annual-cancer-facts-and-figures/2019/cancer-facts-and-figures-2019.pdf.
Athuluri-Divakar et al. "A small molecule RAS-mimetic disrupts RAS association with effector proteins to block signaling." Cell 165(3): 643-655 (2016).
Bacher et al. "NRAS mutations in AML: biology, cytogenetics, and prognosis—a study on 2502 patients" Blood 107: 3847-3853 (2006).
Barbacid. "Ras genes." Annual Review of Biochemistry 56(1): 779-827 (1987).
Barceló et al. "Oncogenic K-ras segregates at spatially distinct plasma membrane signaling platforms according to its phosphorylation status." J Cell Sci 126(20): 4553-4559 (2013).
Barceló et al. "Phosphorylation at Ser-181 of oncogenic KRAS is required for tumor growth." Cancer Research 74(4): 1190-1199 (2014).
Barretina et al. "The Cancer Cell Line Encyclopedia enables predictive modelling of anticancer drug sensitivity." Nature 483(7391): 603-607 (2012).
Berger et al. "Melanoma genome sequencing reveals frequent PREX2 mutations." Nature 485(7399): 502-506 (2012).
Berndt et al. "Targeting protein prenylation for cancer therapy." Nature Reviews Cancer 11(11): 775-791 (2011).
Boeing et al. "Multiomic analysis of the UV-induced DNA damage response." Cell Reports 15(7): 1597-1610 (2016).
Bonilla et al. "Genomic analysis identifies new drivers and progression pathways in skin basal cell carcinoma." Nature genetics 48(4): 398-406 (2016).
BOS. "Ras oncogenes in human cancer: a review." Cancer research 49(17): 4682-4689 (1989).
Brash. "UV signature mutations." Photochemistry and photobiology 91(1): 15-26 (2015).
Brunner et al. "Farnesyltransferase inhibitors: an overview of the results of preclinical and clinical investigations." Cancer Research 63(18): 5656-5668 (2003).
Bunda et al. "Inhibition of SHP2-mediated dephosphorylation of Ras suppresses oncogenesis." Nature Communications 6: 8859 pp. 1-12 (2015).
Bunda et al. "Src promotes GTPase activity of Ras via tyrosine 32 phosphorylation." Proceedings of the National Academy of Sciences 111(36): E3785-E3794 (2014).
Burd et al. "Mutation-specific RAS oncogenicity explains NRAS codon 61 selection in melanoma." Cancer Discovery 4(12): 1418-1429(2014).
Buss et al. "Direct identification of palmitic acid as the lipid attached to P21ras." Molecular and Cellular Biology 6(1): 116-122(1986).
Casey et al. "P21ras is modified by a farnesyl isoprenoid." Proceedings of the National Academy of Sciences 86(21): 8323-8327 (1989).
Chapman et al. "Improved survival with vemurafenib in melanoma with BRAF V600E mutation." New England Journal of Medicine 364(26): 2507-2516 (2011).
Chen et al. "Palmitoylation-dependent activation of MC1R prevents melanomagenesis." Nature 549(7672): 399-403 (2017).
Chiu et al. "Ras signalling on the endoplasmic reticulum and the Golgi." Nature Cell Biology 4(5): 343-350 (2002).
Cox et al. "Drugging the undruggable RAS: mission possible?." Nature Reviews Drug Discovery 13(11): 828-851 (2014).
Dankort et al. "Braf V600E cooperates with Pten loss to induce metastatic melanoma." Nature Genetics 41(5): 544-552 (2009).
Davies et al. "Mutations of the BRAF gene in human cancer." Nature 417(6892): 949-954 (2002).
Deribe et al. "Truncating PREX2 mutations activate its GEF activity and alter gene expression regulation in NRAS-mutant melanoma." Proceedings of the National Academy of Sciences 113(9): E1296-E1305 (2016).
Downward. "Targeting RAS signalling pathways in cancer therapy." Nature Reviews Cancer 3(1): 11-22 (2003).
Ercan et al. "Reactivation of ERK signaling causes resistance to EGFR kinase inhibitors." Cancer Discovery 2(10): 934-947 (2012).
Fargnoli et al. "MC1R variants increase risk of melanomas harboring BRAF mutations." Journal of Investigative Dermatology 128(10): 2485-2490 (2008).
Flaherty et al. "Inhibition of mutated, activated BRAF in metastatic melanoma." New England Journal of Medicine 363(9): 809-819 (2010).
Garraway et al. "Integrative genomic analyses identify MITF as a lineage survival oncogene amplified in malignant melanoma." Nature 436(7047): 117-122 (2005).
Goel et al. "Examination of mutations in BRAF, NRAS, and PTEN in primary cutaneous melanoma." Journal of Investigative Dermatology 126(1): 154-160 (2006).
Gomez-Escobar et al. "The G11 gene located in the major histocompatibility complex encodes a novel nuclear serine/threonine protein kinase" Journal of Biological Chemistry 273(47): 30954-30960 (1998).
Hatzivassiliou et al. "RAF inhibitors prime wild-type RAF to activate the MAPK pathway and enhance growth." Nature 464(7287): 431-435 (2010).
Hayward et al. "Whole-genome landscapes of major melanoma subtypes." Nature 545(7653): 175-180 (2017).
Herlyn et al. "Characteristics of cultured human melanocytes isolated from different stages of tumor progression." Cancer Research 45(11 Part 2): 5670-5676 (1985).
Hodis et al. "A landscape of driver mutations in melanoma." Cell 150(2): 251-263 (2012).
Hugo et al. "Genomic and transcriptomic features of response to anti-PD-1 therapy in metastatic melanoma." Cell 165(1): 35-44 (2016).
Jackson et al. "Farnesol modification of Kirsten-ras exon 4B protein is essential for transformation." Proceedings of the National Academy of Sciences 87(8): 3042-3046 (1990).
Jakob et al. "NRAS mutation status is an independent prognostic factor in metastatic melanoma." Cancer 118(16): 4014-4023 (2012).
Ji et al. "Targeting the RAS pathway in melanoma." Trends in Molecular Medicine 18(1): 27-35 (2012).
Karaman et al. "A quantitative analysis of kinase inhibitor selectivity." Nature Biotechnology 26(1): 127-132 (2008).
Karimkhani et al. "The global burden of melanoma: results from the Global Burden of Disease Study 2015." British Journal of Dermatology 177(1): 134-140 (2017).
Karnoub et al. "Ras oncogenes: split personalities." Nature reviews Molecular Cell Biology 9(7): 517-531 (2008).
Kawakami et al. "A Ras activation pathway dependent on Syk phosphorylation of protein kinase C." Proceedings of the National Academy of Sciences 100(16): 9470-9475 (2003).
Kefford et al. "Phase I/II study of GSK2118436, a selective inhibitor of oncogenic mutant BRAF kinase, in patients with metastatic melanoma and other solid tumors." Journal of Clinical Oncology 28(15_suppl): 8503 (2010).
Kim et al. "Lack of somatic alterations of MC1R in primary melanoma." Pigment Cell & Melanoma Research 21(5): 579-582 (2008).
Godwin et al. "Isolation, culture, and transfection of melanocytes." Current Protocols in Cell Biology 63(1): 1.8.1-1.8.20 (2014).
Krengel et al. "Three-dimensional structures of H-ras p21 mutants: molecular basis for their inability to function as signal switch molecules." Cell 62(3): 539-548 (1990).

(56) References Cited

OTHER PUBLICATIONS

Lee et al. "Frequencies of BRAF and NRAS mutations are different in histological types and sites of origin of cutaneous melanoma: a meta-analysis." British Journal of Dermatology 164(4): 776-784 (2011).
Mainardi et al. "SHP2 is required for growth of KRAS-mutant non-small-cell lung cancer in vivo." Nature Medicine 24(7): 961-967(2018).
Purdie et al. "Isolation and culture of squamous cell carcinoma lines." Methods Mol Biol 731:151-159 (2011).
Krauthammer et al. "Exome sequencing identifies recurrent somatic RAC1 mutations in melanoma." Nature Genetics 44(9): 1006-1014 (2012).
Landi et al. "MC1R germline variants confer risk for BRAF-mutant melanoma." Science 313(5786): 521-522 (2006).
Larkin et al. "Combined vemurafenib and cobimetinib in BRAF-mutated melanoma." New England Journal of Medicine 371(20): 1867-1876 (2014).
Lavoie et al. "Regulation of RAF protein kinases in ERK signalling." Nature Reviews Molecular Cell Biology 16(5): 281-298 (2015).
Lawrence et al. "Discovery and saturation analysis of cancer genes across 21 tumour types." Nature 505(7484): 195-501 (2014).
Liu et al. "Discovery of an in vivo chemical probe of the lysine methyltransferases G9a and GLP." Journal of Medicinal Chemistry 56(21): 8931-8942 (2013).
Long et al. "Adjuvant dabrafenib plus trametinib in stage III BRAF-mutated melanoma." New England Journal of Medicine 377(19): 1813-1823 (2017).
Malumbres et al. "RAS oncogenes: the first 30 years." Nature Reviews Cancer 3(6): 459-465 (2003).
Marais et al. "Ras recruits Raf-1 to the plasma membrane for activation by tyrosine phosphorylation." The EMBO Journal 14(13): 3136-3145 (1995).
Mendoza et al. "The Ras-ERK and PI3K-mTOR pathways: crosstalk and compensation." Trends in Biochemical Sciences 36(6): 320-328 (2011).
Milburn et al. "Molecular switch for signal transduction: structural differences between active and inactive forms of protooncogenic ras proteins." Science 247(4945): 939-945 (1990).
Prior et al. "A comprehensive survey of Ras mutations in cancer." Cancer Research 72(10): 2457-2467 (2012).
Pylayeva-Gupta et al. "RAS oncogenes: weaving a tumorigenic web." Nature Reviews Cancer 11(11): 761-774 (2011).
Rauen. "The rasopathies." Annual Review of Genomics and Human Genetics 14: 355-369 (2013).
Samatar et al. "Targeting RAS-ERK signalling in cancer: promises and challenges." Nature Reviews Drug Discovery 13(12): 928-942 (2014).
Sargent et al. "Characterisation of the novel gene G11 lying adjacent to the complement C4A gene in the human major histocompatibility complex." Human Molecular Genetics 3(3): 481-488 (1994).
Scherer et al. "Association between the germline MC1R variants and somatic BRAF/NRAS mutations in melanoma tumors." The Journal of Investigative Dermatology 130(12): 2844-2848 (2010).
Shinkai et al. "H3K9 methyltransferase G9a and the related molecule GLP." Genes & Development 25(8): 781-788 (2011).
Siegelin et al. "Epidermal growth factor receptor mutations in lung adenocarcinoma." Laboratory Investigation 94(2): 129-137 (2014).
Smith et al. "NMR-based functional profiling of RASopathies and oncogenic RAS mutations." Proceedings of the National Academy of Sciences 110(12): 4574-4579 (2013).
Stephen et al. "Dragging ras back in the ring." Cancer Cell 25(3): 272-281 (2014).
Sweis et al. "Discovery and development of potent and selective inhibitors of histone methyltransferase g9a." ACS Medicinal Chemistry Letters 5(2): 205-209 (2014).
Ting et al. "Tyrosine phosphorylation of RAS by ABL allosterically enhances effector binding." The FASEB Journal 29(9): 3750-3761 (2015).
Tsao et al. "Melanoma: from mutations to medicine." Genes & Development 26(11): 1131-1155 (2012).
Wan et al. "Mechanism of activation of the RAF-ERK signaling pathway by oncogenic mutations of B-RAF." Cell 116(6): 855-867 (2014).
Wellbrock et al. "V599EB-RAF is an oncogene in melanocytes." Cancer Research 64(7): 2338-2342 (2004).
Welsch et al. "Multivalent small-molecule pan-RAS inhibitors." Cell 168(5): 878-889.e29 (2017).
Wong et al. "Targeting wild-type KRAS-amplified gastroesophageal cancer through combined MEK and SHP2 inhibition." Nature Medicine 24(7): 968-977 (2018).
Wright et al. "Thematic review series: lipid posttranslational modifications CAAX modification and membrane targeting of Ras." Journal of Lipid Research 47(5): 883-891 (2006).

\* cited by examiner

FIGS. 1A-1H
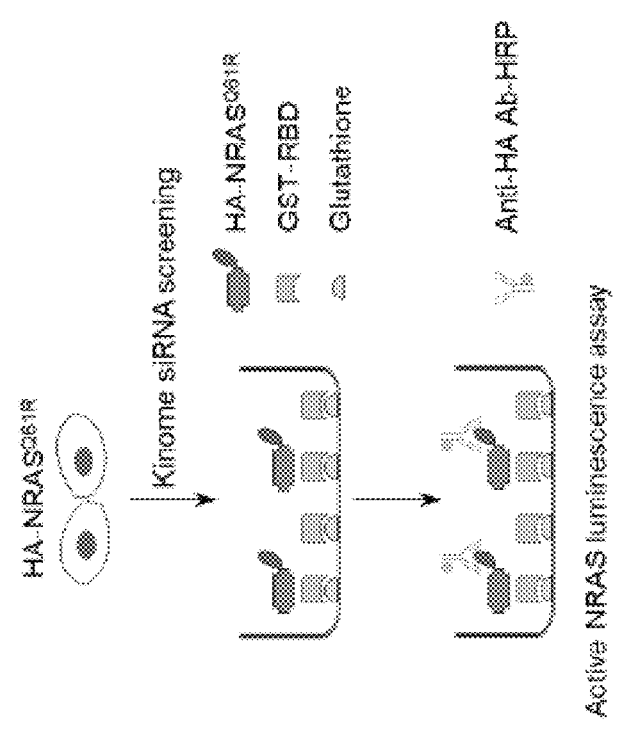
FIG. 1A
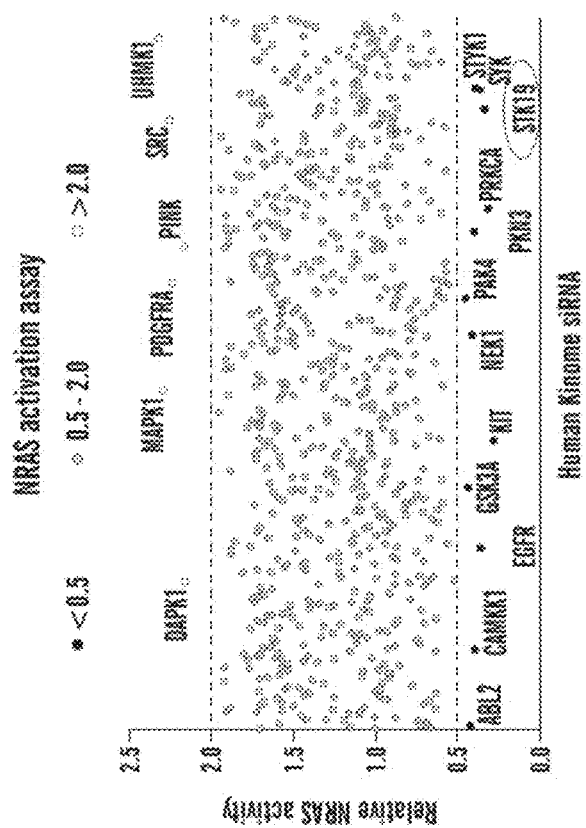
FIG. 1B

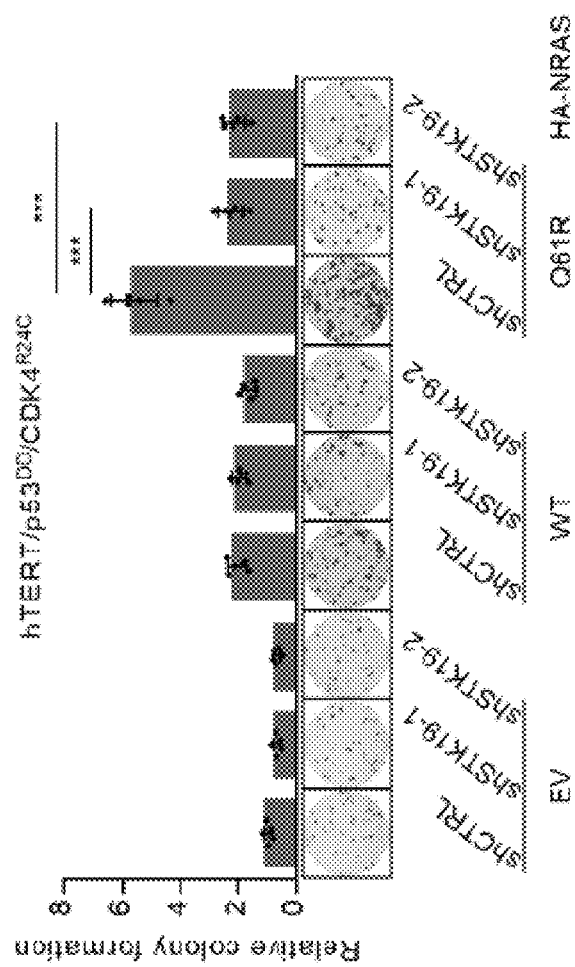
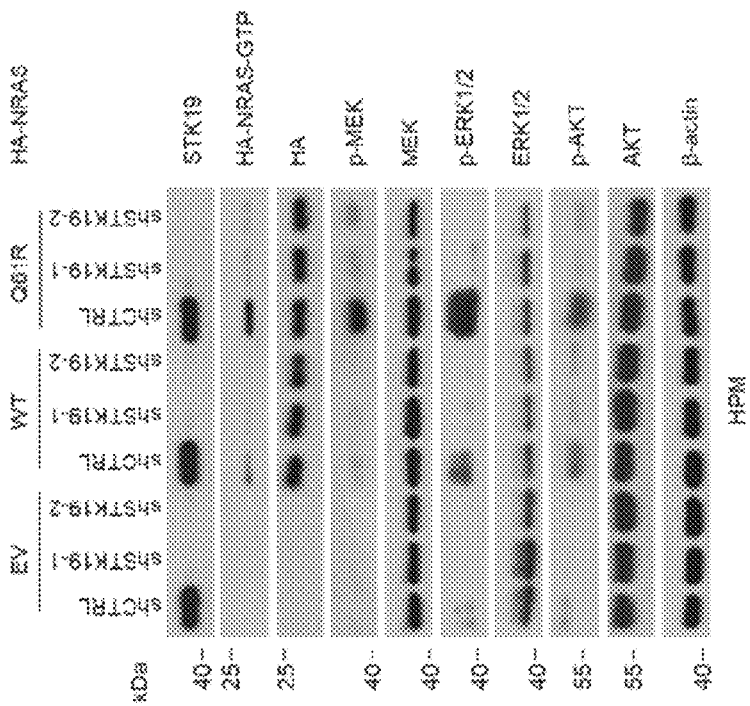
FIG. 1E
FIG. 1D
FIGs. 1A-1H (cont.)

FIGS. 1A-1H (cont.)
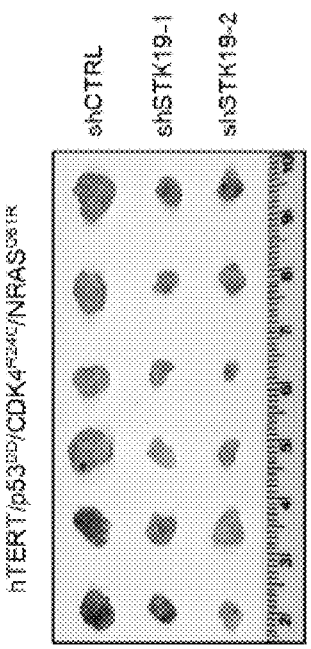
FIG. 1F
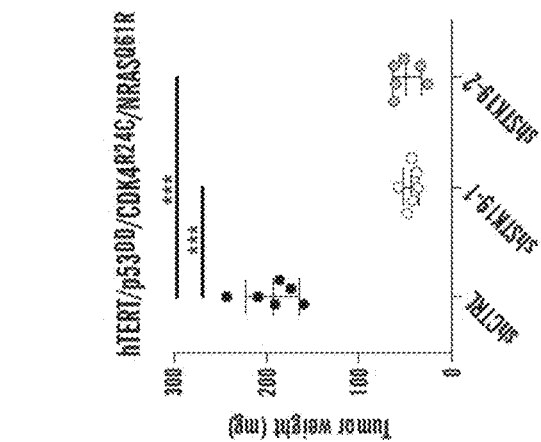
FIG. 1G
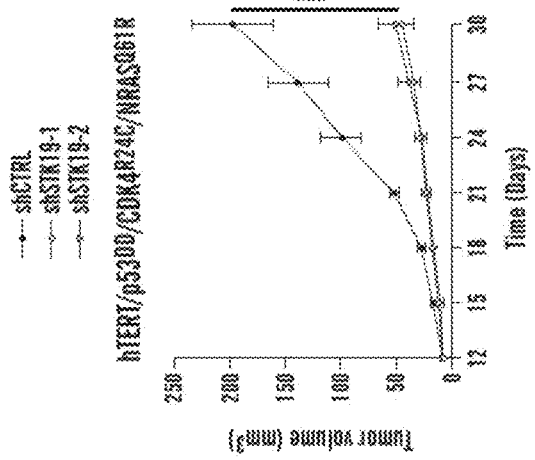
FIG. 1H

FIGs. 2A-2L
Mass spectral peptide count
| Protein | Unique |
|---|---|
| STK19 | 25 |
| NRAS | 13 |
| YWHAE | 8 |
| PABPC1 | 8 |
| ENO1 | 5 |
| PHB2 | 4 |
| PSMC5 | 3 |
| ILF2 | 3 |
| UBAP2L | 3 |
| HNRNPM | 3 |
*FIG. 2A*
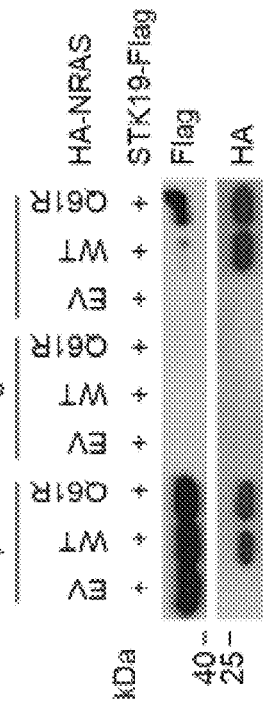
*FIG. 2B*
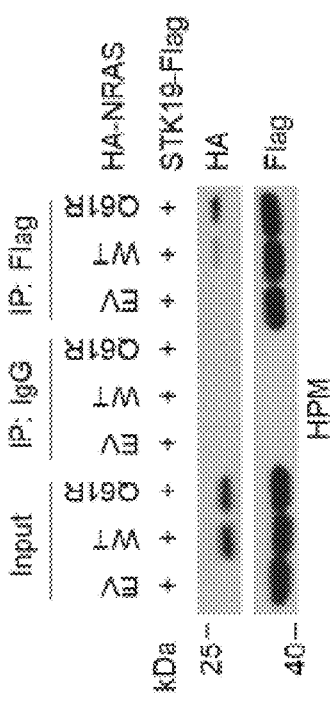
*FIG. 2C*

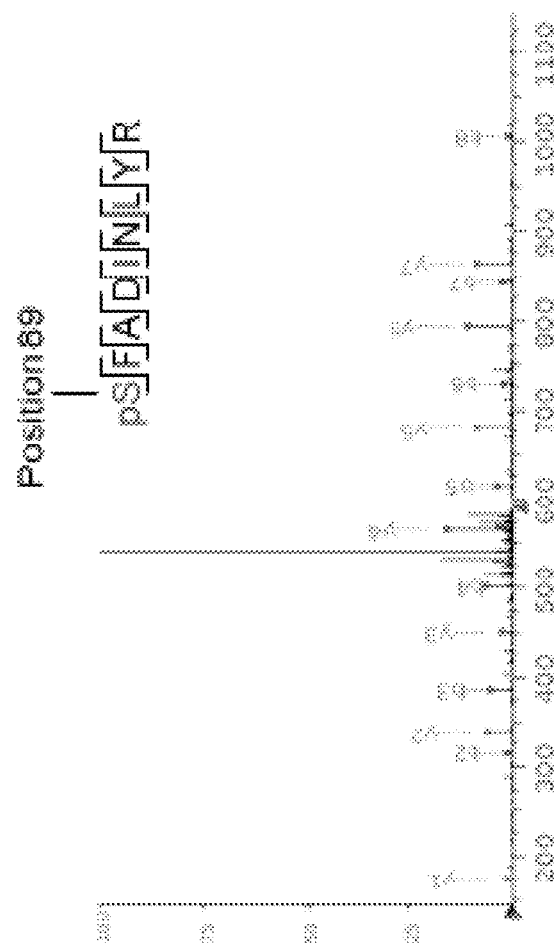
*FIG. 2E*
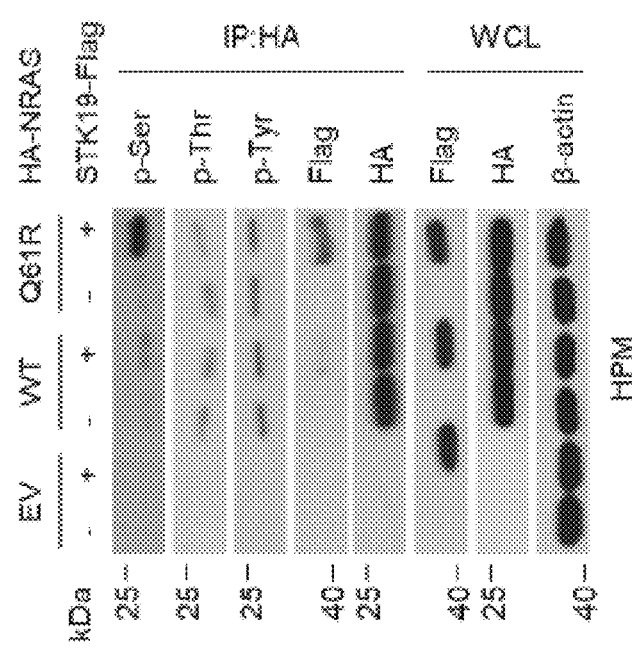
FIGs. 2A-2L (cont.)
*FIG. 2D*

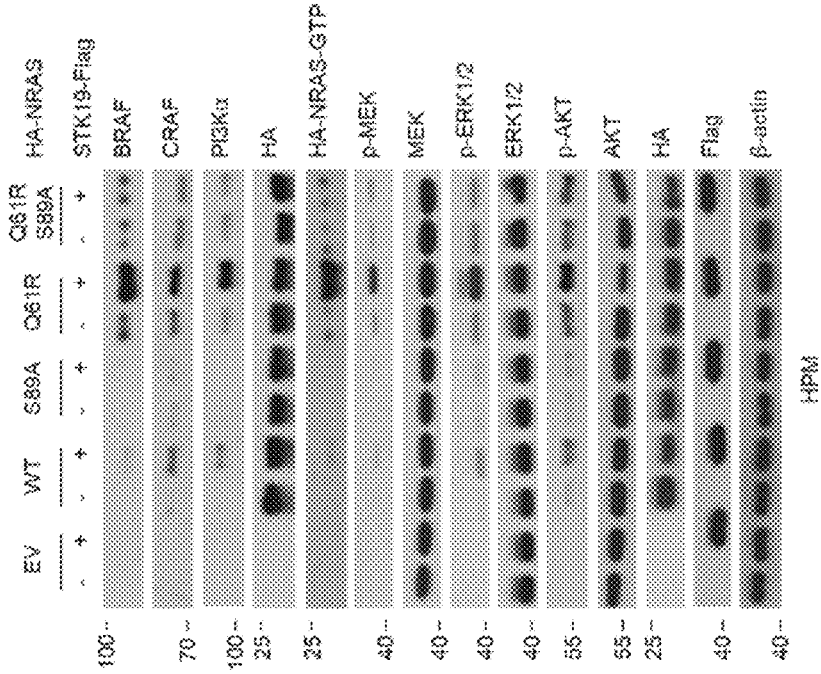
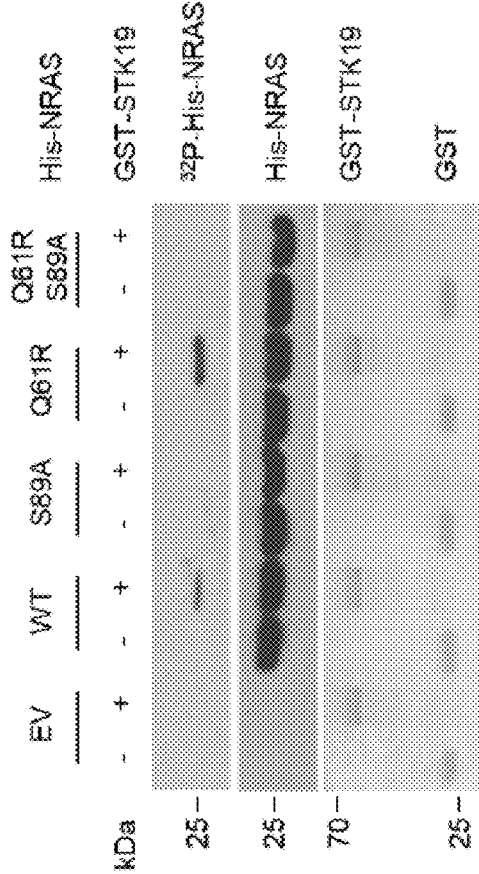
FIGs. 2A-2L (cont.)
FIG. 2F
FIG. 2G
FIG. 2H

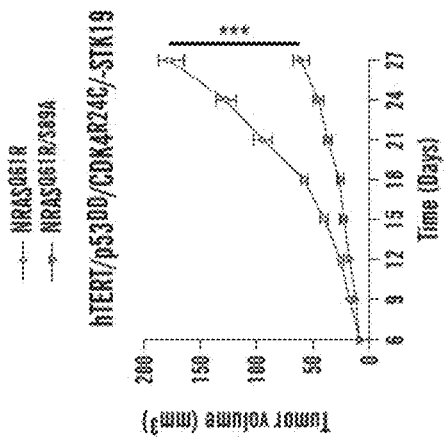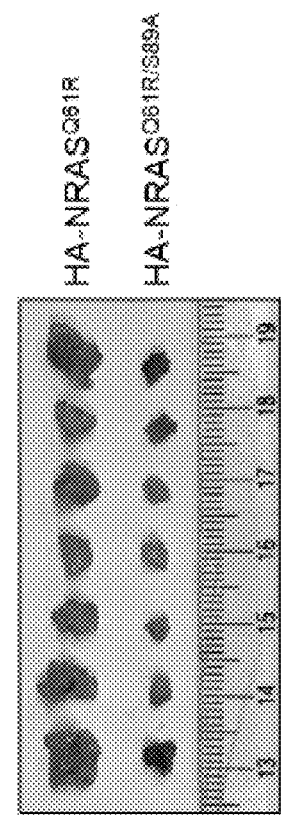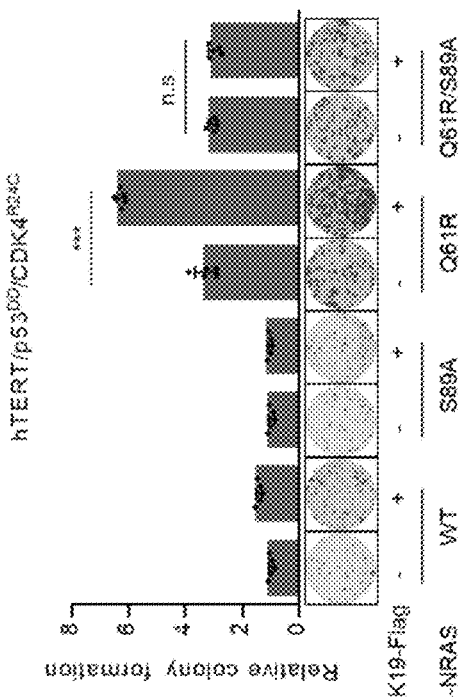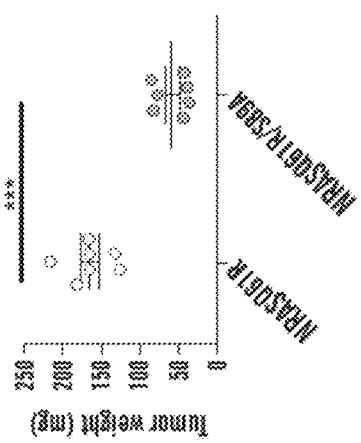
FIG. 2I  FIG. 2J  FIG. 2K  FIG. 2L
FIGs. 2A-2L (cont.)

FIGs. 3A-3G (cont.)
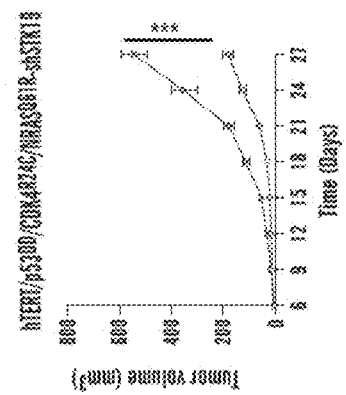
FIG. 3D
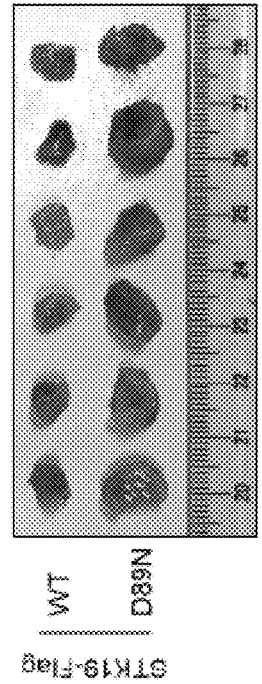
FIG. 3E
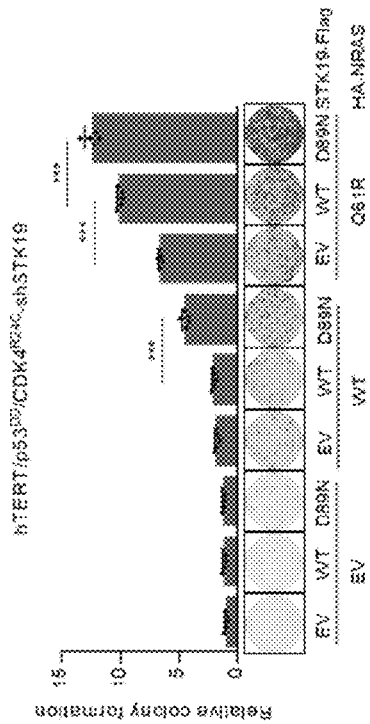
FIG. 3F
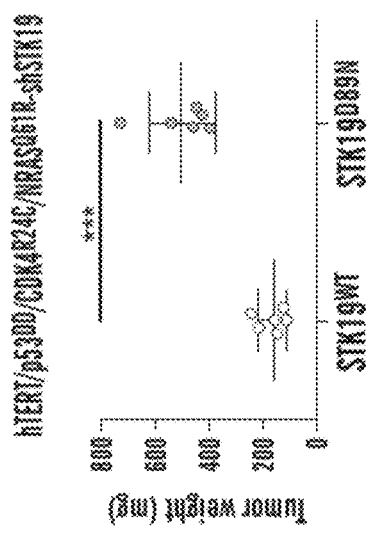
FIG. 3G

FIGs. 4A-4G
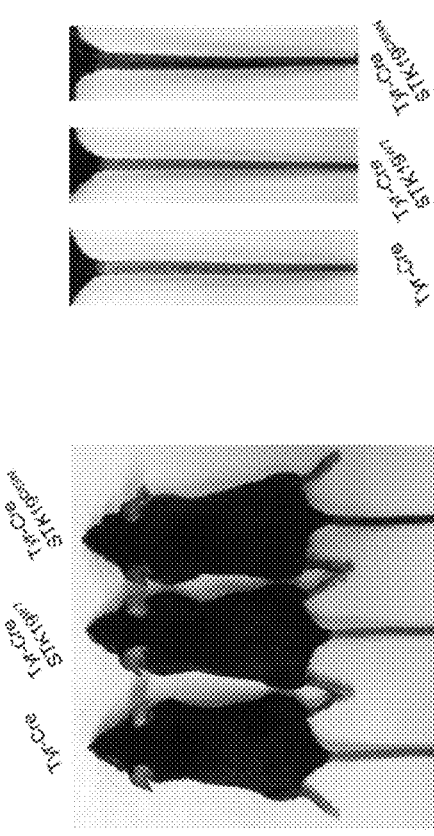
*FIG. 4A*
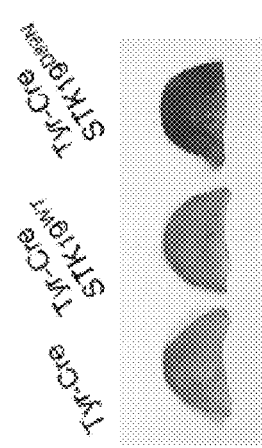
*FIG. 4B*
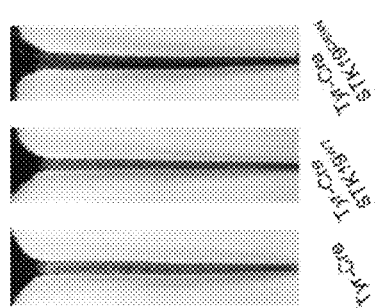
*FIG. 4C*
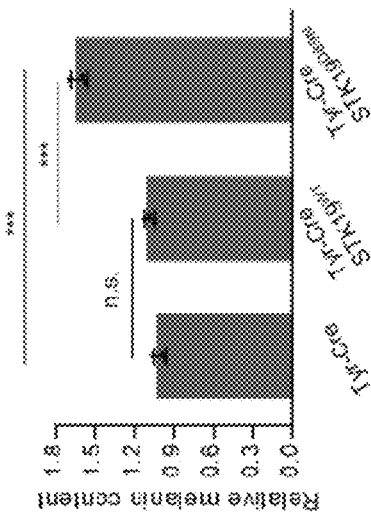
*FIG. 4D*
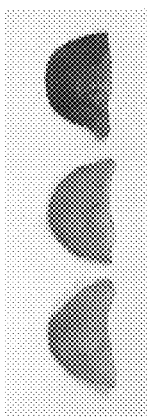
*FIG. 4E*

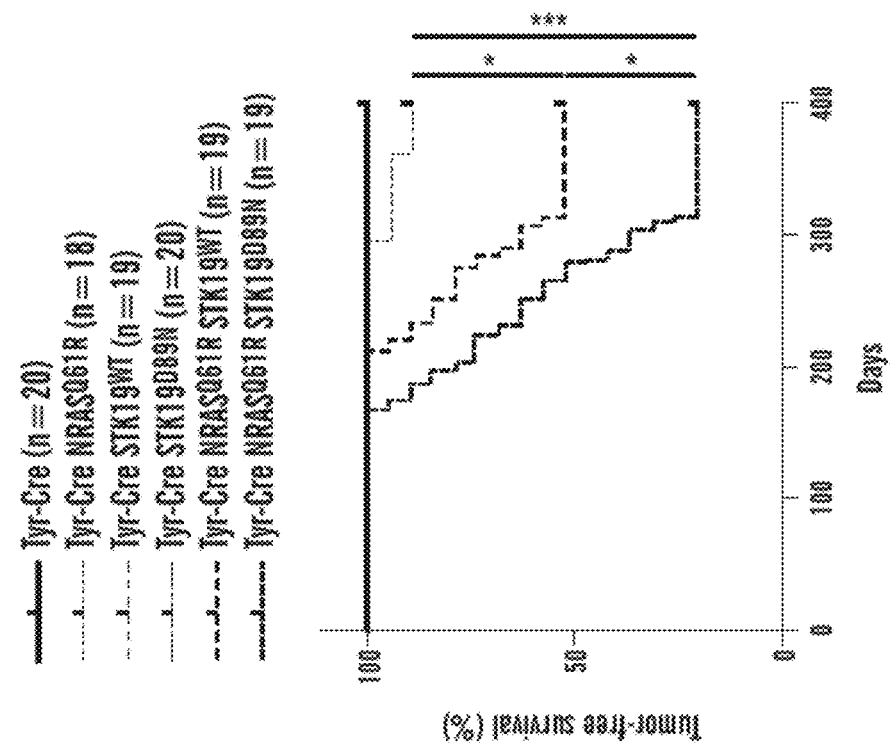
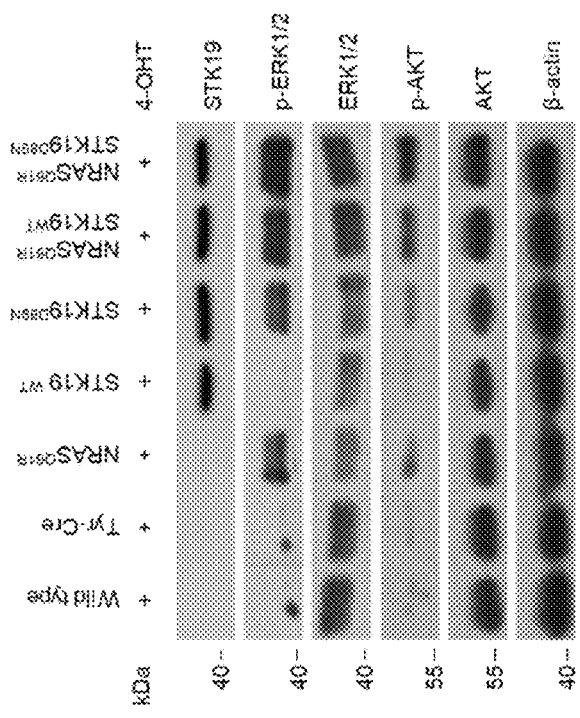
FIGS. 4A-4G (cont.)

FIGS. 5A-5G
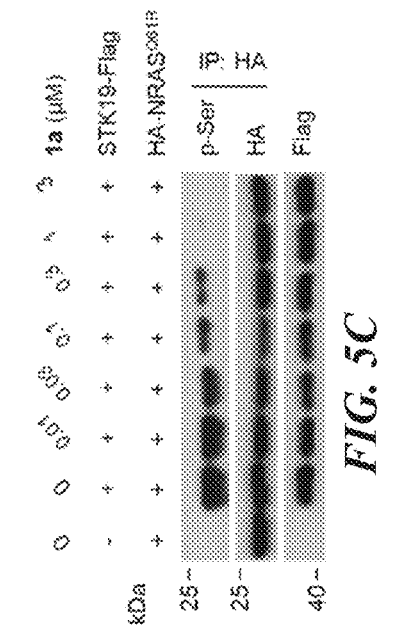
FIG. 5A
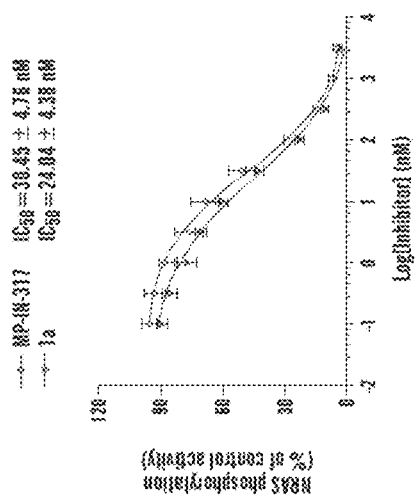
FIG. 5B
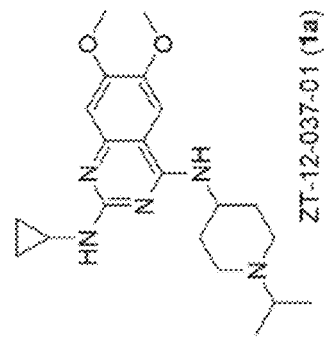
FIG. 5D
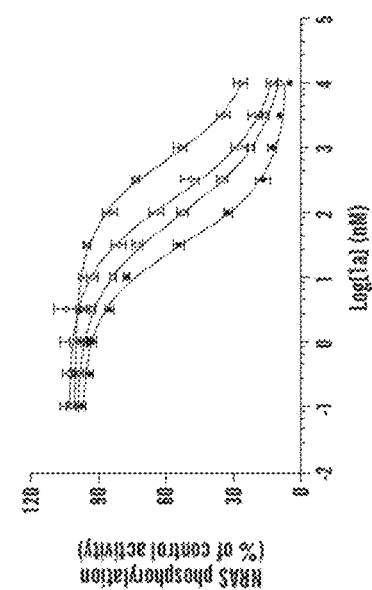
FIG. 5C
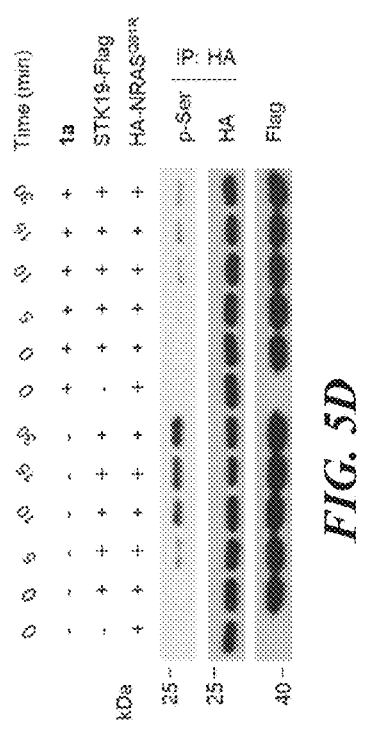
FIG. 5E

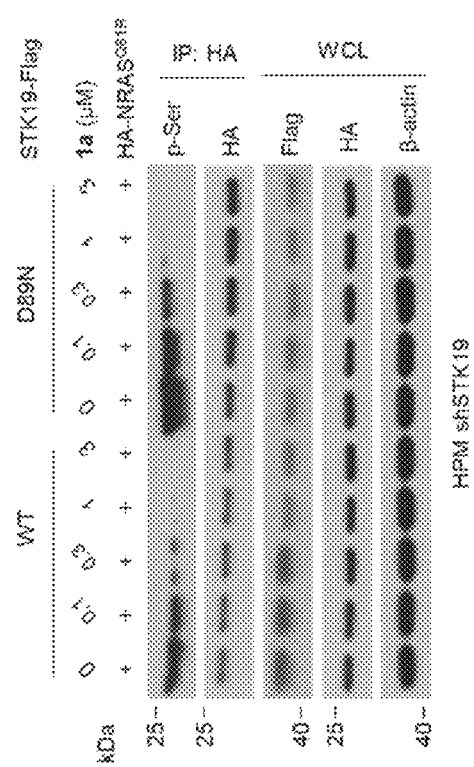
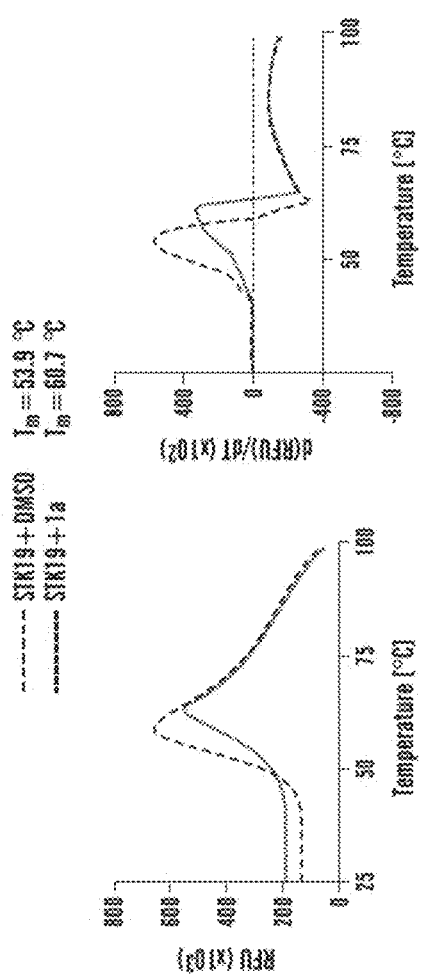
FIGs. 5A-5G (cont.)
FIG. 5F
FIG. 5G

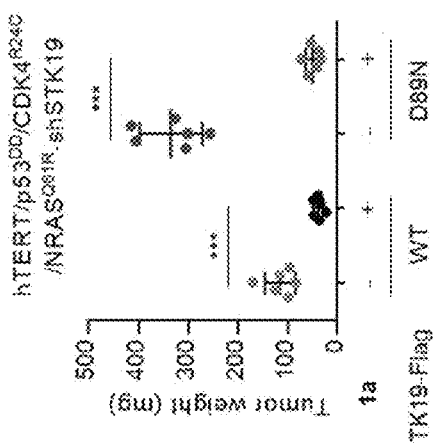
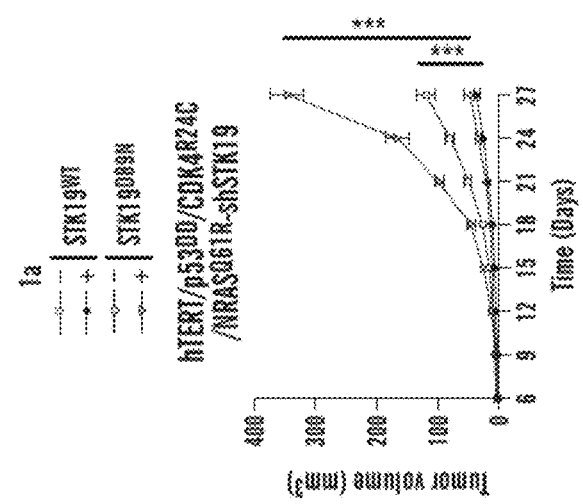
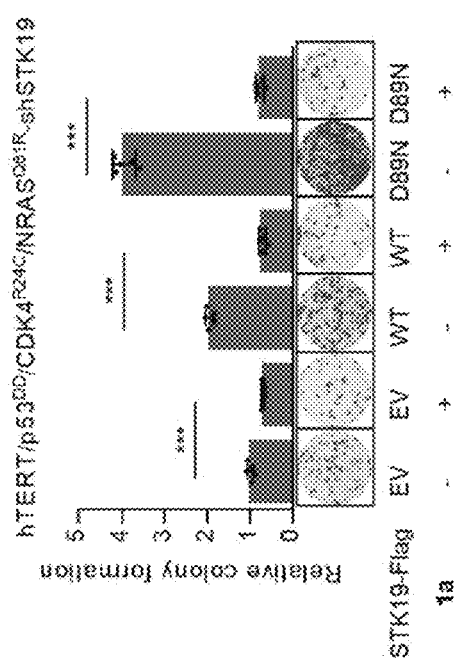
FIGs. 6A-6I
FIG. 6A
FIG. 6B
FIG. 6C

FIGs. 6A-6I (cont.)
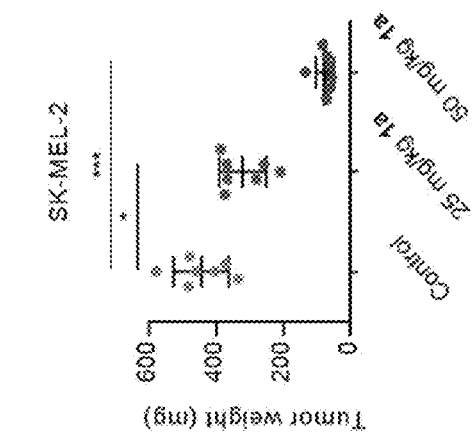
*FIG. 6F*
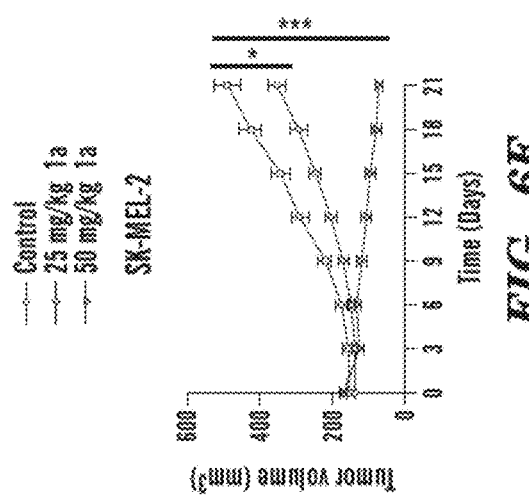
*FIG. 6E*
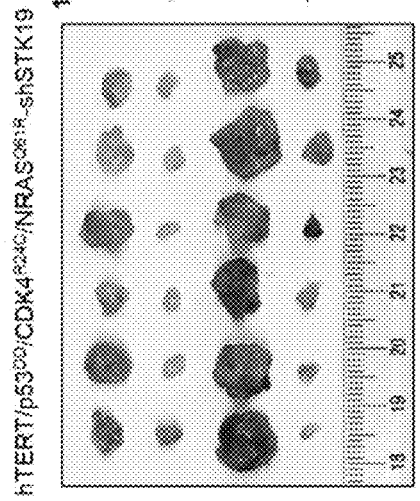
*FIG. 6D*

FIGs. 7A-7H
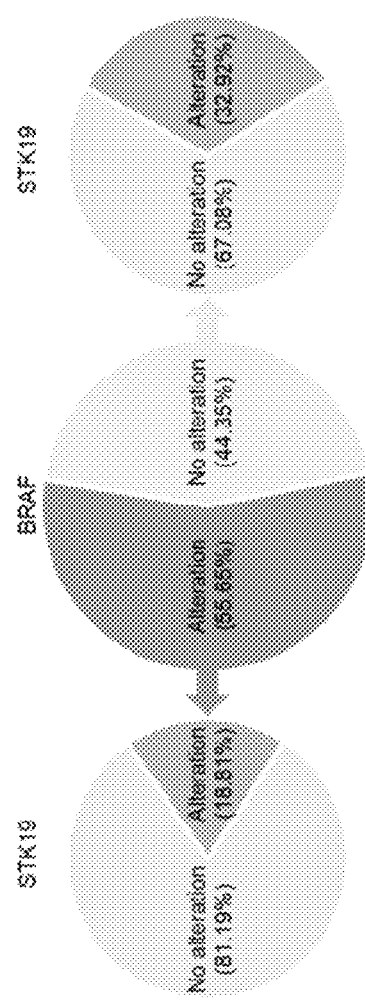
*FIG. 7A*
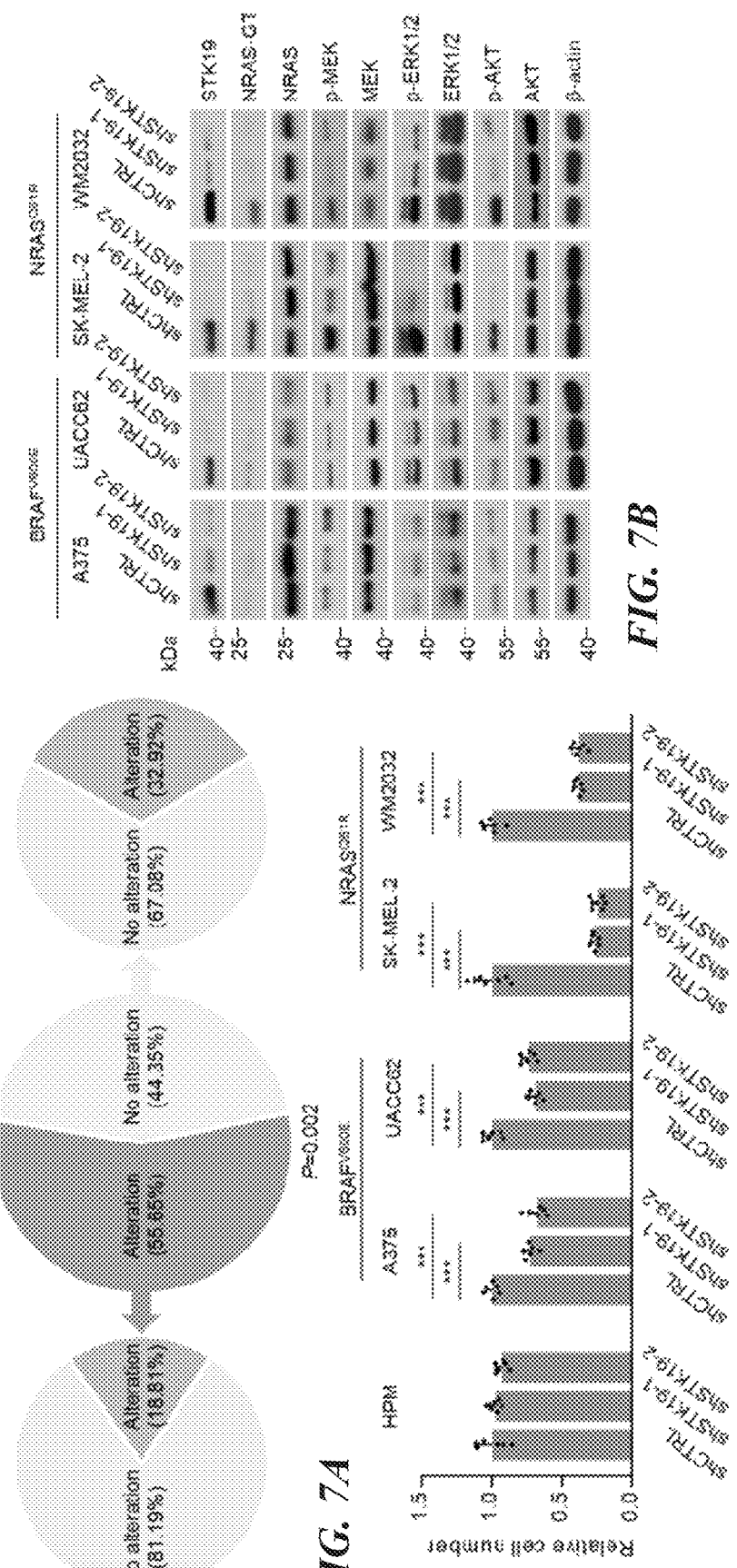
*FIG. 7B*
*FIG. 7C*

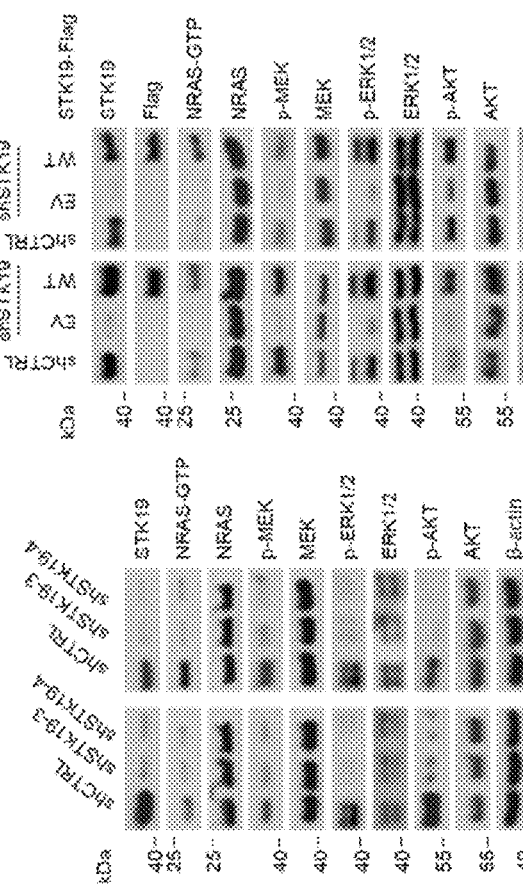
*FIG. 7E*  *FIG. 7F*
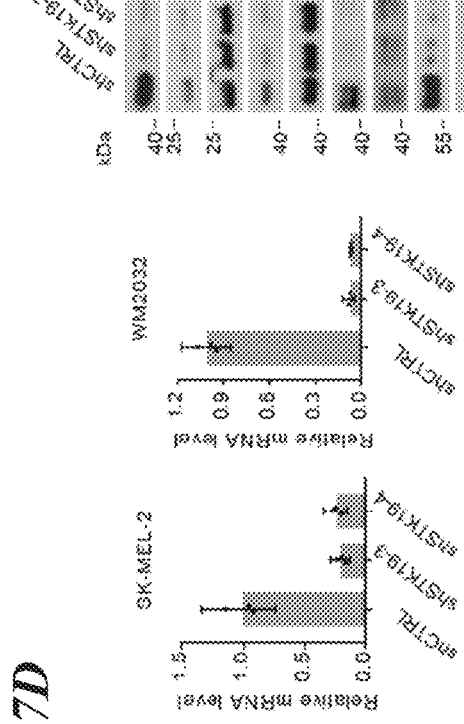
*FIG. 7D*
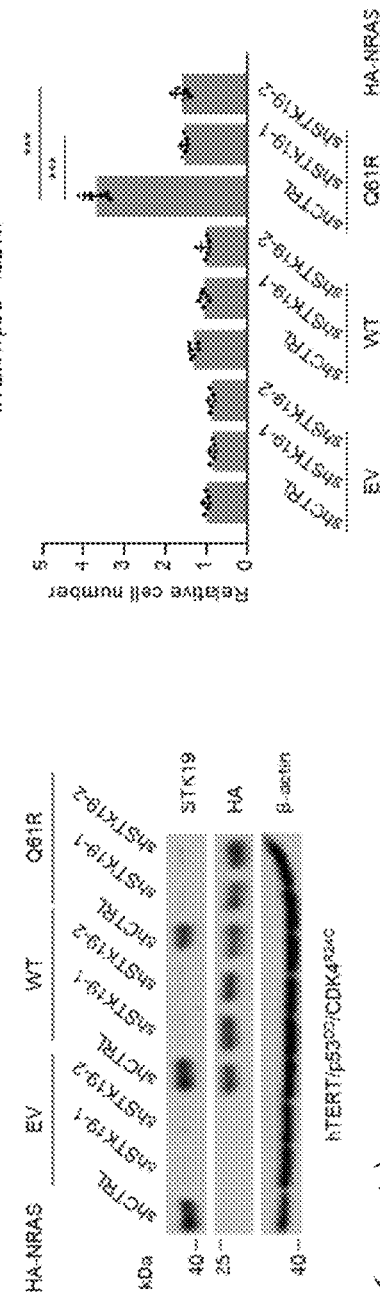
*FIG. 7H*
*FIG. 7G*
*FIGs. 7A-7H (cont.)*

FIGs. 8A-8T
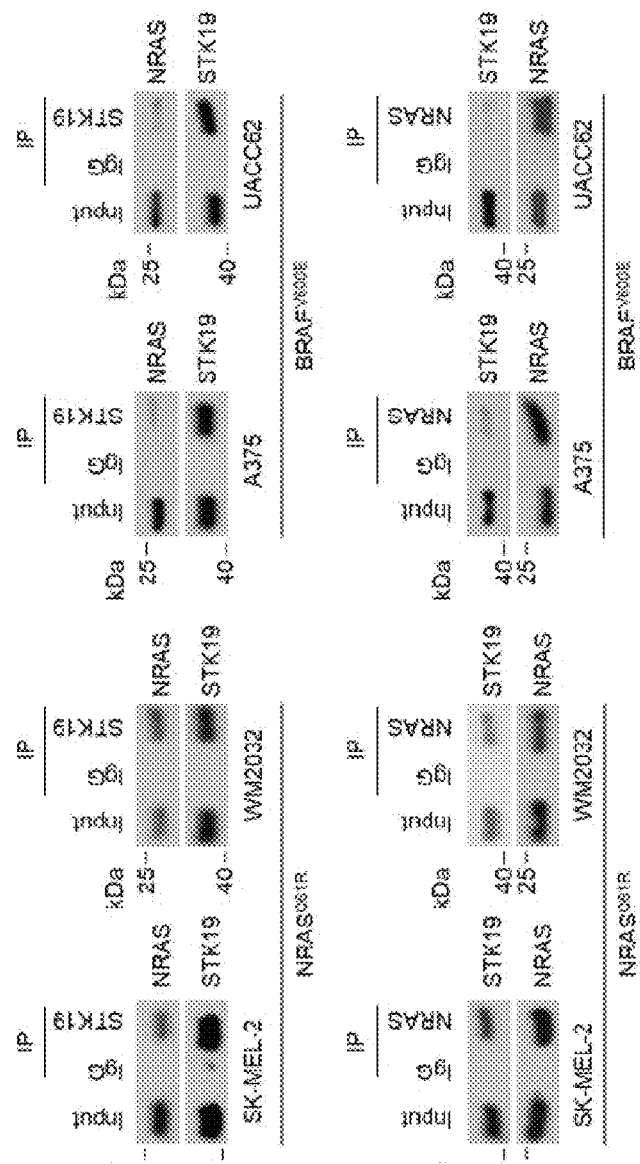
FIG. 8B
FIG. 8C
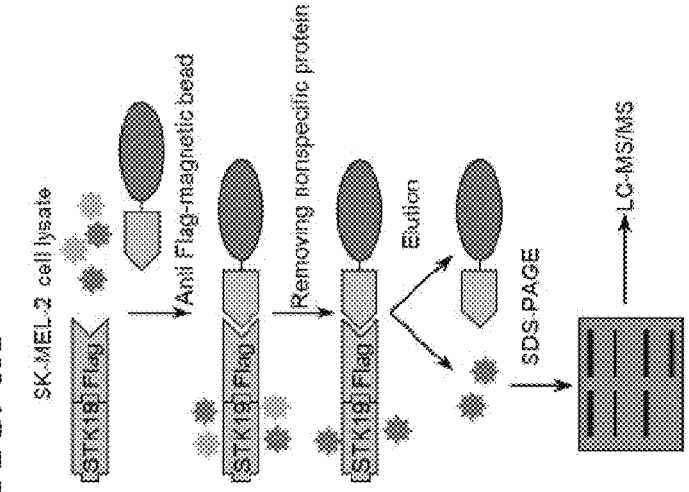
FIG. 8A

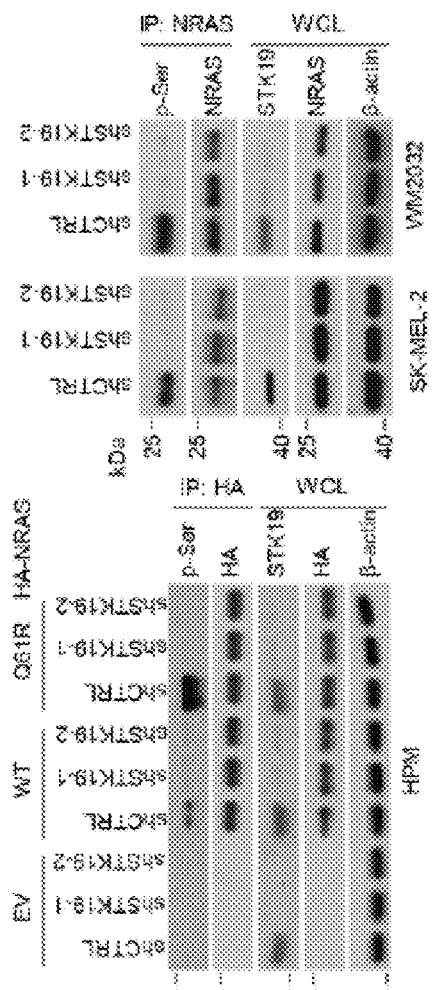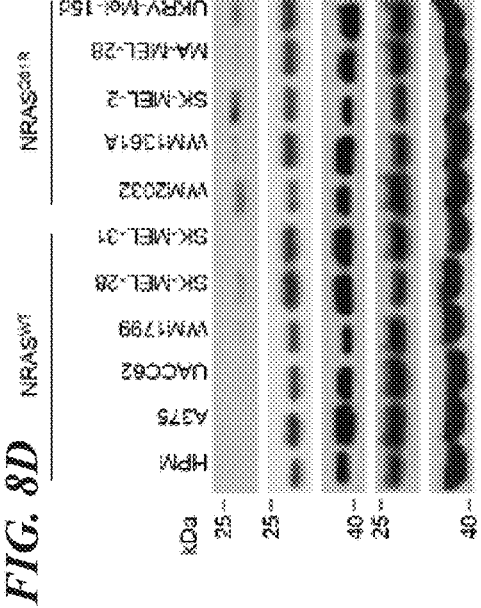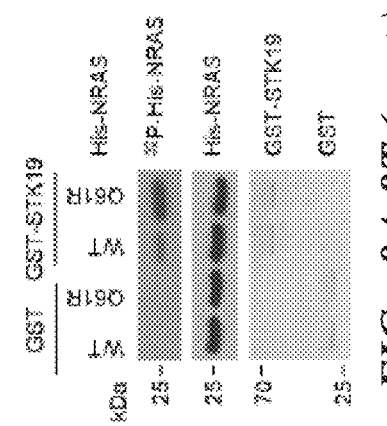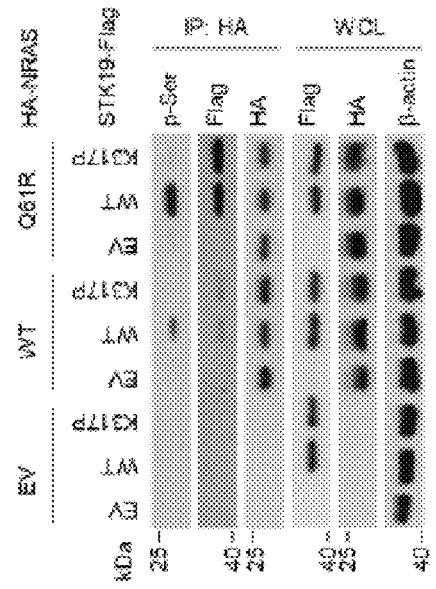
FIGs. 8A-8T (cont.)

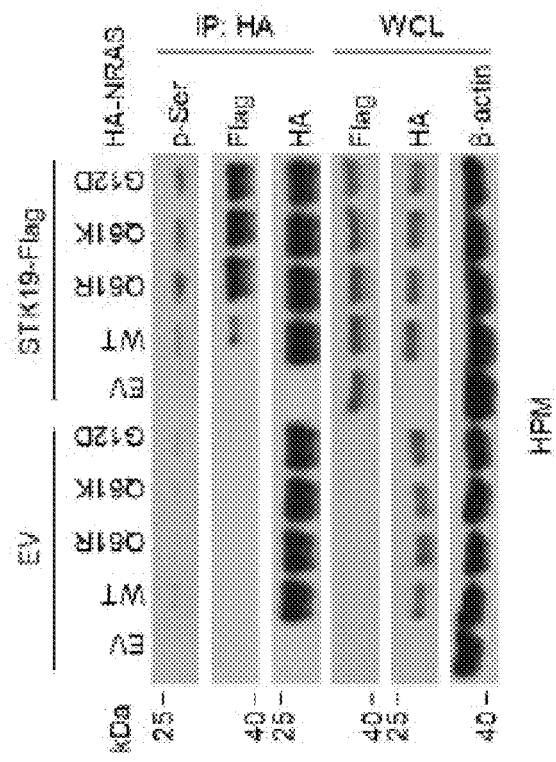
*FIG. 8K*
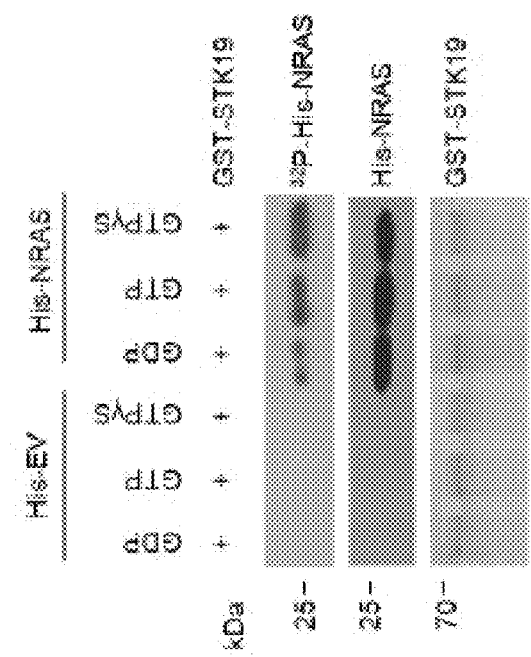
*FIG. 8J*
*FIGS. 8A-8T (cont.)*

FIGs. 8A-8T (cont.)
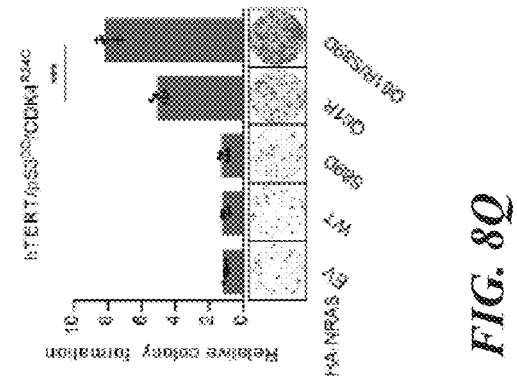
FIG. 8L
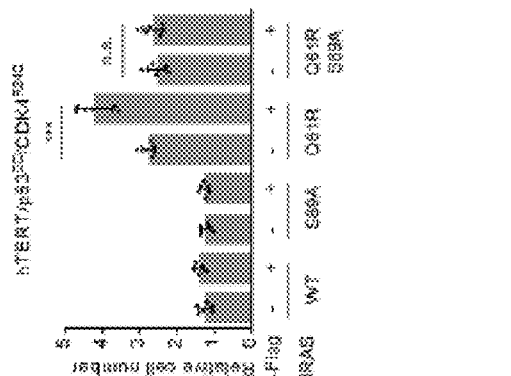
FIG. 8N
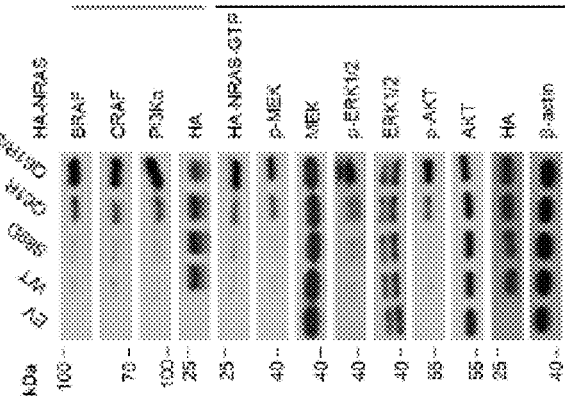
FIG. 8M
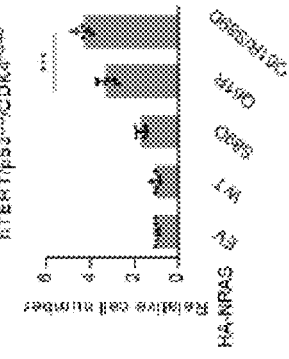
FIG. 8P
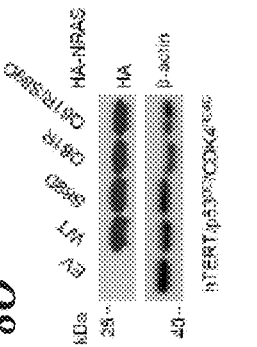
FIG. 8Q
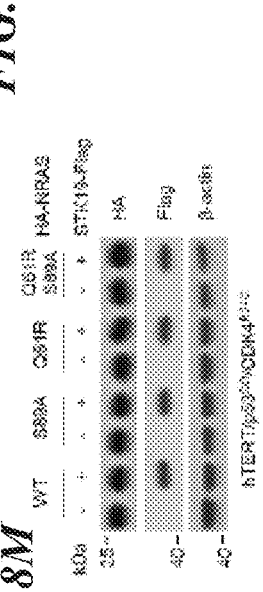
FIG. 8O FIGs. 8A-8T (cont.)
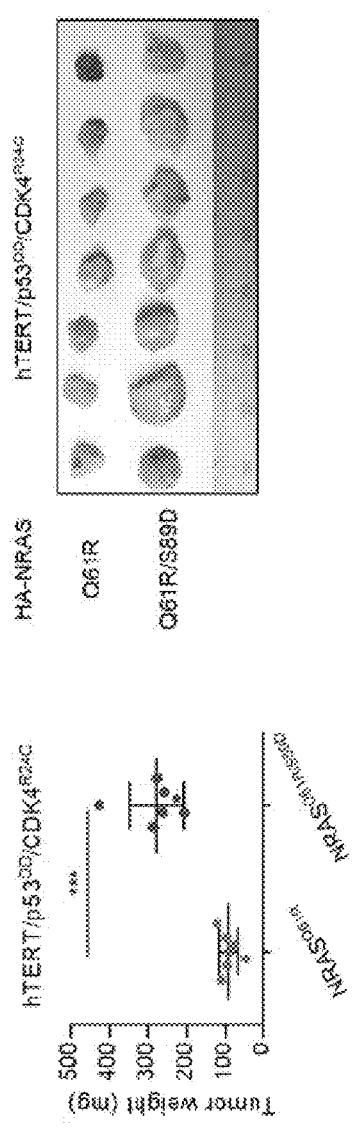
FIG. 8T
FIG. 8S
FIG. 8R
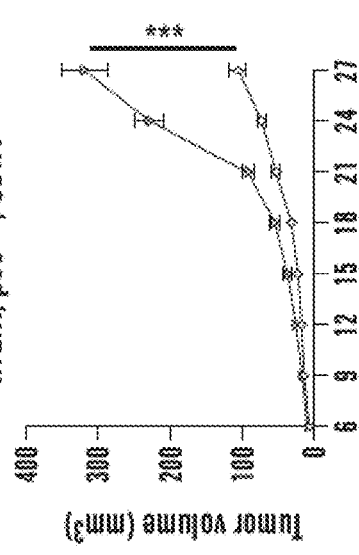

FIGs. 11A-11J (cont.)
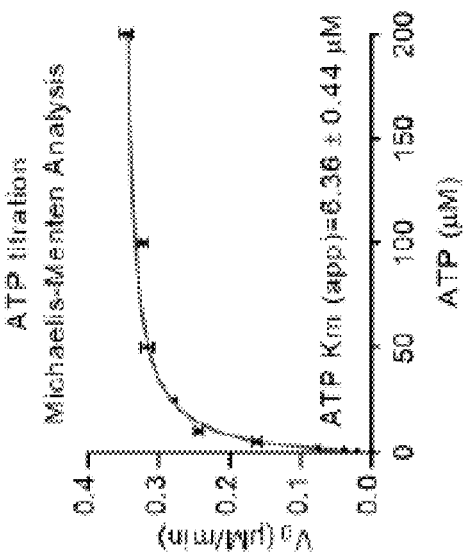
FIG. 11C
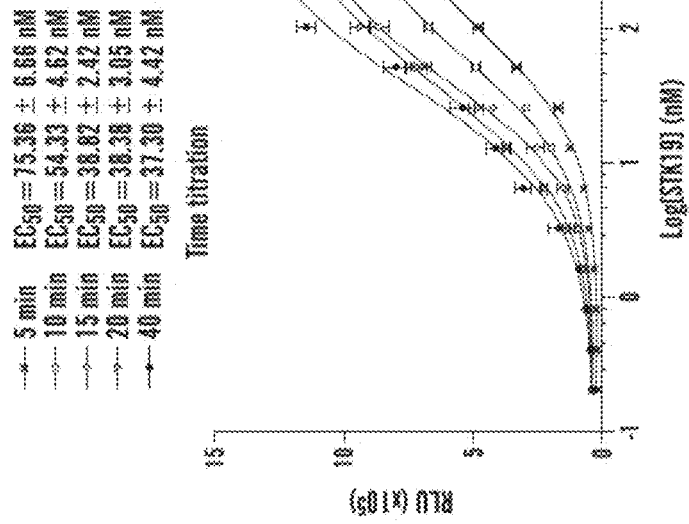
FIG. 11B

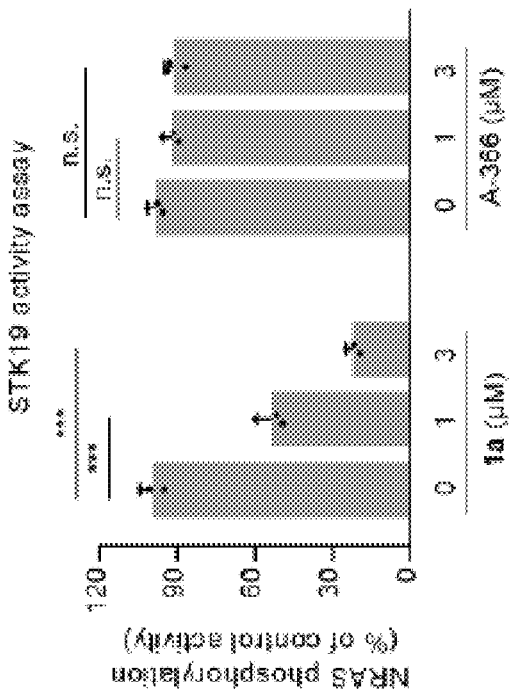
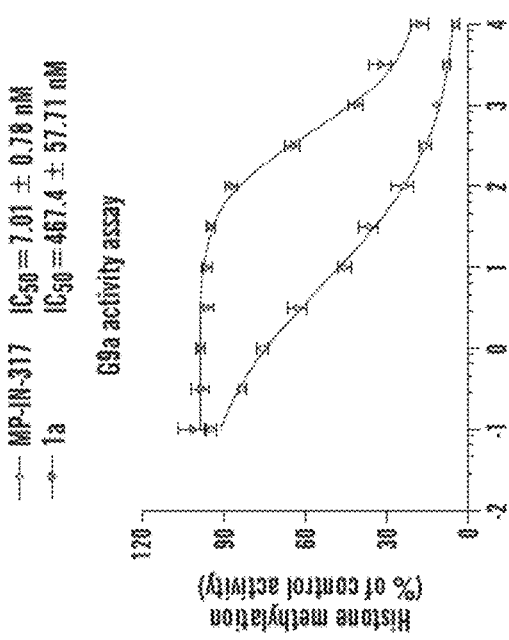
FIGs. 11A-11J (cont.)
FIG. 11D
FIG. 11E

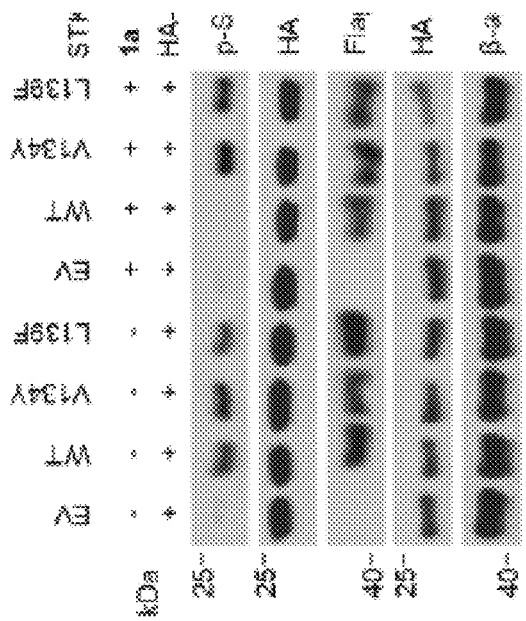
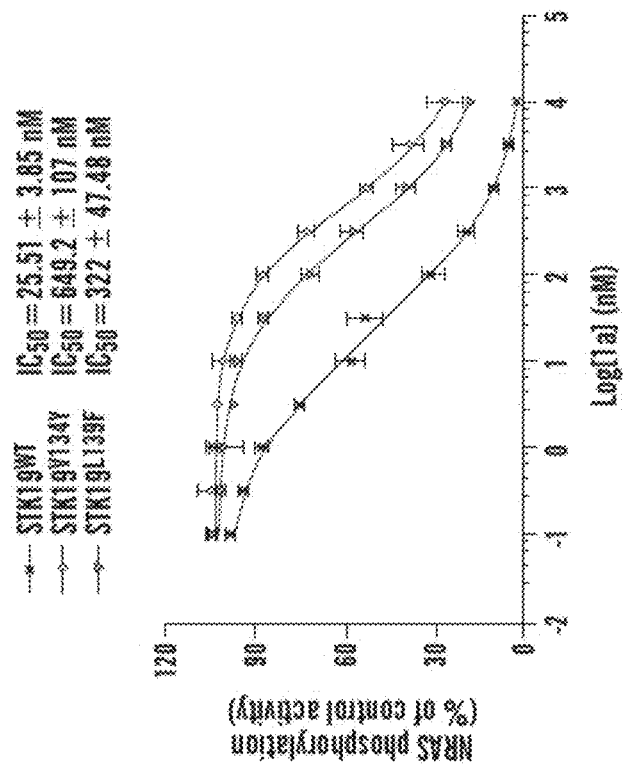
FIGS. 11A-11J (cont.)

FIGS. 11A-11J (cont.)
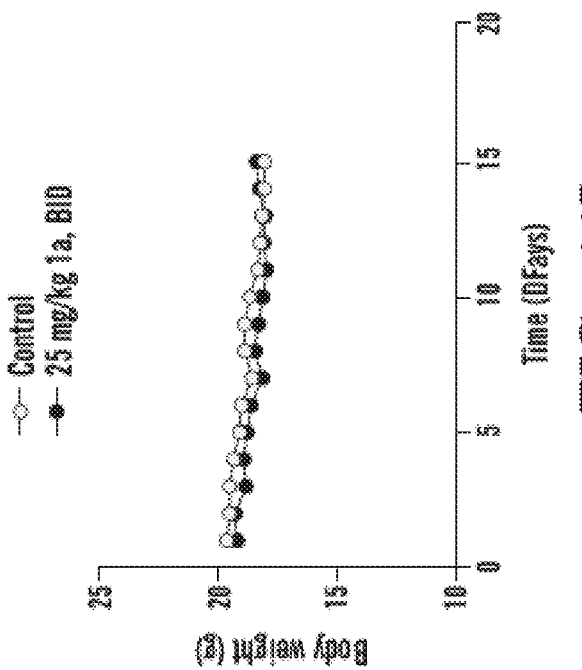
FIG. 11I
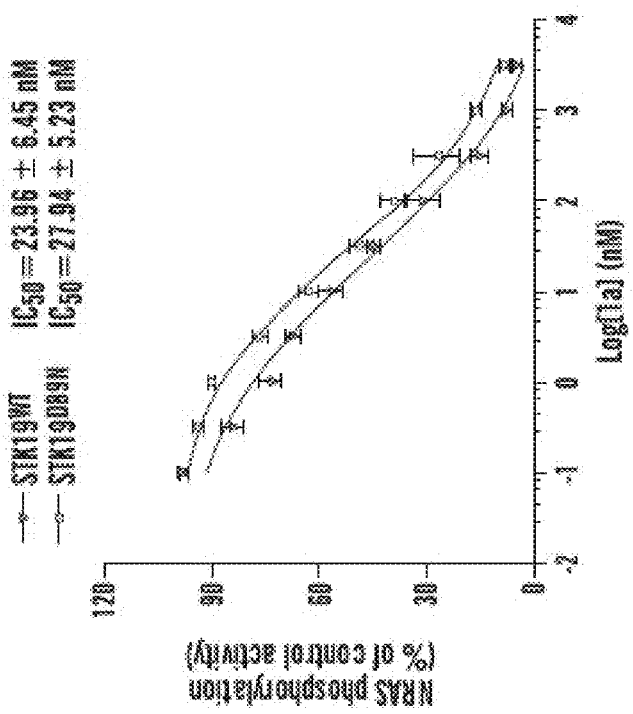
FIG. 11H

FIGs. 12A-12L
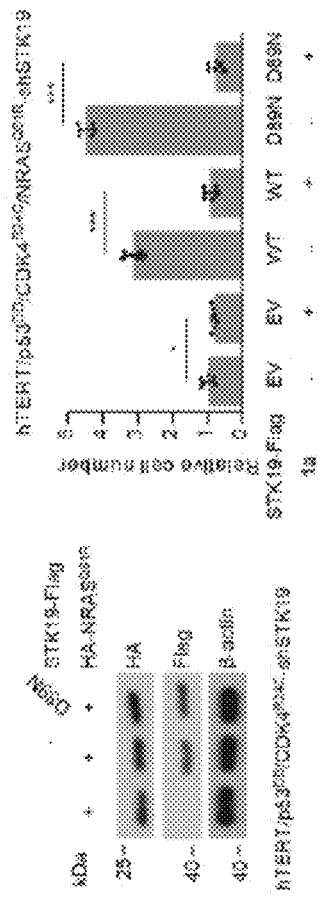
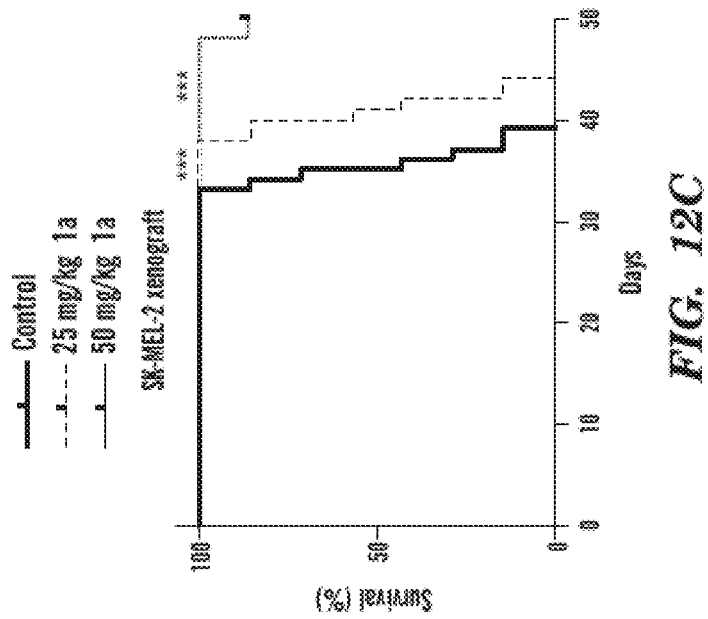

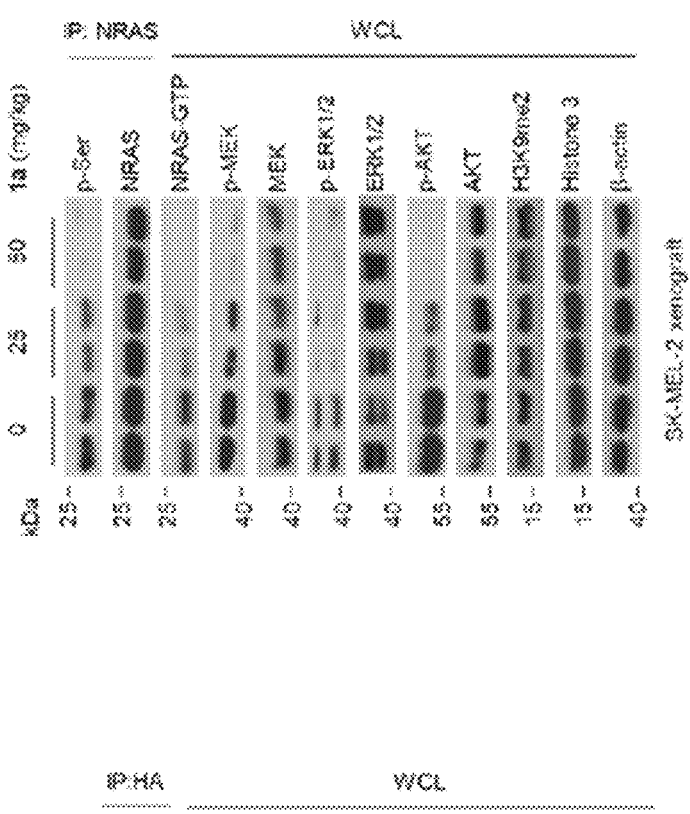
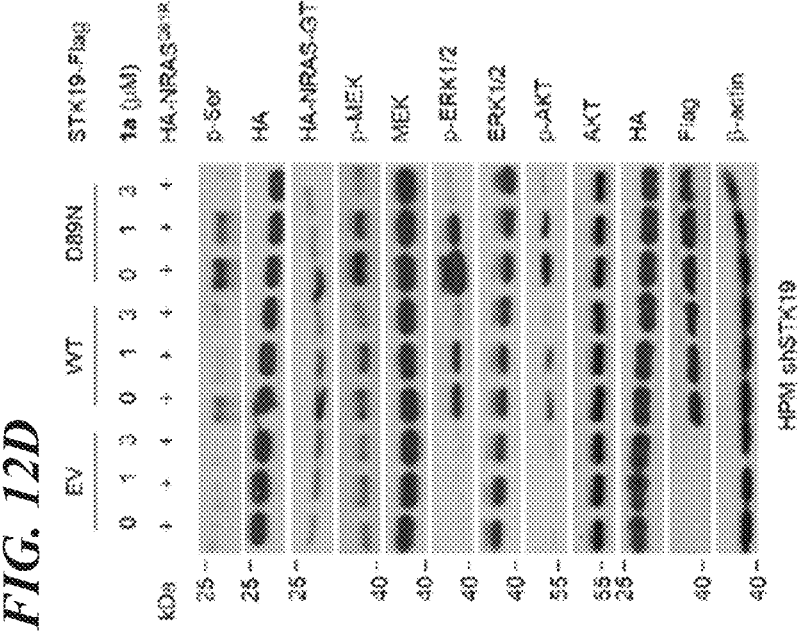
FIGS. 12A-12L (cont.)

FIGS. 12A-12L (cont.)
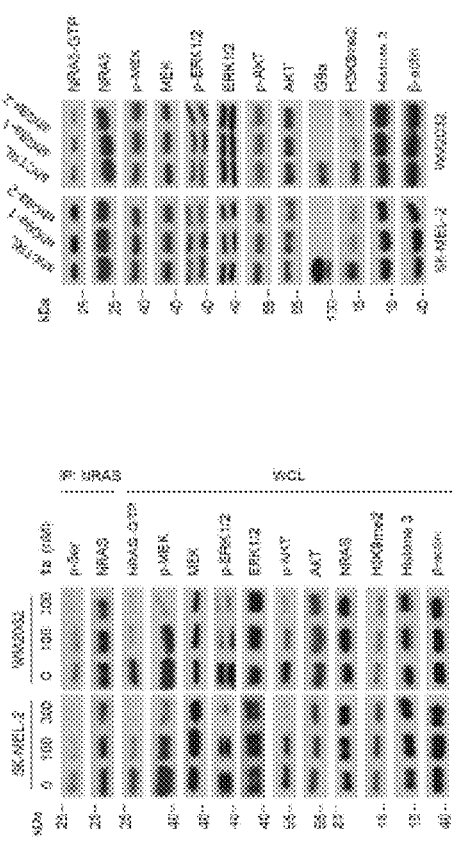
FIG. 12I
FIG. 12J
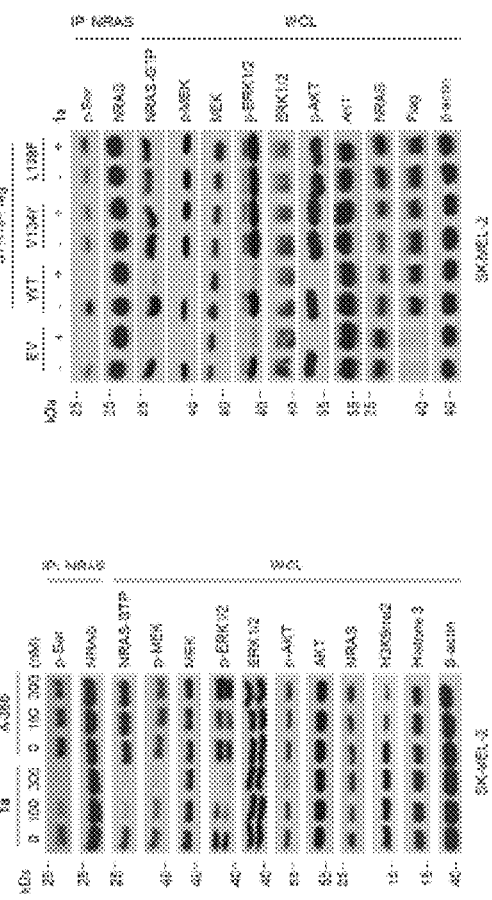
FIG. 12K
FIG. 12L

FIGS. 13A-13C
FIG. 13A
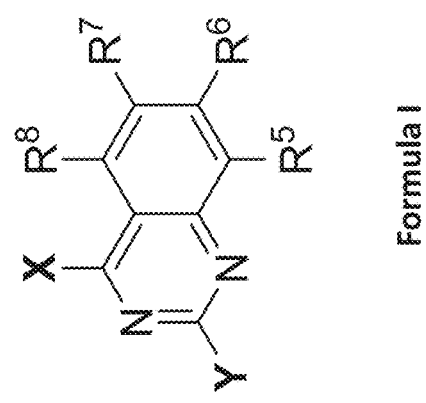
Formula I
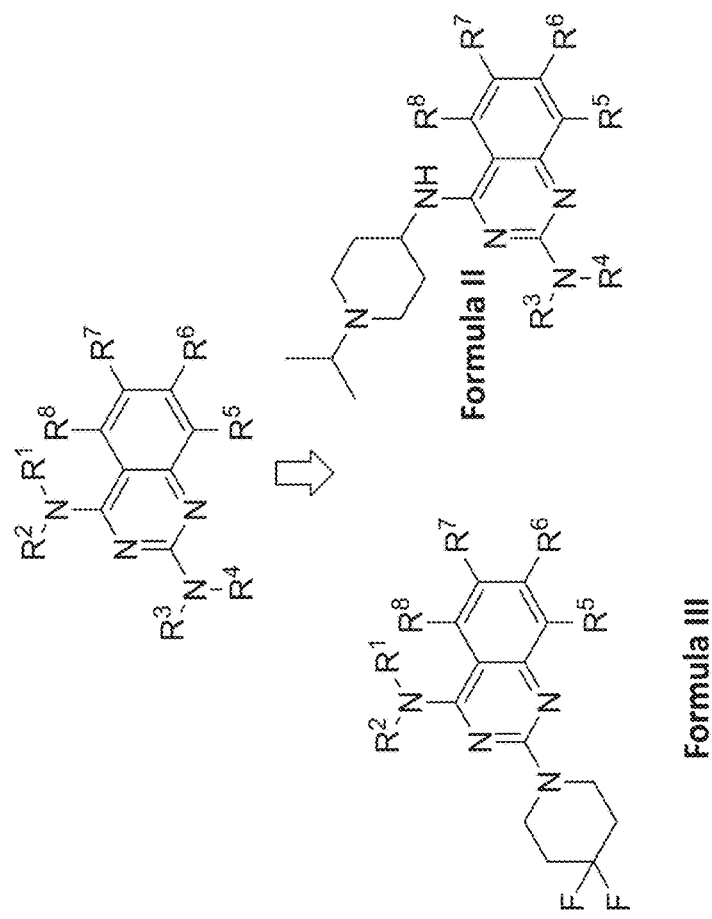
Formula II
Formula III

FIGS. 13A-13C (cont.)
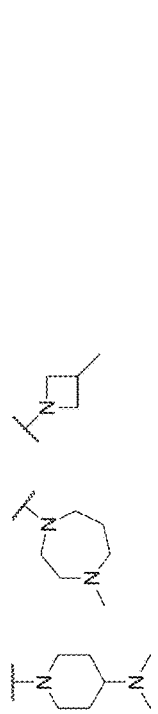
Formula i
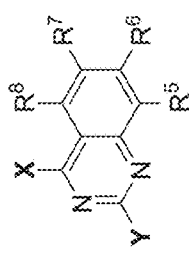
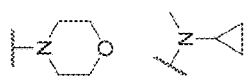
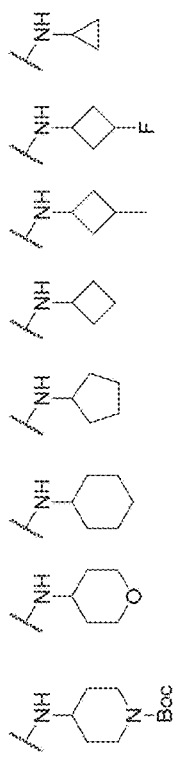
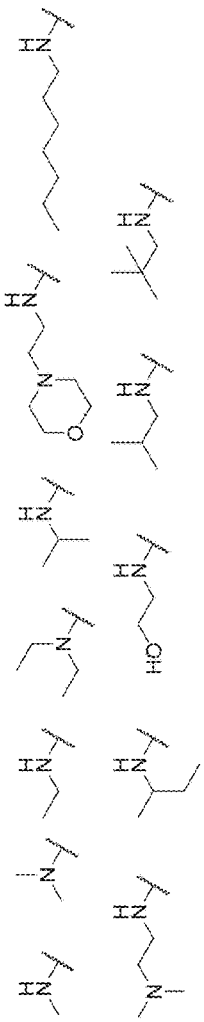
FIG. 13C
X, Y selected from:

SEQUENCE LISTING

<160> NUMBER OF SEQ ID NOS: 14

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Val Gly Ala Gly Gly Val Gly Lys
1               5                   10                  15

-continued

```
Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 2
<211> LENGTH: 364
<212> TYPE: PRT
<213> ORGANISM: Homo sapiens

<400> SEQUENCE: 2

```
Met Gln Lys Trp Phe Ser Ala Phe Asp Asp Ala Ile Ile Gln Arg Gln
1               5                   10                  15

Trp Arg Ala Asn Pro Ser Arg Gly Gly Gly Val Ser Phe Thr Lys
            20                  25                  30

Glu Val Asp Thr Asn Val Ala Thr Gly Ala Pro Pro Arg Arg Gln Arg
        35                  40                  45

Val Pro Gly Arg Ala Cys Pro Trp Arg Glu Pro Ile Arg Gly Arg Arg
    50                  55                  60

Gly Ala Arg Pro Gly Gly Gly Asp Ala Gly Gly Thr Pro Gly Glu Thr
65                  70                  75                  80

Val Arg His Cys Ser Ala Pro Glu Asp Pro Ile Phe Arg Phe Ser Ser
                85                  90                  95

Leu His Ser Tyr Pro Phe Pro Gly Thr Ile Lys Ser Arg Asp Met Ser
            100                 105                 110

Trp Lys Arg His His Leu Ile Pro Glu Thr Phe Gly Val Lys Arg Arg
        115                 120                 125

Arg Lys Arg Gly Pro Val Glu Ser Asp Pro Leu Arg Gly Glu Pro Gly
    130                 135                 140

Ser Ala Arg Ala Ala Val Ser Glu Leu Met Gln Leu Phe Pro Arg Gly
145                 150                 155                 160

Leu Phe Glu Asp Ala Leu Pro Pro Ile Val Leu Arg Ser Gln Val Tyr
                165                 170                 175

Ser Leu Val Pro Asp Arg Thr Val Ala Asp Arg Gln Leu Lys Glu Leu
            180                 185                 190

Gln Glu Gln Gly Glu Ile Arg Ile Val Gln Leu Gly Phe Asp Leu Asp
        195                 200                 205
```

```
Ala His Gly Ile Ile Phe Thr Glu Asp Tyr Arg Thr Arg Val Leu Lys
    210                 215                 220

Ala Cys Asp Gly Arg Pro Tyr Ala Gly Ala Val Gln Lys Phe Leu Ala
225                 230                 235                 240

Ser Val Leu Pro Ala Cys Gly Asp Leu Ser Phe Gln Gln Asp Gln Met
                245                 250                 255

Thr Gln Thr Phe Gly Phe Arg Asp Ser Glu Ile Thr His Leu Val Asn
            260                 265                 270

Ala Gly Val Leu Thr Val Arg Asp Ala Gly Ser Trp Trp Leu Ala Val
        275                 280                 285

Pro Gly Ala Gly Arg Phe Ile Lys Tyr Phe Val Lys Gly Arg Gln Ala
    290                 295                 300

Val Leu Ser Met Val Arg Lys Ala Lys Tyr Arg Glu Leu Leu Leu Ser
305                 310                 315                 320

Glu Leu Leu Gly Arg Arg Ala Pro Val Val Arg Leu Gly Leu Thr
                325                 330                 335

Tyr His Val His Asp Leu Ile Gly Ala Gln Leu Val Asp Cys Ile Ser
                340                 345                 350

Thr Thr Ser Gly Thr Leu Leu Arg Leu Pro Glu Thr
            355                 360

<210> SEQ ID NO 3
<211> LENGTH: 368
<212> TYPE: PRT
<213> ORGANISM: Homo sapiens

<400> SEQUENCE: 3

Met Gln Lys Trp Phe Ser Ala Phe Asp Asp Ala Ile Ile Gln Arg Gln
1               5                   10                  15

Trp Arg Ala Asn Pro Ser Arg Gly Gly Gly Val Ser Phe Thr Lys
            20                  25                  30

Glu Val Asp Thr Asn Val Ala Thr Gly Ala Pro Pro Arg Arg Gln Arg
        35                  40                  45

Val Pro Gly Arg Ala Cys Pro Trp Arg Glu Pro Ile Arg Gly Arg Arg
50                  55                  60

Gly Ala Arg Pro Gly Gly Asp Ala Gly Thr Pro Gly Glu Thr
65                  70                  75                  80

Val Arg His Cys Ser Ala Pro Glu Asp Pro Ile Phe Arg Phe Ser Ser
                85                  90                  95

Leu His Ser Tyr Pro Phe Pro Gly Thr Ile Lys Ser Arg Asp Met Ser
                100                 105                 110

Trp Lys Arg His His Leu Ile Pro Glu Thr Phe Gly Val Lys Arg Arg
            115                 120                 125

Arg Lys Arg Gly Pro Val Glu Ser Asp Pro Leu Arg Gly Glu Pro Gly
        130                 135                 140

Ser Ala Arg Ala Val Ser Glu Leu Met Gln Leu Phe Pro Arg Gly
145                 150                 155                 160

Leu Phe Glu Asp Ala Leu Pro Pro Ile Val Leu Arg Ser Gln Val Tyr
                165                 170                 175

Ser Leu Val Pro Asp Arg Thr Val Ala Asp Arg Gln Leu Lys Glu Leu
            180                 185                 190

Gln Glu Gln Gly Glu Ile Arg Ile Val Gln Leu Gly Phe Asp Leu Asp
        195                 200                 205

Ala His Gly Ile Ile Phe Thr Glu Asp Tyr Arg Thr Arg Val Cys Asp
```

Cys Val Leu Lys Ala Cys Asp Gly Arg Pro Tyr Ala Gly Ala Val Gln
225                 230                 235                 240

Lys Phe Leu Ala Ser Val Leu Pro Ala Cys Gly Asp Leu Ser Phe Gln
            245                 250                 255

Gln Asp Gln Met Thr Gln Thr Phe Gly Phe Arg Asp Ser Glu Ile Thr
                260                 265                 270

His Leu Val Asn Ala Gly Val Leu Thr Val Arg Asp Ala Gly Ser Trp
        275                 280                 285

Trp Leu Ala Val Pro Gly Ala Gly Arg Phe Ile Lys Tyr Phe Val Lys
290                 295                 300

Gly Arg Gln Ala Val Leu Ser Met Val Arg Lys Ala Lys Tyr Arg Glu
305                 310                 315                 320

Leu Leu Leu Ser Glu Leu Leu Gly Arg Arg Ala Pro Val Val Val Arg
                325                 330                 335

Leu Gly Leu Thr Tyr His Val His Asp Leu Ile Gly Ala Gln Leu Val
                340                 345                 350

Asp Cys Ile Ser Thr Thr Ser Gly Thr Leu Leu Arg Leu Pro Glu Thr
            355                 360                 365

<210> SEQ ID NO 4
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Ala Phe Asp Asp Ala Ile Ile Gln Arg Gln Trp Arg Ala Asn Pro
1               5                   10                  15

Ser Arg Gly Gly Gly Gly Val Ser Phe Thr Lys Glu Val Asp Thr Asn
            20                  25                  30

Val Ala Thr Gly Ala Pro Pro Arg Gln Arg Val Pro Gly Arg Ala
        35                  40                  45

Cys Pro Trp Arg Glu Pro Ile Arg Gly Arg Gly Ala Arg Pro Gly
    50                  55                  60

Gly Gly Asp Ala Gly
65

<210> SEQ ID NO 5
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Met Thr Gln Thr Phe Gly Phe Arg Asp Ser Glu Ile Thr His Leu
1               5                   10                  15

Val Asn Ala Gly Val Leu Thr Val Arg Asp Ala Gly Ser Trp Trp Leu
            20                  25                  30

Ala Val Pro Gly Ala Gly Arg Phe Ile Lys Tyr Phe Val Lys Gly Arg
        35                  40                  45

Gln Ala Val Leu Ser Met Val Arg Lys Ala Lys Tyr Arg Glu Leu Leu
    50                  55                  60

Leu Ser Glu Leu Leu Gly Arg Arg Ala Pro Val Val Val Arg Leu Gly

```
                65                  70                  75                  80
Leu Thr Tyr His Val His Asp Leu Ile Gly Ala Gln Leu Val Asp Cys
                    85                  90                  95

Ile Ser Thr Thr Ser Gly Thr Leu Leu Arg Leu Pro Glu Thr
                100                 105                 110

<210> SEQ ID NO 6
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Ala Val Ser Glu Leu Met Gln Leu Phe Pro Arg Gly Leu Phe Glu
1               5                   10                  15

Asp Ala Leu Pro Pro Ile Val Leu Arg Ser Gln Val Tyr Ser Leu Val
                20                  25                  30

Pro Asp Arg Thr Val Ala Asp Arg Gln Leu Lys Glu Leu Gln Glu Gln
            35                  40                  45

Gly Glu Ile Arg Ile Val Gln Leu Gly Phe Asp Leu Asp Ala His Gly
        50                  55                  60

Ile Ile Phe Thr Glu Asp Tyr Arg Thr Arg
65                  70

<210> SEQ ID NO 7
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Ala Phe Asp Asp Ala Ile Ile Gln Arg Gln Trp Arg Ala Asn Pro
1               5                   10                  15

Ser Arg Gly Gly Gly Gly Val Ser Phe Thr Lys Glu Val Asp Thr Asn
                20                  25                  30

Val Ala Thr Gly Ala Pro Pro Arg Arg Gln Arg Val Pro Gly Arg Ala
            35                  40                  45

Cys Pro Trp Arg Glu Pro Ile Arg Gly Arg Arg Gly Ala Arg Pro Gly
        50                  55                  60

Gly Gly Asp Ala Gly
65

<210> SEQ ID NO 8
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Ala Phe Asp Asp Ala Ile Ile Gln Arg Gln Trp Arg Ala Asn Pro
1               5                   10                  15

Ser Arg Gly Gly Gly Gly Val Ser Phe Thr Lys Glu Val Asp Thr Asn
                20                  25                  30

Val Ala Thr Gly Ala Pro Pro Arg Arg Gln Arg Val Pro Gly Arg Ala
            35                  40                  45
```

Cys Pro Trp Arg Glu Pro Ile Arg Gly Arg Arg Gly Ala Arg Pro Gly
            50                  55                  60

Gly Gly Asp Ala Gly
65

<210> SEQ ID NO 9
<211> LENGTH: 9
<212> TYPE: PRT
<213> ORGANISM: Unknown
<220> FEATURE:
<223> OTHER INFORMATION: Description of Unknown:
      NRAS protein sequence

<400> SEQUENCE: 9

Ser Phe Ala Asp Ile Asn Leu Tyr Arg
1               5

<210> SEQ ID NO 10
<211> LENGTH: 20
<212> TYPE: PRT
<213> ORGANISM: Homo sapiens

<400> SEQUENCE: 10

Val Phe Ala Ile Asn Asn Ser Lys Ser Phe Ala Asp Ile Asn Leu Tyr
1               5                   10                  15

Arg Glu Gln Ile
            20

<210> SEQ ID NO 11
<211> LENGTH: 20
<212> TYPE: PRT
<213> ORGANISM: Mus sp.

<400> SEQUENCE: 11

Val Phe Ala Ile Asn Asn Ser Lys Ser Phe Ala Asp Ile Asn Leu Tyr
1               5                   10                  15

Arg Glu Gln Ile
            20

<210> SEQ ID NO 12
<211> LENGTH: 20
<212> TYPE: PRT
<213> ORGANISM: Rattus sp.

<400> SEQUENCE: 12

Val Phe Ala Ile Asn Asn Ser Lys Ser Phe Ala Asp Ile Asn Leu Tyr
1               5                   10                  15

Arg Glu Gln Ile
            20

<210> SEQ ID NO 13
<211> LENGTH: 20
<212> TYPE: PRT
<213> ORGANISM: Cavia porcellus

<400> SEQUENCE: 13

Val Phe Ala Ile Asn Asn Ser Lys Ser Phe Ala Asp Ile Asn Leu Tyr
1               5                   10                  15

Arg Glu Gln Ile
            20

<210> SEQ ID NO 14

```
<211> LENGTH: 20
<212> TYPE: PRT
<213> ORGANISM: Xenopus laevis

<400> SEQUENCE: 14

Val Phe Ala Ile Asn Asn Ser Lys Ser Phe Ala Asp Ile Asn Ala Tyr
1               5                   10                  15

Arg Glu Gln Ile
            20
```

STK19 INHIBITORS FOR TREATMENT OF CANCER

CROSS-REFERENCE TO RELATED APPLICATIONS

This application claims benefit under 35 U.S.C. § 119(e) of U.S. Provisional Application No. 62/782,820 filed Dec. 20, 2018, the content of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 6, 2020, is named 701586-094210WO-PT_SL.txt and is 13,828 bytes in size.

TECHNICAL FIELD

The technical field relates to compositions and methods for the treatment and prevention of cancer, e.g., melanoma.

BACKGROUND

Skin cancer is the most commonly diagnosed cancer in the US. Melanoma, the most serious type of skin cancer, develops in the cells (melanocytes) that produce melanin, the pigment that gives skin its color. The incidence of malignant melanoma has been increasing worldwide, resulting in an important socio-economic problem. About 132,000 new cases of melanoma are diagnosed worldwide each year, according to the World Health Organization. Australia and New Zealand have the highest rates of melanoma in the world. In the United States, melanoma is regarded as the fifth most common cancer in men and the sixth most common cancer in women, where the incidence of malignant melanoma melanoma of the skin has risen rapidly over the past 30 years. Currently, 1 in 63 Americans will develop melanoma during their lifetime. In 2019, it is estimated that there will be 96,480 new cases of melanoma in the United States and 7,230 deaths from the disease.

Although most patients have a localized disease at the time of the diagnosis and are treated by surgical excision of the primary tumor, many patients develop metastases. The Cancer Genome Atlas (TCGA) Network found that whole exome sequence analysis of 333 primary and/or metastatic melanoma patients, melanomas could be classified into four genomic subtypes: mutant BRAF, mutant NRAS, mutant NF1, and triple-wildtype. In melanoma, the activated BRAF mutated kinase can be inhibited by BRAF targeting drugs, and its downstream protein MEK kinase can be inhibited by a MEK targeted drug. The combination of targeted inhibitors have had a very significant impact on survival in patients with BRAF mutant melanoma with a median overall survival exceeding 2 years. On the other hand, the other common genomic subtypes, including mutant NRAS, mutant NF1, and triple-wildtype have thus far not been effectively targeted.

Activating NRAS mutations occur in approximately 20-30% of melanomas. The RAS family includes three primary proto-oncogenes: NRAS, KRAS, and HRAS, that regulate cell proliferation and apoptosis. NRAS mutations constitutively activate the MAPK, PI3K, and other cell signaling pathways causing cell growth, proliferation, and cell cycle dysfunction. Melanomas with NRAS mutations are associated with an aggressive clinical course and poor prognosis. Treatment for NRAS mutant melanoma has been met with limited success to date. There is an unmet medical need for new targeted therapy opportunities in metastatic patients whose tumors harbor an NRAS mutation.

SUMMARY

The inventions described herein relate to several novel agents for the prevention and treatment of a cancer. Specifically, the compounds, compositions and methods described herein have been developed for the prevention and treatment of melanoma. The compounds described herein inhibit the novel serine/threonine kinase STK19 which is upregulated in cancers with mutations in a marker/oncogene described herein, e.g., one or more mutations in NRAS. Accordingly, they are therapeutic for any cancer with NRAS mutations.

In one aspect of any of the embodiments, described herein is a compound of Formula I:

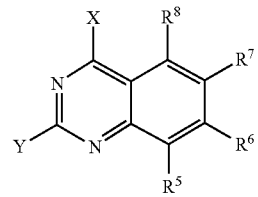

FORMULA I wherein:

X is aryl, or $N(R^1R^2)$;

Y is aryl, or $N(R^3R^4)$;

$R^1$ and $R^2$ are independently hydrogen, alkyl, cyclyl, heterocyclyl, aryl or heteroaryl, each of which can be optionally substituted, or $R^1$ and $R^2$ are connect to form an optionally substituted heterocyclyl;

$R^3$ and $R^4$ are independently hydrogen, alkyl, cyclyl, heterocyclyl, aryl or heteroaryl, each of which can be optionally substituted, or $R^3$ and $R^4$ are connect to form an optionally substituted heterocyclyl $R^5$, $R^6$, $R^7$ and $R^8$ are independently selected from the group consisting of hydrogen, alkyl, halogen, nitro, cyano, hydroxyl, amino, mercapto, formyl, carboxy, alkanoyl, carbamoyl, alkoxy, alkylthio, alkylamino, (alkyl)$_2$amino (dialkylamino), alkylsulfinyl, alkylsulfonyl, arylsulfonyl, cyclyl, heterocyclyl, aryl, or heteroaryl, each of which can be optionally substituted;

provided that at least one of X and Y is independently selected from the group consisting of:

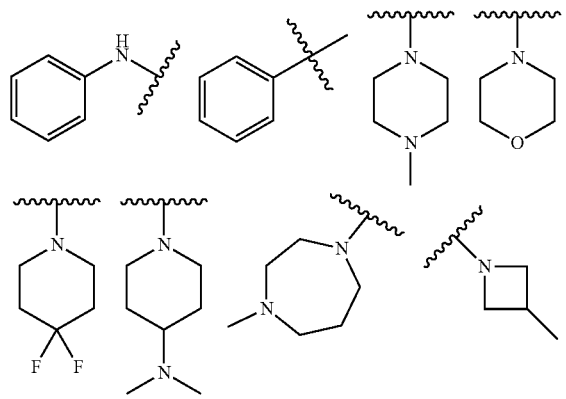

-continued
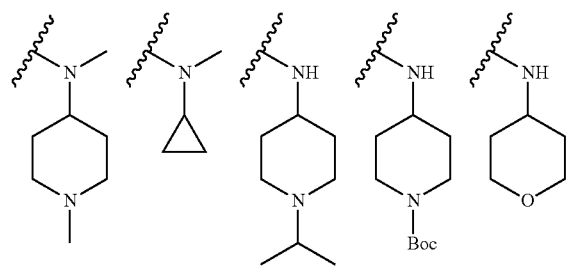
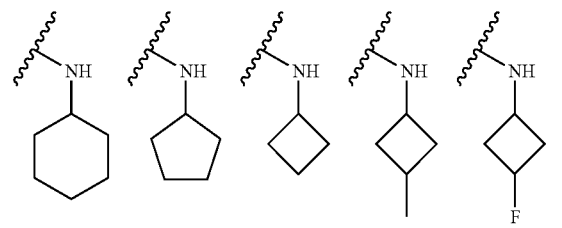
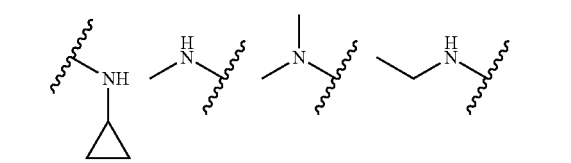
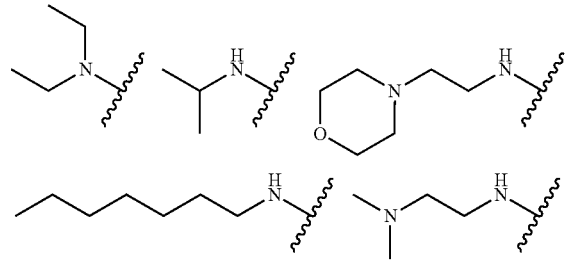
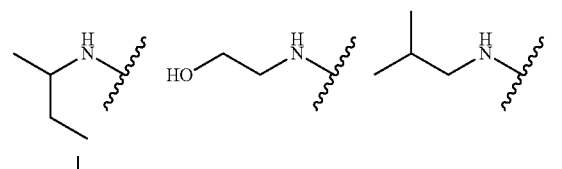
or
isomers, tautomers or a pharmaceutically acceptable salt thereof, provided that the compound is not
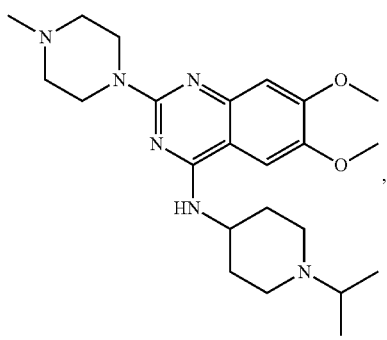
-continued
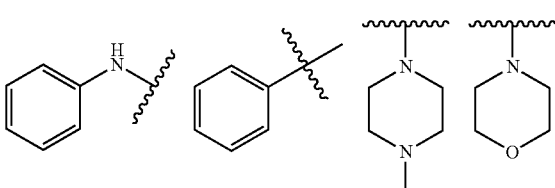
In one embodiment of any of the aspects, the X is selected from the group consisting of:
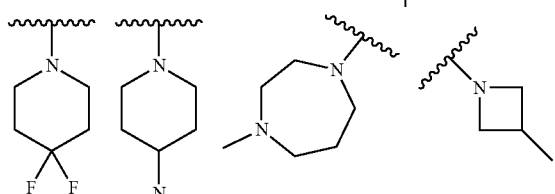
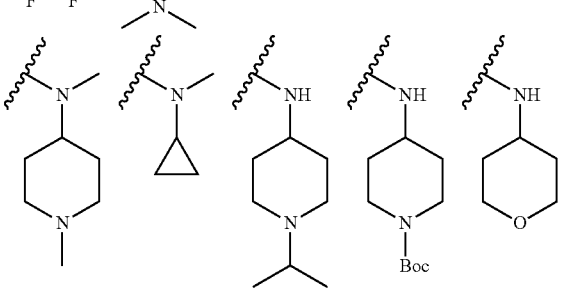

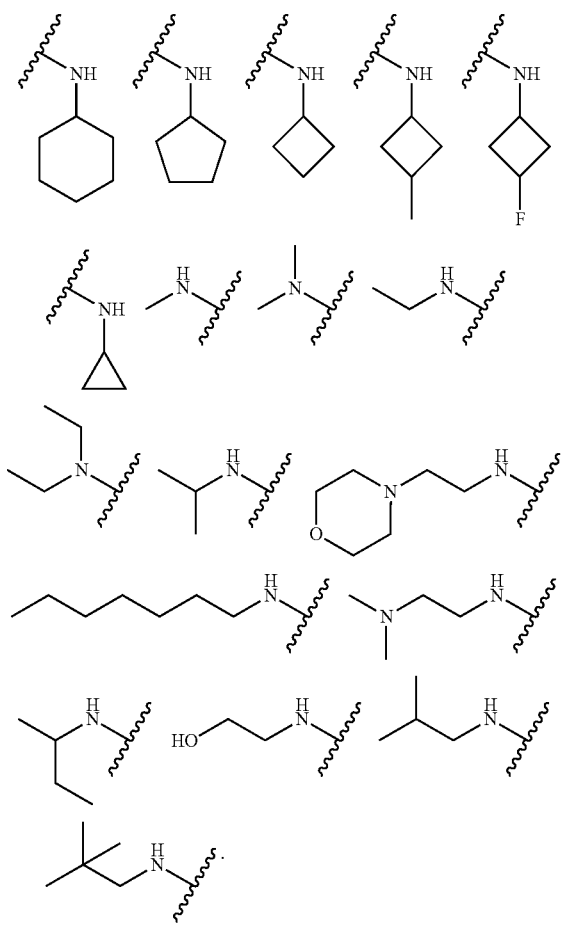
In another embodiment of any of the aspects, the compound of any one of claims 1-2, wherein X is selected from the group consisting of:
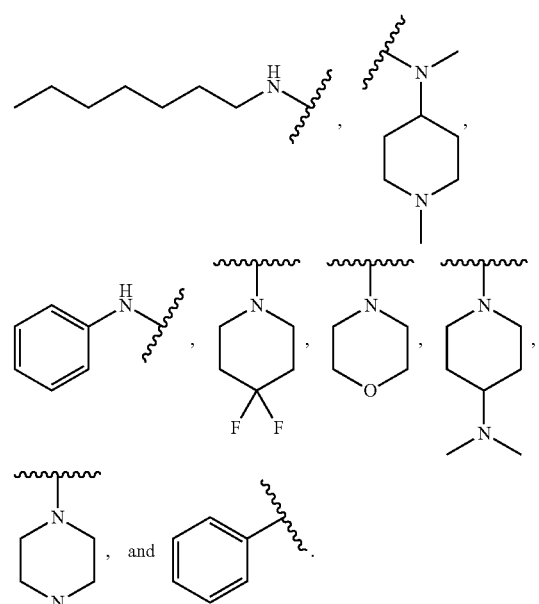
In another embodiment of any of the aspects, the compound is of Formula (II):
FORMULA (II)
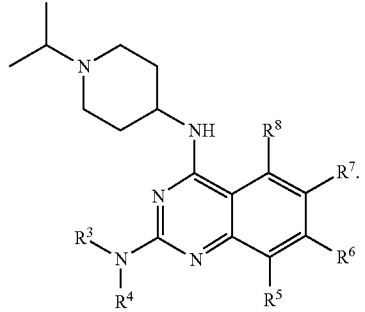
In another embodiment of any of the aspects, the Y is selected from the group consisting of:
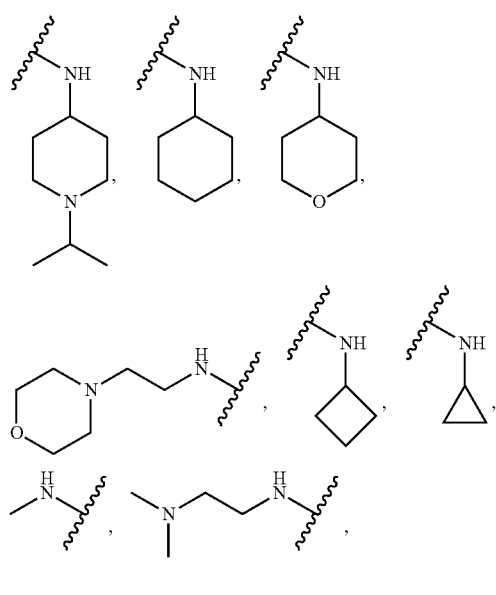

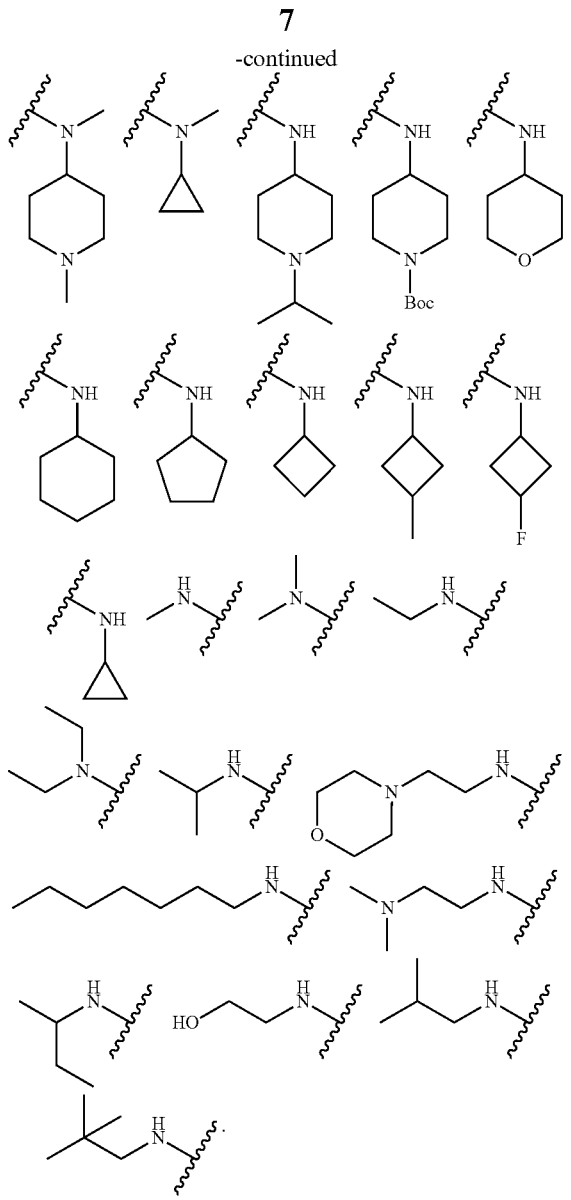

In another embodiment of any of the aspects, the Y is selected from the group consisting of:

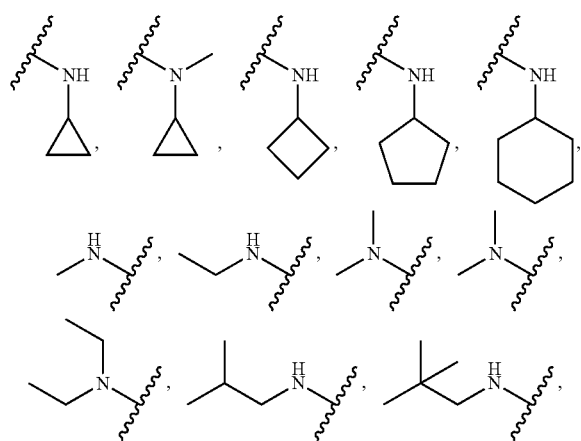

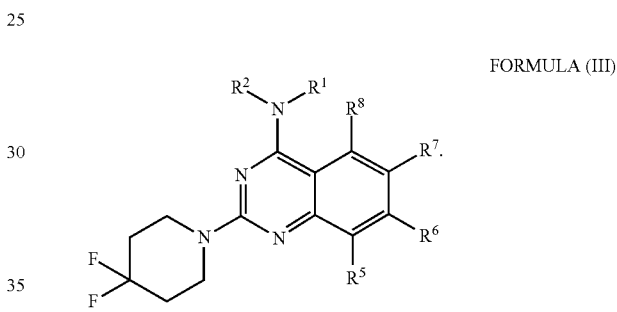

In another embodiment of any of the aspects, the compound is of Formula (III):

FORMULA (III)

In another embodiment of any of the aspects, $R^6$ is H or an optionally substituted alkoxy.

In another embodiment of any of the aspects, $R^6$ is H or —$OR^9$, where $R^9$ is alkyl, cyclyl, heterocyclyl, aryl or heteroaryl, each of which can be optionally substituted.

In another embodiment of any of the aspects, $R^6$ is H or —$OR^9$, where $R^9$ is optionally substituted $C_1$-$C_6$ alkyl.

In another embodiment of any of the aspects, $R^6$ is H or —$OR^9$, where $R^9$ is methyl, ethyl, propyl, isopropyl, 1-mthylpropy, 2-methylpropyl, butyl, t-butyl, pentyl or hexyl.

In another embodiment of any of the aspects, $R^6$ is H or —$OR^9$, where $R^9$ is methyl.

In another embodiment of any of the aspects, $R^7$ is H or an optionally substituted alkoxy.

In another embodiment of any of the aspects, $R^7$ is H or —$OR^{10}$, where $R^{10}$ is alkyl, cyclyl, hetrocyclyl, aryl or heteroaryl, each of which can be optionally substituted.

In another embodiment of any of the aspects, $R^7$ is H or —$OR^{10}$, where $R^{10}$ is optionally substituted $C_1$-$C_6$ alkyl.

In another embodiment of any of the aspects, $R^7$ is H or —$OR^{10}$, where $R^{10}$ is methyl, ethyl, propyl, isopropyl, 1-mthylpropy, 2-methylpropyl, butyl, t-butyl, pentyl or hexyl.

In another embodiment of any of the aspects, $R^7$ is H or —$OR^{10}$, where $R^9$ is methyl.

In another embodiment of any of the aspects, $R^6$ and $R^7$ are H or —$OCH_3$.

In another embodiment of any of the aspects, $R^5$ is hydrogen, alkyl, halogen, nitro, cyano, hydroxyl, alkoxy, carboxy, amino, alkylamino or dialkylamino.

In another embodiment of any of the aspects, $R^5$ is hydrogen, alkyl, halogen, nitro, cyano, hydroxyl, carboxy or amino.

In another embodiment of any of the aspects, $R^5$ is hydrogen.

In another embodiment of any of the aspects, $R^8$ is hydrogen, alkyl, halogen, nitro, cyano, hydroxyl, alkoxy, carboxy, amino, alkylamino or dialkylamino.

In another embodiment of any of the aspects, $R^8$ is hydrogen, alkyl, halogen, nitro, cyano, hydroxyl, carboxy or amino.

In another embodiment of any of the aspects, $R^8$ is hydrogen.

In another embodiment of any of the aspects, $R^5$ and $R^8$ are hydrogen.

In another embodiment of any of the aspects, $R^5$ and $R^8$ are hydrogen, and $R^6$ and $R^7$ are H or —$OCH_3$.

In one aspect of any of the embodiments, described herein is a pharmaceutical composition comprising a compound disclosed herein and a pharmaceutically acceptable carrier or excipient.

In another aspect of any of the embodiments, described herein is a method of treating cancer, the method comprising administering a therapeutically effective dose of a composition disclosed herein to a subject in need of treatment for cancer.

In one embodiment of any of the aspects, the method further comprises a first step of measuring the level of activity and/or expression of a marker in one or more cell types relative to a reference level and the administering step is performed if the level is increased.

In another embodiment of any of the aspects, the one or more marker is a marker of cancer.

In another embodiment of any of the aspects, the cancer marker is a DNA, RNA, or microRNA encoded by one or more of a cancer gene, an oncogene, and a tumor suppressor gene.

In another embodiment of any of the aspects, the marker is a protein or polypeptide encoded by one or more of a cancer gene, an oncogene and/or a tumor suppressor gene.

In another embodiment of any of the aspects, the subject is determined to have an increased level of activity and/or expression of an oncogene in one or more cell types relative to a reference level occurring in a cell selected from the group consisting of: a squamous cell, basal cell and/or melanocyte.

In another embodiment of any of the aspects, the oncogene is selected from the group consisting of:
  NRAS; BRAF; KIT; MAPK1/2; ERBB4; GRIN2A; GRM3; RAC1; PREX2; IDH1; PPP6C; and CDK4.

In one aspect of any of the embodiments, described herein is a method of treating melanoma comprising:
  isolating one or more cells selected from the group consisting of a squamous cell, basal cell and/or melanocyte from a subject in need thereof;
  measuring the expression of one or more cancer genes, oncogenes and/or tumor suppressor genes products in the one or more cells;
  administering a therapeutically effective dose of an inhibitor of immune checkpoint polypeptides to the subject if the expression of one or more cancer genes, oncogenes and/or tumor suppressor gene is not altered or decreased in one or more cells as compared to a reference level; and/or
  administering a therapeutically effective dose of a composition of any of claims 1-26 to the subject if the expression of one or more cancer genes, oncogenes and/or tumor suppressor gene products is elevated in one or more cells as compared to a reference level.

In another embodiment of any of the aspects, the expression product is a nucleic acid.

In another embodiment of any of the aspects, the level of the expression product is determined using a method selected from the group selected from the group consisting of:
  RT-PCR; quantitative RT PCR; Northern Blot; microarray-based expression analysis; next generation sequencing; and RNA in situ hybridization.

In another embodiment of any of the aspects, the level of the expression product is a polypeptide.

In another embodiment of any of the aspects, the level of the expression product is determined using a method selected from the group selected from the group consisting of:
  Western blot; immunoprecipitation; enzyme linked immunosorbent assay (ELISA); radioimmunological assay (RIA); sandwich assay; fluorescence in situ hybridization (FISH); immunohistological staining; radioimmunometric assay; immunofluorescence assay; mass spectrometry; FACS; and immunoelectrophoresis assay.

In another embodiment of any of the aspects, further comprises measuring the level of an expression product of at least one marker gene selected from Table 1.

In another embodiment of any of the aspects, the marker gene is selected from the group consisting of: NRAS; BRAF; KIT; MAPK1/2; ERBB4; GRIN2A; GRM3; RAC1; PREX2; IDH1; PPP6C; and CDK4.

In another embodiment of any of the aspects, the immune checkpoint polypeptide is selected from CTLA4A; CTLA4; Ki-67; CD-28; PD-1; TIM-3; and LAG-3.

In another embodiment of any of the aspects, the inhibitor of immune checkpoint polypeptides is selected from pembrolizumab and nivolumab.

BRIEF DESCRIPTION OF THE DRAWINGS

(FIGS. 1A-1E) Strategy used for identification of kinases regulating NRASQ61R-effector protein: protein interaction. Whole-kinome screen identifies STK19 as a novel regulator of NRASQ61R activity. Active NRAS chemiluminescence assay was performed to screen a total of 709 kinases whose knockdown affects interaction between NRASQ61R and GST-CRAF RBD fusion protein. Vertical axis represents relative level of active NRAS compared to group treated with control siRNA. Data are means of three individual kinase-targeting siRNA. STK19 alterations were identified in 25.07% of 363 melanoma cases (TCGA, Pan-Cancer Atlas). STK19 was depleted in human primary melanocytes infected with retroviruses encoding empty HA, HA-NRASWT, or HA-NRASQ61R. Active HA-NRAS proteins were pulled down by GST-CRAF RBD fusion protein. Active HA-NRAS levels and activation of NRAS downstream signaling were detected by immunoblots. shCTRL, non-targeting shRNA. shSTK19, shRNA targeting STK19. hTERT/p53DD/CDK4(R24C) melanocytes expressing empty HA, HA-NRASWT or HA-NRASQ61R were introduced with control shRNA or STK19 shRNA, and then seeded for colony formation assay. Data are means±SD relative to control group with control shRNA and empty HA (n=6). (FIGS. 1F-1H) Growth curve, tumor weight, and dissected tumors for the xenograft experiments with indicated cells inoculated subcutaneously into flanks of nude mice. Visible tumors were measured every three days. Data are means±SEM relative to control group (n=6).

FIGS. 2A-2L show that STK19 phosphorylates NRAS protein at serine 89. (FIG. 2A) Mass spectral peptide count of STK19-interacting proteins. (FIGS. 2B-2I) Exogenous interactions between HA-NRAS and STK19-Flag were detected by immunoprecipitationvin HPMs with overexpression of STK19-Flag and empty HA, HA-NRASWT or HA-NRASQ61R. HPMs were introduced with retroviruses encoding empty HA, HA-NRASWT or HA-NRASQ61R and/or STK19-Flag. The serine-, threonine- and tyrosine-phosphorylation of HA-NRAS isoforms were detected by immunoblots with specific antibodies. Mass spectrometry analysis to identify serine 89 (S89) as the phosphorylation residue by STK19. Schematic diagram showing the evolutionarily conserved serine residue (S89) in NRAS. An in vitro kinase assay was performed using purified recombinant human STK19 protein and indicated purified recombinant human NRAS isoform proteins, followed by detection of phosphorylation in NRAS. HPMs were introduced with empty HA, HA-NRASWT, HA-NRASS89A, HA-NRASQ61R, or HA-NRASQ61R/S89A. The NRAS-effector protein: protein interaction (including BRAF, CRAF and PI3Kα), active HA-NRAS levels and activation of NRAS downstream signaling were detected by immunoblots after infection with retroviruses encoding empty Flag or Flag-tagged STK19. hTERT/p53DD/CDK4(R24C) melanocytes expressing empty HA, HA-NRASQ61R or HA-NRASQ61R/S89A were introduced with retroviruses encoding empty Flag or Flag-tagged STK19, and then seeded for colony formation assay. Data are means±SD relative to control group with empty HA vector and empty Flag vector (n=6). FIG. 2E discloses SEQ ID NO: 9 and FIG. 2F discloses SEQ ID NOS 10-14, respectively, in order of appearance. (FIGS. 2J-2L) Growth curve, tumor weight, and dissected tumors for the xenograft experiments with indicated cells inoculated subcutaneously into flanks of nude mice. Visible tumors were measured every three days. Data are means±SEM relative to control group (n=7).

(FIGS. 3A-3D) STK19 mutations in TCGA database. An in vitro kinase assay was performed using purified recombinant human STK19WT and STK19D89N proteins and indicated human NRAS isoform proteins, followed by detection of phosphorylation in NRAS. HPMs with depletion of STK19 and overexpression of empty HA, HA-NRASWT, or HA-NRASQ61R were further infected with retroviruses encoding empty Flag, Flag-tagged STK19WT or STK19D89N. Serine phosphorylation of HA-NRAS, active HA-NRAS levels and activation of NRAS downstream signaling were detected by immunoblots. hTERT/p53DD/CDK4(R24C) melanocytes expressing STK19 shRNA and empty HA, HA-NRASWT or HA-NRASQ61R were introduced with retroviruses encoding empty Flag, Flag-tagged STK19WT or STK19D89N, and then seeded for colony formation assay. Data are means±SD relative to control group with empty HA vector and empty Flag vector (n=6). (FIGS. 3E-3G) Growth curve, tumor weight, and dissected tumors for the xenograft experiments with indicated cells inoculated subcutaneously into flanks of nude mice. Visible tumors were measured every three days. Data are means±SEM relative to control group (n=6).

FIGS. 4A-4G show that STK19 D89N induces melanomagenesis in the presence of oncogenic NRAS in vivo. Tyr-Cre, Tyr-Cre-STK19WT and Tyr-Cre-STK19D89N knockin mice. Ears of Tyr-Cre, Tyr-Cre-STK19WT and Tyr-Cre-STK19D89N knockin mice. Tails of Tyr-Cre, Tyr-Cre-STK19WT and Tyr-Cre-STK19D89N knockin mice. Fontana Masson staining of indicated mouse ears. Quantification of skin melanin content in Tyr-Cre, Tyr-Cre-STK19WT and Tyr-Cre-STK19D89N knockin mice. Data are means±SD relative to Tyr-Cre control group (n=3). Primary mouse melanocytes derived from indicated mice were lysed for immunoblot analysis of human STK19 expression and NRAS signaling pathways after treatment of 4-hydroxytamoxifen (4-OHT). Melanoma-free survival. Tyr-Cre, n=20; Tyr-Cre-NRASQ61R, n=18; Tyr-Cre-STK19WT, n=19; Tyr-Cre-STK19D89N, n=20; Tyr-Cre-NRASQ61R-STK19WT, n=19; Tyr-Cre-NRASQ61R-STK19D89N, n=19. By log-rank test, P=0.0116 (Tyr-Cre-NRASQ61R, Tyr-Cre-NRASQ61R-STK19WT), P<0.001 (Tyr-Cre-NRASQ61R, Tyr-Cre-NRASQ61R-STK19D89N), P=0.0269 (Tyr-Cre-NRASQ61R-STK19WT, Tyr-Cre-NRAS Q61R-STK19D89N).

FIGS. 5A-5G show the development of ZT-012-037-1 (IV) as a specific small molecule STK19 inhibitor. The chemical structure of ZT-012-037-1 (IV). The inhibitory activity of MP-IN-317 and IV for STK19, measured as percentage of NRAS phosphorylation. Data are means±SD relative to control group (n=3). IC50 represents median inhibitory concentration. FIGs. C-D. Phosphorylation of HA-NRASQ61R was detected by immunoblots with an in vitro kinase assay at different doses of IV for 15 min or 3 μM of ZT-012-037-1 for different reaction time. IC50 values of IV against STK19 at different ATP concentrations. Data are means±SD relative to control groups (n=3). The thermal denaturation curve shift of STK19 (10 μM) in the presence of IV (100 μM). Immunoblots to detect inhibition of STK19WT and STK19D89N by IV at different concentrations.

(FIGS. 6A-6D) hTERT/p53DD/CDK4(R24C) melanocytes induced with STK19 shRNA and retroviruses encoding empty Flag, Flag-tagged STK19WT or STK19D89N were treated with 3 μM IV or not, and proceeded for colony formation assay. Data are means±SD relative to control group (n=6). FIGS. 6B-6D. Growth curve, tumor weight, and dissected tumors for the xenograft experiments with indicated cells inoculated subcutaneously into flanks of nude mice treated with IV. Visible tumors were measured every three days. Data are means±SEM relative to control group (n=6). (FIGS. 6E-6G) Growth curve, tumor weight, and dissected tumors for the xenograft experiments with SK-MEL-2 cells inoculated subcutaneously into flanks of nude mice treated with IV. Visible tumors were measured every three days. Data are means±SEM relative to control group (n=7). (FIGS. 6H-6I) Effects of IV treatment on in vivo proliferation and apoptosis were evaluated by staining of the sections of tumor collected in G for Ki67 and cleaved caspase-3. The sections were counterstained with DAPI. Data are means±SD (n=7). Representative images were shown. Scale bar, 100 μm.

FIGS. 7A-7H show STK19 is a critical regulator of NRAS function, related to FIGS. 1A-1H. Mutual exclusivity between STK19 and BRAF alterations in TCGA PanCancer Atlas. STK19 was depleted in A375, UACC62, SK-MEL-2 and WM2032 cells. Active NRAS proteins were pulled down by GST-CRAF RBD fusion protein. Active NRAS levels and activation of NRAS downstream signaling were detected by immunoblots. STK19 was depleted in HPM, A375, UACC62, SK-MEL-2 and WM2032 cells, and the cell proliferation rates were measured. Data are means±SD relative to individual control group (n=6). qRT-PCR analysis of STK19 mRNA levels in SK-MEL-2 and WM2032 cells infected with STK19 shRNAs. Error bars indicate 95% confidence interval of triplicates. STK19 was depleted in SK-MEL-2 and WM2032 cells. Active NRAS proteins were pulled down by GST-CRAF RBD fusion protein. Active NRAS levels and activation of NRAS downstream signaling were detected by immunoblots. SK-MEL-2 and WM2032 cells with depletion of STK19 were infected with retroviruses encoding empty Flag or Flag-tagged STK19WT. Active NRAS proteins were pulled down by GST-CRAF RBD fusion protein. Active NRAS levels and activation of NRAS downstream signaling were detected by immunoblots. Immunoblots to show depletion of STK19 and overexpression of HA-NRAS proteins in hTERT/p53DD/CDK4 (R24C) melanocytes. hTERT/p53DD/CDK4(R24C) melanocytes expressing empty HA, HA-NRASWT or HA-NRASQ61R were introduced with control shRNA or STK19 shRNA, and then seeded for cell proliferation assay. Data are means±SD relative to control group (n=6).

FIGS. 8A-8T show that STK19 phosphorylates NRAS protein at serine 89, related to FIGS. 2A-2L. (FIG. 8A) Strategy to identify STK19-interacting proteins by mass spectrometry analysis. (FIGS. 8B-8Q) Endogenous STK19-NRAS interactions were detected by immunoprecipitation in SK-MEL-2, WM2032, A375 and UACC62 cells. The serine phosphorylation of NRAS in a panel of melanoma cells was detected by immunoblots. STK19 was depleted by shSTK19 in HPMs overexpressing empty HA, HA-NRASWT, or HA-NRASQ61R. The serine phosphorylation of HA-NRAS was detected by immunoblots. The serine phosphorylation of NRAS was detected by immunoblots in SK-MEL-2 and WM2032 cells with depletion of endogenous STK19. HPMs with depletion of STK19 and overexpression of HA-tagged empty vector, HA-NRASWT, or HA-NRASQ61R were further infected with retroviruses encoding Flag tagged empty vector, Flag-tagged STK19WT or kinase-dead STK19K317P. The serine phosphorylation of HA-NRAS and STK19-NRAS interactions were detected by immunoblots. The serine phosphorylation of NRAS was detected by immunoblots in SK-MEL-2 and WM2032 cells with depletion of endogenous STK19 and overexpression of empty Flag, Flag-tagged STK19WT or kinase dead STK19K317P. An in vitro kinase assay was performed using purified recombinant human STK19 protein and human NRAS (WT and Q61R) protein followed by detection of phosphorylation in NRAS. Purified recombinant human NRAS protein preloaded with GDP, GTP or GTPγS were incubated with purified recombinant human STK19 protein for in vitro kinase assay followed by detection of phosphorylation in NRAS. HPMs were transduced with indicated NRAS mutant isoforms and Flag-tagged STK19. The serine phosphorylation of HA-NRAS and STK19-NRAS interactions were detected by immunoblots. HPMs were transduced with empty HA, HA-NRASWT, HA-NRASS89D, HA-NRASQ61R, or HA-NRASQ61R/S89D. The NRAS-effector protein: protein interaction (including BRAF, CRAF and PI3Kα), active HA-NRAS levels and activation of NRAS downstream signaling were detected by immunoblots. Immunoblots to show overexpression of HA-NRAS and STK19-Flag isoforms in hTERT/p53DD/CDK4(R24C) melanocytes. hTERT/p53DD/CDK4(R24C) melanocytes expressing empty HA, HA-NRASWT, HA-NRASS89A, HA-NRASQ61R or HA-NRASQ61R/S89A were introduced with retroviruses encoding empty Flag or Flag-tagged STK19, and then seeded for cell proliferation assay. Data are means±SD relative to control group (n=6). Immunoblots to show overexpression of HA-NRAS isoforms in hTERT/p53DD/CDK4(R24C) melanocytes. hTERT/p53DD/CDK4 (R24C) melanocytes were transduced with retroviruses encoding empty HA, HA-NRASWT, HA-NRASS89D, HA-NRASQ61R or HA-NRASQ61R/S89D, and then seeded for colony formation assay. Data are means±SD relative to control group with empty HA vector (n=6). hTERT/p53DD/CDK4(R24C) melanocytes were transduced with retroviruses encoding empty HA, HA-NRASWT, HA-NRASS89D, HA-NRASQ61R or HA-NRASQ61R/ S89D, and then seeded for cell proliferation assay. Data are means±SD relative to control group with empty HA vector (n=6). (FIGS. 8R-8T) Growth curve, tumor weight, and dissected tumors for the xenograft experiments with indicated cells inoculated subcutaneously into flanks of nude mice. Visible tumors were measured every three days. Data are means±SEM relative to control group (n=7).

(FIGS. 9A-9E) SK-MEL-2 and WM2032 cells were treated with indicated conditions, and active NRAS levels and activation of NRAS downstream signaling in the melanoma cells were detected by immunoblots. SK-MEL-2 and WM2032 cells were treated with indicated conditions, and the cell proliferation rates were measured. Data are means±SD relative to individual control group (n=6). Immunoblots to show overexpression of HA-NRAS and STK19-Flag isoforms in hTERT/p53DD/CDK4(R24C) melanocytes. hTERT/p53DD/CDK4(R24C) melanocytes expressing STK19 shRNA and empty HA, HA-NRASWT or HA-NRASQ61R were introduced with retroviruses encoding empty Flag, Flag-tagged STK19WT or STK19D89N, and then seeded for cell proliferation assay. Data are means±SD relative to control group (n=6).

FIGS. 10A-10E show that STK19 D89N induces melanomagenesis in the presence of oncogenic NRAS in vivo, related to FIGS. 4A-4G. Schematic representation to generate the conditional knockin C57BL/6 mice with human STK19WT or STK19D89N. PCR was performed to select mice with expression of STK19WT or STK19D89N in indicated mouse strains. Immunoblots to confirm the expression of STK19WT or STK19D89N protein in indicated mouse strains. Schematic representation to observe melanoma development. Melanoma tissues from Tyr-Cre-NRASQ61R, Tyr-Cre-NRASQ61R-STK19WT and Tyr-Cre-NRASQ61R-STK19D89N knockin mice were collected for immunoblotting. Active NRAS proteins were pulled down by GST-CRAF RBD fusion protein. Active NRAS levels and activation of NRAS downstream signaling were detected by immunoblots.

FIGS. 12A-12L show that ZT-012-037-1 (IV) inhibits oncogenic NRAS-driven melanoma development and growth, related to FIGS. 6A-6I. (FIG. 12A-12L) Immunoblots show overexpression of HA-NRAS and STK19-Flag isoforms in hTERT/p53DD/CDK4(R24C)-shSTK19 melanocytes. hTERT/p53DD/CDK4(R24C) melanocytes infected with STK19 shRNA and retroviruses encoding empty Flag, Flag-tagged STK19WT or STK19D89N were treated with IV (3 µM) or not, and then seeded for cell proliferation assay. Data are means±SD relative to control group (n=6). Survival evaluation of SK-MEL-2 xenograft-bearing mice treated with IV. By log-rank test, P<0.001 (control, 25 mg/kg IV); P<0.001 (control, 50 mg/kg IV). HPMs with depletion of STK19 and overexpression of HA-NRASQ61R were transduced with retroviruses encoding empty Flag, Flag-tagged STK19WT or STK19D89N, and then treated with indicated concentrations of IV. Serine phosphorylation of NRASQ61R, active HA-NRAS levels and activation of NRAS downstream signaling were detected by immunoblots. SK-MEL-2 xenograft tumors from FIG. 6G were collected. Serine phosphorylation of NRASQ61R, active NRAS levels, activation of NRAS downstream signaling and H3K9 methylation were detected by immunoblots. A375, UACC62, SK-MEL-2 and WM2032 cells were treated with indicated concentrations of IV. Serine phosphorylation of NRAS, active NRAS levels and activation of NRAS downstream signaling in these melanoma cells were detected by immunoblots. A375, UACC62, SK-MEL-2 and WM2032 cells were treated with indicated concentrations of IV for 4 days, and the cell proliferation rates were measured. Data are means±SD relative to individual control group (n=6). A375, UACC62, SK-MEL-2 and WM2032 cells were treated with indicated concentrations of IV for 4 days, and the caspase activity assays were performed to investigate apoptosis. Data are means±SD relative to individual control group (n=6). SK-MEL-2 and WM2032 cells were treated with indicated low concentrations of IV. Serine phosphorylation of NRAS, activation of NRAS signaling and H3K9 methylation in these melanoma cells were detected by immunoblots. G9a was depleted in SK-MEL-2 and WM2032 cells. Active NRAS proteins were pulled down by GST-CRAF RBD fusion protein. Active NRAS levels, activation of NRAS downstream signaling and H3K9 methylation were detected by immunoblots. SK-MEL-2 cells were treated with indicated concentrations of IV or A-366. Serine phosphorylation of NRAS, active NRAS levels, activation of NRAS downstream signaling and H3K9 methylation were detected by immunoblots. SK-MEL-2 cells were infected with retroviruses encoding empty Flag, Flag-tagged STK19WT or STK19 mutants, and then treated with IV or not. Serine phosphorylation of NRAS, active NRAS levels, activation of NRAS downstream signaling and H3K9 methylation were detected by immunoblots.

Figures 13A, 13B, 13C:
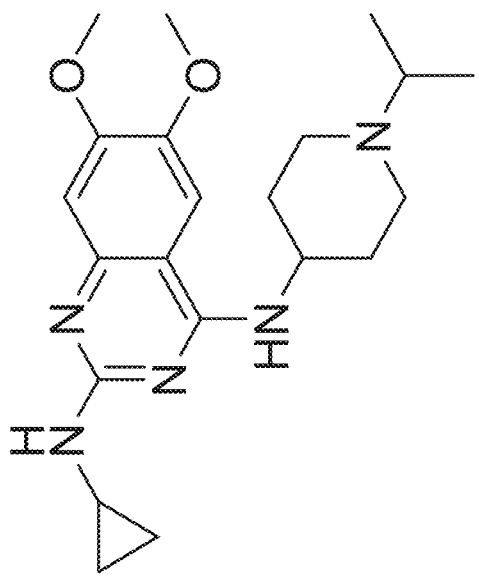

FIGS. 13A-13C depict the chemical structures of Formulas I-IV including ZT-012-037-1 (IV) scaffold and variants thereof.

DETAILED DESCRIPTION

Melanoma is a malignant tumor of melanocytes. Primarily melanoma is a skin tumor, but it is also seen, though less frequently, in the melanocytes of the eye (uveal melanoma). Melanoma underlies the majority of skin cancer-related deaths and despite many years of intensive laboratory and clinical research, there are still limited treatments especially for metasized melanoma.

As described herein, several novel agents have been developed for the prevention and treatment of a cancer. Specifically, the compounds, compositions and methods described herein have been developed for the prevention and treatment of melanoma. The compounds described herein inhibit the novel serine/threonine kinase STK19 which is upregulated in cancers with mutations in a marker/oncogene described herein, e.g., one or more mutations in NRAS. Accordingly, they are therapeutic for any cancer with NRAS mutations.

In some embodiments of the various aspects disclosed herein, the disclosure relates to a compound of the structure of Formula I:

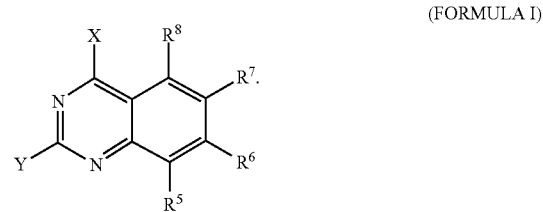

(FORMULA I)

In compounds of Formula I, X can be aryl, heteroaryl, or $N(R^1R^2)$, where $R^1$ and $R^2$ are independently hydrogen, alkyl, cyclyl, heterocyclyl, aryl or heteroaryl, each of which can be optionally substituted; or $R^1$ and $R^2$ are connect to form an optionally substituted heterocyclyl. For example, X can be Cl, Br, I, F or an optionally substituted 3-12 membered aryl, such as an optionally substituted phenyl.

In some embodiments, $R^1$ and $R^2$ are independently H, $C_1$-$C_8$alkyl, 3-12 membered aryl, 3-12 membered heteroaryl, 3-12 membered cycloalkyl, or 3-12 membered heterocyclyl, each of which can be optionally substituted. For example, $R^1$ and $R^2$ are independently H, $C_1$-$C_8$alkyl, 3-12 membered cycloalkyl, or 3-12 membered heterocyclyl, each of which can be optionally substituted.

Exemplary $C_1$-$C_8$alkyls for $R^1$ and $R^2$ include, but are not limited to, methyl, ethyl, propyl, isopropyl, 1-methylpropyl, 2-methylpropyl, 2,3-dimethylpropyl, butyl, t-butyl, hexyl and heptyl, each of which can be optionally substituted. Preferred $C_1$-$C_8$alkyls include, but are not limited to, methyl, ethyl, propyl, 1-methylpropyl, 2-methylpropyl, 2,3-dimethylpropyl, t-butyl, 2-(morpholinyl)ethyl, 2-(dimethylamino)ethyl, and 2-hydroxyethyl. Exemplary cyclyls for $R^1$ and $R^2$ include, but are not limited to, cyclopropyl, cyclobutyl, cyclopentyl, cyclohexyl, each of which can be optionally substituted. Some preferred cyclyls include, but are not limited to, cyclopropyl, cyclobutyl, 3-methylcyclobutyl, 3-fluorocyclobutyl, cyclopentyl, and cyclohexyl. Exemplary heterocyclyls for $R^1$ and $R^2$ include, but are not limited to, aziridine, oxirane, thiiarne, diazridine, oxaziridine, dioxirane, azetidine, oxetane, thietane, diazetidine, dioxetane, dithietane, -pyrrolidine, tetrahydrofuran, tetrahydrothiophene, imidazolidine, pyrazolidine, oxazolidine, isoxazolidine, thiazolidine, isothiazolidine, dioxalane, dithiolane, piperidine, tetrahydropyran, thiane, piperazine, morpholine, thiomorpholine, dioxane, dithiane, hexahydro-1,3,5-triazine, trioxane, trithiane, azepane, oxepane, thiepane, diazepane, azocane, oxocane, thiocane, azonane, oxonane, and thionane, each of which can be optionally substituted. Some preferred heterocyclys include, but are not limited to, N-methylpiperidin-4-yl, N-isopropylpiperidin-4-yl, N-Bocpiperidin-4-yl, and tetrahydropyran-4-yl.

In some embodiments, $R^1$ and $R^2$ are selected independently from the group consisting of H, methyl, ethyl, propyl, 1-methylpropyl, 2-methylpropyl, 2,3-dimethylpropyl, t-butyl, 2-(morpholinyl)ethyl, 2-(dimethylamino)ethyl, 2-hydroxyethyl, cyclopropyl, cyclobutyl, 3-methylcyclobutyl, 3-fluorocyclobutyl, cyclopentyl, cyclohexyl, N-methylpiperidin-4-yl, N-isopropylpiperidin-4-yl, N-Bocpiperidin-4-yl, and tetrahydropyran-4-yl.

It is noted that $R^1$ and $R^2$ can be same or different. For example, only one of $R^1$ and $R^2$ can be H or neither $R^1$ nor $R^2$ is H.

In some compounds of Formula I, $R^1$ and $R^2$ are connect to form an optionally substituted 3-12 membered heterocyclyl. Exemplary heterocyclyls include, but are not limited to, aziridine, oxirane, thiiarne, diazridine, oxaziridine, dioxirane, azetidine, oxetane, thietane, diazetidine, dioxetane, dithietane, -pyrrolidine, tetrahydrofuran, tetrahydrothiophene, imidazolidine, pyrazolidine, oxazolidine, isoxazolidine, thiazolidine, isothiazolidine, dioxalane, dithiolane, piperidine, tetrahydropyran, thiane, piperazine, morpholine, thiomorpholine, dioxane, dithiane, hexahydro-1,3,5-triazine, trioxane, trithiane, azepane, oxepane, thiepane, diazepane, azocane, oxocane, thiocane, azonane, oxonane, and thionane, each of which can be optionally substituted. Preferably, $R^1$ and $R^2$ are connect to form an heterocyclyl selected from the group consisting of piperzinyl, N-methylpiperzinyl, 4,4-dimethylpiperzinyl, 4-(dimethylamino)piperzinyl, morpholinyl, diazepanyl, and N-methyldiazepanyl.

In compounds of Formula I, Y can be aryl, heteroaryl, or $N(R^3R^4)$, where $R^3$ and $R^4$ are independently hydrogen, alkyl, cyclyl, heterocyclyl, aryl or heteroaryl, each of which can be optionally substituted; or $R^3$ and $R^4$ are connect to form an optionally substituted heterocyclyl. For example, Y can be Cl, Br, I, F or an optionally substituted 3-12 membered aryl, such as an optionally substituted phenyl.

In some embodiments, $R^3$ and $R^4$ are independently H, $C_1$-$C_8$alkyl, 3-12 membered aryl, 3-12 membered heteroaryl, 3-12 membered cycloalkyl, or 3-12 membered heterocyclyl, each of which can be optionally substituted. For example, $R^3$ and $R^4$ are independently H, $C_1$-$C_8$alkyl, 3-12 membered cycloalkyl, or 3-12 membered heterocyclyl, each of which can be optionally substituted.

Exemplary $C_1$-$C_8$ alkyls for $R^3$ and $R^4$ include, but are not limited to, methyl, ethyl, propyl, isopropyl, 1-methylpropyl, 2-methylpropyl, 2,3-dimethylpropyl, butyl, t-butyl, hexyl and heptyl, each of which can be optionally substituted. Preferred $C_1$-$C_8$alkyls include, but are not limited to, methyl, ethyl, propyl, 1-methylpropyl, 2-methylpropyl, 2,3-dimethylpropyl, t-butyl, 2-(morpholinyl)ethyl, 2-(dimethylamino)ethyl, and 2-hydroxyethyl. Exemplary cyclyls for $R^1$ and $R^2$ include, but are not limited to, cyclopropyl, cyclobutyl, cyclopentyl, cyclohexyl, each of which can be optionally substituted. Some preferred cyclyls include, but are not limited to, cyclopropyl, cyclobutyl, 3-methylcyclobutyl, 3-fluorocyclobutyl, cyclopentyl, and cyclohexyl. Exemplary heterocyclyls for $R^3$ and $R^4$ include, but are not limited to, aziridine, oxirane, thiiarne, diazridine, oxaziridine, dioxirane, azetidine, oxetane, thietane, diazetidine, dioxetane, dithietane, -pyrrolidine, tetrahydrofuran, tetrahydrothiophene, imidazolidine, pyrazolidine, oxazolidine, isoxazolidine, thiazolidine, isothiazolidine, dioxalane, dithiolane, piperidine, tetrahydropyran, thiane, piperazine, morpholine, thiomorpholine, dioxane, dithiane, hexahydro-1,3,5-triazine, trioxane, trithiane, azepane, oxepane, thiepane, diazepane, azocane, oxocane, thiocane, azonane, oxonane, and thionane, each of which can be optionally substituted. Some preferred heterocyclys include, but are not limited to, N-methylpiperidin-4-yl, N-isopropylpiperidin-4-yl, N-Bocpiperidin-4-yl, and tetrahydropyran-4-yl.

In some embodiments, $R^3$ and $R^4$ are selected independently from the group consisting of H, methyl, ethyl, propyl, 1-methylpropyl, 2-methylpropyl, 2,3-dimethylpropyl, t-butyl, 2-(morpholinyl)ethyl, 2-(dimethylamino)ethyl, 2-hydroxyethyl, cyclopropyl, cyclobutyl, 3-methylcyclobutyl, 3-fluorocyclobutyl, cyclopentyl, cyclohexyl, N-methylpiperidin-4-yl, N-isopropylpiperidin-4-yl, N-Bocpiperidin-4-yl, and tetrahydropyran-4-yl.

It is noted that $R^3$ and $R^4$ can be same or different. For example, only one of $R^3$ and $R^4$ can be H or neither $R^3$ nor $R^4$ is H.

In some compounds of Formula I, $R^3$ and $R^4$ are connect to form an optionally substituted 3-12 membered heterocyclyl. Exemplary heterocyclyls include, but are not limited to, aziridine, oxirane, thiiarne, diazridine, oxaziridine, dioxirane, azetidine, oxetane, thietane, diazetidine, dioxetane, dithietane, pyrrolidine, tetrahydrofuran, tetrahydrothiophene, imidazolidine, pyrazolidine, oxazolidine, isoxazolidine, thiazolidine, isothiazolidine, dioxalane, dithiolane, piperidine, tetrahydropyran, thiane, piperazine, morpholine, thiomorpholine, dioxane, dithiane, hexahydro-1,3,5-triazine, trioxane, trithiane, azepane, oxepane, thiepane, diazepane, azocane, oxocane, thiocane, azonane, oxonane, and thionane, each of which can be optionally substituted. Preferably, $R^3$ and $R^4$ are connect to form an heterocyclyl selected from the group consisting of piperzinyl, N-methylpiperzinyl, 4,4-dimethylpiperzinyl, 4-(dimethylamino)piperzinyl, morpholinyl, diazepanyl, and N-methyldiazepanyl.

In some embodiments, the compound is of structure:

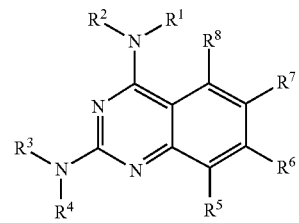

In some embodiments, at least one of, e.g., both X and Y are selected independently from the group consisting of

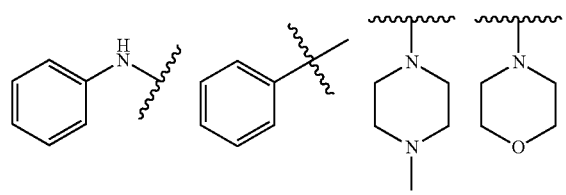

-continued
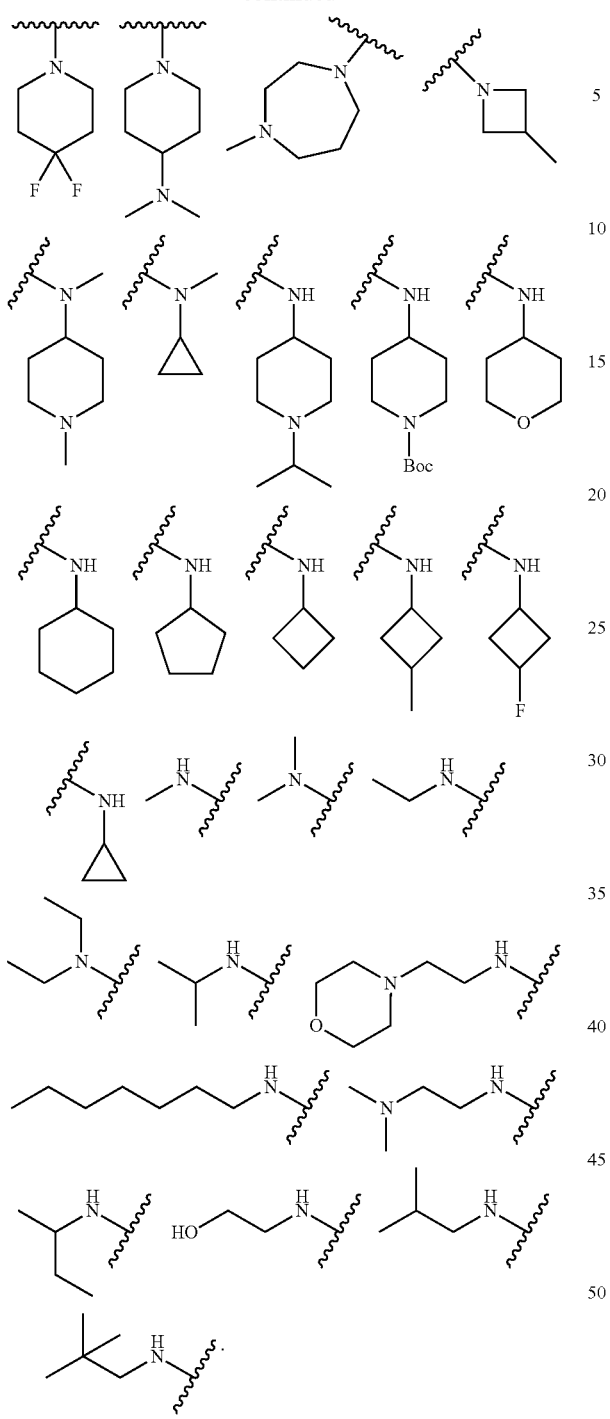
In some embodiments, X is selected form the group consisting of:
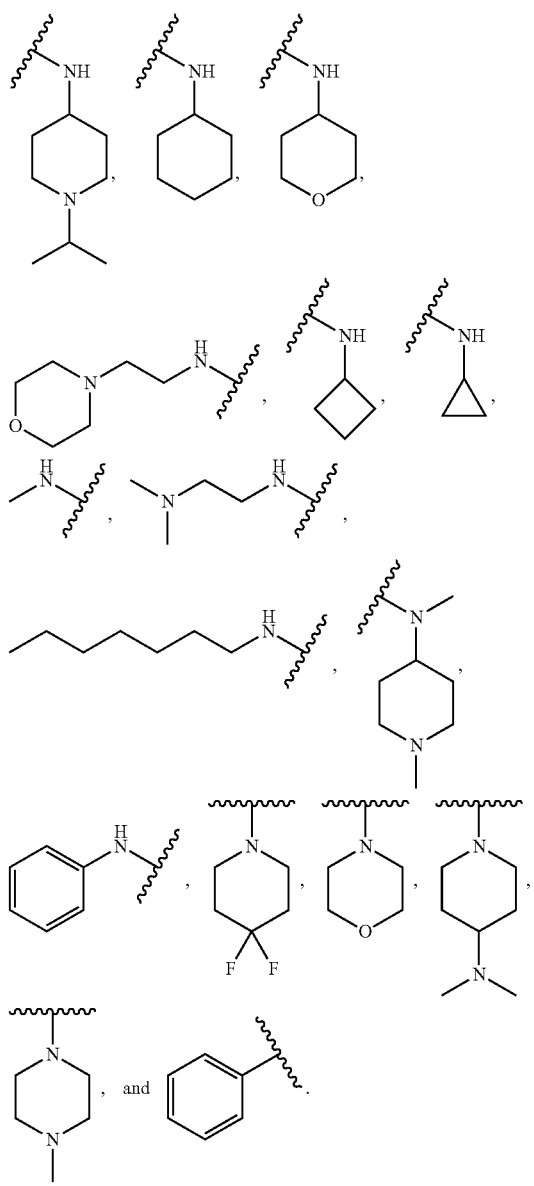
In some embodiments, Y is selected form the group consisting of:
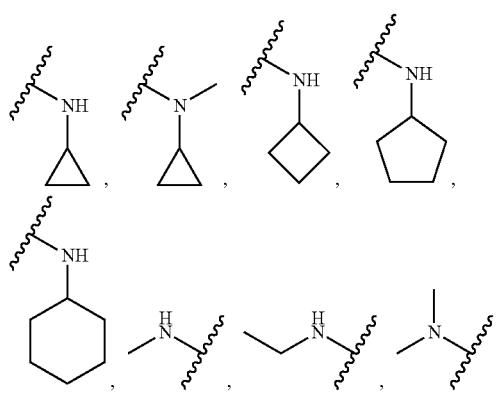

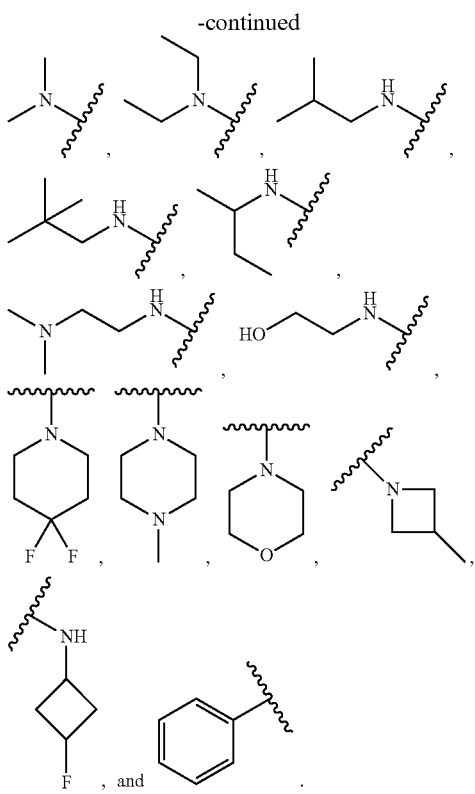

In compounds of Formula I, $R^5$ can be H, halogen, OH, nitro, cyano, carboxy, amino, ($C_1$-$C_6$ alkyl)amino, di($C_1$-$C_6$alkyl)amino, $C_1$-$C_6$alkyl, 3-12 membered aryl, 3-12 membered heteroaryl, 3-12 membered cycloalkyl, 3-12 membered heterocyclyl, acyl, $C_1$-$C_6$alkoxy, CN, $CF_3$, each of which can be optionally substituted. For example, $R^5$ can be H, $C_1$-$C_6$alkyl, halogen, nitro, cyano, hydroxyl, carboxy or amino. In some compounds of Formula I, $R^5$ is H, OH, $CF_3$, CN, $NH_2$, Cl, F, I or Br. Preferably, $R^5$ is H.

In compounds of Formula I, $R^6$ can be H, halogen, OH, nitro, cyano, carboxy, amino, ($C_1$-$C_6$alkyl)amino, di($C_1$-$C_6$alkyl)amino, $C_1$-$C_6$alkyl, 3-12 membered aryl, 3-12 membered heteroaryl, 3-12 membered cycloalkyl, 3-12 membered heterocyclyl, acyl, $C_1$-$C_6$alkoxy, CN, $CF_3$, each of which can be optionally substituted. For example, $R^6$ can be H, $C_1$-$C_6$alkyl, $C_1$-$C_6$alkoxy, halogen, nitro, cyano, hydroxyl, carboxy or amino. In some embodiments, $R^6$ is H or —$OR^9$, where $R^9$ is alkyl, cyclyl, heterocyclyl, aryl or heteroaryl, each of which can be optionally substituted. For Example, $R^6$ can be H or —$OR^9$, where $R^9$ is optionally substituted $C_1$-$C_6$alkyl. Exemplary alkyls for $R^9$ include, but are not limited to, methyl, ethyl, propyl, isopropyl, 1-mthylpropy, 2-methylpropyl, butyl, t-butyl, pentyl or hexyl. Preferably $R^9$ is methyl.

In compounds of Formula I, $R^7$ can be H, halogen, OH, nitro, cyano, carboxy, amino, ($C_1$-$C_6$alkyl)amino, di($C_1$-$C_6$alkyl)amino, $C_1$-$C_6$alkyl, 3-12 membered aryl, 3-12 membered heteroaryl, 3-12 membered cycloalkyl, 3-12 membered heterocyclyl, acyl, $C_1$-$C_6$alkoxy, CN, $CF_3$, each of which can be optionally substituted. For example, $R^7$ can be H, $C_1$-$C_6$alkyl, $C_1$-$C_6$alkoxy, halogen, nitro, cyano, hydroxyl, carboxy or amino. In some embodiments, $R^7$ is H or —$OR^{10}$, where $R^{10}$ is alkyl, cyclyl, heterocyclyl, aryl or heteroaryl, each of which can be optionally substituted. For Example, $R^7$ can be H or —$OR^{10}$, where $R^{10}$ is optionally substituted $C_1$-$C_6$alkyl. Exemplary alkyls for $R^{10}$ include, but are not limited to, methyl, ethyl, propyl, isopropyl, 1-mthylpropy, 2-methylpropyl, butyl, t-butyl, pentyl or hexyl. Preferably $R^{10}$ is methyl.

It is noted that $R^6$ and $R^7$ can be same or different. For example, $R^6$ and $R^7$ can be selected independently from the group consisting of H, halogen, OH, nitro, cyano, carboxy, amino, ($C_1$-$C_6$alkyl)amino, di($C_1$-$C_6$alkyl)amino, $C_1$-$C_6$alkyl, 3-12 membered aryl, 3-12 membered heteroaryl, 3-12 membered cycloalkyl, 3-12 membered heterocyclyl, acyl, $C_1$-$C_6$alkoxy, CN, $CF_3$, each of which can be optionally substituted. For example, $R^6$ and $R^7$ can be independently H, $C_1$-$C_6$alkyl, $C_1$-$C_6$alkoxy, halogen, nitro, cyano, hydroxyl, carboxy or amino. In some embodiments, $R^6$ and $R^7$ are selected independently from the H or —OR, where R is optionally substituted $C_1$-$C_6$alkyl. Exemplary alkyls for R include, but are not limited to, methyl, ethyl, propyl, isopropyl, 1-mthylpropy, 2-methylpropyl, butyl, t-butyl, pentyl or hexyl. Preferably R is methyl. Preferably, $R^6$ and $R^7$ are H or methoxy.

In compounds of Formula I, $R^8$ selected independently from the group consisting of H, halogen, OH, nitro, cyano, carboxy, amino, ($C_1$-$C_6$alkyl)amino, di($C_1$-$C_6$alkyl)amino, $C_1$-$C_6$alkyl, 3-12 membered aryl, 3-12 membered heteroaryl, 3-12 membered cycloalkyl, 3-12 membered heterocyclyl, acyl, $C_1$-$C_6$alkoxy, CN, $CF_3$, each of which can be optionally substituted. For example, $R^8$ can be H, $C_1$-$C_6$alkyl, halogen, nitro, cyano, hydroxyl, carboxy or amino. In some embodiments, $R^8$ is H, OH, $CF_3$, CN, $NH_2$, Cl, F, I and Br. Preferably, $R^8$ is H.

It is noted that $R^5$ and $R^8$ can be same or different. For example, $R^5$ and $R^8$ can be H, halogen, OH, nitro, cyano, carboxy, amino, ($C_1$-$C_6$alkyl)amino, di($C_1$-$C_6$alkyl)amino, $C_1$-$C_6$alkyl, 3-12 membered aryl, 3-12 membered heteroaryl, 3-12 membered cycloalkyl, 3-12 membered heterocyclyl, acyl, $C_1$-$C_6$alkoxy, CN, $CF_3$, each of which can be optionally substituted. For example, $R^5$ and $R^8$ can be independently H, $C_1$-$C_6$alkyl, halogen, nitro, cyano, hydroxyl, carboxy or amino. In some embodiments, $R^5$ and $R^8$ are selected independently from the group consisting of H, OH, $CF_3$, CN, $NH_2$, Cl, F, I and Br. Preferably, $R^5$ and $R^8$ are H It is noted that $R^5$, $R^6$, $R^7$ and $R^8$ can be same, all different or some same and some different. For example, $R^5$ and $R^8$ can be same. In another example, $R^6$ and $R^7$ are same. In some embodiments, $R^5$ and $R^8$ are H; and $R^6$ and $R^7$ are H or $OCH_3$.

In some embodiments, the compound is of Formula II:

(FORMULA II)

In some embodiments, the compound is of Formula III:

(FORMULA III)

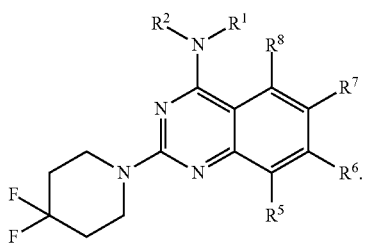

In some embodiments, the compound is selected from Formula IV-LI:

| Formula number | Chemical Structure | H NMR and MS |
|---|---|---|
| IV | TFA salt | $^1$H NMR (600 MHz, Chloroform-d) δ 8.89 (s, 1H), 7.71 (s, 1H), 7.28 (s, 1H), 6.85 (s, 1H), 4.49-4.32 (m, 1H), 3.97 (s, 3H), 3.93 (s, 3H), 3.40-3.28 (m, 2H), 3.29-3.17 (m, 1H), 2.85-2.74 (m, 1H), 2.78-2.64 (m, 2H), 2.35-2.27 (m, 2H), 2.28-2.14 (m, 2H), 1.31-1.23 (m, 6H), 0.81-0.70 (m, 2H), 0.72-0.61 (m, 2H). MS (ESI) m/z: 386[M + H]$^+$. |
| V | 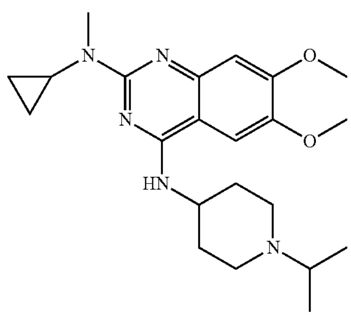 [SMILES: COc1cc2nc(N(C)C3CC3)nc(NC3CCN(C(C)C)CC3)c2cc1OC] | $^1$H NMR (600 MHz, Chloroform-d) δ 7.08 (s, 1H), 6.86 (s, 1H), 4.24-4.12 (m, 1H), 3.96 (s, 3H), 3.95 (s, 3H), 3.19 (s, 3H), 3.07-2.97 (m, 2H), 2.87 (p, J = 6.6 Hz, 1H), 2.82-2.75 (m, 1H), 2.46-2.31 (m, 2H), 2.30-2.15 (m, 2H), 1.81-1.68 (m, 2H), 1.12 (d, J = 6.6 Hz, 6H), 0.91-0.85 (m, 2H), 0.75-0.65 (m, 2H). MS (ESI) m/z: 400[M + H]$^+$. |
| VI | TFA salt | $^1$H NMR (600 MHz, DMSO-d$_6$) δ 9.75 (s, 1H), 8.95 (s, 1H), 7.77 (s, 1H), 6.87 (s, 1H), 4.55-4.37 (m, 1H), 4.39-4.30 (m, 1H), 3.90-3.88 (m, 3H), 3.87 (s, 1H), 3.85 (s, 3H), 3.58-3.45 (m, 2H), 3.25-2.98 (m, 2H), 2.41-2.30 (m, 2H), 2.31-2.20 (m, 2H), 2.13-1.99 (m, 2H), 2.01-1.89 (m, 2H), 1.86-1.64 (m, 2H), 1.30 (d, J = 6.6 Hz, 6H). MS (ESI) m/z: 400[M + H]$^+$. |

| Formula number | Chemical Structure | H NMR and MS |
|---|---|---|
| VII | 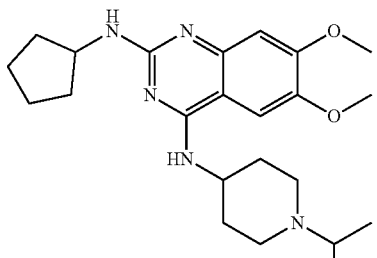<br>TFA salt | ¹H NMR (600 MHz, DMSO-d₆) δ 7.78 (s, 1H), 6.89 (s, 1H), 4.46-4.27 (m, 1H), 3.89 (s, 3H), 3.86 (s, 3H), 3.59-3.49 (m, 3H), 3.46-3.27 (m, 2H), 3.21-3.00 (m, 2H), 2.31-2.24 (m, 2H), 2.04-1.87 (m, 3H), 1.79-1.66 (m, 2H), 1.64-1.51 (m, 4H), 1.29 (d, J = 6.6 Hz, 6H). MS (ESI) m/z: 414[M + H]⁺. |
| VIII | 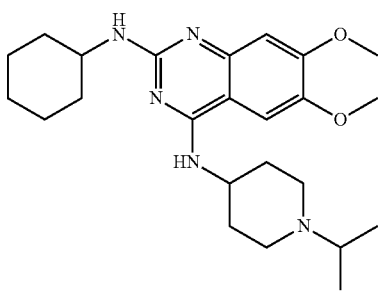<br>TFA salt | ¹H NMR (600 MHz, Chloroform-d) δ 9.07 (s, 1H), 8.19 (s, 1H), 7.35 (s, 1H), 6.89 (s, 1H), 4.55-4.44 (m, 1H), 3.99 (s, 3H), 3.91 (s, 3H), 3.81-3.69 (m, 1H), 3.59-3.51 (m, 2H), 2.99-2.78 (m, 2H), 2.58-2.40 (m, 2H), 2.39-2.27 (m, 2H), 2.26-2.13 (m, 4H), 2.03-1.92 (m, 2H), 1.89-1.77 (m, 2H), 1.69-1.55 (m, 1H), 1.40 (d, J = 6.0 Hz, 6H). MS (ESI) m/z: 428[M + H]⁺. |
| IX | 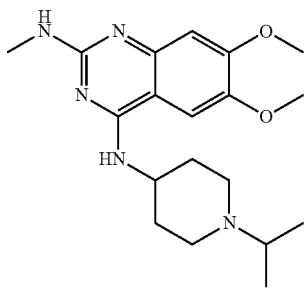 [SMILES: CNc1nc(NC2CCN(C(C)C)CC2)c2cc(OC)c(OC)cc2n1] | ¹H NMR (600 MHz, DMSO-d₆) δ 7.46 (s, 1H), 7.29 (s, 1H), 6.72 (s, 1H), 6.25 (s, 1H), 4.15-4.02 (m, 1H), 3.81 (s, 3H), 3.80 (s, 3H), 2.98-2.86 (m, 2H), 2.87-2.80 (m, 1H), 2.79 (d, J = 4.8 Hz, 3H), 2.37-2.19 (m, 2H), 2.00-1.92 (m, 2H), 1.68-1.53 (m, 2H), 1.02 (d, J = 6.6 Hz, 6H). MS (ESI) m/z: 360[M + H]⁺. |
| X | 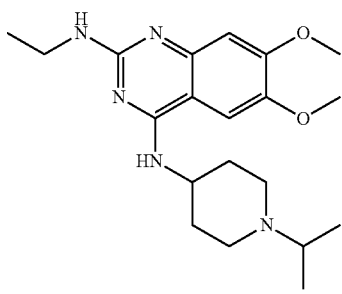<br>TFA salt | ¹H NMR (600 MHz, Methanol-d₄) δ 7.71 (s, 1H), 6.98 (s, 1H), 4.60-4.48 (m, 1H), 3.97 (s, 3H), 3.93 (s, 3H), 3.65-3.49 (m, 5H), 3.23 (t, J = 12.8 Hz, 2H), 2.48-2.36 (m, 2H), 2.20-1.99 (m, 2H), 1.41 (d, J = 6.6 Hz, 6H), 1.30 (t, J = 7.2 Hz, 3H).. MS (ESI) m/z: 374[M + H]⁺. |

| Formula number | Chemical Structure | H NMR and MS |
|---|---|---|
| XI | 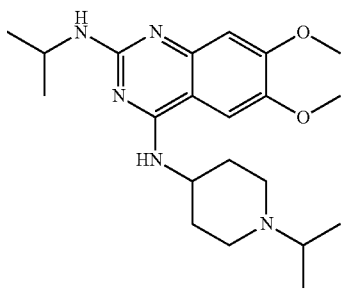<br>TFA salt | ¹H NMR (600 MHz, Chloroform-d) δ 8.64 (s, 1H), 8.31 (s, 1H), 7.40 (s, 1H), 6.86 (s, 1H), 4.55-4.44 (m, 1H), 4.22-4.05 (m, 1H), 3.97 (s, 3H), 3.88 (s, 3H), 3.60-3.42 (m, 3H), 3.01-2.84 (m, 2H), 2.57-2.36 (m, 2H), 2.36-2.22 (m, 2H), 1.39 (d, J = 6.0 Hz, 6H), 1.27 (d, J = 6.4 Hz, 6H).. MS (ESI) m/z: 388[M + H]⁺. |
| XII | 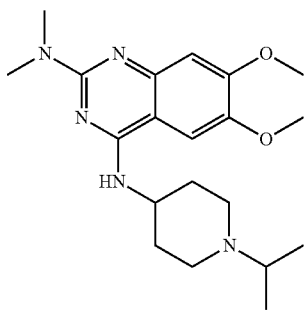<br>TFA salt | ¹H NMR (600 MHz, DMSO-d₆) δ 7.79 (s, 1H), 7.30 (s, 1H), 4.47-4.29 (m, 1H), 3.89 (s, 3H), 3.86 (s, 3H), 3.56-3.45 (m, 3H), 3.27 (s, 6H), 3.23-3.10 (m, 2H), 2.32-2.21 (m, 2H), 2.02-1.87 (m, 2H), 1.29 (d, J = 6.6 Hz, 6H).. MS (ESI) m/z: 374[M + H]⁺. |
| XIII | 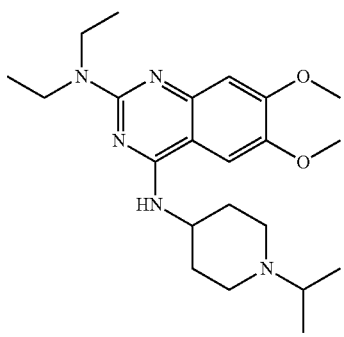<br>TFA salt | ¹H NMR (600 MHz, Chloroform-d) δ 7.15 (s, 1H), 7.12 (s, 1H), 4.13 (tt, J = 9.7, 4.9 Hz, 1H), 3.90 (s, 3H), 3.89 (s, 3H), 3.65 (q, J = 7.1 Hz, 4H), 3.13-3.04 (m, 2H), 3.03-2.93 (m, 1H), 2.56-2.41 (m, 2H), 2.25-2.12 (m, 2H), 1.93-1.82 (m, 2H), 1.21 (t, J = 7.1 Hz, 6H), 1.14 (d, J = 6.6 Hz, 6H).. MS (ESI) m/z: 402[M + H]⁺. |
| XIV | 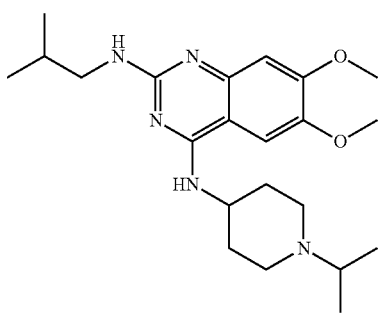<br>TFA salt | ¹H NMR (600 MHz, Chloroform-d) δ 8.73 (s, 1H), 8.14 (s, 1H), 7.34 (s, 1H), 6.86 (s, 1H), 4.59-4.44 (m, 1H), 3.97 (s, 3H), 3.89 (s, 3H), 3.63-3.53 (m, 3H), 3.31-3.19 (m, 2H), 3.02-2.85 (m, 2H), 2.51-2.37 (m, 2H), 2.39-2.24 (m, 2H), 1.99-1.79 (m, 1H), 1.45-1.34 (m, 6H), 0.94 (d, J = 6.5 Hz, 6H).. MS (ESI) m/z: 402[M + H]⁺. |

-continued

| Formula number | Chemical Structure | H NMR and MS |
|---|---|---|
| XV | 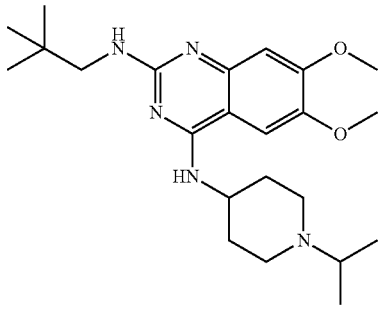 [SMILES: COc1cc2nc(NCC(C)(C)C)nc(NC3CCN(C(C)C)CC3)c2cc1OC] | $^1$H NMR (600 MHz, Chloroform-d) δ 6.91 (s, 1H), 6.85 (s, 1H), 4.21-4.11 (m, 1H), 3.93 (s, 3H), 3.91 (s, 3H), 3.33-3.25 (m, 2H), 3.00-2.87 (m, 2H), 2.84-2.71 (m, 1H), 2.38-2.28 (m, 2H), 2.18-2.07 (m, 2H), 1.75-1.60 (m, 2H), 1.07 (d, J = 6.6 Hz, 6H), 0.96 (s, 9H). MS (ESI) m/z: 416[M + H]$^+$. |
| XVI | 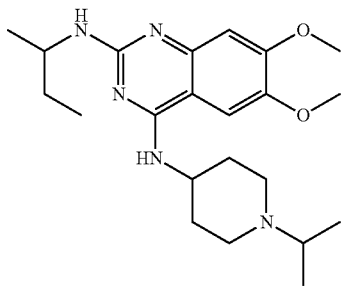 [SMILES: CCC(C)Nc1nc(NC2CCN(C(C)C)CC2)c2cc(OC)c(OC)cc2n1] | $^1$H NMR (600 MHz, Chloroform-d) δ 7.09 (s, 1H), 6.90 (s, 1H), 4.35-4.18 (m, 1H), 3.97 (s, 3H), 3.93 (s, 3H), 3.72-3.58 (m, 1H), 3.25-3.10 (m, 2H), 3.10-2.94 (m, 1H), 2.60-2.47 (m, 2H), 2.28-2.13 (m, 2H), 2.09-1.91 (m, 3H), 1.75-1.47 (m, 2H), 1.26-1.24 (m, 2H), 1.18 (d, J = 6.7 Hz, 6H), 0.99-0.90 (m, 3H). MS (ESI) m/z: 402[M + H]$^+$. |
| XVII | 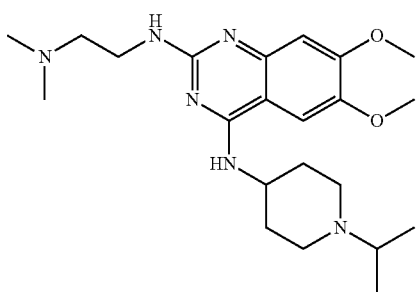 [SMILES: COc1cc2nc(NCCN(C)C)nc(NC3CCN(C(C)C)CC3)c2cc1OC] | $^1$H NMR (600 MHz, Chloroform-d) δ 7.05 (s, 1H), 6.83 (s, 1H), 4.24-4.09 (m, 1H), 3.91 (s, 3H), 3.89 (s, 3H), 3.63-3.44 (m, 2H), 2.98-2.88 (m, 2H), 2.88-2.73 (m, 1H), 2.55-2.47 (m, 2H), 2.40-2.30 (m, 2H), 2.26 (s, 6H), 2.15-2.07 (m, 2H), 1.79-1.65 (m, 2H), 1.07 (d, J = 6.6 Hz, 6H).. MS (ESI) m/z: 417[M + H]$^+$. |
| XVIII | 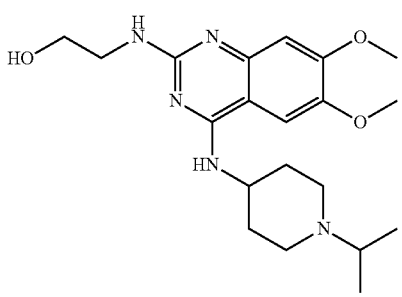 [SMILES: COc1cc2nc(NCCO)nc(NC3CCN(C(C)C)CC3)c2cc1OC] | $^1$H NMR (600 MHz, Chloroform-d) δ 6.83 (s, 1H), 6.78 (s, 1H), 5.38 (s, 1H), 4.21-4.06 (m, 1H), 3.93 (s, 3H), 3.92 (s, 3H), 3.87-3.82 (m, 2H), 3.62-3.55 (m, 2H), 2.98-2.89 (m, 2H), 2.87-2.72 (m, 1H), 2.42-2.30 (m, 2H), 2.20-2.07 (m, 2H), 1.72-1.61 (m, 2H), 1.09 (d, J = 6.5 Hz, 6H). MS (ESI) m/z: 390[M + H]$^+$. |

-continued

| Formula number | Chemical Structure | H NMR and MS |
|---|---|---|
| XIX | 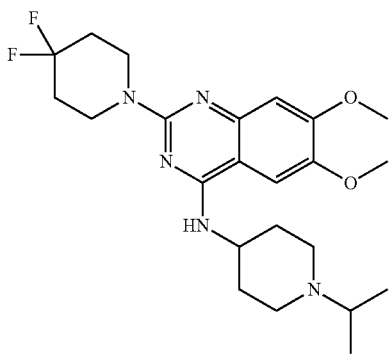<br>TFA salt | $^1$H NMR (600 MHz, Methanol-d$_4$) δ 7.75 (s, 1H), 7.19 (s, 1H), 4.69-4.51 (m, 1H), 4.10-4.03 (m, 4H), 3.99 (s, 3H), 3.96 (s, 3H), 3.65-3.54 (m, 3H), 3.36-3.29 (m, 2H), 2.44-2.37 (m, 2H), 2.25-2.14 (m, 4H), 2.16-2.05 (m, 2H), 1.43 (d, J = 6.7 Hz, 6H). MS (ESI) m/z: 450[M + H]$^+$. |
| XX | 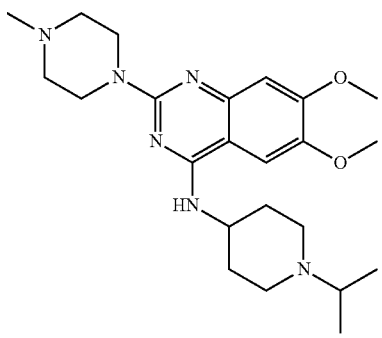<br>TFA salt | $^1$H NMR (600 MHz, Methanol-d$_4$) δ 7.44 (s, 1H), 6.89 (s, 1H), 4.66 (s, 1H), 4.31-4.13 (m, 1H), 3.90 (d, J = 5.0 Hz, 6H), 3.86-3.79 (m, 4H), 3.23-3.14 (m, 2H), 2.70-2.59 (m, 2H), 2.57-2.49 (m, 4H), 2.35 (s, 3H), 2.26-2.16 (m, 2H), 1.87-1.71 (m, 2H), 1.21 (d, J = 6.6 Hz, 6H). MS (ESI) m/z: 429[M + H]$^+$. |
| XXI | 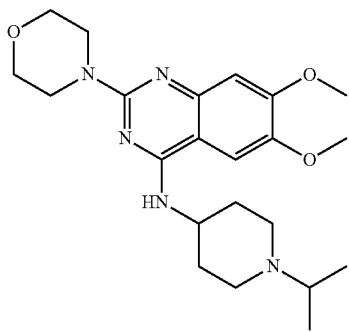<br>TFA salt | $^1$H NMR (600 MHz, Chloroform-d) δ 6.98-6.86 (m, 2H), 4.37-4.25 (m, 1H), 3.97-3.93 (m, 6H), 3.82-3.76 (m, 8H), 3.44-3.17 (m, 3H), 2.78-2.65 (m, 2H), 2.34-2.23 (m, 2H), 2.14-1.97 (m, 2H), 1.28 (d, J = 6.7 Hz, 6H). MS (ESI) m/z: 416[M + H]$^+$. |
| XXII | 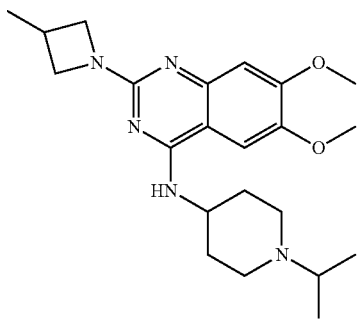 [SMILES: COc1cc2nc(N3CC(C)C3)nc(NC3CCN(C(C)C)CC3)c2cc1OC] | $^1$H NMR (600 MHz, Chloroform-d) δ 6.98 (s, 1H), 6.78 (s, 1H), 5.34 (s, 1H), 4.27 (t, J = 8.1 Hz, 2H), 4.21-4.12 (m, 1H), 3.95-3.88 (m, 6H), 3.78-3.68 (m, 2H), 3.03-2.92 (m, 2H), 2.89-2.81 (m, 1H), 2.80-2.69 (m, 1H), 2.44-2.34 (m, 2H), 2.24-2.15 (m, 2H), 1.73-1.61 (m, 2H), 1.31-1.27 (m, 3H), 1.13-1.06 (m, 6H). MS (ESI) m/z: 400[M + H]$^+$. |

| Formula number | Chemical Structure | H NMR and MS |
|---|---|---|
| XXIII | 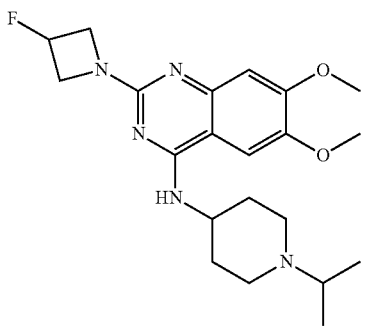 [SMILES: COc1cc2nc(N3CC(F)C3)nc(NC3CCN(C(C)C)CC3)c2cc1OC] | ¹H NMR (600 MHz, Chloroform-d) δ 6.94 (s, 1H), 6.80 (s, 1H), 5.39-5.25 (m, 1H), 4.48-4.35 (m, 2H), 4.33-4.18 (m, 2H), 4.19-4.09 (m, 1H), 3.94-3.89 (m, 6H), 2.96-2.91 (m, 2H), 2.87-2.66 (m, 1H), 2.41-2.29 (m, 2H), 2.22-2.11 (m, 2H), 1.71-1.50 (m, 2H), 1.08 (d, J = 6.5 Hz, 6H). MS (ESI) m/z: 404[M + H]⁺. |
| XXIV | 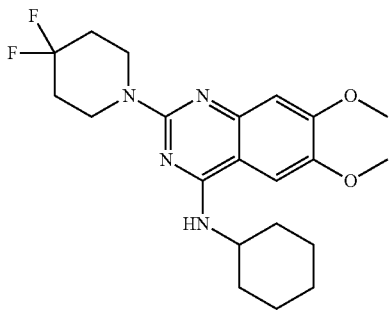<br>TFA salt | ¹H NMR (600 MHz, DMSO-d₆) δ 8.90 (s, 1H), 7.77 (s, 1H), 7.21 (s, 1H), 4.21-4.03 (m, 1H), 3.96-3.90 (m, 3H), 3.88 (s, 2H), 3.86 (s, 2H), 3.61-3.28 (m, 2H), 2.22-2.05 (m, 4H), 2.01-1.93 (m, 2H), 1.85-1.76 (m, 2H), 1.51-1.28 (m, 4H). MS (ESI) m/z: 407[M + H]⁺. |
| XXV | 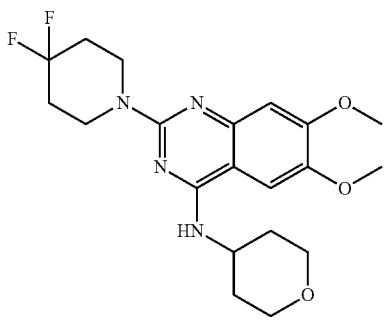<br>TFA salt | ¹H NMR (600 MHz, Methanol-d₄) δ 7.72 (s, 1H), 7.14 (s, 1H), 4.57-4.43 (m, 1H), 4.05-3.99 (m, 4H), 3.97 (s, 3H), 3.94 (s, 3H), 3.66-3.54 (m, 2H), 3.38-3.23 (m, 2H), 2.25-2.10 (m, 4H), 2.07-1.94 (m, 2H), 1.91-1.74 (m, 2H). MS (ESI) m/z: 409[M + H]⁺. |
| XXVI | 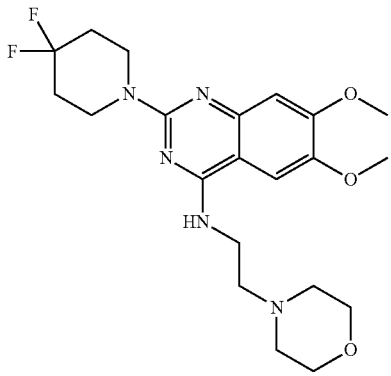<br>TFA salt | ¹H NMR (600 MHz, Chloroform-d) δ 9.85 (s, 1H), 7.42 (s, 1H), 7.14 (s, 1H), 4.11-4.03 (m, 2H), 4.01-3.98 (m, 4H), 3.97-3.94 (m, 4H), 3.92 (s, 3H), 3.91 (s, 3H), 3.63-3.48 (m, 2H), 3.47-3.33 (m, 2H), 3.13-2.85 (m, 2H), 2.18-1.99 (m, 4H). MS (ESI) m/z: 438[M + H]⁺. |

| Formula number | Chemical Structure | H NMR and MS |
|---|---|---|
| XXVII | 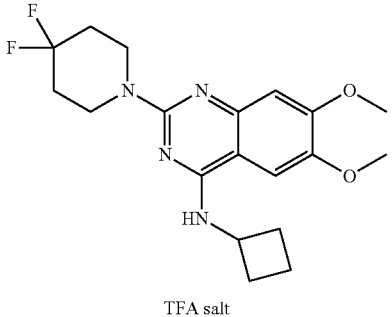 [SMILES: COc1cc2nc(N3CCC(F)(F)CC3)nc(NC3CCC3)c2cc1OC]<br>TFA salt | ¹H NMR (600 MHz, Chloroform-d) δ 9.21 (s, 1H), 7.56 (s, 1H), 6.80 (s, 1H), 4.39-4.24 (m, 1H), 3.97-3.90 (m, 4H), 3.87 (s, 3H), 3.86 (s, 3H), 2.36 (s, 2H), 2.21 (t, J = 10.1 Hz, 2H), 2.11-2.00 (m, 4H), 1.95-1.76 (m, 2H). MS (ESI) m/z: 379[M + H]⁺. |
| XXVIII | 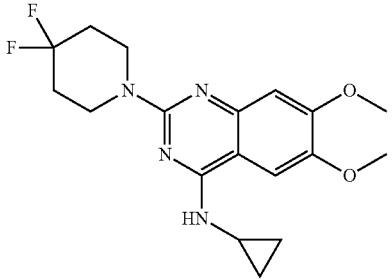<br>TFA salt | ¹H NMR (600 MHz, Chloroform-d) δ 9.19 (s, 1H), 7.44 (s, 1H), 6.83 (s, 1H), 4.03-3.93 (m, 4H), 3.88 (s, 3H), 3.85 (s, 3H), 3.08-2.77 (m, 1H), 2.21-1.91 (m, 4H), 0.96-0.66 (m, 4H). MS (ESI) m/z: 365[M + H]⁺. |
| XXIX | 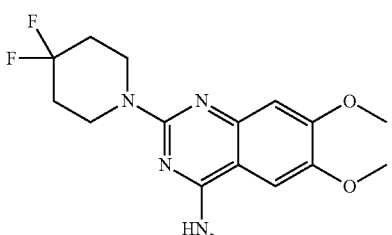 | ¹H NMR (600 MHz, Chloroform-d) δ 6.92 (s, 1H), 6.77 (s, 1H), 4.03 (t, J = 5.9 Hz, 4H), 3.96 (s, 3H), 3.93 (s, 3H), 3.13 (d, J = 4.7 Hz, 3H), 2.03 (tt, J = 13.5, 5.8 Hz, 4H). MS (ESI) m/z: 339[M + H]⁺. |
| XXX | 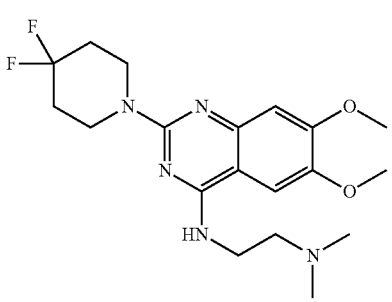 [SMILES: COc1cc2nc(N3CCC(F)(F)CC3)nc(NCCN(C)C)c2cc1OC] | ¹H NMR (600 MHz, Chloroform-d) δ 6.93-6.81 (m, 2H), 6.07 (s, 1H), 4.03-3.99 (m, 4H), 3.96 (s, 3H), 3.94 (s, 3H), 3.65 (d, J = 5.3 Hz, 2H), 2.63 (p, J = 5.3, 4.5 Hz, 2H), 2.39-2.23 (m, 6H), 2.08-1.92 (m, 4H). MS (ESI) m/z: 396[M + H]⁺. |
| XXXI | 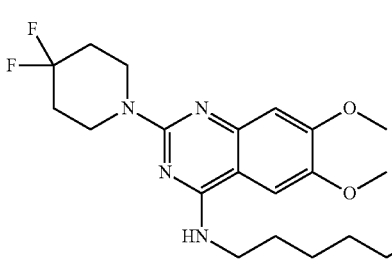<br>TFA salt | ¹H NMR (600 MHz, Chloroform-d) δ 8.88 (s, 1H), 7.38 (s, 1H), 6.86 (s, 1H), 3.98-3.91 (m, 4H), 3.88 (s, 3H), 3.87 (s, 3H), 3.49-3.30 (m, 2H), 2.33 (s, 2H), 2.15-1.96 (m, 4H), 1.65 (p, J = 7.2 Hz, 2H), 1.32-1.27 (m, 4H), 0.88 (t, 3H).<br>MS (ESI) m/z: 409[M + H]⁺. |

| Formula number | Chemical Structure | H NMR and MS |
|---|---|---|
| XXXII | 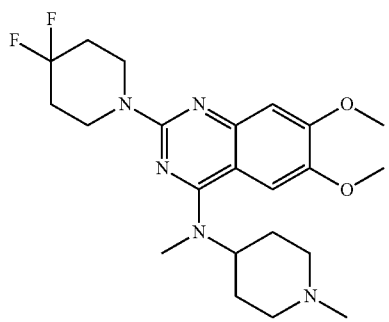<br>TFA salt | $^1$H NMR (600 MHz, Methanol-d$_4$) δ 7.45 (s, 1H), 7.21 (s, 1H), 4.08-4.00 (m, 7H), 3.96 (s, 3H), 3.75-3.67 (m, 2H), 3.48 (s, 3H), 3.34-3.30 (m, 2H), 2.96 (s, 3H), 2.32-2.25 (m, 4H), 2.25-2.16 (m, 4H), 1.45-1.36 (m, 1H). MS (ESI) m/z: 436[M + H]$^+$. |
| XXXIII | 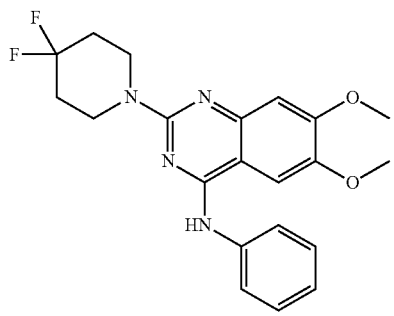<br>TFA salt | $^1$H NMR (600 MHz, Chloroform-d) δ 10.71 (s, 1H), 7.85 (d, J = 7.9 Hz, 2H), 7.69 (s, 1H), 7.41 (t, J = 7.8 Hz, 2H), 7.25-7.20 (m, 1H), 6.75 (s, 1H), 3.93 (s, 3H), 3.74-3.68 (m, 4H), 3.65 (s, 3H), 2.19-1.83 (m, 4H). MS (ESI) m/z: 401[M + H]$^+$. |
| XXXIV | 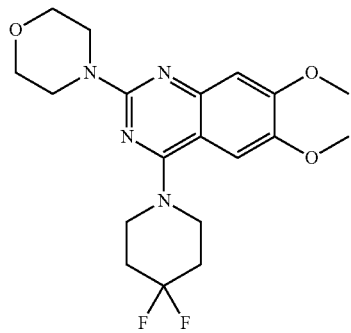<br>TFA salt | $^1$H NMR (600 MHz, DMSO-d$_6$) δ 7.28 (s, 1H), 7.22 (s, 1H), 4.06-3.98 (m, 4H), 3.93 (s, 3H), 3.90 (s, 3H), 3.84-3.78 (m, 4H), 3.78-3.72 (m, 4H), 2.30-2.08 (m, 4H). MS (ESI) m/z: 395[M + H]$^+$. |
| XXXV | 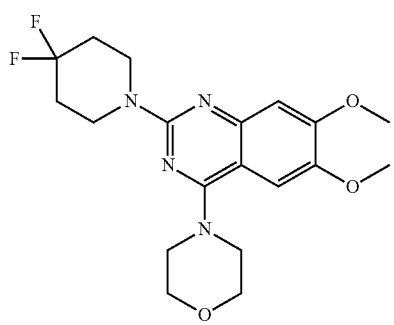<br>TFA salt | $^1$H NMR (600 MHz, DMSO-d$_6$) δ 7.28-7.15 (m, 2H), 4.00-3.95 (m, 4H), 3.95-3.92 (m, 4H), 3.91 (s, 3H), 3.87 (s, 3H), 3.78-3.71 (m, 4H), 2.24-1.98 (m, 4H). MS (ESI) m/z: 395[M + H]$^+$. |

| Formula number | Chemical Structure | H NMR and MS |
|---|---|---|
| XXXVI | 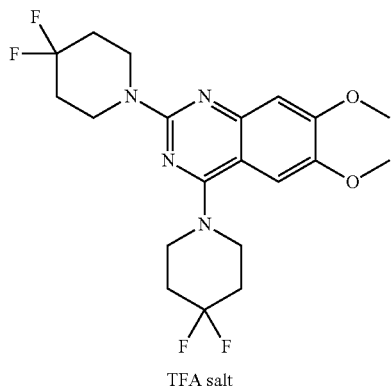 [SMILES: COc1cc2nc(N3CCC(F)(F)CC3)nc(N3CCC(F)(F)CC3)c2cc1OC]<br>TFA salt | $^1$H NMR (600 MHz, DMSO-d$_6$) δ 7.69-6.70 (m, 2H), 4.02-3.93 (m, 8H), 3.92 (s, 3H), 3.88 (s, 3H), 2.27-2.17 (m, 4H), 2.17-2.08 (m, 4H). MS (ESI) m/z: 429[M + H]$^+$. |
| XXXVII | 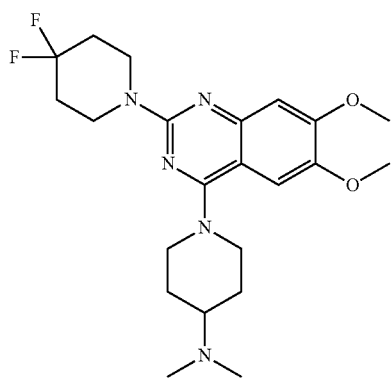 [SMILES: COc1cc2nc(N3CCC(F)(F)CC3)nc(N3CCC(N(C)C)CC3)c2cc1OC] | $^1$H NMR (600 MHz, Chloroform-d) δ 6.98 (s, 1H), 6.92 (s, 1H), 4.22-4.12 (m, 2H), 4.03-3.98 (m, 4H), 3.97 (s, 3H), 3.92 (s, 3H), 3.05-2.94 (m, 2H), 2.52-2.42 (m, 1H), 2.38 (s, 6H), 2.08-1.91 (m, 6H), 1.78-1.62 (m, 2H). MS (ESI) m/z: 436[M + H]$^+$. |
| XXXVIII | 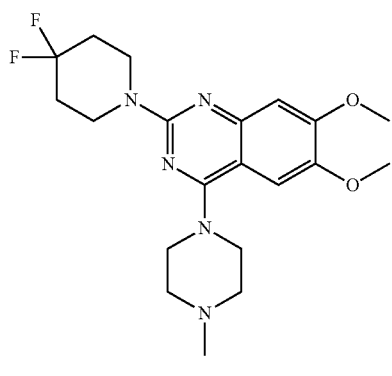<br>TFA salt | $^1$H NMR (600 MHz, DMSO-d$_6$) δ 7.22 (s, 1H), 7.15 (s, 1H), 4.66-4.40 (m, 2H), 3.96 (t, J = 5.7 Hz, 4H), 3.91 (s, 3H), 3.89 (s, 3H), 3.72-3.42 (m, 4H), 3.34-3.15 (m, 2H), 2.86 (s, 3H), 2.17-2.04 (m, 4H)..MS (ESI) m/z: 408[M + H]$^+$. |
| XXXIX | 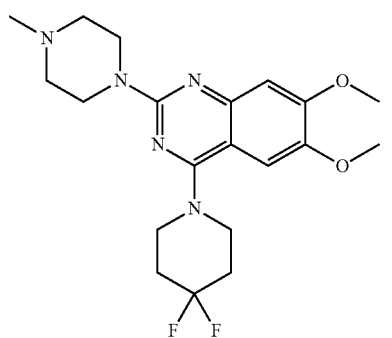 | $^1$H NMR (600 MHz, Chloroform-d) δ 6.92-6.90 (m, 2H), 3.94 (s, 3H), 3.88 (s, 3H), 3.87-3.81 (m, 4H), 3.68 (t, J = 5.7 Hz, 4H), 2.47 (t, J = 5.1 Hz, 4H), 2.32 (s, 3H), 2.21-2.06 (m, 4H), MS (ESI) m/z: 408[M + H]$^+$. |

-continued

| Formula number | Chemical Structure | H NMR and MS |
|---|---|---|
| XL | 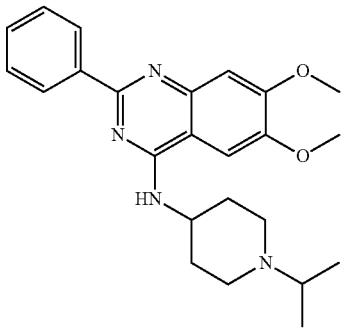 [SMILES: COc1cc2nc(-c3ccccc3)nc(NC3CCN(C(C)C)CC3)c2cc1OC] | $^1$H NMR (600 MHz, Methanol-d$_4$) δ 8.25 (d, J = 7.0 Hz, 2H), 7.46 (s, 1H), 7.43-7.33 (m, 3H), 7.11 (s, 1H), 4.37-4.23 (m, 1H), 3.88 (s, 3H), 3.87 (s, 3H), 3.11-2.94 (m, 2H), 2.89-2.76 (m, 1H), 2.59-2.37 (m, 2H), 2.19-2.07 (m, 2H), 1.79-1.56 (m, 2H), 1.08 (d, J = 6.6 Hz, 6H). MS (ESI) m/z: 407[M + H]$^+$. |
| XLI | 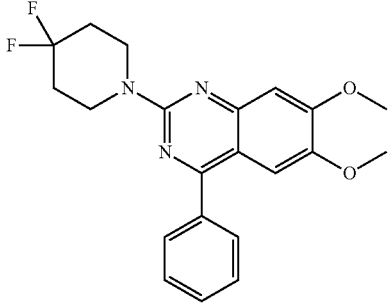 | $^1$H NMR (600 MHz, Chloroform-d) δ 7.81-7.69 (m, 2H), 7.61-7.47 (m, 3H), 7.15 (s, 1H), 7.03 (s, 1H), 4.14-4.09 (m, 4H), 4.03 (s, 3H), 3.83 (s, 3H), 2.16-1.95 (m, 4H). MS (ESI) m/z: 386[M + H]$^+$. |
| XLII | 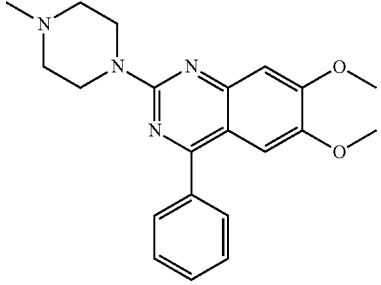 | $^1$H NMR (600 MHz, Methanol-d$_4$) δ 7.76-7.71 (m, 2H), 7.63-7.53 (m, 3H), 7.16 (s, 1H), 7.10 (s, 1H), 3.96 (s, 3H), 3.74 (s, 3H), 3.70-3.39 (m, 4H), 3.42-3.10 (m, 4H), 2.97 (s, 3H). MS (ESI) m/z: 365[M + H]$^+$. |
| XLIII | 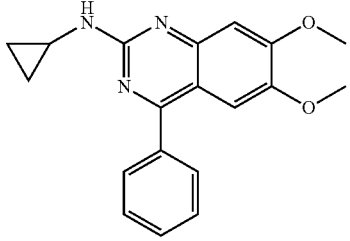<br>TFA salt | $^1$H NMR (600 MHz, Chloroform-d) δ 10.26 (s, 1H), 7.86-7.80 (m, 2H), 7.69-7.55 (m, 3H), 7.23 (s, 1H), 7.16 (s, 1H), 4.09 (s, 3H), 3.85 (s, 3H), 3.15-3.06 (m, 1H), 0.92-0.84 (m, 2H), 0.82-0.75 (m, 2H). MS (ESI) m/z: 322[M + H]$^+$. |
| XLIV | 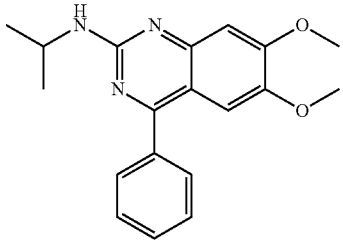<br>TFA salt | $^1$H NMR (600 MHz, Methanol-d$_4$) δ 7.87-7.79 (m, 2H), 7.71-7.67 (m, 1H), 7.66-7.61 (m, 3H), 7.29 (s, 1H), 4.43-4.30 (m, 1H), 4.07 (s, 3H), 3.82 (s, 3H), 1.38 (d, J = 6.5 Hz, 6H). MS (ESI) m/z: 324[M + H]$^+$. |

| Formula number | Chemical Structure | H NMR and MS |
|---|---|---|
| XLV | 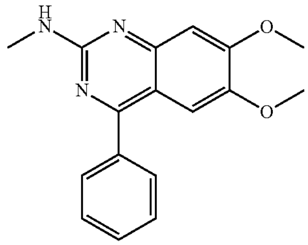 | ¹H NMR (600 MHz, Chloroform-d) δ 7.74-7.66 (m, 2H), 7.57-7.49 (m, 3H), 7.11-7.06 (m, 2H), 5.29 (s, 1H), 4.03 (s, 3H), 3.81 (s, 3H), 3.11 (d, J = 5.1 Hz, 3H). MS (ESI) m/z: 296[M + H]⁺. |
| XLVI | 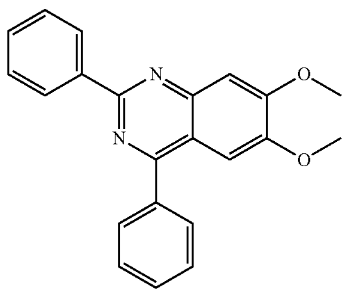 [SMILES: COc1cc2nc(-c3ccccc3)nc(-c3ccccc3)c2cc1OC] | ¹H NMR (600 MHz, Chloroform-d) δ 8.65-8.61 (m, 2H), 7.91-7.87 (m, 2H), 7.65-7.54 (m, 4H), 7.56-7.42 (m, 4H), 4.10 (s, 3H), 3.91 (s, 3H). MS (ESI) m/z: 343[M + H]⁺. |
| XLVII | 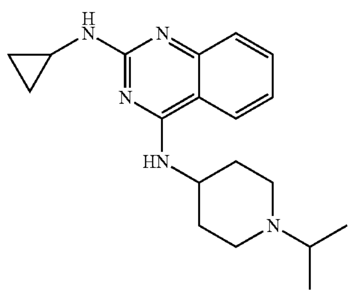 [SMILES: CC(C)N1CCC(Nc2nc(NC3CC3)nc3ccccc23)CC1] | ¹H NMR (600 MHz, Chloroform-d) δ 8.30 (dd, J = 4.2, 1.5 Hz, 1H), 7.75 (d, J = 8.4 Hz, 1H), 7.41 (dd, J = 8.5, 4.2 Hz, 1H), 6.91 (d, J = 7.9 Hz, 1H), 5.37 (s, 1H), 4.25-3.78 (m, 1H), 2.94-2.82 (m, 2H), 2.80-2.68 (m, 1H), 2.39-2.26 (m, 2H), 2.18-2.06 (m, 2H), 1.72-1.59 (m, 2H), 1.06 (d, J = 6.6 Hz, 6H), 0.82-0.75 (m, 2H), 0.59-0.52 (m, 2H). MS (ESI) m/z: 326[M + H]⁺. |
| XLVIII<br>TFA salt | | ¹H NMR (600 MHz, Methanol-d₄) δ 8.28 (dd, J = 8.3, 1.2 Hz, 1H), 7.83 (ddd, J = 8.3, 7.2, 1.3 Hz, 1H), 7.68 (d, J = 8.3 Hz, 1H), 7.51-7.45 (m, 1H), 4.71-4.56 (m, 1H), 4.17-4.01 (m, 4H), 3.64-3.54 (m, 3H), 3.36-3.32 (m, 2H), 2.45-2.33 (m, 2H), 2.25-2.15 (m, 4H), 2.15-2.07 (m, 2H), 1.41 (d, J = 6.6 Hz, 6H). MS (ESI) m/z: 390[M + H]⁺. |

| Formula number | Chemical Structure | H NMR and MS |
|---|---|---|
| XLIX | 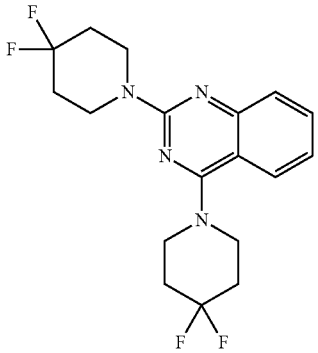 TFA salt | $^1$H NMR (600 MHz, DMSO-$d_6$) δ 8.05-7.98 (m, 1H), 7.90-7.83 (m, 1H), 7.75 (d, J = 8.3 Hz, 1H), 7.44 (t, J = 7.6 Hz, 1H), 4.13-3.94 (m, 8H), 2.37-2.07 (m, 8H). MS (ESI) m/z: 369[M + H]$^+$. |
| L | 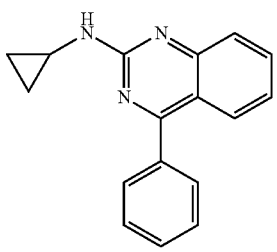 [SMILES: c1ccc(-c2nc(NC3CC3)nc3ccccc23)cc1] | $^1$H NMR (600 MHz, Chloroform-d) δ 10.68 (s, 1H), 8.00 (d, J = 8.2 Hz, 1H), 7.90-7.78 (m, 4H), 7.69 (t, J = 7.4 Hz, 1H), 7.63 (t, J = 7.4 Hz, 2H), 7.41 (t, J = 7.5 Hz, 1H), 3.35-3.06 (m, 1H), 1.02-0.69 (m, 4H). MS (ESI) m/z: 262[M + H]$^+$. |
| LI | 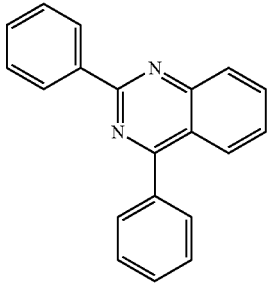 [SMILES: c1ccc(-c2nc(-c3ccccc3)c3ccccc3n2)cc1] | $^1$H NMR (600 MHz, Chloroform-d) δ 8.74-8.67 (m, 2H), 8.21-8.10 (m, 2H), 7.92-7.85 (m, 3H), 7.66-7.57 (m, 3H), 7.58-7.47 (m, 4H). MS (ESI) m/z: 283[M + H]$^+$. |

For administration to a subject, the compounds of Formula (I)-(LI) can be provided in pharmaceutically acceptable compositions. These pharmaceutically acceptable compositions comprise a compound of Formula (I)-(LI), formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Examples of solid carriers include starch, sugar, bentonite, silica, and other commonly used carriers. Further non-limiting examples of carriers and diluents which can be used in the formulations comprising a $PrP^C$ ligand as disclosed herein of the present invention include saline, syrup, dextrose, and water.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The phrase "therapeutically-effective amount" as used herein means that amount of a compound or composition which is effective for producing some desired therapeutic effect in at least a sub-population of cells in an animal at a reasonable benefit/risk ratio applicable to any medical treatment. According, a "therapeutically effective amount" refers to an amount effective, at dosage and periods of time necessary, to achieve a desired therapeutic result. A therapeutic result can be, e.g., lessening of symptoms, prolonged survival, improved mobility, and the like. A therapeutic result need not be a "cure."

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The administration of a compound or composition as described herein may be for either "prophylactic" or "therapeutic" purpose. When provided prophylactically, therapy is provided in advance of any symptom. The prophylactic administration of the therapy serves to prevent formation of melanoma. Prophylactic administration may be given to a patient with, for example, a family history of cancer, or a patient that has had a melanoma removed surgically. Alternatively, administration of the combination therapy may be given to a patient with rising cancer marker protein levels, for example melanoma markers described in WO 2008/141275, WO 2009/073513, or in U.S. Pat. No. 7,442,507

The compounds can be formulated in a gelatin capsule, in tablet form, dragee, syrup, suspension, topical cream, suppository, injectable solution, or kits for the preparation of syrups, suspension, topical cream, suppository or injectable solution just prior to use. Also, compounds can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17th edition, Nema et al., *PDA J. Pharm. Sci. Tech.* 1997 51:166-171. Methods to make invention formulations include the step of bringing into association or contacting an ActRIIB compound with one or more excipients or carriers. In general, the formulations are prepared by uniformly and intimately bringing into association one or more compounds with liquid excipients or finely divided solid excipients or both, and then, if appropriate, shaping the product.

The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

Examples of injectable form include solutions, suspensions and emulsions. Injectable forms also include sterile powders for extemporaneous preparation of injectable solutions, suspensions or emulsions. The compounds of the present invention can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin. A suitable carrier is 5% dextrose in saline. Frequently, it is desirable to include additives in the carrier such as buffers and preservatives or other substances to enhance isotonicity and chemical stability.

In some embodiments, compounds can be administered encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., a pituitary cell) can also be used as pharmaceutically acceptable carriers.

In one embodiment, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and Primogel™, and the like.

The compounds can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these compounds may be incorporated with excipients and used in the form of tablets, capsules, elixirs, suspensions, syrups, and the like. Such compositions and preparations should contain at least 0.1% of compound. The percentage of the agent in these compositions may, of course, be varied and may conveniently be between about 2% to about 60% of the weight of the unit. The amount of compound in such therapeutically useful compositions is such that a suitable dosage will be obtained. Preferred compositions according to the present invention are prepared so that an oral dosage unit contains between about 100 and 2000 mg of compound.

Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The compositions can be given as a bolus dose, to maximize the circulating levels for the greatest length of time after the dose. Continuous infusion may also be used after the bolus dose.

The compounds can also be administrated directly to the airways in the form of an aerosol. For administration by inhalation, the compounds in solution or suspension can be delivered in the form of an aerosol spray from pressured container or dispenser which contains a suitable propellant, e.g., a gas such as carbon dioxide, or hydrocarbon propellant like propane, butane or isobutene. The compounds can also be administrated in a no-pressurized form such as in an atomizer or nebulizer.

The compounds can also be administered parenterally. Solutions or suspensions of these compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of compound calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

For oral or enteral formulations as disclosed herein for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982.

As regards formulations for administering a compound of Formula I as disclosed herein, one particularly useful embodiment is a tablet formulation comprising a compound of Formula I with an enteric polymer casing. An example of such a preparation can be found in WO2005/021002. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropylcellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient, e.g., compound of Formula I preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg of the active ingredient. Particularly preferably, the core contains 20, 30, 40, 50, 60, 80 or 100 mg of the active ingredient. The active ingredient can be present as is or as any pharmaceutically acceptable salt. If the active ingredient is present as a salt, the weight is adjusted such that the tablet contains the desired amount of active ingredient, calculated as free base or free acid of the salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1, 2-, 3, 4-diepoxybutane. The casing can also include starch and/or dextrin.

In some embodiments, an enteric coating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or Citroflex® or Citroflex® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticizers and up to around 50 wt % of anti-tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

A seal coat can also be included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876. Other enteric-coated preparations of this sort can be prepared by one skilled in the art, using these materials or their equivalents.

In one aspect, described herein is a method of treating cancer (e.g. melanoma), the method comprising administering a therapeutically effective dose of a composition of any of one of the compounds described herein or any of the pharmaceutical compositions described herein to a subject in need of treatment for cancer.

As used herein, a "subject in need of treatment for cancer" encompasses an individual who has received a diagnosis (e.g., including but not limited to a CT scan showing a mass; the presence of benign, pre-cancerous or cancerous tissue and or the increased or decreased expression of a cancer marker gene as including but not limited to those disclosed in table 1). The term further includes people who once had cancer (e.g., an individual in remission). Cancers may be characterized by the identification of the expression of one or more cancer marker genes, including but not limited to, the cancer markers disclosed herein in table 1.

As used herein, the term "marker of a cancer" or "cancer marker" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient.

In one embodiment of any of the aspects, the method further comprises a first step of measuring the level of activity and/or expression of a marker in one or more cell types relative to a reference level and the administering step is performed if the level is increased. In one embodiment of any of the aspects, the subject is one who has been determined (e.g., previously determined to have an increased level of activity and/or expression of a marker in one or more cell types relative to a reference level. In some embodiments of any of the aspects, the marker is a mutation in a marker/oncogene described herein, e.g., one or more mutations in NRAS.

In some embodiments, the one or more marker is a marker of cancer. The method of any of the preceding claims, wherein the cancer marker is a DNA, RNA, or microRNA encoded by one or more of a cancer gene, an oncogene, and a tumor suppressor gene.

In one embodiment of any of the aspects, the marker is a protein or polypeptide encoded by one or more of a cancer gene, an oncogene and/or a tumor suppressor gene.

In one embodiment of any of the aspects, the subject is determined to have an increased level of activity and/or expression of an oncogene in one or more cell types relative to a reference level occurring in a cell selected from the group consisting of: a squamous cell, basal cell and/or melanocyte.

In one embodiment of any of the aspects, the method of any of the preceding claims, wherein the marker or oncogene is selected from the group consisting of: NRAS, BRAF, KIT, MAPK1/2, ERBB4, GRIN2A, GRM3, RAC1, PREX2, IDH1, PPP6C, and CDK4 (see also list of exemplary cancer marker genes, Gene IDs and Polypeptide sequences and NCBI reference sequence ID as disclosed in table 1).

TABLE 1

Exemplary list of cancer marker genes

| Gene name | Gene ID | NCBI Reference Sequence ID |
| --- | --- | --- |
| NRAS | 4893 | e.g. NP_002515.1 |
| BRAF | 673 | e.g. NP_001341538.1 |
| KIT | 3815 | e.g. NP_000213.1 |
| MAPK1 | 5594 | e.g. NP_002736.3 |
| ERBB4 | 2066 | e.g. NP_001036064.1 |
| GRIN2A | 2903 | e.g. NP_000824.1 |
| GRM3 | 2913 | e.g. NP_000831.2 |
| RAC1 | 5879 | e.g. NP_008839.2; e.g. NP_061485.1 |
| PREX2 | 80243 | e.g. NP_079146.2; e.g. NP_079446.3 |
| IDH1 | 3418 | e.g. NP_001276839.1; e.g. NP_001277043.1; e.g. NP_002159.2 |
| PPP6C | 5537 | e.g. NP_001116827.1; e.g. NP_001116841.1; e.g NP_002712.1 |
| CDK4 | 1019 | e.g. NP_000066.1 |

In one aspect, described herein is a method of treating melanoma.

The term "melanoma" as used herein includes all types of melanoma, including, for example, melanoma skin cancer, ocular melanoma, and mucosal melanoma. Melanoma is caused by changes melanocytes that produce melanin. There are four major types of melanoma: 1) superficial spreading melanoma, which is usually flat and irregular in shape and color, with different shades of black and brown and is most common in Caucasians, 2) nodular melanoma, which usually starts as a raised area that is dark blackish-blue or bluish-red, but can be colorless, 3) Lentigo maligna melanoma, which usually occurs in the elderly and is most common in sun-damaged skin on the face, neck, and arms. The abnormal skin areas are usually large, flat, and tan with areas of brown, 4) Acral lentiginous melanoma, which is the least common form and usually occurs on the palms, soles, or under the nails and is more common in African Americans. Melanomas may also appear in the mouth, iris of the eye, or retina at the back of the eye and can be found during dental or eye examinations. Although very rare, melanoma can also develop in the vagina, esophagus, anus, urinary tract, and small intestine.

The presence of melanoma can be determined by means well known to those of skill in the art, e.g. tissue biopsies and in situ assays in which malignant melanoma (malignant melanocytes scattered in all epidermal layers) show atrophic epidermis, prominent dermal solar elastosis and almost always lymphocytic infiltration. Invasion of the dermis by melanocytes may occur in lentigo maligna melanoma. In addition, melanoma may be detected by methods that include, but are not limited, immunohistochemistry using the melanoma specific antibody HMB-45, or RT-PCR with different melanoma associated antigens (MAA) including, but not limited to tyrosinase, MART-1/Melan A, Pmel-17, TRP-1, and TRP-2 (see, e.g., Hatta N., et al., J Clin Pathol. 1998 August; 51(8):597-601). Biomarkers for melanoma are also known and can be used for example to assess subjects at risk of melanoma. Non-limiting example biomarkers for melanoma are described in WO 2008/141275, WO 2009/073513, or in U.S. Pat. No. 7,442,507, which are herein incorporated by reference in their entirety.

Symptoms of melanoma include, but are not limited to, a mole, sore, lump, or growth on the skin that may bleed, or exhibit change in skin coloring. Often patients are told of an ABCDE system the can help them remember possible symptoms of melanoma to watch out for: Asymmetry: a mole where one half of the abnormal area is different from the other half; Borders, the edges of the growth are irregular; Color, the color changes from one area to another, with shades of tan, brown, or black, and sometimes white, red, or blue, e.g. a mixture of colors may appear within one sore; Diameter, the spot is usually (but not always) larger than 6 mm in diameter, about the size of a pencil eraser; and Evolution, the mole keeps changing appearance.

As used herein, "treatment", "treating", "prevention" or "amelioration" of melanoma refers to inhibition of growth of a melanoma, inhibiting metastasis of melanoma, delaying or preventing the onset of melanoma, or reversing, alleviating, ameliorating, inhibiting, slowing down, or stopping the progression of melanoma. The term "treatment" as used herein is not intended encompass 100% cure of melanoma. However, in one embodiment, the therapeutic methods described herein may result in 100% reversal of disease.

In one embodiment of the methods described herein, at least one symptom of melanoma is alleviated by at least 5%, at least 10%, at least 20%, at least 30%, at least 40%, at least 50%, at least 60%, at least 70%, at least 80%, or at least 90%. In such an embodiment, the clinical signs and/or the symptoms associated with the melanoma are lessened as a result of the administration of the inhibitor/s. The signs or symptoms to be monitored are characteristic of a particular melanoma and are known to the skilled clinician, as well as the methods for monitoring the signs and conditions.

In one embodiment of the methods described herein, the melanoma lesion size is reduced by at least 5%, at least 10%, at least 20%, at least 30%, at least 40%, at least 50%, at least 60%, at least 70%, at least 80%, or at least 90%.

In one embodiment of the methods describe herein, melanoma cell proliferation, or melanoma growth, is inhibited by at least 5%, at least 10%, at least 20%, at least 30%, at least 40%, at least 50%, at least 60%, at least 70%, at least 80%, or at least 90%. The skilled clinician may monitor the size or rate of growth of a tumor using a diagnostic imaging method typically used for the particular tumor (e.g., using ultrasound or magnetic resonance image (MRI) to monitor a tumor).

In one aspect described herein is a treatment for melanomas with NRAS mutations.

Activating mutations in NRAS account for 20-30% of melanoma, but despite decades of research no effective anti-NRAS therapies have been forthcoming.

As used herein, "NRAS", "NS6", "CMNS", or "NRAS proto-oncogene, GTPase" refers to a N-ras oncogene encoding a membrane protein that shuttles between the Golgi apparatus and the plasma membrane. NRAS has intrinsic GTPase activity, is activated by a guanine nucleotide-exchange factor and inactivated by a GTPase activating protein. Mutations in this gene have been associated with somatic rectal cancer, follicular thyroid cancer, autoimmune lymphoproliferative syndrome, Noonan syndrome, and juvenile myelomonocytic leukemia. Sequences for NRAS are known for a number of species, e.g., human NRAS (the NCBI Gene ID is 4893), mRNA sequences (e.g., NM_002524.5) and polypeptide sequences (e.g., NP_002515.1 (SEQ ID NO: 1) are known in the art. These, together with any naturally occurring allelic, splice variants, and processed forms thereof that catalyze the same reaction are contemplated for use in the methods and compositions described herein.

| Gene name and Gene ID | Polypeptide sequences and NCBI Reference Sequence ID |
|---|---|
| human NRAS Gene ID 4893 | e.g. NP_002515.1 (SEQ ID: 1): MTEYKLVVVGAGGVGKSALTIQLIQNHFVDEYDPT IEDSYRKQVVIDGETCLLDILDTAGQEEYSAMRDQ YMRTGEGFLCVFAINNSKSFADINLYREQIKRVKD SDDVPMVLVGNKCDLPTRTVDTKQAHELAKSYGIP FIETSAKTRQGVEDAFYTLVREIRQYRMKKLNSSD DGTQGCMGLPCVVM |

RAS genes were originally identified as retroviral oncogenes in the 1960/70s from the genome of Harvey and Kirsten rat sarcoma viruses RAS proteins control cellular signaling pathways responsible for growth, migration, adhesion, cytoskeletal integrity, survival and differentiation. RAS proteins belong to the large family of small GTPases, which are activated in response to various extracellular stimuli. The activation of RAS proteins is tightly controlled in normal cells since defects in RAS signaling result in malignant transformation.

In normal cells, RAS proteins switch between active GTP-bound forms and inactive GDP-bound forms. The transition between the active and inactive state is mediated by GTPase-activating proteins (GAPs).

As used herein, a "GTPase-activating protein" or "GAP" refers to a family of regulatory proteins whose members can bind to activated G proteins and stimulate their GTPase activity.

As used herein, a "Regulator of G protein signaling proteins" or RGS protein refers to multi-functional, GTPase-accelerating proteins that promote GTP hydrolysis by the α-subunit of heterotrimeric G proteins, thereby inactivating the G protein and rapidly switching off G protein-coupled receptor signaling pathways.

Non-limiting examples of downstream effectors of NRAS include RAF kinases (e.g. the Serine/threonine-protein kinase A-Raf (ARAF), the seine/threonine-protein kinas B-Raf (BRAF), and serine/threonine-protein kinase C-Raf (CRAF), phosphatidylinositol 3-kinase (PI3K), and the RAS-like protein (RAL) Guanine nucleotide exchange factors.

In one aspect described herein are compounds, compositions and methods of inhibiting the novel serine/threonine kinase STK19 for the treatment for melanomas.

In one embodiment of any of the aspects described herein are compounds, compositions and methods of inhibiting the novel serine/threonine kinase STK19 for the treatment for melanomas with NRAS mutations.

Non limiting examples of NRAS mutations include but are not limited to a point mutation. As used herein, a "point mutation" refers to the identity of the nucleotide present at a site of a mutation in the mutant copy of a genomic locus (including insertions and deletions), i.e. it refers to an alteration in the sequence of a nucleotide at a single base position from the wild type sequence. A SNP (single nucleotide polymorphism) is one type of point mutation that occurs at the same genomic locus between different individuals in a population. Point mutations may be somatic in that they occur between different cells in the same individual.

In some embodiments, a NRAS point mutation can be a point mutation resulting in one of the following amino acid residue changes. Non-limiting examples of NRAS point mutations include e.g. G12D; G12S; G13A; G13C; G13D; G12R; G13V; Q61H; Q61K; Q61L; Q61R and S89A.

In one embodiment of any of the aspects described herein are compounds, compositions and methods of inhibiting the novel serine/threonine kinase STK19 for the treatment for melanomas with BRAF mutations.

In some embodiments, a BRAF point mutation can be a point mutation resulting in one of the following amino acid residue changes: V600D TG/AT; V600E T/A; V600E TG/AA; and V600K GT/AA.

As used herein, "STK19", "G11", "D6S60", or "Serine/threonine kinase 19" refers to a serine/threonine kinase which localizes predominantly to the nucleus which is thought to be involved in transcriptional regulation. The gene localizes to the major histocompatibility complex (MHC) class III region on chromosome 6 and expresses at least two transcript variants. Sequences for STK19 are known for a number of species, e.g., human STK19 (the NCBI Gene ID is 8859), mRNA sequences (e.g., NM_004197.1 and/or NM_032454.1) and polypeptide sequences (e.g., NP_004188.1 (SEQ ID NO: 2) and/or NP_115830.1 (SEQ ID NO: 3) are known in the art. These, together with any naturally occurring allelic, splice variants, and processed forms thereof that catalyze the same reaction are contemplated for use in the methods and compositions described herein.

| Gene name and Gene ID | Polypeptide sequences and NCBI Reference Sequence ID |
|---|---|
| Human STK19 Gene ID 8859 | e.g., NP_004188.1 (SEQ ID NO: 2): MQKWFSAFDDAIIQRQWRANPSRGGGGVSFTKEVD TNVATGAPPRRQRVPGRACPWREPIRGRRGARPGG GDAGGTPGETVRHCSAPEDPIFRFSSLHSYPFPGT IKSRDMSWKRHHLIPETFGVKRRRKRGPVESDPLR GEPGSARAAVSELMQLFPRGLFEDALPPIVLRSQV YSLVPDRTVADRQLKELQEQGEIRIVQLGFDLDAH GIIFTEDYRTRVLKACDGRPYAGAVQKFLASVLPA CGDLSFQQDQMTQTFGFRDSEITHLVNAGVLTVRD AGSWWLAVPGAGRFIKYFVKGRQAVLSMVRKAKYR ELLLSELLGRRAPVVVRLGLTYHVHDLIGAQLVDC ISTTSGTLLRLPET or: <br><br>NP_115830.1 (SEQ ID NO: 3): MQKWFSAFDDAIIQRQWRANPSRGGGGVSFTKEVD TNVATGAPPRRQRVPGRACPWREPIRGRRGARPGG GDAGGTPGETVRHCSAPEDPIFRFSSLHSYPFPGT IKSRDMSWKRHHLIPETFGVKRRRKRGPVESDPLR GEPGSARAAVSELMQLFPRGLFEDALPPIVLRSQV YSLVPDRTVADRQLKELQEQGEIRIVQLGFDLDAH GIIFTEDYRTRVCDCVLKACDGRPYAGAVQKFLAS VLPACGDLSFQQDQMTQTFGFRDSEITHLVNAGVL TVRDAGSWWLAVPGAGRFIKYFVKGRQAVLSMVRK |

-continued

| Gene name and Gene ID | Polypeptide sequences and NCBI Reference Sequence ID |
|---|---|
| | AKYRELLLSELLGRRAPVVVRLGLTYHVHDLIGAQ LVDCISTTSGTLLRLPET |

As used herein, a "serine/threonine protein kinase" refers to enzymes classified under Enzyme Commission number (EC) 2.7.11. Serine/threonine protein kinases phosphorylates the OH (hydroxyl) group on the side chain of one or more serine or threonine amino acid residue in a protein.

As described herein, the serine/threonine kinase STK19 phosphorylates and thereby activates NRAS to enhance its binding to its downstream effectors and promotes oncogenic NRAS-mediated melanocyte malignant transformation. As disclosed herein, a D89N point mutation in STK19 was identified in 25% of human melanomas. STK19 D89N represents a gain-of-function mutation that interacts better with NRAS to enhance melanocyte transformation. A STK19D89N knockin mouse model leads to skin hyperpigmentation and promotes NRASQ61R-driven melanomagenesis in vivo.

Where the treatment of melanoma can benefit from interventions that promote the activation of NRAS (e.g. by phosphorylation) to enhance its binding to downstream effectors and to promote e.g. oncogenic NRAS-mediated melanocyte malignant transformation, compositions and antibody agents targeting STK19, as described herein, are well-suited for treating melanoma.

Antibody agents that target STK19 are known in the art. For example, Table 2 provides exemplary antibodies that target STK19.

As used herein, the term "antibody agent" refers to a polypeptide that includes at least one immunoglobulin variable domain or immunoglobulin variable domain sequence and that specifically binds a given antigen on STK19. An antibody agent can comprise a monoclonal antibody or a polypeptide comprising an antigen-binding domain of a monoclonal antibody. In another example, an antibody agent can include two heavy (H) chain variable regions and two light (L) chain variable regions. The term "antibody agent" encompasses antigen-binding portions or fragments of antibodies (e.g., single chain antibodies, Fab and sFab fragments, F(ab')2, Fd fragments, Fv fragments, scFv, and single domain antibody (dAb) fragments (see, e.g., de Wildt et al., Eur J. Immunol. 1996; 26(3):629-39; which is incorporated by reference herein in its entirety)), as well as complete antibodies.

TABLE 2

Exemplary anti-STK19 antibodies

| Antibody | Source | Clonality | SEQ ID NO: | Immunogen sequence |
|---|---|---|---|---|
| PA5-56764 | Thermo Fisher Scientific | polyclonal | 4 | SAFDDAIIQR QWRANPSRGG GGVSFTKEVD TNVATGAPPR RQRVPGRACP WREPIRGRRG ARPGGGDAG |
| 4E11 | Novus Biologicals | monoclonal | 5 | QMTQTFGFRDSEITHLVNAG VLTVRDAGSWWLAVPGAGR FIKYFVKGRQAVLSMVRKA KYRELLLSELLGRRAPVVVR LGLTYHVHDLIGAQLVDCIS TTSGTLLRLPET |
| HPA068559 | Atlas Antibodies | polyclonal | 6 | AAVSELMQLFPRGLFEDALP PIVLRSQVYSLVPDRTVADR QLKELQEQGEIRIVQLGFDLD AHGIIFTEDYRTR |
| 3B6 | Santa Cruz | monoclonal | | |
| HPA031510 | Sigma Aldrich | polyclonal | 7 | SAFDDAIIQRQWRANPSRGG GGVSFTKEVDTNVATGAPPR RQRVPGRACPWREPIRGRRG ARPGGGDAG |
| ab251814 | Abcam | polyclonal | 8 | SAFDDAIIQRQWRANPSRGG GGVSFTKEVDTNVATGAPPR RQRVPGRACPWREPIRGRRG ARPGGGDAG |

In one embodiment of any of the aspects, the method of treating melanoma comprises the isolation of one or more cells selected from the group consisting of a squamous cell, basal cell and/or melanocyte from a subject in need thereof.

As used herein, the term "squamous cell" refers to flat, thin cells that make up the middle and outer layers of the skin. Squamous cell carcinoma of the skin occurs when squamous cells develop mutations in their DNA e.g. caused by ultraviolet (UV) radiation. Squamous cell carcinoma (SCC) is a malignant neoplasm of epithelial cells, e.g., keratinocytes, bronchial epithelia, etc. SCCs can include, for example, skin, oral, lung, cervical, and colorectal carcinomas. SCC cells readily grow and expand in culture, and continuously passage. Methods to isolate SCC cells are well known in the art. A non-limiting example for the isolation of SCC cells is described e.g. in Methods Mol Biol. 2011; 731:151-9., incorporated by reference in its entirety.

As used herein, the term "basal cell" refers to any stratified or pseudostratified epithelium. Bsal cells are cells that are juxtaposed to the basement membrane and under one or more additional epithelial layers. Mammary tissue can have both a two cell layer epithelium (basal and luminal cells) or in the duct system, a single layered epithelium. In the two cell layer, the cells adjacent to the basement membrane are termed "basal cells" and express basal cell markers (e.g., including but not limited to cytokeratin 17 and cytokeratin 5/6). Basal cell carcinoma (BCC) is a type of skin cancer that begins in the basal cells. BCC is the most common type of skin cancer. Methods to isolate basal cells are well known in the art. A non-limiting example for the isolation of basal cells is described, e.g. in Succony L et al., Methods to isolate basal cells from the respiratory epithelium, available on the world wide web at https://thorax.bmj.com/content/thoraxjnl/69/Suppl_2/A59.2.full.pdf.

As used herein, the term "Melanocyte" refers to melanin-producing cells located in the bottom layer of the skin's epidermis, including but not limited to the middle layer of the eye, the inner ear, vaginal epithelium, meninges, bone, and heart. The precursor of the melanocyte is the melanoblast. Methods to isolate melanocytes and/or melanoblasts are well known in the art. A non-limiting example for the isolation of melanocytes and/or meanoblasts is described, e.g. in Godwin L S, et al., Isolation, culture, and trsnafection of melanocytes, Curr Protoc Cell Biol. 2014 Jun. 3; 63:1.8.1-20, incorporated by reference in its entirety.

In one embodiment of any of the aspects, the one or more cells isolated can be a human cell or mammalian cell, for example, a canine, avian, feline, equine, bovine, porcine, primate, rodent, or bat cell.

In one aspect, described herein is a method of treating melanoma comprising: isolating one or more cells selected from the group consisting of a squamous cell, basal cell and/or melanocyte from a subject in need thereof; measuring the expression of one or more cancer genes, oncogenes and/or tumor suppressor genes products in the one or more cells; administering a therapeutically effective dose of an inhibitor of immune checkpoint polypeptides to the subject if the expression of one or more cancer genes, oncogenes and/or tumor suppressor gene is not altered or decreased in one or more cells as compared to a reference level; or administering a therapeutically effective dose of any of the compositions disclosed herein to the subject if the expression of one or more cancer genes, oncogenes and/or tumor suppressor gene products is elevated in one or more cells as compared to a reference level.

In one embodiment of any of the aspects, the expression product is a nucleic acid.

In one embodiment of any of the aspects, the level of the expression product is determined using a method selected from the group selected from the group consisting of: RT-PCR; quantitative RT PCR; Northern Blot; microarray-based expression analysis; next generation sequencing; and RNA in situ hybridization.

In one embodiment of any of the aspects, the level of the expression product is a polypeptide.

In one embodiment of any of the aspects, the level of the expression product is determined using a method selected from the group selected from the group consisting of: Western blot; immunoprecipitation; enzyme linked immunosorbent assay (ELISA); radioimmunological assay (RIA); sandwich assay; fluorescence in situ hybridization (FISH); immunohistological staining; radioimmunometric assay; immunofluorescence assay; mass spectrometry; FACS; and immunoelectrophoresis assay.

In one embodiment of any of the aspects, the method comprises measuring the level of an expression product of at least one marker gene selected from Table 1.

In one embodiment of any of the aspects, the marker gene is selected from the group consisting of: NRAS, BRAF, KIT, MAPK1/2, ERBB4, GRIN2A, GRM3, RAC1, PREX2, IDH1, PPP6C, and CDK4 (as disclosed e.g. in Table 1).

In one embodiment of any of the aspects, the immune checkpoint polypeptides are selected from CTLA4A, CTLA4, Ki-67, CD-28, PD-1, TIM-3, and LAG-3.

In one embodiment of any of the aspects, the inhibitor of immune checkpoint polypeptides are selected from Pembrolizumab and Nivolumab.

As used herein, "immune checkpoint protein" refers to a protein which, when active, exhibits an inhibitory effect on immune activity, e.g., T cell activity. Exemplary immune checkpoint proteins can include PD-1 (e.g., NCBI Gene ID: 5133); PD-L1 (e.g., NCBI Gene ID: 29126); PD-L2 (e.g., NCBI Gene ID: 80380); TIM-3 (e.g., NCBI Gene ID: 84868); CTLA4 (e.g., NCBI Gene ID: 1493); TIGIT (e.g., NCBI Gene ID: 201633); KIR (e.g., NCBI Gene ID: 3811); LAG3 (e.g., NCBI Gene ID: 3902); DD1-α (e.g., NCBI Gene ID: 64115); A2AR (e.g., NCBI Gene ID: 135); B7-H3 (e.g., NCBI Gene ID: 80381); B7-H4 (e.g., NCBI Gene ID: 79679); BTLA (e.g., NCBI Gene ID: 151888); IDO (e.g., NCBI Gene ID: 3620); TDO (e.g., NCBI Gene ID: 6999); HVEM (e.g., NCBI Gene ID: 8764); GAL9 (e.g., NCBI Gene ID: 3965); 2B4 (belongs to the CD2 family of molecules and is expressed on all NK, γδ, and memory CD8+ (αβ) T cells) (e.g., NCBI Gene ID: 51744); CD160 (also referred to as BY55) (e.g., NCBI Gene ID: 11126); and various B-7 family ligands. B7 family ligands include, but are not limited to, B7-1, B7-2, B7-DC, B7-H1, B7-H2, B7-H3, B7-H4, B7-H5, B7-H6 and B7-H7.

PD-1 blockade can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; which are incorporated by reference herein in their entireties. In certain embodiments the PD-1 inhibitors include anti-PD-L1 antibodies. In certain other embodiments the PD-1 inhibitors include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224, a fusion protein of B7-DC; an antibody Fc portion; BMS-936559 (MDX-1105-01) for PD-L1 (B7-H1) blockade.

Examples of anti-CTLA-4 antibodies are described in U.S. Pat. Nos. 5,811,097; 5,811,097; 5,855,887; 6,051,227; 6,207,157; 6,682,736; 6,984,720; and 7,605,238; which are incorporated by reference herein in their entireties. One anti-CDLA-4 antibody is tremelimumab, (ticilimumab, CP-675,206). In one embodiment, the anti-CTLA-4 antibody is ipilimumab (also known as 10D1, MDX-D010) a fully human monoclonal IgG antibody that binds to CTLA-4. Ipilimumab is marketed under the name YERVOY™ and has been approved for the treatment of unresectable or metastatic melanoma.

Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94).

Non-limiting examples of immune checkpoint inhibitors (with checkpoint targets and manufacturers noted in parantheses) can include:MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3: Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CellDex); MEDI-6769 (Ox40; MedImmune); CP-870,893 (CD40; Genentech); tremelimumab (CTLA-4; Medimmune); pidilizumab (PD-1; Medivation); MPDL3280A (PD-L1; Roche); MED14736 (PD-L1; AstraZeneca); MSB0010718C (PD-L1; EMD Serono); AUNP12 (PD-1; Aurigene); avelumab (PD-L1; Merck); durvalumab (PD-L1; Medimmune).

In some embodiments, prodrugs of compounds of Formula (I)-(LI) also fall within the scope of the invention. As used herein, a "prodrug" refers to a compound that can be converted via some chemical or physiological process (e.g., enzymatic processes and metabolic hydrolysis) to a compound compounds of Formula (I)-(LI). Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al., "Application of Physical Organic Principles to Prodrug Design" in E. B. Roche ed. Design of Biopharmaceutical Properties through Prodrugs and Analogs, *APHA Acad. Pharm. Sci.* 40 (1977); Bioreversible Carriers in Drug in Drug Design, Theory and Application, E. B. Roche, ed., *APHA Acad. Pharm. Sci.* (1987); Design of Prodrugs, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11,:345-365; Gaignault et al. (1996) "Designing Prodrugs and Bioprecursors I. Carrier Prodrugs," *Pract. Med. Chem.* 671-696; Asgharnejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs-principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [Symp.] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J Clin. Pharmac.* 28: 497-507 (1989), and Sofia et al. "Tyrosinase activated melanoma prodrugs.", *Anticancer Agents Med Chem.* 2009 September; 9(7): 717-27., contents of all of which are herein incorporated by reference in their entireties.

As used herein, the term "administering" refers to the placement of a therapeutic (e.g., a compound, composition, pharmaceutical composition, or an agent described herein)

into a subject by a method or route which results in at least partial localization of the composition at a desired site such that desired effect is produced. A therapeutic (e.g., a compound, composition, pharmaceutical composition, or an agent described herein) described herein can be administered by any appropriate route known in the art including, but not limited to, oral or parenteral routes, including intravenous, intramuscular, parenteral, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are orally administered. Without limitations, oral administration can be in the form of solutions, suspensions, tablets pills, capsules, sustained-release formulations, oral rinses, powders and the like.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

In jurisdictions that forbid the patenting of methods that are practiced on the human body, the meaning of "administering" of a therapeutic to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of therapeutic includes both methods practiced on the human body and also the foregoing activities.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The term "effective amount" is used interchangeably with the term "therapeutically effective amount" or "amount sufficient" and refers to the amount of at least one therapeutic (e.g., a compound, composition, pharmaceutical composition, or an agent described herein) at dosages and for periods of time necessary to achieve the desired therapeutic result, for example, to "attenuate", reduce or stop at least one symptom of a cancer, e.g., melanoma. For example, an effective amount using the methods as disclosed herein would be considered as the amount sufficient to reduce one or more symptoms of melanoma by at least 10%. An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from melanoma. The effective dosage range for the administration of the inhibitors depends upon the form of the inhibitor and its potency. It is an amount large enough to produce the desired effect in which symptoms of melanoma are ameliorated (e.g. inhibition of tumor growth). The phrase "therapeutically-effective amount" as used herein means that amount of inhibitory compound or composition comprising the inhibitor/s which is effective for producing the desired therapeutic effect, in at least a sub-population of cells, in a subject at a reasonable benefit/risk ratio applicable to any medical treatment. For example, an amount of a compound administered to a subject that is sufficient to produce a statistically significant, measurable change in at least one symptom of melanoma. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. There are preclinical melanoma models that are well known to those of skill in the art which can be used to determine therapeutically effective amounts of the compound or agents and to optimize administration regimes. See for example Yang et al. (2010) RG7204 (PLX4032), The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of use or administration utilized.

As used herein, the term ED denotes "effective dose" and is used in connection with animal models. The term EC denotes "effective concentration" and is used in connection with in vitro models.

The data obtained from the cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay (e.g. the Promega ADP-Glo® kinase assay according to the manufacture's protocol available on the world wide web at https://www.promega.com/resources/protocols/technical-manuals/0/adp-glo-kinase-assay-protocol/(and further described e.g. in Example 2 herein).

The dosage of a therapeutic (e.g., a compound, composition, pharmaceutical composition, or an agent described herein) may be determined by a physician and adjusted, as necessary, to suit observed effects of the treatment. Generally, the compositions are administered so that the compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that therapeutic (e.g., a compound, composition, pharmaceutical composition, or an agent described herein) or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compound. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

In one embodiment of any of the aspects, the agent or composition is administered continuously (e.g., at constant levels over a period of time). Continuous administration of an agent can be achieved, e.g., by epidermal patches, continuous release formulations, or on-body injectors.

The compound can be administered as a single bolus or multiple boluses, as a continuous infusion, or a combination thereof. For example, the compound can be administered as a single bolus initially, and then administered as a continuous infusion following the bolus. The rate of the infusion can be any desired rate. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The terms "co-administration" or the like, as used herein, are meant to encompass administration of the selected therapeutic agents to a single patient and are intended to include treatment regimens in which the agents are administered by the same or different route of administration or at the same or different time.

"Unit dosage form" as the term is used herein refers to a dosage for suitable one administration. By way of example a unit dosage form can be an amount of therapeutic disposed in a delivery device, e.g., a syringe or intravenous drip bag. In one embodiment of any of the aspects, a unit dosage form is administered in a single administration. In another embodiment of any of the aspects, more than one-unit dosage form can be administered simultaneously.

The dosage of the therapeutic as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

The efficacy of a therapeutic described herein, e.g., for the treatment of melanoma, can be determined by the skilled practitioner. However, a treatment is considered "effective treatment," as the term is used herein, if one or more of the signs or symptoms of cancer (e.g., melanoma) are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., immune function. Efficacy can also be measured by a failure of an individual to worsen as assessed by hospitalization, or need for medical interventions (i.e., progression of the symptoms). Methods of measuring these indicators are known to those of skill in the art and/or are described herein.

Efficacy can be assessed in animal models of a condition described herein, for example, a mouse model or an appropriate animal model of a cancer, e.g., melanoma, as the case may be. When using an experimental animal model (e.g a Xenograft models of melanoma (e.g. human melanoma cells are transplanted into immune-deficient mice). Efficacy of treatment is evidenced when a statistically significant change in a marker is observed, e.g., reduced melanoma or reduced levels of a biomarker of melanoma. Non-limiting example biomarkers for melanoma e.g. lactate dehydrogenase, tyrosinase, S100 family of calcium-binding proteins, cyclooxygenase-2, matrix metalloproteinases are described in WO 2008/141275, WO 2009/073513, or in U.S. Pat. No. 7,442,507, which are herein incorporated by reference in their entirety.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

"Alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

"Alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

"Cycloalkyl" refers to a non-aromatic mono- or multicyclic ring system of about 3 to about 12 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

"Heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Aryl" refers to an aromatic carbocyclic radical containing about 3 to about 13 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Heteroaryl" refers to an aromatic 3-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively.

Exemplary aryl and heteroaryls include, but are not limited to, phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application.

The term "haloalkyl" as used herein refers to an alkyl structure with at least one substituent of fluorine, chorine, bromine or iodine, or with combinations thereof. Exemplary halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($CF_3$), perfluoroethyl, 2,2,2-trifluoroethyl, 2,2,2-trifluoro-1,1-dichloroethyl, and the like).

As used herein, the term "amino" means —$NH_2$. The term "alkylamino" means a nitrogen moiety having one straight or branched unsaturated aliphatic, cyclyl, or heterocyclyl radicals attached to the nitrogen, e.g., —NH(alkyl). The term "dialkylamino" means a nitrogen moiety having at two straight or branched unsaturated aliphatic, cyclyl, or heterocyclyl radicals attached to the nitrogen, e.g., —N(alkyl)(alkyl). The term "alkylamino" includes "alkenylamino," "alkynylamino," "cyclylamino," and "heterocyclylamino." The term "arylamino" means a nitrogen moiety having at least one aryl radical attached to the nitrogen. For example, -NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like. Exemplary alkylamino includes, but is not limited to, NH($C_1$-$C_{10}$alkyl), such as —$NHCH_3$, —$NHCH_2CH_3$, —$NHCH_2CH_2CH_3$, and —$NHCH(CH_3)_2$. Exemplary dialkylamino includes, but is not limited to, —N($C_1$-$C_{10}$alkyl)$_2$, such as N($CH_3$)$_2$, —N($CH_2CH_3$)$_2$, —N($CH_2CH_2CH_3$)$_2$, and —N($CH(CH_3)_2$)$_2$.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The terms "hydroxy" and "hydroxyl" mean the radical —OH.

The terms "alkoxyl" or "alkoxy" as used herein refers to an alkyl group, as defined above, having an oxygen radical attached thereto, and can be represented by one of —O-alkyl, —O— alkenyl, and —O-alkynyl. Aroxy can be represented by —O-aryl or O-heteroaryl, wherein aryl and heteroaryl are as defined herein. The alkoxy and aroxy groups can be substituted as described above for alkyl. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. As used herein, a carboxy group includes —COOH, i.e., carboxyl group.

The term "cyano" means the radical —CN.

The term "nitro" means the radical —$NO_2$.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N═, —NR, —N+(O—)═, —O—, —S— or —S(O)$_2$—, —OS(O)$_2$—, and —SS—, wherein $R^N$ is H or a further substituent.

The terms "alkylthio" and "thioalkoxy" refer to an alkoxy group, as defined above, where the oxygen atom is replaced with a sulfur. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

In some embodiments, the compound of Formula I is selected from the group of the following compounds

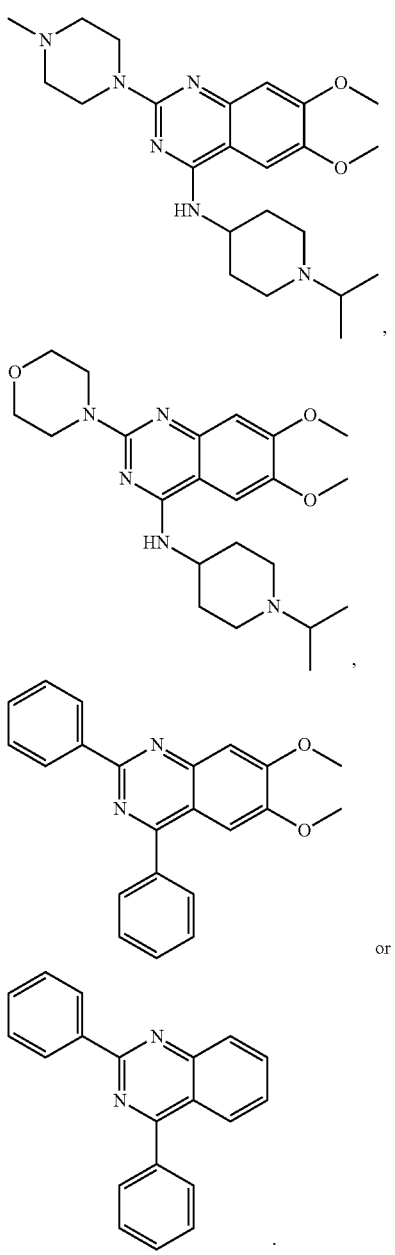

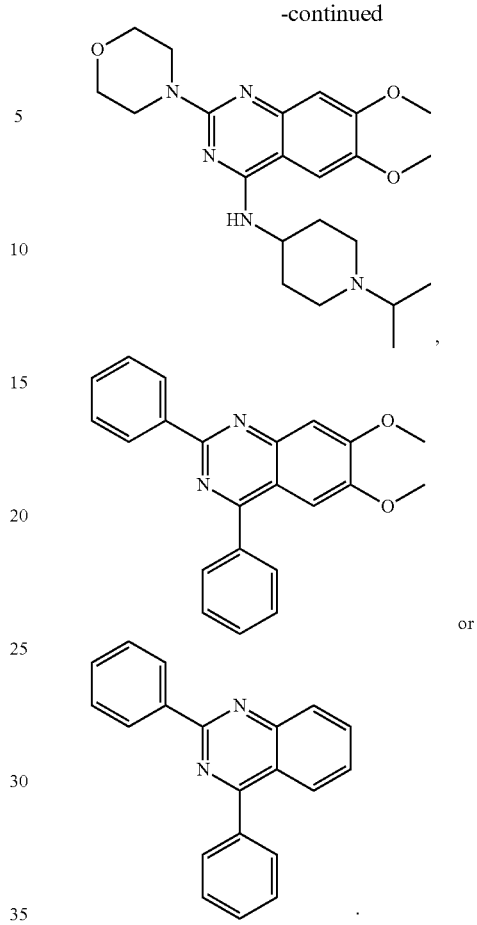

In some embodiments, the compound of Formula I is not compound

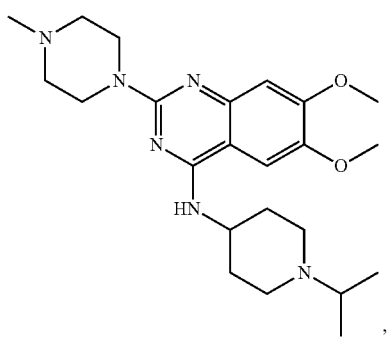

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Aroyl" means an aryl-CO— group, wherein aryl is as previously described. Exemplary aroyl groups include benzoyl and 1- and 2-naphthoyl.

"Arylthio" refers to an aryl-S— group, wherein the aryl group is as previously described. Exemplary arylthio groups include phenylthio and naphthylthio.

"Aralkyl" refers to an aryl-alkyl-group, wherein aryl and alkyl are as previously described. Exemplary aralkyl groups include benzyl, phenylethyl and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H2N—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described. "Acylamino" refers to an acyl-NH— group, wherein acyl is as previously described. "Aroylamino" refers to an aroyl-NH— group, wherein aroyl is as previously described.

The term "optionally substituted" means that the specified group or moiety is unsubstituted or is substituted with one or more (typically 1, 2, 3, 4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

For example, any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$ alkyl, $SO_2NH(C_1-C_4)$alkyl, halogen, carbonyl, thiol, cyano, $NH_2$, $NH(C_1-C_4)$alkyl, $N[(C_1-C_4)alkyl]_2$, $C(O)NH_2$, COOH, COOMe, acetyl, $(C_1-C_5)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)— alkyl, C(O)— alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo; "m" and "p" are independently 1, 2, 3, 4, 5 or 6.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. The term "tautomer," as used herein, refers to one of two or more structural isomers which exist in equilibrium and which are readily converted from one isomeric form to another, for example, a keto-enol pair.

The term "pharmaceutically acceptable salt" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

As used herein, the terms "treat" "treatment," "treating," or "amelioration" refer to therapeutic treatments, wherein the object is to reverse, alleviate, ameliorate, inhibit, slow down or stop the progression or severity of a condition associated with a disease or disorder, e.g. the inhibition of growth of melanoma, inhibiting metastasis of melanoma, delaying or preventing the onset of melanoma, or reversing, alleviating, ameliorating, inhibiting, slowing down, or stopping the progression of melanoma. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "prevent" or "preventing" refers to the prevention of at least one symptom associated with melanoma, or delaying or preventing the onset of melanoma or the complete prevention of melanoma, or the lessening of the severity of melanoma (e.g., the inhibition of growth of melanoma, inhibiting metastasis of melanoma, or reversing, alleviating, ameliorating, inhibiting, slowing down, or stopping the progression of melanoma) in a subject, and/or delaying one or more symptoms of melanoma, and/or delaying the onset of melanoma.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments of any of the aspects, administration comprises physical human activity, e.g., an injection, act of ingestion, an act of application, and/or manipulation of a delivery device or machine. Such activity can be performed, e.g., by a medical professional and/or the subject being treated.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., Xenograft models of melanoma (e.g. human melanoma cells are transplanted into immune-deficient mice). A subject can be male or female.

A subject can be one who has been previously diagnosed with or identified as suffering from or having a disease or disorder in need of treatment (e.g., melanoma) or one or more complications related to such a disease or disorder, and optionally, have already undergone treatment for the disease or disorder or the one or more complications related to the disease or disorder. A subject can be resistant to at least one treatment for the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

As used herein, the term "agent" or "compound" refers to any organic or inorganic molecule, including modified and unmodified nucleic acids such as antisense nucleic acids, RNAi, such as siRNA or shRNA, peptides, small molecules peptidomimetics, receptors, ligands, and antibodies. e.g. including but not limited to molecules and/or compositions that inhibit STK19 activity or inhibit NRAS activity. The compounds/agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies, or fragments thereof.

The term "agent" as used herein means any compound or substance such as, but not limited to, a small molecule, nucleic acid, polypeptide, peptide, gene editing system, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

As used herein, a "compound" refers to any chemical, test chemical, drug, new chemical entity (NCE) or other moiety. For example, a compound can be any foreign chemical not normally present in a subject such as mammals including humans. A compound can also be an endogenous chemical that is normally present and synthesized in biological systems, such as mammals including humans.

As used herein, an "inhibitor" refers to any agent, compound, or composition that reduces the levels or activity of a polypeptide (e.g. including but not limited to reducing the levels or activity of a STK19 or NRAS polypeptide).

The terms "polypeptide," "peptide" and "protein" refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acids.

The terms "marker", "cancer marker" or "biomarker" refer to a DNA, RNA or microRNA that is encoded by one or more of a cancer gene, an oncogene, and a tumor suppressor gene and/or a protein or polypeptide encoded by one or more of a cancer gene, an oncogene and/or a tumor suppressor gene.

As used herein, the term "cancer marker" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. Biomarkers for melanoma are well known in the art and can be used for example to assess subjects at risk of melanoma. Non-limiting example biomarkers for melanoma are described in PCT Publications WO 2008/141275, WO 2009/073513, or in U.S. Pat. No. 7,442,507, which are herein incorporated by reference in their entirety.

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to an appropriate control.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a cancer (e.g melanoma) or prior to receiving a given treatment, or a biological sample that has not been contacted with an agent disclosed herein).

As used herein, an "appropriate control" refers to an untreated, otherwise identical cell or population (e.g., a subject who was not administered an agent described herein, or was administered by only a subset of agents described herein, as compared to a non-control cell).

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments of any of the aspects, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A compound of Formula I:

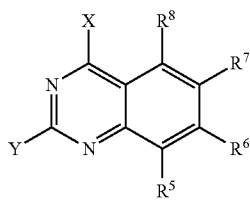

FORMULA I wherein:

X is aryl, or $N(R^1R^2)$;

Y is aryl, or $N(R^3R^4)$;

$R^1$ and $R^2$ are independently hydrogen, alkyl, cyclyl, heterocyclyl, aryl or heteroaryl, each of which can be optionally substituted, or $R^1$ and $R^2$ are connect to form an optionally substituted heterocyclyl;

$R^3$ and $R^4$ are independently hydrogen, alkyl, cyclyl, heterocyclyl, aryl or heteroaryl, each of which can be optionally substituted, or $R^3$ and $R^4$ are connect to form an optionally substituted heterocyclyl $R^5$, $R^6$, $R^7$ and $R^8$ are independently selected from the group consisting of hydrogen, alkyl, halogen, nitro, cyano, hydroxyl, amino, mercapto, formyl, carboxy, alkanoyl, carbamoyl, alkoxy, alkylthio, alkylamino, (alkyl)$_2$amino (dialkylamino), alkylsulfinyl, alkylsulfonyl, arylsulfonyl, cyclyl, heterocyclyl, aryl, or heteroaryl, each of which can be optionally substituted;

provided that at least one of X and Y is independently selected from the group consisting of:

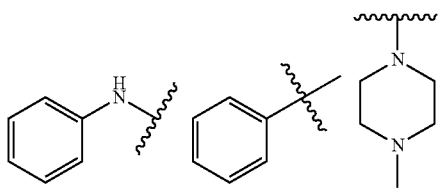

-continued

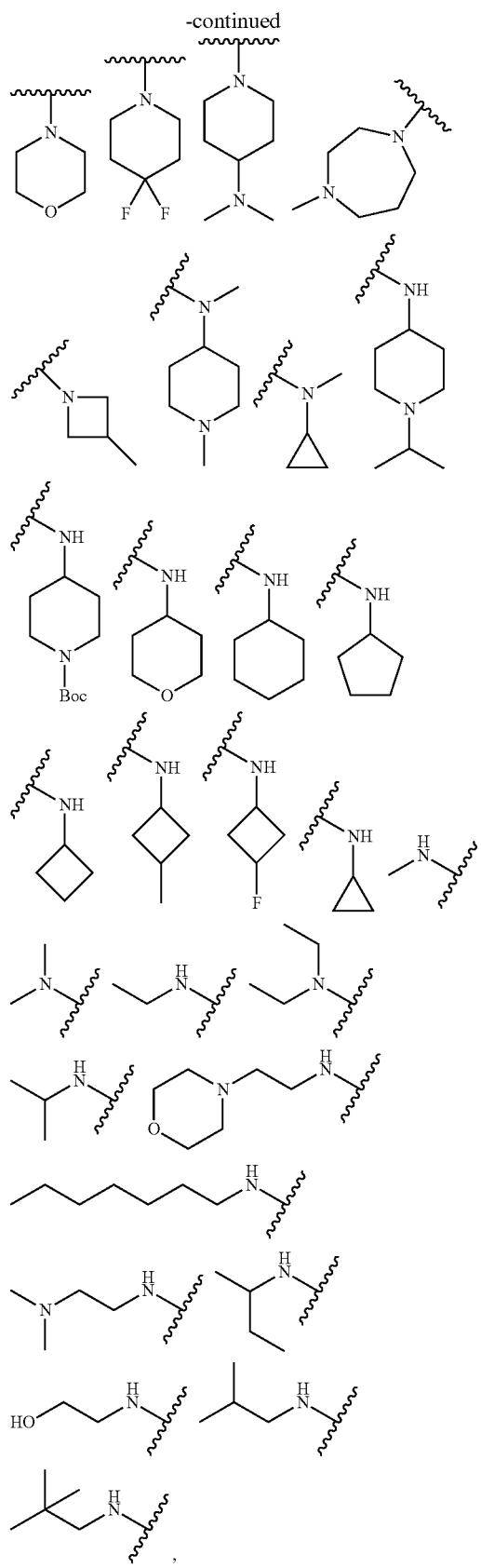

or isomers, tautomers or a pharmaceutically acceptable salt thereof, provided that the compound is not

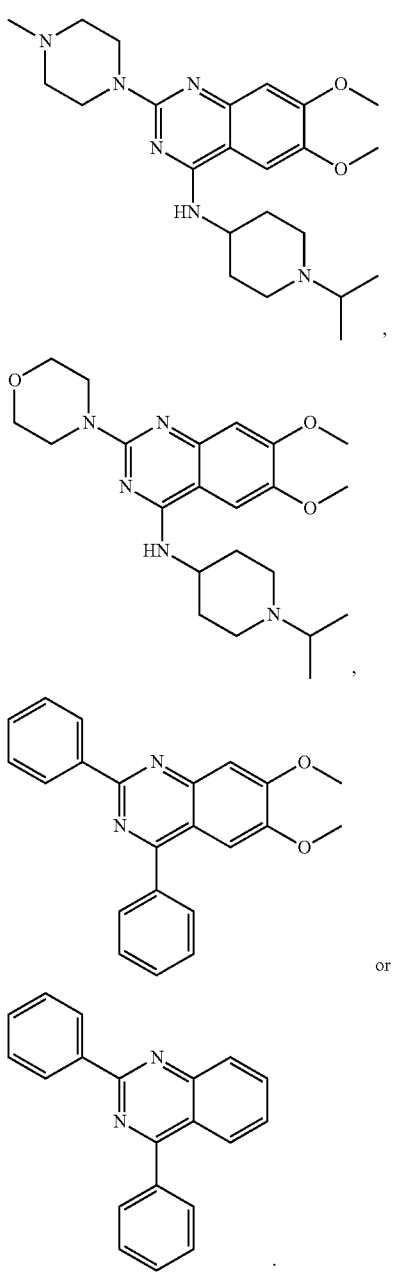
2. The compound of claim 1, wherein X is selected from the group consisting of:
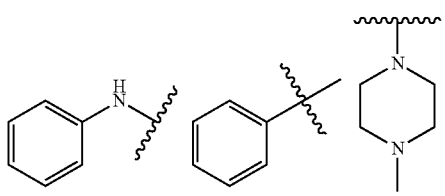
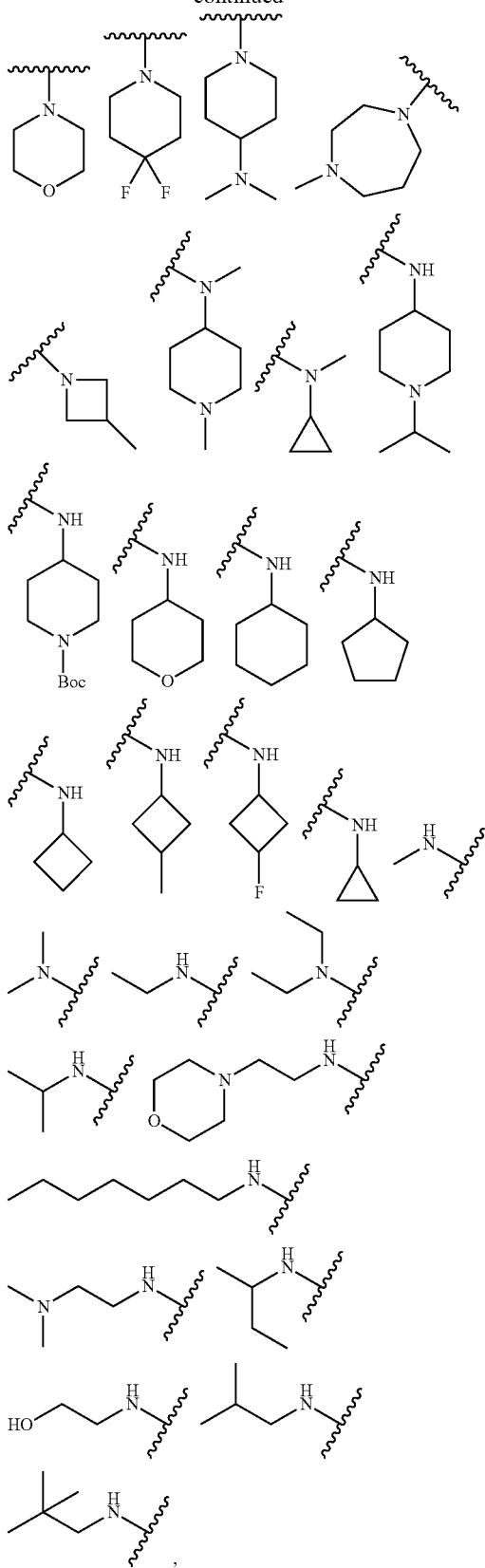
3. The compound of any one of paragraphs 1-2, wherein X is selected from the group consisting of:

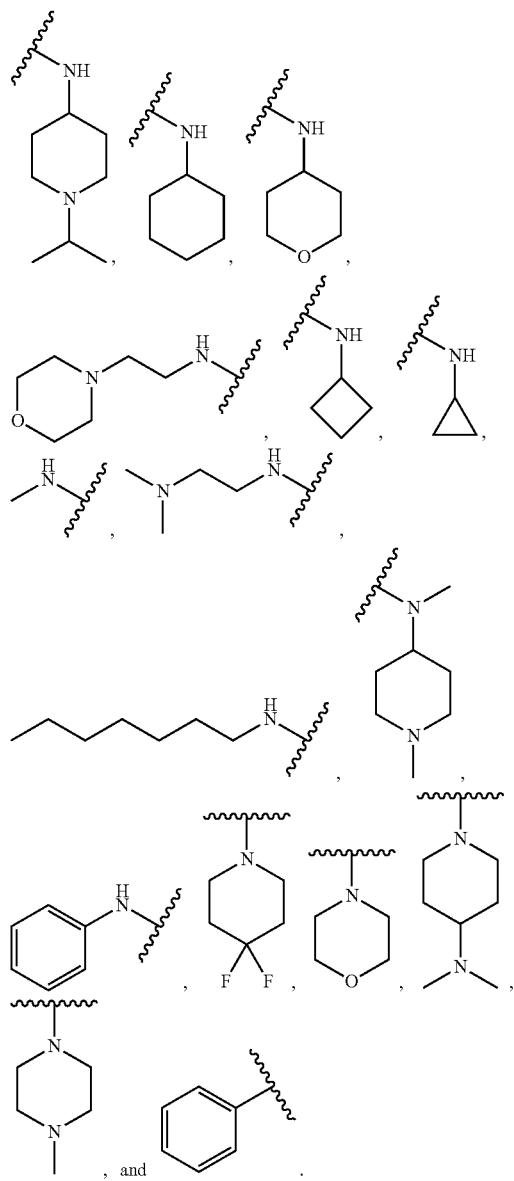
4. The compound of any one of paragraphs 1-3, wherein the compound is of Formula (II):
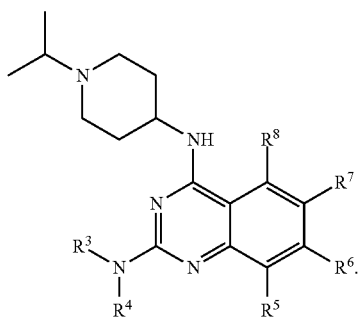
FORMULA (II)
5. The compound of any one of paragraphs 1-4, wherein Y is selected from the group consisting of:
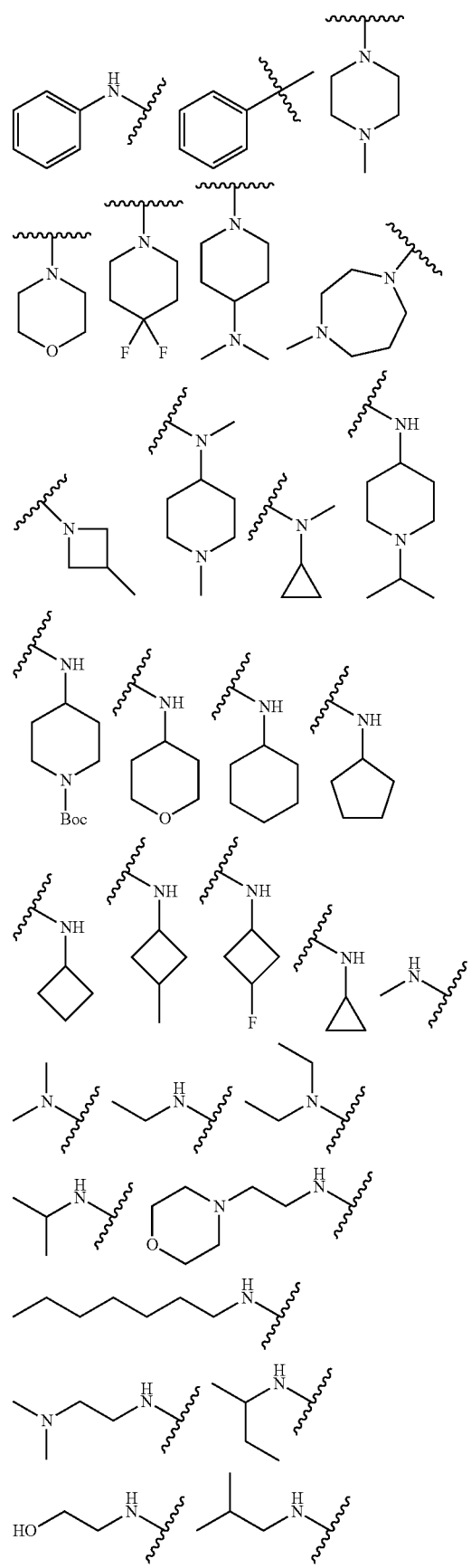

-continued

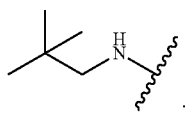

6. The compound of any one of paragraphs 1-5, wherein Y is selected from the group consisting of:

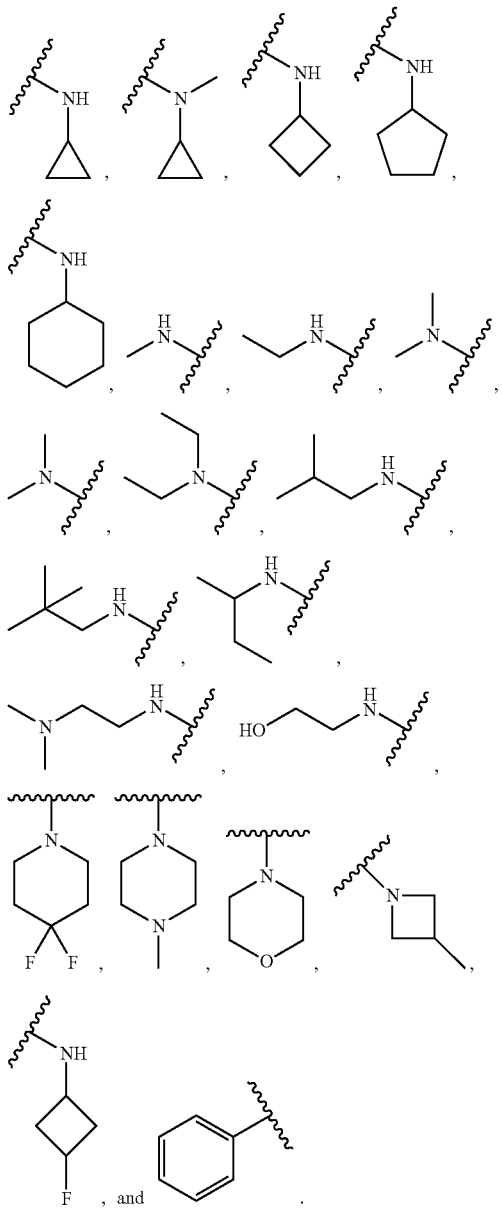

7. The compound of any one of paragraphs 1-6, wherein the compound is of Formula (III):

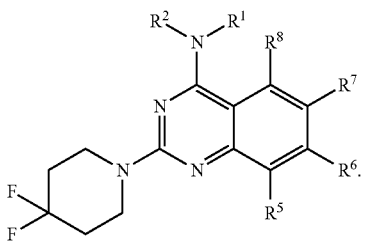

FORMULA (III)

8. The compound of any one of paragraphs 1-7, wherein $R^6$ is H or an optionally substituted alkoxy.
9. The compound of any one of paragraphs 1-8, wherein $R^6$ is H or —$OR^9$, where $R^9$ is alkyl, cyclyl, heterocyclyl, aryl or heteroaryl, each of which can be optionally substituted.
10. The compound of any one of paragraphs 1-9, wherein $R^6$ is H or —$OR^9$, where $R^9$ is optionally substituted $C_1$-$C_6$alkyl.
11. The compound of any one of paragraphs 1-10, wherein $R^6$ is H or —$OR^9$, where $R^9$ is methyl, ethyl, propyl, isopropyl, 1-mthylpropy, 2-methylpropyl, butyl, t-butyl, pentyl or hexyl.
12. The compound of any one of paragraphs 1-11, wherein $R^6$ is H or —$OR^9$, where $R^9$ is methyl.
13. The compound of any one of paragraphs 1-12, wherein $R^7$ is H or an optionally substituted alkoxy.
14. The compound of any one of paragraphs 1-13, wherein $R^7$ is H or —$OR^{10}$, where $R^{10}$ is alkyl, cyclyl, hetrocyclyl, aryl or heteroaryl, each of which can be optionally substituted.
15. The compound of any one of paragraphs 1-14, wherein $R^7$ is H or —$OR^{10}$, where $R^{10}$ is optionally substituted $C_1$-$C_6$alkyl.
16. The compound of any one of paragraphs 1-15, wherein $R^7$ is H or —$OR^{10}$, where $R^{10}$ is methyl, ethyl, propyl, isopropyl, 1-mthylpropy, 2-methylpropyl, butyl, t-butyl, pentyl or hexyl.
17. The compound of any one of paragraphs 1-16, wherein $R^7$ is H or —$OR^{10}$, where $R^9$ is methyl.
18. The compound of any one of paragraphs 1-17, wherein $R^6$ and $R^7$ are H or —$OCH_3$.
19. The compound of any one of paragraphs 1-18, wherein $R^5$ is hydrogen, alkyl, halogen, nitro, cyano, hydroxyl, alkoxy, carboxy, amino, alkylamino or dialkylamino.
20. The compound of any one of paragraphs 1-19, wherein $R^5$ is hydrogen, alkyl, halogen, nitro, cyano, hydroxyl, carboxy or amino.
21. The compound of any one of paragraphs 1-20, wherein $R^5$ is hydrogen.
22. The compound of any one of paragraphs 1-21, wherein $R^8$ is hydrogen, alkyl, halogen, nitro, cyano, hydroxyl, alkoxy, carboxy, amino, alkylamino or dialkylamino.
23. The compound of any one of paragraphs 1-22, wherein $R^8$ is hydrogen, alkyl, halogen, nitro, cyano, hydroxyl, carboxy or amino.
24. The compound of any one of paragraphs 1-23, wherein $R^8$ is hydrogen.
25. The compound of any one of paragraphs 1-24, wherein $R^5$ and $R^8$ are hydrogen.
26. The compound of any one paragraphs 1-26, wherein $R^5$ and $R^8$ are hydrogen, and $R^6$ and $R^7$ are H or —$OCH_3$.
27. A pharmaceutical composition comprising a compound of any one of paragraphs 1-26 and a pharmaceutically acceptable carrier or excipient.

28. A method of treating cancer, the method comprising administering a therapeutically effective dose of a composition of any of paragraphs 1-26 to a subject in need of treatment for cancer.

29. The method of any of the preceding paragraphs, wherein the method further comprises a first step of measuring the level of activity and/or expression of a marker in one or more cell types relative to a reference level and the administering step is performed if the level is increased.

30. The method of claim 29, wherein the one or more marker is a marker of cancer.

31. The method of any of the preceding paragraphs, wherein the cancer marker is a DNA, RNA, or microRNA encoded by one or more of a cancer gene, an oncogene, and a tumor suppressor gene.

32. The method of any of the preceding paragraphs, wherein the marker is a protein or polypeptide encoded by one or more of a cancer gene, an oncogene and/or a tumor suppressor gene.

33. The method of any of the preceding paragraphs, wherein the subject is determined to have an increased level of activity and/or expression of an oncogene in one or more cell types relative to a reference level occurring in a cell selected from the group consisting of: a squamous cell, basal cell and/or melanocyte.

34. The method of any of the preceding paragraphs, wherein the oncogene is selected from the group consisting of: NRAS; BRAF; KIT; MAPK1/2; ERBB4; GRIN2A; GRM3; RAC1; PREX2; IDH1; PPP6C; and CDK4.

35. A method of treating melanoma comprising:
  isolating one or more cells selected from the group consisting of a squamous cell, basal cell and/or melanocyte from a subject in need thereof;
  measuring the expression of one or more cancer genes, oncogenes and/or tumor suppressor genes products in the one or more cells;
  administering a therapeutically effective dose of an inhibitor of immune checkpoint polypeptides to the subject if the expression of one or more cancer genes, oncogenes and/or tumor suppressor gene is not altered or decreased in one or more cells as compared to a reference level; and/or
  administering a therapeutically effective dose of a composition of any of paragraphs 1-26 to the subject if the expression of one or more cancer genes, oncogenes and/or tumor suppressor gene products is elevated in one or more cells as compared to a reference level.

36. The method of claim 35, wherein the expression product is a nucleic acid.

37. The method of any of the preceding paragraphs, wherein the level of the expression product is determined using a method selected from the group selected from the group consisting of:
RT-PCR; quantitative RT PCR; Northern Blot; microarray-based expression analysis; next generation sequencing; and RNA in situ hybridization.

38. The method of any of the preceding paragraphs, wherein the level of the expression product is a polypeptide.

39. The method of any of the preceding paragraphs, wherein the level of the expression product is determined using a method selected from the group selected from the group consisting of:
Western blot; immunoprecipitation; enzyme linked immunosorbent assay (ELISA); radioimmunological assay (RIA); sandwich assay; fluorescence in situ hybridization (FISH); immunohistological staining; radioimmunometric assay; immunofluorescence assay; mass spectrometry; FACS; and immunoelectrophoresis assay.

40. The method of any of the preceding paragraphs, further comprising measuring the level of an expression product of at least one marker gene selected from Table 1.

41. The method of any of the preceding paragraphs, wherein the marker gene is selected from the group consisting of: NRAS; BRAF; KIT; MAPK1/2; ERBB4; GRIN2A; GRM3; RAC1; PREX2; IDH1; PPP6C; and CDK4.

42. The method of any of the preceding paragraphs, wherein the immune checkpoint polypeptide is selected from CTLA4A; CTLA4; Ki-67; CD-28; PD-1; TIM-3; and LAG-3.

43. The method of any of the preceding paragraphs, wherein the inhibitor of immune checkpoint polypeptides is selected from pembrolizumab and nivolumab.

EXAMPLES

Example 1: Pharmacological Targeting of STK19 Inhibits Oncogenic NRAS Driven Melanomagenesis Activating mutations in NRAS account for 20-30% of melanoma, but despite decades of research and in contrast to BRAF, no effective anti-NRAS therapies have been forthcoming. Here the inventors identify a previously uncharacterized serine/threonine kinase STK19 as a novel NRAS activator. STK19 phosphorylates NRAS to enhance its binding to its downstream effectors and promotes oncogenic NRAS-mediated melanocyte malignant transformation. A recurrent D89N substitution in STK19 whose alterations were identified in 25% of human melanomas represents a gain-of-function mutation that interacts better with NRAS to enhance melanocyte transformation. STK19D89N knockin leads to skin hyperpigmentation and promotes NRASQ61R-driven melanomagenesis in vivo. Finally, the inventors developed ZT-12-037-01 (IV) as a specific STK19-targeted inhibitor and showed that it effectively blocks oncogenic NRAS-driven melanocyte malignant transformation and melanoma growth in vitro and in vivo. Together, our findings provide a new and viable therapeutic strategy for melanomas harboring NRAS mutations.

RAS proteins are small membrane-bound guanine nucleotide-binding GTPases, acting as molecular switches by converting between GDP-bound inactive state and GTP-bound active state (Bos, 1989; Downward, 2003; Milburn et al., 1990; Pylayeva-Gupta et al., 2011). They play a central role in the regulation of cell proliferation, differentiation and survival by activating different downstream signaling pathways including RAF-MEK-ERK and PI3K-AKT pathways (Downward, 2003; Lavoie and Therrien, 2015; Mendoza et al., 2011; Samatar and Poulikakos, 2014). The RAS family has three major isoforms, KRAS, HRAS and NRAS (Barbacid, 1987; Malumbres and Barbacid, 2003) that share 92-98% sequence identity in the amino-terminal 1-165 residues but substantially diverge in the carboxy-terminal 23-24 residues of hypervariable region (HVR) (Krengel et al., 1990; Prior et al., 2012). Oncogenic mutations of RAS family members are commonly found in 20% to 30% of all human tumors (Prior et al., 2012; Stephen et al., 2014). Despite the highly conserved sequence similarity, the three major RAS isoforms exhibit distinct preferences in coupling to particular cancer types (Pylayeva-Gupta et al., 2011; Stephen et al., 2014). For instance, oncogenic mutations of KRAS are most identified in pancreatic ductal adenocarcinomas (PDAC) and colorectal adenocarcinomas (CRC) (Cox et al., 2014), HRAS mutations are frequently associated with bladder cancer (Cox et al., 2014; Prior et al., 2012), whereas NRAS mutations occur most frequently in cutaneous melanomas and acute myeloid leukemia (Bacher et al., 2006; Goel et al., 2006; Prior et al., 2012).

The prevailing NRAS mutation in melanoma occurs at position 61, where glutamine is substituted by arginine/lysine/leucine (Q61R/K/L) (Bos, 1989; Hayward et al., 2017; Jakob et al., 2012). This mutation impairs the intrinsic GTP hydrolysis activity and traps NRAS in a constitutive GTP-bound active conformation, which recruits RAF to the inner membrane for dimerization and activation (Marais et al., 1995; Smith et al., 2013). The most frequent mutation of BRAF (approximately 90%) is the substitution of valine to glutamate at position 600 (Davies et al., 2002). The BRAFV600E mutation increases its kinase activity more than 10.7-fold and stimulates constitutive activation of the downstream MEK-ERK signaling (Davies et al., 2002; Wan et al., 2004; Wellbrock et al., 2004). The oncogenic activation of NRAS and BRAF leads to growth factor-independent proliferation of melanocytes and finally transformation to melanoma (Davies et al., 2002; Ji et al., 2012). Thus, NRAS Q61 mutations and BRAFV600E mutation are key drivers of melanomagenesis and important therapeutic targets. Unlike the well-defined BRAF inhibitors, the development of direct NRAS-selective inhibitors has been unsuccessful in the past decades (Cox et al., 2014).

Oncogenic activity of RAS depends on its localization at the inner face of the plasma membrane and its subsequent association with major effectors for downstream signal transduction, which are modulated by RAS posttranslational modifications including prenylation, palmitoylation and phosphorylation (Ahearn et al., 2011; Barcelo et al., 2013; Berndt et al., 2011; Chiu et al., 2002; Jackson et al., 1990). Prenylation at the CAAX box cysteine and addition of a palmitic moiety to a second cysteine residue in the C-terminal hypervariable region (HVR) result in hydrophobic anchors to localize RAS to the plasma membrane (Buss and Sefton, 1986; Casey et al., 1989; Wright and Philips, 2006). RAS phosphorylation at different sites also distinctly regulates RAS activity. Phosphorylation at tyrosine 32 by SRC promotes the intrinsic GTPase activity of RAS to downregulate RAS signaling pathway (Bunda et al., 2014), whereas phosphorylation at tyrosine 137 by ABL allosterically enhances the binding of RAS to RAF (Ting et al., 2015). Phosphorylation at serine 181 of oncogenic KRAS is required for tumor growth and apoptosis inhibition (Barcelo et al., 2014). Therefore, targeting the regulators of RAS modification may provide a novel perspective to develop anti-RAS therapies for cancer treatment.

The human STK19 gene (also named as G11 or RP1) localizes in the class III region of the major histocompatibility complex (MHC) (Sargent et al., 1994). STK19 protein consists of 368 amino acids and two major functional domains: the regulatory domain (1-110 aa) and the catalytic kinase domain (111-368 aa) (Gomez-Escobar et al., 1998). STK19 was originally reported to phosphorylate α-casein at serine/threonine residues and histones at serine residues (Gomez-Escobar et al., 1998). Recently, it has been reported to involve in transcription-related DNA damage response (Boeing et al., 2016). However, the role of STK19 in cancer initiation and development is poorly appreciated. Importantly, STK19 harbors significant somatic hot spot mutations in 5% of melanoma (Hodis et al., 2012) and 10% of skin basal cell carcinoma (Bonilla et al., 2016) respectively, and is listed among the top melanoma driver genes (Lawrence et al., 2014). This strong genetic evidence implies an important, but uncharacterised role of STK19 in melanocyte malignant transformation and melanoma progression.

In this study, the inventors set out to use melanoma as a model to identify novel strategies for targeting oncogenic RAS signaling by identifying kinases that regulate NRAS activity and leading to the discovery of STK19. The inventors demonstrated that STK19 phosphorylates NRAS at serine 89, and consequently enhanced binding between NRAS and its effectors and activated NRAS downstream signaling pathways to induce melanocyte malignant transformation. The inventors also showed that the frequent D89N substitution detected in melanoma patients represents a gain-of-function mutation in STK19 that in knock-in mice causes skin hyperpigmentation and promotes oncogenic NRAS-driven melanomagenesis. By developing a specific and novel STK19-targeted inhibitor, ZT-12-037-01 (IV), the inventors were able to effectively blockade oncogenic NRAS-driven melanocyte malignant transformation and melanoma growth. The results described herein reveal how targeting STK19 may provide an effective therapeutic strategy for NRAS mutant melanomas.

STK19 is a critical regulator of NRAS function

Figures 1A, 1B, 1C, 1D, 1E, 1F, 1G, 1H:
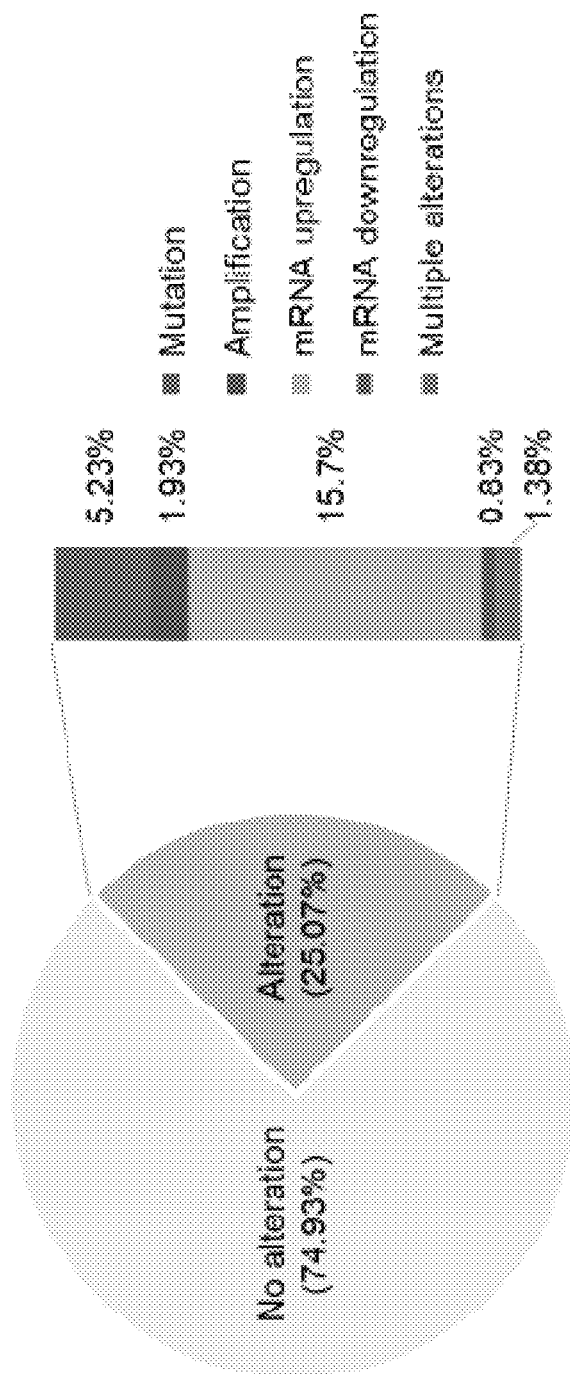
FIGS. 1A-1H show that STK19 is a critical regulator of NRAS function.

Activation of NRAS signaling depends on its association with effector proteins, such as RAF and PI3K, that contain a common RAS-binding domain (RBD) (Pylayeva-Gupta et al., 2011). Disrupting the NRAS-RBD protein interaction would represent an effective therapy in NRAS mutant melanoma. To achieve this objective, the inventors screened for kinases that could regulate the activity of NRASQ61R, the most prevalent NRAS mutation found in melanoma (Jakob et al., 2012). The inventors therefore established HEK293FT cells expressing HA-tagged NRASQ61R and screened a primary human kinome siRNA library using a modified active NRAS chemiluminescence assay as a readout. Specifically, HA-NRASQ61R from siRNA-transfected cells was captured using a GST-CRAF-RBD fusion protein on glutathione-coated plates, and detected with an anti-HA tag antibody conjugated with horseradish peroxidase for luminescence quantification (FIG. 1A). The inventors initially identified 12 kinases whose knockdown led to more than 50% inhibition of NRASQ61R activity, and six kinases whose knockdown led to at least two-fold upregulation of NRASQ61R activity (FIG. 1B). Among these genes, EGFR, SYK and SRC are well-known regulators of NRAS functions (Bunda et al., 2014; Downward, 2003; Kawakami et al., 2003). However, of all the hits, STK19 was one of the candidates whose knockdown caused the highest inhibition on NRAS activity (35.1% of control group) (FIG. 1B). To identify the status of STK19 in human melanomas, the inventors investigated STK19 alteration in the TCGA melanoma cohort (PanCancer Atlas) and found STK19 to be altered in 91 of 363 (25.07%) sequenced skin cutaneous melanoma cases (FIG. 1C). This is consistent with the analysis of large-scale melanoma exome data that discovered STK19 as one of six novel melanoma genes (PPP6C, RAC1, SNX31, TACC1, STK19, and ARID2) with a statistically significant functional mutation burden (Hodis et al., 2012). As such, STK19 has been listed as an oncogenic candidate among the Broad Institute melanoma driver genes (Lawrence et al., 2014). Analysis of STK19 alteration in melanomas collected in different cBioPortal for Cancer Genomics databases further confirmed this discovery (Berger et al., 2012; Hodis et al., 2012; Hugo et al., 2016). However, the function of STK19 is largely uncharacterized, particularly in melanoma initiation and progression. The inventors found that STK19 alteration was significantly mutually exclusive with BRAF in human melanomas (P=0.002) (FIG. 7A), consistent with BRAF lying downstream from NRAS activation (Lavoie and Therrien, 2015). Given these observations, the inventors further investigated the potential role of STK19 in regulating NRAS functions in melanomas.

Oncogenic NRAS plays a critical role in melanoma cell growth, which is mediated by its downstream signaling pathways including RAF-MEK-ERK and PI3K-AKT pathways (Ji et al., 2012). To confirm whether STK19 knockdown inhibits NRAS activity, the inventors investigated whether the downstream signaling of NRAS was inhibited after STK19 silencing. Retroviruses encoding empty HA, HA-tagged wild-type NRAS or NRASQ61R were introduced into human primary melanocytes (HPMs) depleted of STK19. The active-RAS pull-down assay indicated that depletion of STK19 markedly decreased the active fraction of both wild type and oncogenic NRAS, and that consequently signaling downstream from NRAS via the RAF-MEK-ERK and PI3K-AKT pathways was diminished (FIG. 1D). The inventors also used melanoma cells with different NRAS mutation status to identify the role of STK19 in regulating endogenous NRAS. To this end, STK19 was silenced in A375 and UACC62 cells, both with BRAFV600E and wild-type NRAS, or SK-MEL-2 and WM2032 cells that both express NRASQ61R and wild-type BRAF (Barretina et al., 2012; Herlyn et al., 1985). Interestingly, inhibition of active NRAS and its downstream effectors (p-MEK, p-ERK1/2, p-AKT) was highly efficient in SK-MEL-2 and WM2032 (NRASQ61R, BRAFWT) cells, but the inhibition was much weaker in A375 and UACC62 (BRAFV600E, NRASWT) cells (FIG. 7B). Consistently, depletion of STK19 significantly decreased the growth rate of SK-MEL-2 and WM2032 (NRASQ61R, BRAFWT) cells, but had a much smaller effect on the BRAFV600E, NRASWT cells or primary melanocytes (FIG. 7C). To confirm that inhibition of NRAS signaling was mediated by STK19 knockdown, two new sets of STK19-targeted shRNA were exploited and the resulting depletion of STK19 notably inhibited NRAS activity and its downstream signaling in SK-MEL-2 and WM2032 cells (FIGS. 7D and 7E). Furthermore, the inventors performed rescue experiments and infected the STK19-depleted melanoma cells with retroviruses encoding empty Flag or Flag-tagged STK19. The ectopic expression of STK19-Flag restored the activation of NRAS signaling (FIG. 7F), confirming that the inhibition of NRAS signaling using STK19-specific shRNAs was mediated by knockdown of STK19 rather than the off-target effects. Collectively, these results suggest that STK19 has a crucial role in activating oncogenic NRASQ61R-driven signaling.

To explore the potential role of STK19 in NRASQ61R-driven tumorigenesis, the role of STK19 in melanocyte proliferation and malignant transformation was evaluated using genetically engineered human immortalized melanocytes (hTERT/p53DD/CDK4(R24C)) (Lissanu Deribe et al., 2016) expressing NRASQ61R together with STK19 silencing. The results indicated that silencing STK19 (FIG. 7G) substantially inhibited the colony formation capacity of NRASQ61R-transformed melanocytes (FIG. 1E), as well as their proliferation (FIG. 7H) and tumor-forming ability in xenografts (FIGS. 1F-1H). These results suggest that STK19 is critical for NRASQ61R-driven melanomagenesis.

STK19 phosphorylates NRAS protein at serine 89

To identify the direct substrates of STK19, cell lysates collected from SK-MEL-2 cells expressing human recombinant Flag-tagged STK19 protein were purified using anti-Flag beads and the interaction factors analyzed by liquid chromatography/tandem mass spectrometry (LC-MS/MS) to identify STK19-interacting proteins (FIG. 8A). NRAS was identified as one of the most abundant STK19-interacting proteins on the basis of total number of unique peptides (13) (FIG. 2A). Reciprocal co-immunoprecipitation confirmed that endogenous STK19 strongly interacted with NRAS in SK-MEL-2 and WM2032 cells (NRASQ61R), but bound less well in A375 and UACC62 cells (expressing wild type NRAS) (FIGS. 8B and 8C). The NRASQ61R-STK19 interaction was confirmed by reciprocal co-immuno-precipitation from HPMs exogenously expressing STK19-Flag and HA-NRAS WT or Q61R mutant (FIGS. 2B and 2C). These results indicate that STK19 directly interacts with NRAS, and especially with NRASQ61R.

To address the significance of the STK19-NRASQ61R interaction, the inventors asked whether NRAS was an STK19 substrate. Phosphorylated-serine, -threonine and -tyrosine in NRAS were detected in cellular lysates collected from HPMs expressing ectopic STK19 and NRAS (WT or Q61R) after NRAS immunoprecipitation (FIG. 2D). Strikingly, serine, but not threonine or tyrosine phosphorylation of NRASQ61R mutant was substantially increased by STK19 expression, and only a marginal increase in phosphorylation of NRASWT was detected. The inventors also observed robust endogenous NRAS phosphorylation in a panel of melanoma cells expressing NRASQ61R (FIG. 8D) whereas phosphorylation of NRAS at serine residues was barely detectable in cells following STK19 silencing (FIGS. 8E and 8F). The upregulation of phosphorylated serine levels in NRAS was also diminished by overexpression of a kinase-dead STK19 K317P mutant (Gomez-Escobar et al., 1998) (FIGS. 8G and 8H). These results suggest that STK19 phosphorylates NRAS at serine residues.

The preferential phosphorylation of NRASQ61R compared to NRASWT was also observed using an in vitro kinase assay (FIG. 8I), suggesting that STK19 has a stronger preference towards GTP-loaded active NRAS. To verify this, the inventors further performed an in vitro kinase assay using purified NRAS recombinant protein preloaded with GDP, GTP or GTPγS in the presence of recombinant STK19. The inventors found a higher STK19-induced phosphorylation of the GTP- and GTPγS-loaded NRAS than GDP-loaded NRAS (FIG. 8J). This was confirmed in experiments that showed STK19-induced phosphorylation of different NRAS mutant isoforms was more efficient than that of NRASWT (FIG. 8K).

To identify the specific NRAS serine residue(s) phosphorylated by STK19, the inventors performed mass spectrometry after in vitro phosphorylation of recombinant NRASQ61R by purified recombinant STK19 protein. This approach identified phosphorylation of the evolutionarily conserved NRAS serine 89 (S89) (FIGS. 2E and 2F). In agreement with this observation, mutation of S89 to alanine (S89A) abolished phosphorylation of NRASWT and NRASQ61R (FIG. 2G).

To confirm that STK19 upregulates NRAS activity through phosphorylating NRAS protein at S89, HA-NRASWT, HA-NRASS89A, HA-NRASQ61R or HA-NRASQ61R/S89A were expressed in HPMs expressing ectopic STK19-Flag. After immunoprecipitation of NRAS WT or mutants, immunoblots were performed to detect interactions between NRAS and its effectors, including BRAF, CRAF and PI3Kα. The inventors found that STK19 overexpression dramatically enhanced the interaction between NRASQ61R and its effectors, and also stimulated signaling downstream of NRAS as detected by immunoblotting whole cell extracts (FIG. 2H). No effects of STK19 were observed on a phosphorylation-defective form of NRAS (NRASS89A) or its signaling. By contrast, the introduction of phosphomimetic NRASQ61R/S89D enhanced NRAS interaction with its effectors and its downstream signaling (FIG. 8L). These data strongly suggest that STK19-regulated NRASQ61R activity is largely dependent on the phosphorylation at NRAS S89. Using HPMs expressing NRASWT, NRASQ61R and NRASQ61R/S89A mutants alone or together with STK19 (FIG. 8M) revealed that STK19-stimulated NRAS-driven melanocyte proliferation and malignant transformation were inhibited by the NRAS S89A mutation in assays for colony formation (FIG. 2I), cell proliferation (FIG. 8N), and xenograft tumor assays (FIGS. 2J-2L). Moreover, mutation of S89 to phosphomimetic aspartate in the NRASQ61R mutant (FIG. 8O) strongly promoted melanocyte colony formation (FIG. 8P), proliferation (FIG. 8Q) and tumor formation (FIGS. 8R-8T). Taken together, our data indicate that STK19-mediated phosphorylation of NRAS at S89 activates oncogenic NRAS-driven melanomagenesis.

STK19 D89N is a recurrent gain-of-function mutation

Figures 3A, 3B, 3C, 3D, 3E, 3F, 3G:
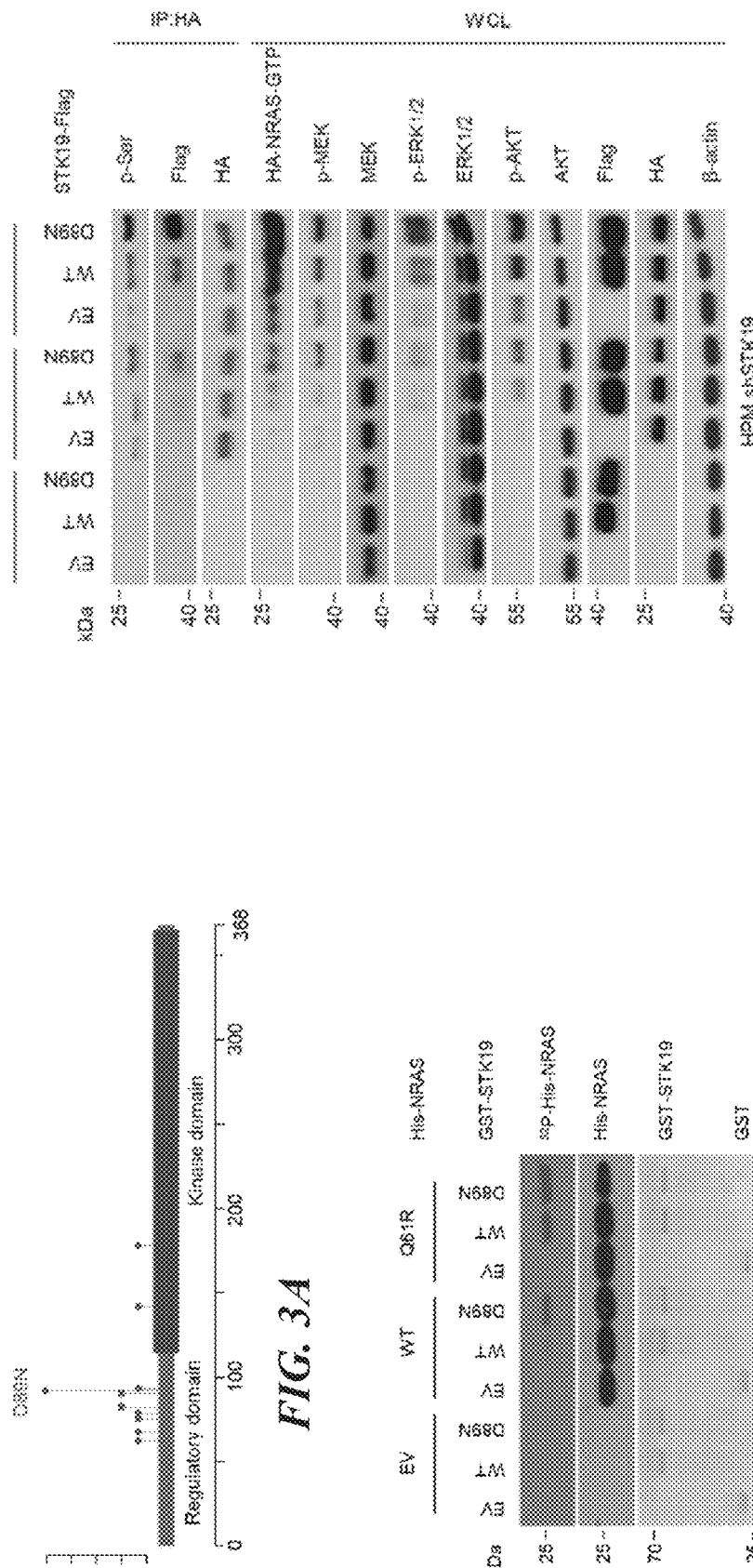
FIGS. 3A-3G show that STK19 D89N is a recurrent gain-of-function mutation.
Figures 9A, 9B, 9C, 9D, 9E:
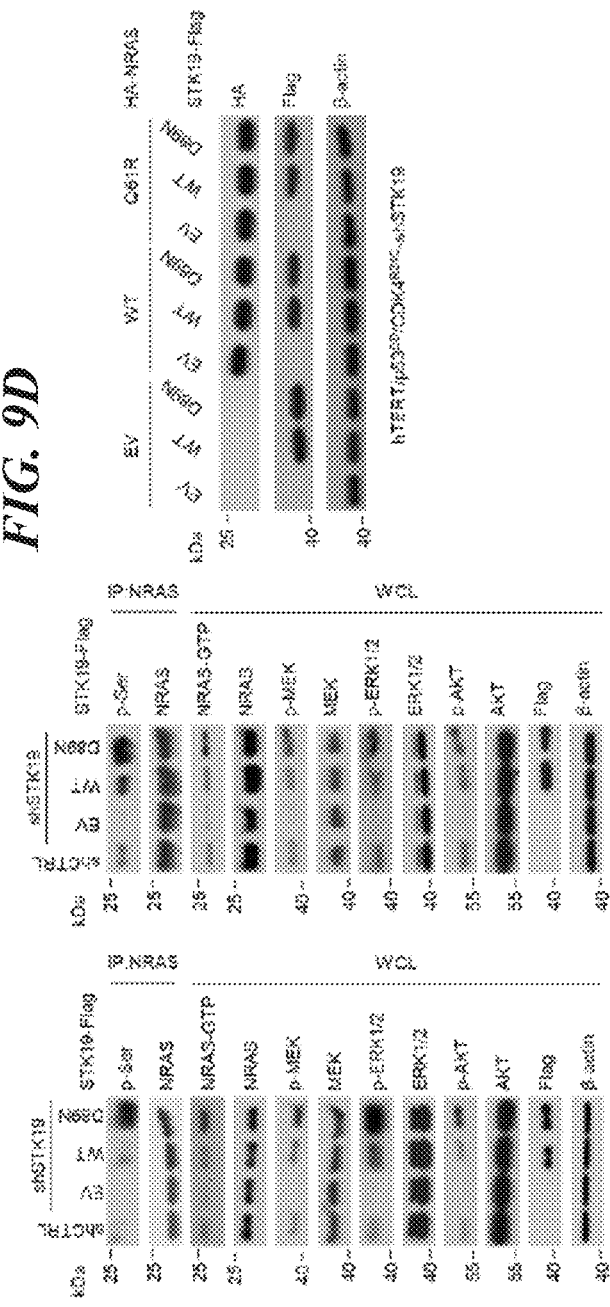
FIGS. 9A-9E show that STK19 D89N is a recurrent gain-of-function mutation, related to FIGS. 3A-3G.

STK19 has a statistically significant mutation burden in melanoma, and a total of 19 mutations were identified in the TCGA melanoma database as of December of 2017. Strikingly, 8 of them (~42%) were the same mutation (D89N), and most of the other mutations were adjacent to this region (FIG. 3A), suggesting STK19 D89 is a dominant mutant site in melanoma. These findings are consistent with Hodis et al's exon sequence discovery that STK19 is an important cancer gene with a hot spot mutation pattern in melanoma (Hodis et al., 2012). The inventors have shown that STK19 phosphorylates NRAS to activate its downstream signaling (FIGS. 1 and 2). However, it remained unclear how the STK19D89N might affect NRAS protein modification and activation. The inventors therefore performed an in vitro kinase assay to compare the activity of STK19WT and STK19D89N mutant. The inventors found that phosphorylation of purified recombinant NRAS was enhanced by STK19D89N to a higher extent than by STK19WT (FIG. 3B). Accordingly, compared to STK19WT, the STK19D89N mutant co-immunoprecipitated more efficiently with NRAS, enhanced NRAS phosphorylation and activated higher NRAS downstream signaling (FIGS. 3C, 9A and 9B), and also promoted proliferation of SK-MEL-2 and WM2032 melanoma cells (FIG. 9C). These data suggest that the recurrent STK19D89N mutation represents a gain-of-function mutation that operates by enhancing NRAS signaling.

To identify the role for STK19D89N in driving melanocyte malignant transformation, STK19D89N was expressed in human immortalized primary melanocytes (hTERT/p53DD/CDK4(R24C)) expressing wild type or mutant NRAS with endogenous STK19 silenced (FIG. 9D) and the resulting cells assayed for colony formation, proliferation and tumor formation. The results revealed that in the presence of oncogenic NRASQ61R, STK19D89N significantly promoted melanocyte colony formation (FIG. 3D), proliferation (FIG. 9E) and tumor formation (FIGS. 3E-3G). Collectively these data indicate that STK19D89N, a gain-of-function mutation, contributes to melanomagenesis in the presence of activated NRAS.

STK19 D89N induces melanomagenesis in the presence of oncogenic NRAS in vivo.

Figures 10A, 10B, 10C, 10D, 10E:
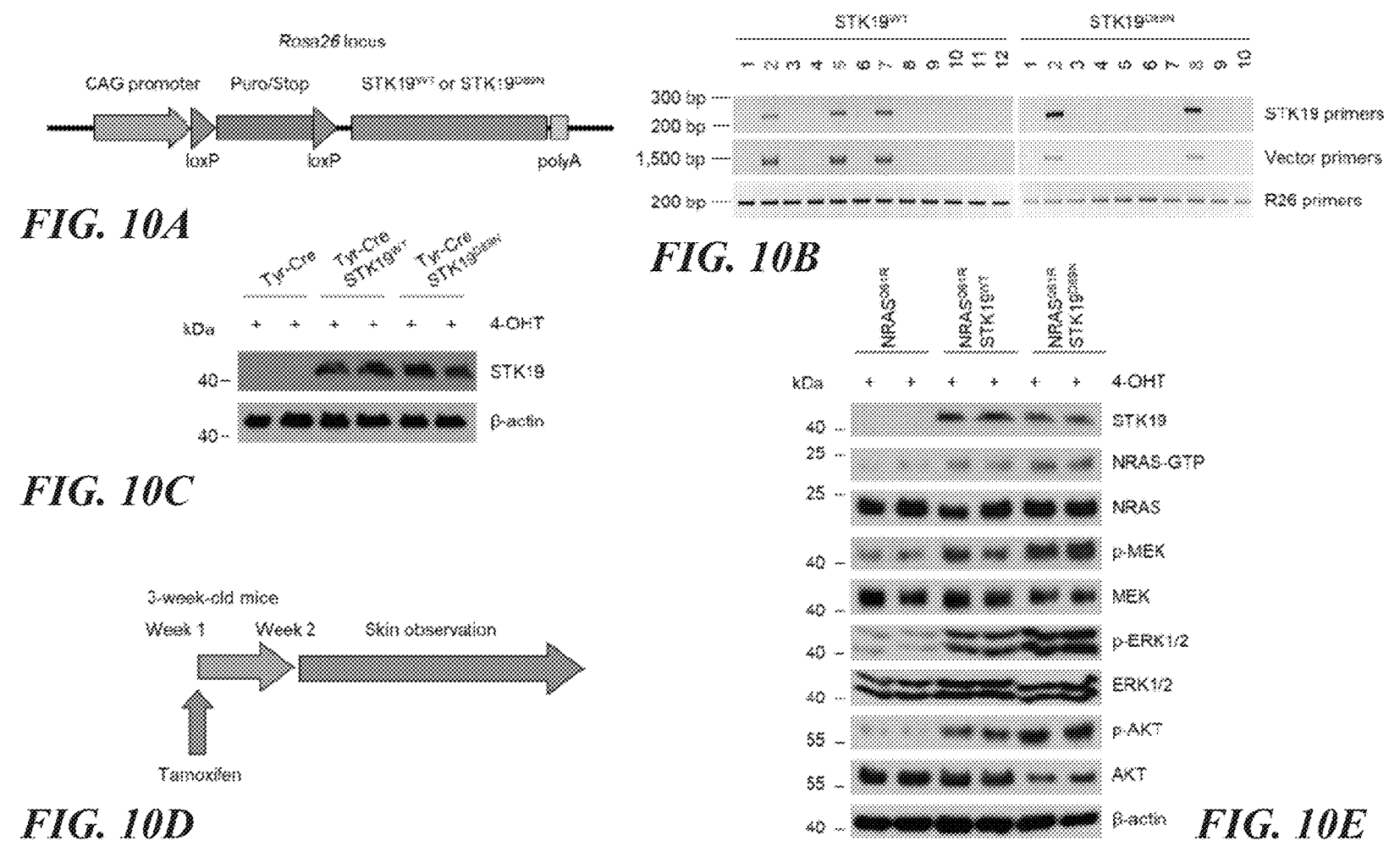

To better understand the role of STK19 in melanocytes and melanomagenesis in vivo, the inventors generated STK19WT or STK19D89N CRISPR-knockin mice. cDNA encoding human STK19WT or STK19D89N was subcloned into a CRISPR/Cas9-mediated homologous recombination vector targeting the ROSA26 locus and injected into single-cell embryos of C57BL/6J mice (Chu et al., 2016). The exogenous transcription of the knockin alleles was controlled by using the CAG hybrid promoter. To spatiotemporally control knockin gene expression, a loxP-flanked transcriptional stop element was placed downstream of the CAG promoter (FIG. 10A). The ROSA26 locus targeting of STK19WT and STK19D89N allele was confirmed by PCR (FIG. 10B). Both STK19WT and STK19D89N knockin mice develop normally. The knockin mice with correct insertion were further intercrossed with the Tyr-CreERT2 mouse strain expressing Cre recombinase directed by the melanocyte-specific tyrosinase promoter/enhancer to achieve Tyr-Cre-STK19WT and Tyr-Cre-STK19D89N mice and the expression of STK19WT and STK19D89N protein was confirmed by immunoblotting (FIG. 10C). Remarkably, the Tyr-Cre-STK19D89N mice, but not the STK19WT mice, exhibited hyperpigmentation of the skin, ears and tail, and the melanin content in skin was significantly increased after tamoxifen induction (FIGS. 4A-4E), similar to the hyperpigmentation observed when oncogenic NRAS is targeted to the melanocyte lineage (Ackermann et al., 2005; Burd et al., 2014b).

To determine whether the overexpression of STK19WT and STK19D89N contributes to melanomagenesis in the presence of oncogenic NRASQ61R, Tyr-Cre-STK19WT or -STK19D89N mice were crossed with loxP/STOP/loxP NRASQ61R knockin (LSL-NRASQ61R) mice (Ackermann et al., 2005; Burd et al., 2014a) to generate Tyr-Cre-NRASQ61R-STK19WT or Tyr-Cre-NRASQ61R-STK19D89N knockin mice. The effects of STK19WT or STK19D89N knockin in activating NRAS signaling pathways were detected and confirmed by immunoblot analysis of primary mouse melanocytes derived from the relevant engineered mice. The results obtained using antibodies to detect phosphorylated ERK1/2 and AKT indicated that STK19, and especially the STK19 D89N mutant, enhanced oncogenic NRAS signaling (FIG. 4F). By observing melanoma incidence and other skin abnormalities after tamoxifen induction for one year (FIG. 10D), the inventors found that exogenous expression of STK19WT and STK19D89N accelerated initiation and incidence of melanoma in NRASQ61R knockin mice (FIG. 4G). Specifically, melanoma was first diagnosed 295, 211 and 166 days after the tamoxifen injection in Tyr-Cre-NRASQ61R, Tyr-Cre-NRASQ61R-STK19WT and Tyr-Cre-NRASQ61R-STK19D89N knockin mice, respectively. Significantly, melanoma was diagnosed in 78.9% of Tyr-Cre-NRASQ61R-STK19D89N knockin mice and 47.4% of Tyr-Cre-NRASQ61R-STK19WT mice (P=0.0269) compared to 11.1% of Tyr-Cre-NRASQ61R mice (P<0.001 and P=0.0116, respectively). Thus, the STK19D89N mutation increased melanoma incidence 7-fold on the NRASQ61R background versus NRASQ61R alone. The melanoma tissues from Tyr-Cre-NRASQ61R, Tyr-Cre-NRASQ61R-STK19WT, and Tyr-Cre-NRASQ61R-STK19D89N mice were also collected for immunoblot analysis to investigate activities of NRAS signaling. The results revealed that STK19WT and especially STK19D89N strongly enhanced signaling downstream from NRAS (FIG. 10E). These results confirm that STK19, and particularly the STK19D89N mutant, promotes oncogenic NRAS-driven melanomagenesis in vivo.

Development of ZT-012-037-1 (IV) as a specific small molecule STK19 inhibitor

Figures 11A, 11B, 11C, 11D, 11E, 11F, 11G, 11H, 11I, 11J:
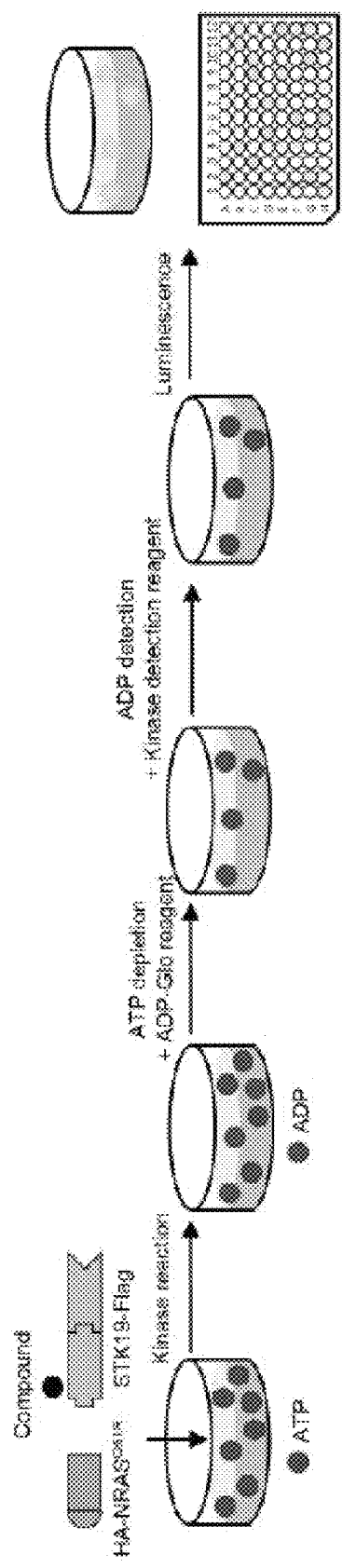
FIGS. 11A-11J shows the development of ZT-012-037-1 (IV) as a specific small molecule STK19 inhibitor, related to FIGS. 5A-5G. Schematic representation of the in vitro STK19 kinase activity assay using HA-NRASQ61R as the substrate. The kinase assays were performed using gradient concentrations of STK19-Flag for the indicated reaction time with 100 µM ATP concentration to establish the optimal STK19 concentration (12.5 nM) and reaction time (15 min). Data are means±SD (n=3). Gradient concentrations of ATP (0.5 µM to 200 µM) were incubated with 12.5 nM STK19-Flag for 15 min for the STK19 kinase activity assay. ATP Km (app) was calculated by fitting the data with Michaelis-Menten equation. Data are means±SD (n=3). IC50 of MP-IN-317 and ZT-012-037-1 (IV) for inhibition of G9a enzyme activity with in vitro methyltransferase assay. Data are means±SD relative to control group (n=3). Relative inhibition of STK19 enzyme by ZT-012-037-1 (IV) and A-366 was calculated following in vitro kinase assay. Data are means±SD relative to control group (n=3). IC50 values for the inhibition of STK19 WT or mutants STK19 V134Y and L139F by IV. Data are means±SD relative to control groups (n=3). Phosphorylation of HA-NRasQ61R was detected by immunoblots in HPMs with knockdown of STK19 and overexpression of HA-NRasQ61R and indicated STK19 isoforms. IC50 values for the inhibition of STK19WT or STK19D89N by IV. Data are means±SD relative to control groups (n=3). Body weight measurements of C57BL/6J mice treated with 0 or 25 mg/kg IV (BID) for 15 days. Data are means±SEM relative to control groups (n=8). H&E staining of tissues in C57BL/6J mice treated with 0 or 25 mg/kg IV (BID) for 15 days. Scale bar, 250 m.
Figures 11A, 11B, 11C, 11D, 11E, 11F, 11G, 11H, 11I, 11J:
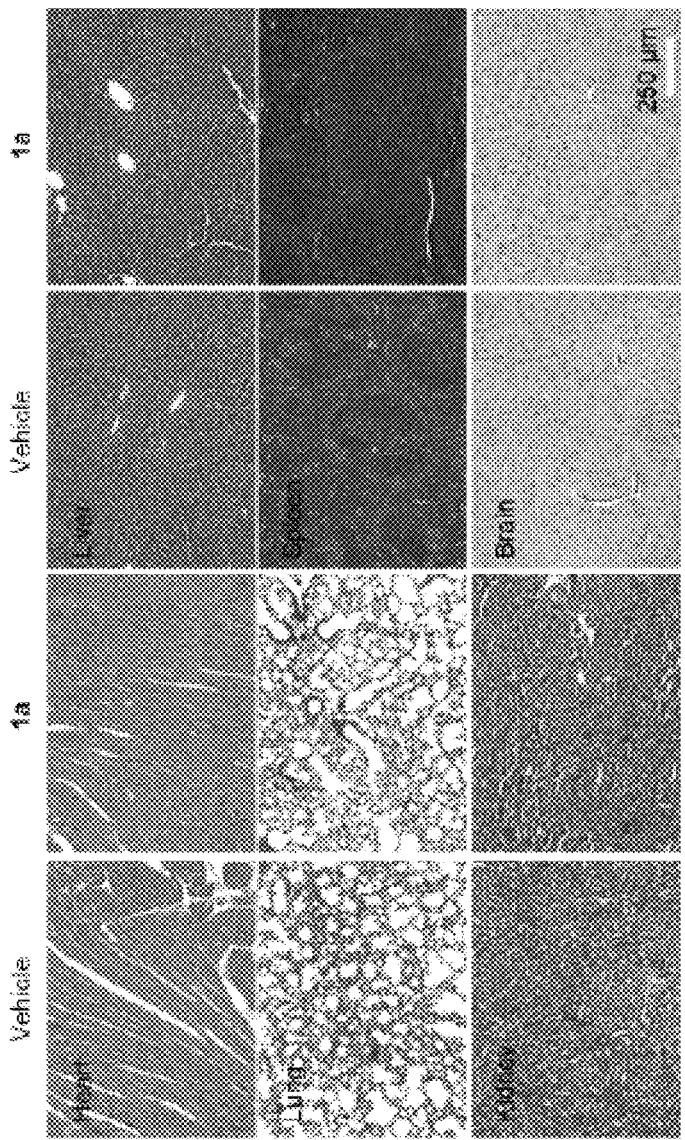

Given the pivotal role of NRAS signaling in melanomagenesis and the prominent role of STK19 in NRAS activation, targeting STK19 would represent a potential new therapeutic strategy in melanoma, especially in those with NRAS mutations. Therefore, to identify pharmacological inhibitors of STK19 kinase activity, the inventors screened an in-house library of small molecule compounds based on an optimized biochemical ADP generation assay using recombinant purified human STK19 and NRASQ61R proteins (FIG. 11A). The optimal kinase reaction conditions were chosen through multiple rounds of optimization and validation (FIGS. 11B and 11C). MP-IN-317, also known as UNC0642, a selective G9a and GLP histone lysine methyltransferase inhibitor (Liu et al., 2013), was initially identified as the best hit. The inventors then performed structure-activity relationship (SAR) studies to improve the selectivity and reduce off-target effects towards STK19. After iterative rounds of medicinal chemistry optimization, ZT-12-037-01 (IV) was obtained (FIG. 5A) with similar potent inhibitory activity against STK19 compared to MP-IN-317 with an IC50 of 24.04 nM and 30.45 nM respectively (FIG. 5B), but remarkably decreased inhibitory activity towards the G9a histone lysine methyltransferase with an IC50 of 467.4 nM and 7.01 nM (FIG. 11D). On the other hand, another G9a/GLP specific inhibitor A-366 with different chemical scaffold (Sweis et al., 2014), showed little inhibitory potential toward STK19 (FIG. 11E). Additionally, IV was determined to have extremely high kinase selectivity using KINOMEscan (Table 6), which profiled the inhibitor at a concentration of 1 µM against a panel of 468 diverse kinases using an in vitro ATP-site competition binding assay (Karaman et al., 2008). IV was therefore picked to be further validated for STK19-targeted inhibition and experimental therapy in melanoma.

ZT-12-037-01 (IV) treatment efficiently inhibited phosphorylation of NRAS in a dose- and time-dependent manner (FIGS. 5C and 5D). Furthermore, with increasing ATP concentrations, the IC50 of IV against STK19 accordingly increased (FIG. 5E), indicating that IV is an ATP-competitive inhibitor for STK19. IV also showed a high-affinity interaction with STK19 protein, as demonstrated by a shift of 6.8° C. in the melting temperature of STK19 (FIG. 5F). To develop inhibitor-resistant alleles of STK19 that compromise the inhibitor binding, the inventors performed a series of mutagenesis and biochemical studies based on the functional motifs and the hinge region (R131 to V150) within STK19. Introduction of single mutation of valine 134 to tyrosine (V134Y) or lysine 139 to phenylalanine (L139F) had minimal effects on STK19 kinase activity, but remarkably compromised the inhibitory potential of IV for STK19 (FIGS. 11F and 11G). These results demonstrate that IV is on-target to STK19. The inventors also found that IV has similar IC50 for STK19WT and STK19D89N (23.96 nM and 27.94 nM, respectively) (FIG. 11H). The consistent inhibitory effects of IV on STK19WT and STK19D89N-activated NRAS phosphorylation were also detected in HPMs (FIG. 5G). These data suggest that the inhibitory ability of IV on STK19 was not dependent on a region around D89 within STK19. Importantly, IV did not affect mouse weight (FIG. 11I), serum transaminase levels (Table 5) or histology of mouse tissues (FIG. 11J), suggesting that ZT-12-037-01 (IV) is a highly potent STK19 inhibitor with low in vivo toxicity.

Figures 6A, 6B, 6C, 6D, 6E, 6F, 6G, 6H, 6I:
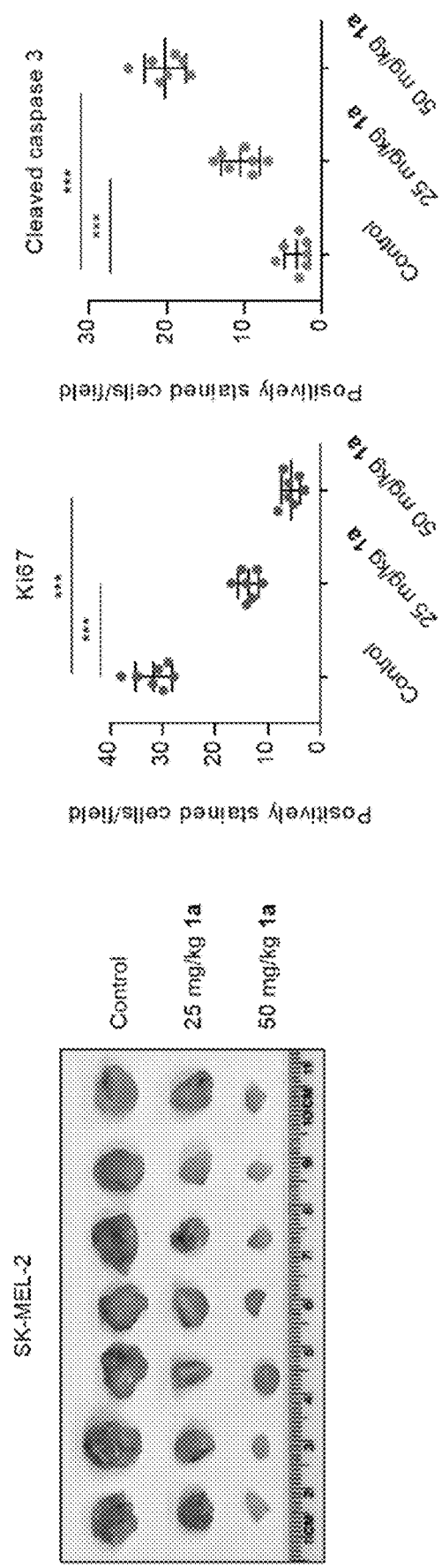
FIGS. 6A-6I show that ZT-012-037-1 (IV) inhibits oncogenic NRAS-driven melanoma development and growth.
Figures 6A, 6B, 6C, 6D, 6E, 6F, 6G, 6H, 6I:
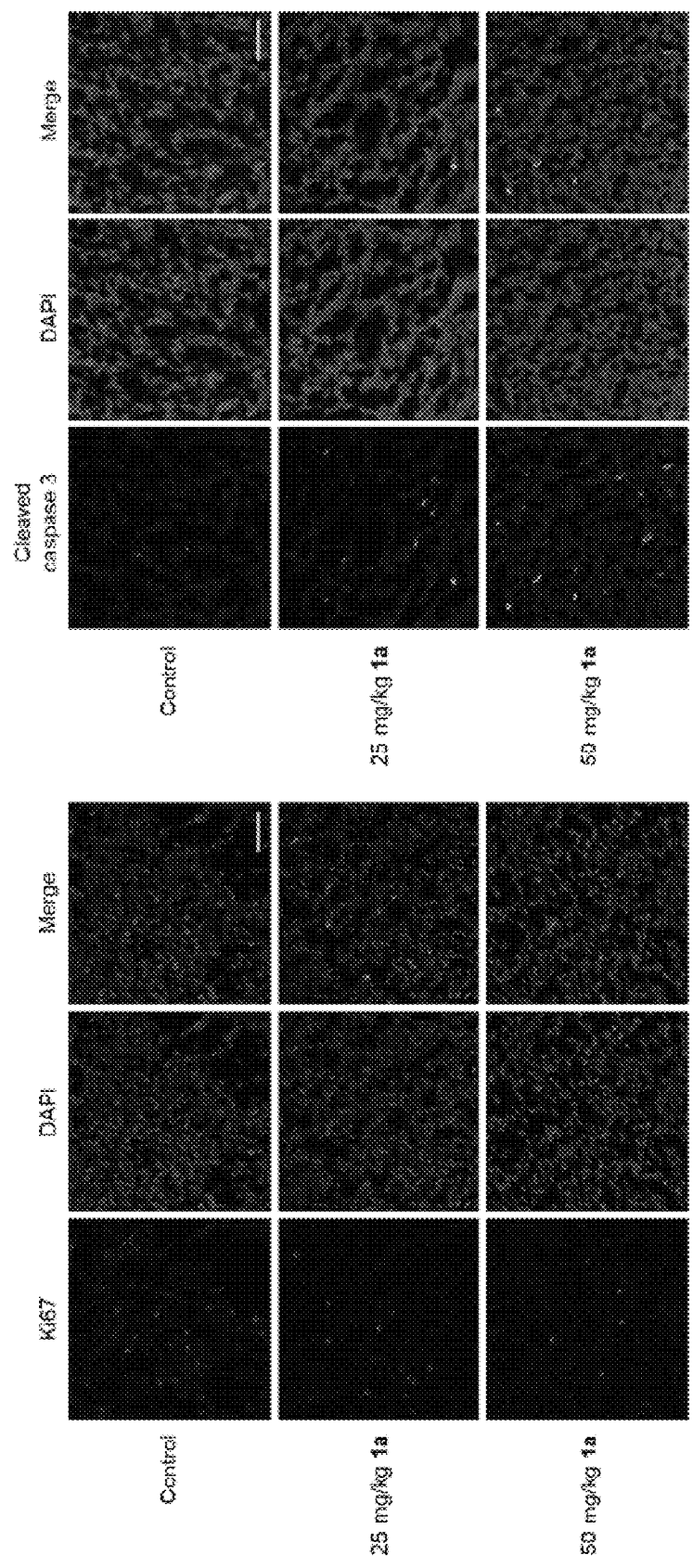
Figures 12A, 12B, 12C, 12D, 12E, 12F, 12G, 12H, 12I, 12J, 12K, 12L:
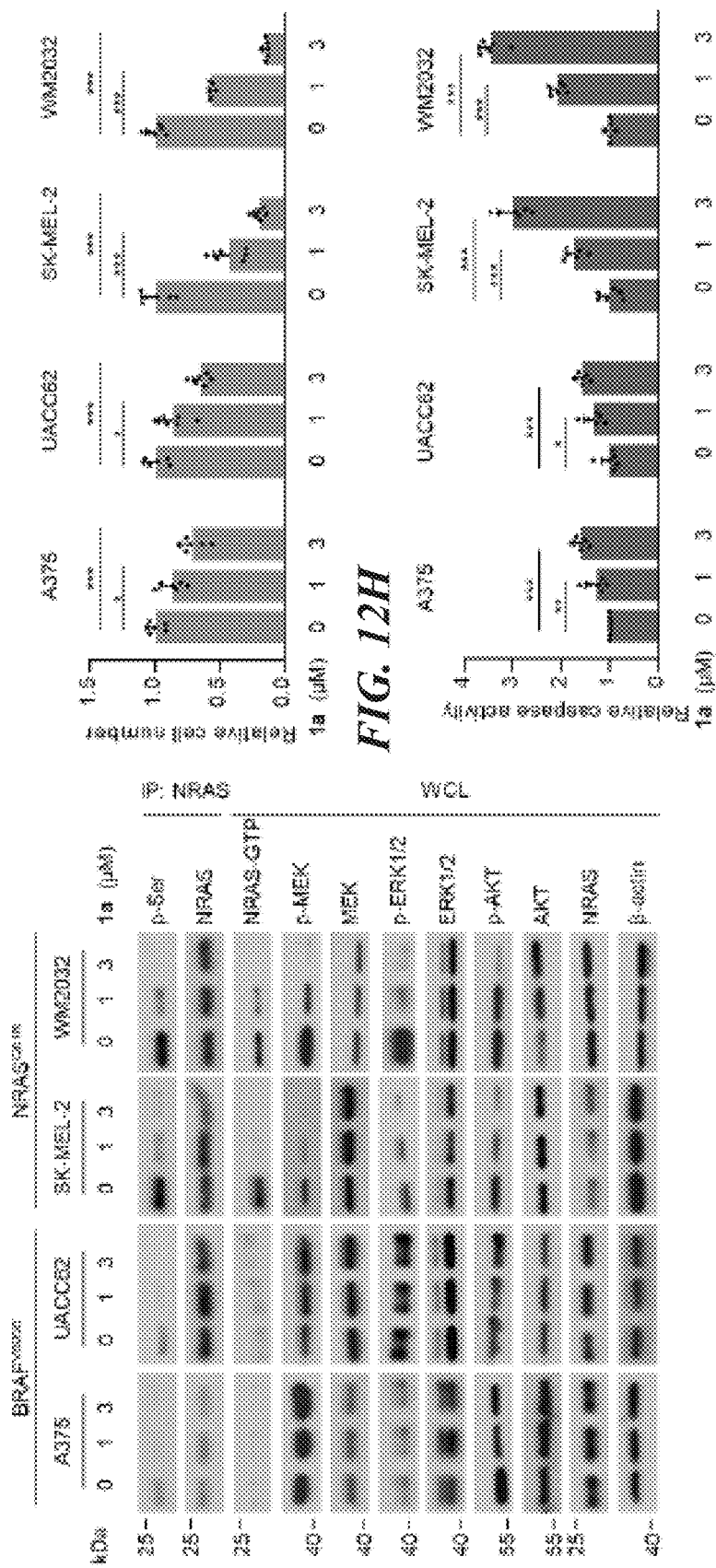

ZT-012-037-1 (IV) inhibits oncogenic NRAS-driven melanoma development and growth To determine whether ZT-12-037-01 (IV) represented a potential therapeutic option for NRAS mutant melanoma, genetically engineered NRASQ61R-expressing human immortal melanocytes (hTERT/p53DD/CDK4(R24C)) ectopically expressing STK19WT or STK19D89N (FIG. 12A) were treated with IV. The inventors found that IV treatment significantly inhibited mutant NRAS/STK19-driven melanocyte colony formation (FIG. 6A), proliferation (FIG. 12B) and tumor formation (FIGS. 6B-6D). IV treatment also inhibited growth of SK-MEL-2 xenograft melanoma (with NRASQ61R) in a dose-dependent manner (FIGS. 6E-6G). The inventors also performed immunofluorescence on SK-MEL-2 xenograft tumors to investigate the effects of IV on in vivo proliferation and apoptosis, represented by Ki67 and cleaved caspase-3 staining. The inventors observed that IV treatment effectively inhibited cell proliferation and induced apoptosis of SK-MEL-2 tumors (FIGS. 6H and 6I), confirming the in vivo efficacy of IV. The inventors then assessed the effects of IV on survival rate of SK-MEL-2 xenograft tumor-bearing mice and observed that IV significantly prolonged the survival of recipients compared with controls (FIG. 12C). Taken together these data indicate the potential therapeutic benefits of targeting STK19 with ZT-12-037-01 (IV) in melanomas with mutant NRAS.

Next, the inventors determined whether the treatment effects of IV are mediated by inhibiting NRAS signaling. Different doses of IV (0 µM, 1 µM, or 3 µM) were used to treat STK19-depleted HPMs ectopically expressing NRASQ61R that were infected with retroviruses encoding empty Flag, Flag-tagged STK19WT, or STK19D89N. The inventors found that IV effectively inhibited STK19WT- and STK19D89N-induced NRAS phosphorylation and activation of its downstream signaling (FIG. 12D). The inventors also collected SK-MEL-2 xenograft tumors with treatment of different doses of IV for immunoblot analysis to confirm that IV targeted STK19 to inhibit NRAS signaling but not G9a activity. Consistently, IV inhibited NRAS activity in a dose-dependent manner, but did not affect the levels of H3K9 methylation (FIG. 12E), a downstream marker of G9a activity (Shinkai and Tachibana, 2011).

In addition, the inventors investigated the growth inhibitory effects of IV in melanoma cells with different NRAS and BRAF status, including A375 and UACC62 (NRASWT, BRAFV600E), and SK-MEL-2 and WM2032 (NRASQ61R, BRAFWT). The inventors found that IV effectively inhibited NRAS signaling, including the MEK-ERK and PI3K pathways in SK-MEL-2 and WM2032 cells (with NRASQ61R), but the inhibition was much less effective in A375 or UACC62 cells (with NRASWT) (FIG. 12F). Consistently, IV effectively inhibited cell growth (FIG. 12G) and induced apoptosis (FIG. 12H) of SK-MEL-2 and WM2032 melanoma cells, but exhibited a reduced impact on A375 or UACC62 cells. These results indicate that pro-apoptotic effect of ZT-12-037-01 (IV) is dramatically enhanced in cells expressing oncogenic NRAS.

To confirm the specificity of the targeted inhibition of STK19 by IV, lower concentrations of IV (100 nM and 300 nM) were evaluated in SK-MEL-2 and WM2032 melanoma cells and the levels of H3K9 methylation and NRAS phosphorylation and activity were investigated by immunoblotting. The inventors found up to 300 nM, IV had no obvious effects on H3K9 methylation but still effectively decreased NRAS phosphorylation and activity (FIG. 12I). To further confirm the pharmacological effects of IV derive from STK19 inhibition and not G9a inhibition, the inventors investigated the role of G9a in NRAS signaling activation. G9a was silenced by G9a-specific shRNA or inhibited by a specific inhibitor, A-366, in SK-MEL-2 and WM2032 melanoma cells. The inventors observed the inhibition of G9a activity by knockdown (FIG. 12J) or treatment with A-366 (FIG. 12K) markedly repressed H3K9 methylation levels but not NRAS signaling, indicating that IV inhibited NRAS activity via targeting STK19 but not G9a. The inventors also found that IV-mediated inhibition of oncogenic NRAS signaling was rescued by introduction of IV-resistant STK19 V134Y or L139F, confirming the inhibition specificity of IV towards STK19 (FIG. 12L). In summary, ZT-12-037-01 (IV) is a specific STK19-targeted inhibitor to block oncogenic NRAS-driven melanocyte malignant transformation and melanoma growth.

DISCUSSION

The development of targeted cancer therapies is facilitated by understanding the functional consequences of genetic driver mutations that lead to overactive signaling pathways. The three RAS genes (KRAS, HRAS and NRAS) are frequently activated by mutation in about 25% of all cancers including melanomas, pancreatic ductal adenocarcinomas, colorectal adenocarcinomas and lung adenocarcinomas (Cox et al., 2014; Lee et al., 2011; Stephen et al., 2014). Activating mutations in RAS family members and components of the downstream MEK/ERK signaling pathway also account for development of a group of genetic syndromes known as RASopathies (Rauen, 2013). However, unlike the downstream effectors of RAS, such as BRAF and MEK whose targeted therapy has been extensively exploited through the successful development of several small molecule inhibitors (Chapman et al., 2011; Flaherty et al., 2010; Kefford et al., 2010; Larkin et al., 2014; Long et al., 2017a, b), little progress has been made towards targeting activation of RAS proteins.

For example, since the activation of oncogenic RAS depends on the protein's localization at the inner face of plasma membrane for effector binding, efforts have been made towards targeting the hydrophobic modifications of the C-terminal HVR domain necessary for RAS plasma membrane association (Ahearn et al., 2011; Barcelo et al., 2013; Berndt et al., 2011; Buss and Sefton, 1986; Casey et al., 1989; Wright and Philips, 2006). Moreover, the observation that RAS proteins are prenylated for plasma membrane localization and activation initially led to the development of farnesyltransferase inhibitors (FTIs) aimed at preventing RAS localization to the plasma membrane (Brunner et al., 2003). However, these attempts were unsuccessful in clinical trials because RAS proteins are also modified by geranylgeranyl isoprenoid to retain their membrane association (Karnoub and Weinberg, 2008). It has also recently been reported that a small molecule RAS-mimetic rigosertib and pan-RAS ligands block RAS binding to effector proteins, bringing new possibilities for anti-RAS therapy (Athuluri-Divakar et al., 2016; Welsch et al., 2017). In addition to these strategies, others have also considered targeting kinases/phosphatases that regulate RAS activity. Phosphorylation of NRAS at Y32 by the kinase SRC, which was recognized as a proto-oncogene protein to activate RAS and MEK/ERK signaling, was reported to inhibit RAS activity through GTP hydrolysis and dissociation of RAF binding (Bunda et al., 2014). Consequently, inhibition of SHP2 which mediates RAS dephosphorylation can suppress tumor growth in multiple cancers (Bunda et al., 2015; Mainardi et al., 2018; Wong et al., 2018).

In this study, rather than targeting RAS directly the inventors identified and characterized the poorly studied serine/threonine kinase STK19 as a novel activator of NRAS. Our observations suggest that for activated NRAS to signal effectively and exert its oncogenic effects on melanocytes it needs to be phosphorylated on the S89 by STK19. Phosphorylation at S89 then promotes NRAS interaction with its downstream effector and accordingly STK19 activates NRAS signaling via the MEK/ERK and PI3K pathways. The identification of STK19 as a critical kinase upstream from NRAS indicated that STK19 would represent a therapeutic vulnerability in NRAS-driven melanomas. Consistent with this, the selective STK19 inhibitor ZT-12-037-01 (IV) developed here exhibits impressive inhibitory effects on STK19-induced NRAS phosphorylation and NRAS-driven melanoma progression in vitro and in vivo. Our results therefore offer a preclinical proof of concept for therapeutic targeting of the STK19 kinase in melanomas with NRAS mutations. Significantly, although the inventors have focused on NRAS, the inventors note that S89, the key residue in NRAS phosphorylated by STK19, is conserved in all the three RAS proteins. Since depletion or inhibition of STK19 limits the transforming potential of oncogenic NRAS in melanocytes and inhibits growth of NRAS mutant melanoma, our results indicate that targeting STK19 represent a promising therapeutic approach for anti-RAS therapies in general.

Many different genetic driver mutations have been identified in melanomagenesis, most notably those affecting BRAF, NRAS, INK4a, PTEN and p14ARF (Fargnoli et al., 2008; Kim et al., 2008; Landi et al., 2006; Scherer et al.; Tsao et al., 2012). Our knowledge of driver genes in melanoma has recently been augmented by large-scale massively parallel sequencing studies that have identified additional significantly mutated genes include NF1, ARID2, PPP6C, SNX31, TACC1, STK19, and RAC1 from the initial large-scale melanoma exome data (Hodis et al., 2012; Krauthammer et al., 2012), as well as MAP2K1, IDH1, RB1, and DDX3X in the Cancer Genome Atlas Skin Cutaneous Melanoma (SKCM-TCGA) exome sequencing dataset (Akbani et al., 2015). Here our cellular and genetic studies extended these observations to identify the STK19D89N mutant as a gain-of-function mutation in melanomas which accelerates oncogenic NRAS-driven melanomagenesis in vivo. The inventors also found that overexpression and mutations of STK19 were detected in about 25% of human melanomas and that higher STK19 expression conferred a substantially increased risk of mortality in patients with primary melanomas. However, no melanoma was observed in mice with an STK19D89N knockin alone. Our data therefore suggest that the STK19 mutant is not a typical driver, but is perhaps a helper mutation that facilitates melanoma development by activation of NRAS signaling. Notably, unlike those mutations activating NRAS (Q61R/L/K) or BRAF (V600E), the significant hotspot D89N in STK19 corresponds to cytosine to a thymidine (C>T transition) UVR signature mutation in melanoma (Brash, 2015). As such our results explain the association of NRAS mutation-associated melanoma with UVR if STK19 accelerates UVR-driven melanomagenesis in individuals with NRAS mutations.

Targeted therapies have significantly improved clinical outcomes in patients with various cancers such as BRAF inhibitors for metastatic melanoma and epidermal growth factor receptor (EGFR) inhibitors for EGFR mutant non-small cell lung cancer (NSCLC) (Chapman et al., 2011; Siegelin and Borczuk, 2014). However, the efficacy is almost always ultimately compromised by the acquisition of drug resistance, which frequently involves RAS mutations or reactivation of the MEK/ERK and PI3K pathways (Ercan et al., 2012; Hatzivassiliou et al., 2010). The ability to target RAS signaling using the STK19 inhibitor ZT-12-037-01 (IV) developed here can overcome or prevent drug-resistance in patients with RAS mutation cancers.

REFERENCES

Ackermann, J., Frutschi, M., Kaloulis, K., McKee, T., Trumpp, A., and Beermann, F. (2005). Metastasizing melanoma formation caused by expression of activated N-RasQ61K on an INK4a-deficient background. Cancer Res 65, 4005-4011.

Ahearn, I. M., Haigis, K., Bar-Sagi, D., and Philips, M. R. (2011). Regulating the regulator: post-translational modification of RAS. Nat Rev Mol Cell Biol 13, 39-51.

Akbani, R., Akdemir, K. C., Aksoy, B. A., Albert, M., Ally, A., Amin, S. B., Arachchi, H., Arora, A., Auman, J. T., Ayala, B., et al. (2015). Genomic Classification of Cutaneous Melanoma. Cell 161, 1681-1696.

Athuluri-Divakar, S. K., Vasquez-Del Carpio, R., Dutta, K., Baker, S. J., Cosenza, S. C., Basu, I., Gupta, Y. K., Reddy, M. V., Ueno, L., Hart, J. R., et al. (2016). A Small Molecule RAS-Mimetic Disrupts RAS Association with Effector Proteins to Block Signaling. Cell 165, 643-655.

Bacher, U., Haferlach, T., Schoch, C., Kern, W., and Schnittger, S. (2006). Implications of NRAS mutations in AML: a study of 2502 patients. Blood 107, 3847-3853.

Barbacid, M. (1987). ras genes. Annu Rev Biochem 56, 779-827.

Barcelo, C., Paco, N., Beckett, A. J., Alvarez-Moya, B., Garrido, E., Gelabert, M., Tebar, F., Jaumot, M., Prior, I., and Agell, N. (2013). Oncogenic K-ras segregates at spatially distinct plasma membrane signaling platforms according to its phosphorylation status. J Cell Sci 126, 4553-4559.

Barcelo, C., Paco, N., Morell, M., Alvarez-Moya, B., Bota-Rabassedas, N., Jaumot, M., Vilardell, F., Capella, G., and Agell, N. (2014). Phosphorylation at Ser-181 of Oncogenic KRAS Is Required for Tumor Growth. Cancer Research 74, 1190-1199.

Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anticancer drug sensitivity. Nature 483, 603-607.

Berger, M. F., Hodis, E., Heffernan, T. P., Deribe, Y. L., Lawrence, M. S., Protopopov, A., Ivanova, E., Watson, I. R., Nickerson, E., Ghosh, P., et al. (2012). Melanoma genome sequencing reveals frequent PREX2 mutations. Nature 485, 502-506.

Berndt, N., Hamilton, A. D., and Sebti, S. M. (2011). Targeting protein prenylation for cancer therapy. Nature Reviews Cancer 11, 775-791.

Boeing, S., Williamson, L., Encheva, V., Gori, I., Saunders, R. E., Instrell, R., Aygun, O., Rodriguez-Martinez, M., Weems, J. C., Kelly, G. P., et al. (2016). Multiomic Analysis of the UV-Induced DNA Damage Response. Cell Rep 15, 1597-1610.

Bonilla, X., Parmentier, L., King, B., Bezrukov, F., Kaya, G., Zoete, V., Seplyarskiy, V. B., Sharpe, H. J., McKee, T., Letourneau, A., et al. (2016). Genomic analysis identifies new drivers and progression pathways in skin basal cell carcinoma. Nat Genet 48, 398-406.

Bos, J. L. (1989). ras oncogenes in human cancer: a review. Cancer Res 49, 4682-4689.

Brash, D. E. (2015). U V signature mutations. Photochem Photobiol 91, 15-26.

Brunner, T. B., Hahn, S. M., Gupta, A. K., Muschel, R. J., McKenna, W. G., and Bernhard, E. J. (2003). Farnesyltransferase inhibitors: an overview of the results of preclinical and clinical investigations. Cancer Res 63, 5656-5668.

Bunda, S., Burrell, K., Heir, P., Zeng, L., Alamsahebpour, A., Kano, Y., Raught, B., Zhang, Z. Y., Zadeh, G., and Ohh, M. (2015). Inhibition of SHP2-mediated dephosphorylation of Ras suppresses oncogenesis. Nat Commun 6, 8859. Bunda, S., Heir, P., Srikumar, T., Cook, J. D., Burrell, K., Kano, Y., Lee, J. E., Zadeh, G., Raught, B., and Ohh, M. (2014). Src promotes GTPase activity of Ras via tyrosine 32 phosphorylation. P Natl Acad Sci USA 111, E3785-E3794. Burd, C. E., Liu, W., Huynh, M. V., Waqas, M. A., Gillahan, J. E., Clark, K. S., Fu, K., Martin, B. L., Jeck, W. R., Souroullas, G. P., et al. (2014a). Mutation-Specific RAS Oncogenicity Explains NRAS Codon 61 Selection in Melanoma. Cancer Discov 4, 1418-1429.

Burd, C. E., Liu, W., Huynh, M. V., Waqas, M. A., Gillahan, J. E., Clark, K. S., Fu, K., Martin, B. L., Jeck, W. R., Souroullas, G. P., et al. (2014b). Mutation-specific RAS oncogenicity explains NRAS codon 61 selection in melanoma. Cancer Discov 4, 1418-1429.

Buss, J. E., and Sefton, B. M. (1986). Direct Identification of Palmitic Acid as the Lipid Attached to P21ras. Mol Cell Biol 6, 116-122.

Casey, P. J., Solski, P. A., Der, C. J., and Buss, J. E. (1989). P21ras Is Modified by a Farnesyl Isoprenoid. P Natl Acad Sci USA 86, 8323-8327.

Chapman, P. B., Hauschild, A., Robert, C., Haanen, J. B., Ascierto, P., Larkin, J., Dummer, R., Garbe, C., Testori, A., Maio, M., et al. (2011). Improved survival with vemurafenib in melanoma with BRAF V600E mutation. N Engl J Med 364, 2507-2516.

Chen, S., Zhu, B., Yin, C., Liu, W., Han, C., Chen, B., Liu, T., Li, X., Chen, X., Li, C., et al. (2017). Palmitoylation-dependent activation of MC1R prevents melanomagenesis. Nature 549, 399-403.

Chiu, V. K., Bivona, T., Hach, A., Sajous, J. B., Silletti, J., Wiener, H., Johnson, R. L., Cox, A. D., and Philips, M. R. (2002). Ras signalling on the endoplasmic reticulum and the Golgi. Nat Cell Biol 4, 343-350.

Chu, V., Weber, T., Graf, R., Sommermann, T., Petsch, K., Sack, U., Volchkov, P., Rajewsky, K., and Kuhn, R. (2016). Efficient generation of Rosa26 knock-in mice using CRISPR/Cas9 in C57BL/6 zygotes. Bmc Biotechnol 16.

Cox, A. D., Fesik, S. W., Kimmelman, A. C., Luo, J., and Der, C. J. (2014). Drugging the undruggable RAS: Mission possible? Nat Rev Drug Discov 13, 828-851.

Dankort, D., Curley, D. P., Cartlidge, R. A., Nelson, B., Karnezis, A. N., Damsky, W. E., You, M. J., DePinho, R. A., McMahon, M., and Bosenberg, M. (2009). Braf (V600E) cooperates with Pten loss to induce metastatic melanoma. Nature Genetics 41, 544-552.

Davies, H., Bignell, G. R., Cox, C., Stephens, P., Edkins, S., Clegg, S., Teague, J., Woffendin, H., Garnett, M. J., Bottomley, W., et al. (2002). Mutations of the BRAF gene in human cancer. Nature 417, 949-954.

Downward, J. (2003). Targeting RAS signalling pathways in cancer therapy. Nat Rev Cancer 3, 11-22.

Ercan, D., Xu, C., Yanagita, M., Monast, C. S., Pratilas, C. A., Montero, J., Butaney, M., Shimamura, T., Sholl, L., Ivanova, E. V., et al. (2012). Reactivation of ERK signaling causes resistance to EGFR kinase inhibitors. Cancer Discov 2, 934-947.

Fargnoli, M. C., Pike, K., Pfeiffer, R. M., Tsang, S., Rozenblum, E., Munroe, D. J., Golubeva, Y., Calista, D., Seidenari, S., Massi, D., et al. (2008). MC1R variants increase risk of melanomas harboring BRAF mutations. J Invest Dermatol 128, 2485-2490.

Flaherty, K. T., Puzanov, I., Kim, K. B., Ribas, A., McArthur, G. A., Sosman, J. A., O'Dwyer, P. J., Lee, R. J., Grippo, J. F., Nolop, K., et al. (2010). Inhibition of Mutated, Activated BRAF in Metastatic Melanoma. New Engl J Med 363, 809-819.

Garraway, L. A., Widlund, H. R., Rubin, M. A., Getz, G., Berger, A. J., Ramaswamy, S., Beroukhim, R., Milner, D. A., Granter, S. R., Du, J. Y., et al. (2005). Integrative genomic analyses identify MITF as a lineage survival oncogene amplified in malignant melanoma. Nature 436, 117-122.

Goel, V. K., Lazar, A. J., Warneke, C. L., Redston, M. S., and Haluska, F. G. (2006). Examination of mutations in BRAF, NRAS, and PTEN in primary cutaneous melanoma. J Invest Dermatol 126, 154-160.

Gomez-Escobar, N., Chou, C. F., Lin, W. W., Hsieh, S. L., and Campbell, R. D. (1998). The G11 gene located in the major histocompatibility complex encodes a novel nuclear serine/threonine protein kinase. J Biol Chem 273, 30954-30960.

Hatzivassiliou, G., Song, K., Yen, I., Brandhuber, B. J., Anderson, D. J., Alvarado, R., Ludlam, M. J., Stokoe, D., Gloor, S. L., Vigers, G., et al. (2010). RAF inhibitors prime wild-type RAF to activate the MAPK pathway and enhance growth. Nature 464, 431-435.

Hayward, N. K., Wilmott, J. S., Waddell, N., Johansson, P. A., Field, M. A., Nones, K., Patch, A. M., Kakavand, H., Alexandrov, L. B., Burke, H., et al. (2017). Whole-genome landscapes of major melanoma subtypes. Nature 545, 175-180.

Herlyn, M., Thurin, J., Balaban, G., Bennicelli, J. L., Herlyn, D., Elder, D. E., Bondi, E., Guerry, D., Nowell, P., Clark, W. H., et al. (1985). Characteristics of cultured human melanocytes isolated from different stages of tumor progression. Cancer Res 45, 5670-5676.

Hodis, E., Watson, I. R., Kryukov, G. V., Arold, S. T., Imielinski, M., Theurillat, J. P., Nickerson, E., Auclair, D., Li, L., Place, C., et al. (2012). A landscape of driver mutations in melanoma. Cell 150, 251-263.

Hugo, W., Zaretsky, J. M., Sun, L., Song, C., Moreno, B. H., Hu-Lieskovan, S., Berent-Maoz, B., Pang, J., Chmielowski, B., Cherry, G., et al. (2016). Genomic and Transcriptomic Features of Response to Anti-PD-1 Therapy in Metastatic Melanoma. Cell 165, 35-44.

Jackson, J. H., Cochrane, C. G., Bourne, J. R., Solski, P. A., Buss, J. E., and Der, C. J. (1990). Farnesol Modification of Kirsten-Ras Exon 4b-Protein Is Essential for Transformation. P Natl Acad Sci USA 87, 3042-3046.

Jakob, J. A., Bassett, R. L., Ng, C. S., Curry, J. L., Joseph, R. W., Alvarado, G. C., Rohlfs, M. L., Richard, J., Gershenwald, J. E., Kim, K. B., et al. (2012). NRAS mutation status is an independent prognostic factor in metastatic melanoma. Cancer-Am Cancer Soc 118, 4014-4023.

Ji, Z., Flaherty, K. T., and Tsao, H. (2012). Targeting the RAS pathway in melanoma. Trends Mol Med 18, 27-35.

Karaman, M. W., Herrgard, S., Treiber, D. K., Gallant, P., Atteridge, C. E., Campbell, B. T., Chan, K. W., Ciceri, P., Davis, M. I., Edeen, P. T., et al. (2008). A quantitative analysis of kinase inhibitor selectivity. Nat Biotechnol 26, 127-132.

Karnoub, A. E., and Weinberg, R. A. (2008). Ras oncogenes: split personalities. Nat Rev Mol Cell Biol 9, 517-531.

Kawakami, Y., Kitaura, J., Yao, L., McHenry, R. W., Kawakami, Y., Newton, A. C., Kang, S., Kato, R. M., Leitges, M., Rawlings, D. J., et al. (2003). A Ras activation pathway dependent on Syk phosphorylation of protein kinase C. Proc Natl Acad Sci USA 100, 9470-9475.

Kefford, R., Arkenau, H., Brown, M. P., Millward, M., Infante, J. R., Long, G. V., Ouellet, D., Curtis, M., Lebowitz, P. F., and Falchook, G. S. (2010). Phase I/II study of GSK2118436, a selective inhibitor of oncogenic mutant BRAF kinase, in patients with metastatic melanoma and other solid tumors. J Clin Oncol 28.

Kim, R. D., Curtin, J. A., and Bastian, B. C. (2008). Lack of somatic alterations of MC1R in primary melanoma. Pigment Cell Melanoma Res 21, 579-582.

Krauthammer, M., Kong, Y., Ha, B. H., Evans, P., Bacchiocchi, A., McCusker, J. P., Cheng, E., Davis, M. J., Goh, G., Choi, M., et al. (2012). Exome sequencing identifies recurrent somatic RAC1 mutations in melanoma. Nat Genet 44, 1006-1014.

Krengel, U., Schlichting, I., Scherer, A., Schumann, R., Frech, M., John, J., Kabsch, W., Pai, E. F., and Wittinghofer, A. (1990). 3-Dimensional Structures of H-Ras P21 Mutants-Molecular-Basis for Their Inability to Function as Signal Switch Molecules. Cell 62, 539-548.

Landi, M. T., Bauer, J., Pfeiffer, R. M., Elder, D. E., Hulley, B., Minghetti, P., Calista, D., Kanetsky, P. A., Pinkel, D., and Bastian, B. C. (2006). MC1R germline variants confer risk for BRAF-mutant melanoma. Science 313, 521-522.

Larkin, J., Ascierto, P. A., Dreno, B., Atkinson, V., Liszkay, G., Maio, M., Mandala, M., Demidov, L., Stroyakovskiy, D., Thomas, L., et al. (2014). Combined vemurafenib and cobimetinib in BRAF-mutated melanoma. N Engl J Med 371, 1867-1876.

Lavoie, H., and Therrien, M. (2015). Regulation of RAF protein kinases in ERK signalling. Nat Rev Mol Cell Biol 16, 281-298.

Lawrence, M. S., Stojanov, P., Mermel, C. H., Robinson, J. T., Garraway, L. A., Golub, T. R., Meyerson, M., Gabriel, S. B., Lander, E. S., and Getz, G. (2014). Discovery and saturation analysis of cancer genes across 21 tumour types. Nature 505, 495-501.

Lee, J. H., Choi, J. W., and Kim, Y. S. (2011). Frequencies of BRAF and NRAS mutations are different in histological types and sites of origin of cutaneous melanoma: a meta-analysis. Br J Dermatol 164, 776-784.

Lissanu Deribe, Y., Shi, Y., Rai, K., Nezi, L., Amin, S. B., Wu, C. C., Akdemir, K. C., Mahdavi, M., Peng, Q., Chang, Q. E., et al. (2016). Truncating PREX2 mutations activate its GEF activity and alter gene expression regulation in NRAS-mutant melanoma. Proc Natl Acad Sci USA 113, E1296-1305.

Liu, F., Barsyte-Lovejoy, D., Li, F. L., Xiong, Y., Korboukh, V., Huang, X. P., Allali-Hassani, A., Janzen, W. P., Roth, B. L., Frye, S. V., et al. (2013). Discovery of an in Vivo Chemical Probe of the Lysine Methyltransferases G9a and GLP. J Med Chem 56, 8931-8942.

Long, G. V., Hauschild, A., Santinami, M., Atkinson, V., Mandala, M., Chiarion-Sileni, V., Larkin, J., Nyakas, M., Dutriaux, C., Haydon, A., et al. (2017a). Adjuvant Dabrafenib plus Trametinib in Stage III BRAF-Mutated Melanoma. N Engl J Med.

Long, G. V., Hauschild, A., Santinami, M., Atkinson, V., Mandala, M., Chiarion-Sileni, V., Larkin, J., Nyakas, M., Dutriaux, C., Haydon, A., et al. (2017b). Adjuvant Dabrafenib plus Trametinib in Stage III BRAF-Mutated Melanoma. N Engl J Med 377, 1813-1823.

Mainardi, S., Mulero-Sanchez, A., Prahallad, A., Germano, G., Bosma, A., Krimpenfort, P., Lieftink, C., Steinberg, J. D., de Wit, N., Goncalves-Ribeiro, S., et al. (2018). SHP2 is required for growth of KRAS-mutant non-small-cell lung cancer in vivo. Nat Med.

Malumbres, M., and Barbacid, M. (2003). RAS oncogenes: the first 30 years. Nat Rev Cancer 3, 459-465.

Marais, R., Light, Y., Paterson, H. F., and Marshall, C. J. (1995). Ras recruits Raf-1 to the plasma membrane for activation by tyrosine phosphorylation. EMBO J 14, 3136-3145.

Mendoza, M. C., Er, E. E., and Blenis, J. (2011). The Ras-ERK and PI3K-mTOR pathways: cross-talk and compensation. Trends Biochem Sci 36, 320-328.

Milburn, M. V., Tong, L., Devos, A. M., Brunger, A., Yamaizumi, Z., Nishimura, S., and Kim, S. H. (1990). Molecular Switch for Signal Transduction—Structural Differences between Active and Inactive Forms of Protooncogenic Ras Proteins. Science 247, 939-945.

Prior, I. A., Lewis, P. D., and Mattos, C. (2012). A comprehensive survey of Ras mutations in cancer. Cancer Res 72, 2457-2467.

Pylayeva-Gupta, Y., Grabocka, E., and Bar-Sagi, D. (2011). RAS oncogenes: weaving a tumorigenic web. Nat Rev Cancer 11, 761-774.

Rauen, K. A. (2013). The RASopathies. Annu Rev Genomics Hum Genet 14, 355-369.

Samatar, A. A., and Poulikakos, P. I. (2014). Targeting RAS-ERK signalling in cancer: promises and challenges. Nat Rev Drug Discov 13, 928-942.

Sargent, C. A., Anderson, M. J., Hsieh, S. L., Kendall, E., Gomez-Escobar, N., and Campbell, R. D. (1994). Characterisation of the novel gene G11 lying adjacent to the complement C4A gene in the human major histocompatibility complex. Hum Mol Genet 3, 481-488.

Scherer, D., Rachakonda, P. S., Angelini, S., Mehnert, F., Sucker, A., Egberts, F., Hauschild, A., Hemminki, K., Schadendorf, D., and Kumar, R. Association between the germline MC1R variants and somatic BRAF/NRAS mutations in melanoma tumors. J Invest Dermatol 130, 2844-2848.

Shinkai, Y., and Tachibana, M. (2011). H3K9 methyltransferase G9a and the related molecule GLP. Genes Dev 25, 781-788.

Siegelin, M. D., and Borczuk, A. C. (2014). Epidermal growth factor receptor mutations in lung adenocarcinoma. Lab Invest 94, 129-137.

Smith, M. J., Neel, B. G., and Ikura, M. (2013). NMR-based functional profiling of RASopathies and oncogenic RAS mutations. Proc Natl Acad Sci USA 110, 4574-4579.

Stephen, A. G., Esposito, D., Bagni, R. K., and McCormick, F. (2014). Dragging ras back in the ring. Cancer Cell 25, 272-281.

Sweis, R. F., Pliushchev, M., Brown, P. J., Guo, J., Li, F., Maag, D., Petros, A. M., Soni, N. B., Tse, C., Vedadi, M., et al. (2014). Discovery and development of potent and selective inhibitors of histone methyltransferase g9a. ACS Med Chem Lett 5, 205-209.

Ting, P. Y., Johnson, C. W., Fang, C., Cao, X. Q., Graeber, T. G., Mattos, C., and Colicelli, J. (2015). Tyrosine phosphorylation of RAS by ABL allosterically enhances effector binding. Faseb J 29, 3750-3761.

Tsao, H., Chin, L., Garraway, L. A., and Fisher, D. E. (2012). Melanoma: from mutations to medicine. Genes Dev 26, 1131-1155.

Wan, P. T., Garnett, M. J., Roe, S. M., Lee, S., Niculescu-Duvaz, D., Good, V. M., Jones, C. M., Marshall, C. J., Springer, C. J., Barford, D., et al. (2004). Mechanism of activation of the RAF-ERK signaling pathway by oncogenic mutations of B-RAF. Cell 116, 855-867.

Wellbrock, C., Ogilvie, L., Hedley, D., Karasarides, M., Martin, J., Niculescu-Duvaz, D., Springer, C. J., and Marais, R. (2004). B-V599E-RAF is an oncogene in melanocytes. Cancer Research 64, 2338-2342.

Welsch, M. E., Kaplan, A., Chambers, J. M., Stokes, M. E., Bos, P. H., Zask, A., Zhang, Y., Sanchez-Martin, M., Badgley, M. A., Huang, C. S., et al. (2017). Multivalent Small-Molecule Pan-RAS Inhibitors. Cell 168, 878-889 e829.

Wong, G. S., Zhou, J., Liu, J. B., Wu, Z., Xu, X., Li, T., Xu, D., Schumacher, S. E., Puschhof, J., McFarland, J., et al. (2018). Targeting wild-type KRAS-amplified gastroesophageal cancer through combined MEK and SHP2 inhibition. Nat Med.

Wright, L. P., and Philips, M. R. (2006). Thematic review series: lipid posttranslational modifications. CAAX modification and membrane targeting of Ras. J Lipid Res 47, 883-891.

American Cancer Society®, Cancer Facts & FIGs., 2019; available on the world wide web at https://www.cancer.org/content/dam/cancer-org/research/cancer-facts-and-statistics/annual-cancer-facts-and-FIGs./2019/cancer-facts-and-FIGs.-2019.pdf Br J Dermatol. 2017 July; 177(1):134-140. doi: 10.1111/bjd.15510. Epub 2017 Jun. 12.

Purdie K J et al., Methods Mol Biol. 2011; 731:151-9. doi: 10.1007/978-1-61779-080-5_14.

WO 2008/141275

WO 2009/073513

U.S. Pat. No. 7,442,507

Godwin L S et al., Curr Protoc Cell Biol. 2014 Jun. 3; 63:1.8.1-20.

Example 2: General Synthetic Methods for the Synthesis of Compounds of at Least Formula I-V Synthetic scheme 1, the general synthetic route for compounds IV-XXXIX and XLVII-XLXI.

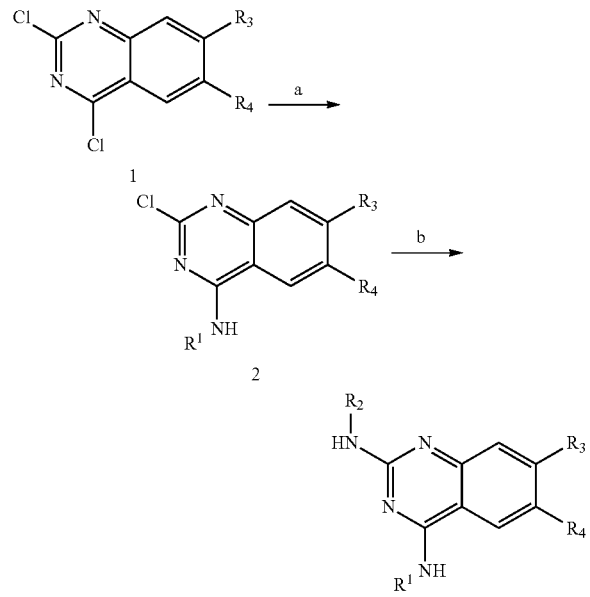

Reagents and Conditions:
a) R¹—NH₂, DMF, K₂CO₃, rt. 6 h; b) R²—NH₂, TFA, Microwave (MW), 110° C., 30 min

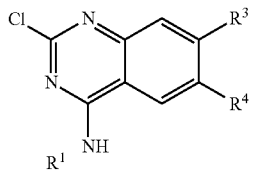

1

To a solution of compound 1 (1 mmol) in DMF (5 mL) were added K2CO₃ (207.03 mg, 1.5 mmol) and R¹—NH₂ (1.2 mmol). The resulting mixture was stirred at room temperature (rt) for 6 h, then the reaction was quenched with water and extracted with EtOAc (3×10 mL). The combined organic layer was washed with brine and dried over anhydrous Na₂SO₄, filtered, and concentrated under reduced pressure. The crude residue was purified by silica gel chromatography with the eluent of ammonia methanol solution and dichloromethane (MeOH (1.75 N NH₃)/CH₂Cl₂=1: 10, v/v] to yield the title compound 2 as white crystal.

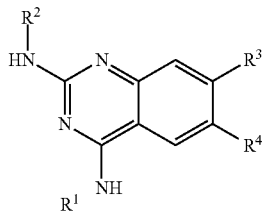

I-1 ~ I-36 and II-1 ~ II-3

The mixture of compound 2 (0.1 mmol) and R²—NH₂ (0.5 mmol) was added TFA (37.2 uL, 0.5 mmol) at rt, then the reaction was heated in a microwave reactor at 110° C. for 30 min. After the reaction was complete monitored by TLC, the resulting mixture was concentrated under reduced pressure. The crude product was purified by preparative HPLC with the eluent of MeOH and H₂O (containing 0.035% TFA) to yield the title compound IV-XXXIX and XLVII-XLXI.

Synthetic Scheme 2, the Synthetic Route for XL:

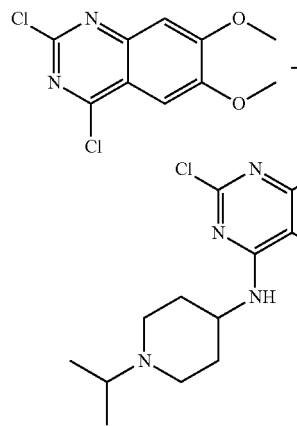

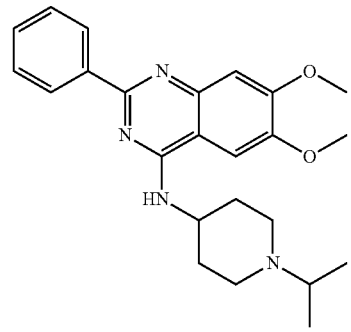

I-37

Reagents and Conditions:
a) R¹—NH₂, DMF, K2CO₃, rt. 6 h; c) K₂CO₃(aq), 60° C., Dioxane, 4 h, phenylboronic acid, PdCl₂(dppf).CH₂Cl₂

Compound 3 was synthesized using the same procedure of compound 2.

(Formula XL)

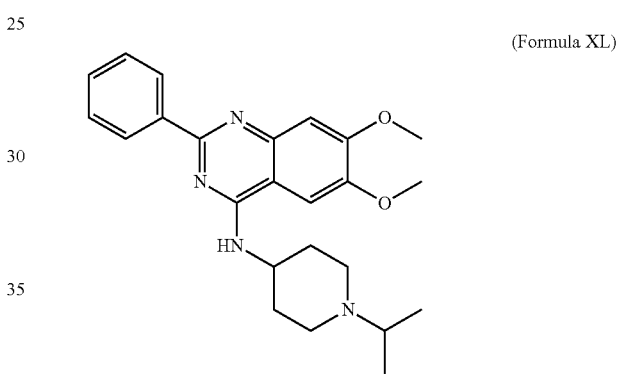

I-37

The mixture of compound 3 (0.15 mmol), phenylboronic acid (0.225 mmol), K₂CO₃ (0.45 mmol), and PdCl₂(dppf) .CH₂Cl₂ (20% m %) in mixed solvent of dioxane (1 mL) and H₂O (0.33 mL) was stirred at 60° C. under N₂ atmosphere for 4 h. After the reaction was complete monitored by LC-MS, the reaction was cooled and diluted with H₂O (10 mL). The aqueous layer was extracted with EtOAc (2×10 mL), and the combined organic layer was dried over anhydrous Na₂SO₄, filtered, and concentrated under reduced pressure. The crude product was purified by silica gel chromatography with the eluent of ammonia methanol solution and dichloromethane (MeOH (1.75 N NH₃)/CH₂Cl₂=1: 10, v/v] to yield the title compound XL as white crystal.

Synthetic Scheme 3, the Synthetic Route for XLI-XLV and L:

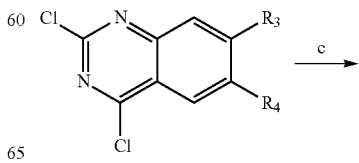

1

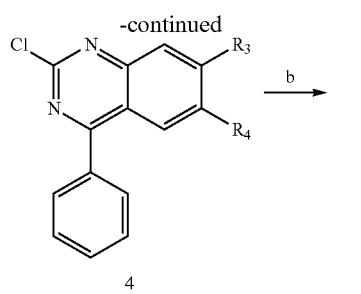

4

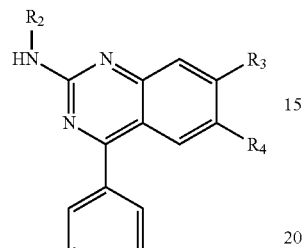

I-38 ~ I-42 and II-4

Reagents and Conditions:

c) $K_2CO_3$(aq), 60° C., Dioxane, 4 h, phenylboronic acid, $PdCl_2$(dppf).$CH_2Cl_2$; b) $R^2$—$NH_2$, TFA, MW, 110° C., 30 min. Compound 4 was synthesized using the same procedure of XL.

Compounds XLI-XLV and L were synthesized following the synthetic procedure of IV~XXXIX and XLVII~XLIX.

Synthetic Scheme 4, the Synthetic Route for XLVI and VIII:

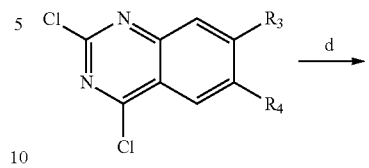

1

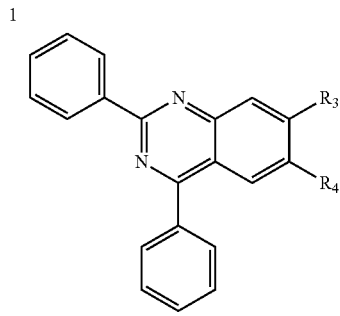

I-43 and II-5

Reagents and Conditions:

d) $K_2CO_3$(aq), 80° C., Dioxane, 6 h, phenylboronic acid, $PdCl_2$(dppf).$CH_2Cl_2$.

The synthesis of XLVI and VIII are the same as XL.

Table 3 lists the formula number of the compounds, their chemical structures, and the H NMR and MS data.

| Formula number | Chemical Structure | H NMR and MS |
|---|---|---|
| IV | TFA salt | $^1$H NMR (600 MHz, Chloroform-d) δ 8.89 (s, 1H), 7.71 (s, 1H), 7.28 (s, 1H), 6.85 (s, 1H), 4.49-4.32 (m, 1H), 3.97 (s, 3H), 3.93 (s, 3H), 3.40-3.28 (m, 2H), 3.29-3.17 (m, 1H), 2.85-2.74 (m, 1H), 2.78-2.64 (m, 2H), 2.35-2.27 (m, 2H), 2.28-2.14 (m, 2H), 1.31-1.23 (m, 6H), 0.81-0.70 (m, 2H), 0.72-0.61 (m, 2H). MS (ESI) m/z: 386[M + H]$^+$. |
| V | 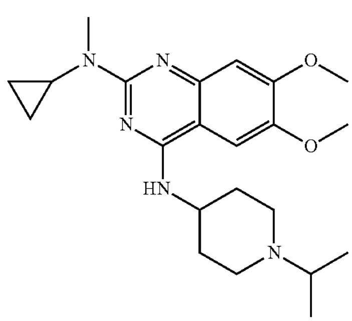 [SMILES: COc1cc2nc(N(C)C3CC3)nc(NC3CCN(C(C)C)CC3)c2cc1OC] | $^1$H NMR (600 MHz, Chloroform-d) δ 7.08 (s, 1H), 6.86 (s, 1H), 4.24-4.12 (m, 1H), 3.96 (s, 3H), 3.95 (s, 3H), 3.19 (s, 3H), 3.07-2.97 (m, 2H), 2.87 (p, J = 6.6 Hz, 1H), 2.82-2.75 (m, 1H), 2.46-2.31 (m, 2H), 2.30-2.15 (m, 2H), 1.81-1.68 (m, 2H), 1.12 (d, J = 6.6 Hz, 6H), 0.91-0.85 (m, 2H), 0.75-0.65 (m, 2H). MS (ESI) m/z: 400[M + H]$^+$. |

-continued

| Formula number | Chemical Structure | H NMR and MS |
|---|---|---|
| VI | 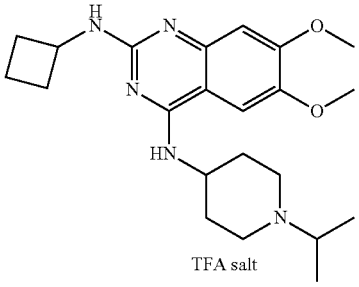 [SMILES: COc1cc2nc(NC3CCC3)nc(NC3CCN(C(C)C)CC3)c2cc1OC]<br>TFA salt | $^1$H NMR (600 MHz, DMSO-$d_6$) δ 9.75 (s, 1H), 8.95 (s, 1H), 7.77 (s, 1H), 6.87 (s, 1H), 4.55-4.37 (m, 1H), 4.39-4.30 (m, 1H), 3.90-3.88 (m, 3H), 3.87 (s, 1H), 3.85 (s, 3H), 3.58-3.45 (m, 2H), 3.25-2.98 (m, 2H), 2.41-2.30 (m, 2H), 2.31-2.20 (m, 2H), 2.13-1.99 (m, 2H), 2.01-1.89 (m, 2H), 1.86-1.64 (m, 2H), 1.30 (d, J = 6.6 Hz, 6H). MS (ESI) m/z: 400[M + H]$^+$. |
| VII | 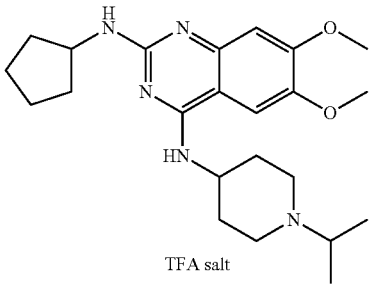 [SMILES: COc1cc2nc(NC3CCCC3)nc(NC3CCN(C(C)C)CC3)c2cc1OC]<br>TFA salt | $^1$H NMR (600 MHz, DMSO-$d_6$) δ 7.78 (s, 1H), 6.89 (s, 1H), 4.46-4.27 (m, 1H), 3.89 (s, 3H), 3.86 (s, 3H), 3.59-3.49 (m, 3H), 3.46-3.27 (m, 2H), 3.21-3.00 (m, 2H), 2.31-2.24 (m, 2H), 2.04-1.87 (m, 3H), 1.79-1.66 (m, 2H), 1.64-1.51 (m, 4H), 1.29 (d, J = 6.6 Hz, 6H). MS (ESI) m/z: 414[M + H]$^+$. |
| VIII | 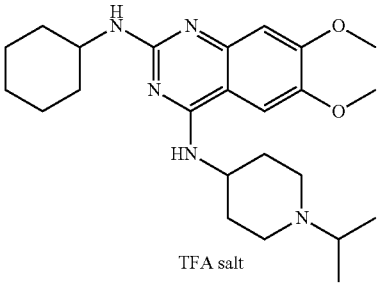 [SMILES: COc1cc2nc(NC3CCCCC3)nc(NC3CCN(C(C)C)CC3)c2cc1OC]<br>TFA salt | $^1$H NMR (600 MHz, Chloroform-d) δ 9.07 (s, 1H), 8.19 (s, 1H), 7.35 (s, 1H), 6.89 (s, 1H), 4.55-4.44 (m, 1H), 3.99 (s, 3H), 3.91 (s, 3H), 3.81-3.69 (m, 1H), 3.59-3.51 (m, 2H), 2.99-2.78 (m, 2H), 2.58-2.40 (m, 2H), 2.39-2.27 (m, 2H), 2.26-2.13 (m, 4H), 2.03-1.92 (m, 2H), 1.89-1.77 (m, 2H), 1.69-1.55 (m, 1H), 1.40 (d, J = 6.0 Hz, 6H). MS (ESI) m/z: 428[M + H]$^+$. |
| IX | 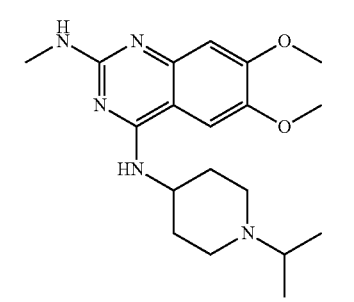 [SMILES: CNc1nc(NC2CCN(C(C)C)CC2)c2cc(OC)c(OC)cc2n1] | $^1$H NMR (600 MHz, DMSO-$d_6$) δ 7.46 (s, 1H), 7.29 (s, 1H), 6.72 (s, 1H), 6.25 (s, 1H), 4.15-4.02 (m, 1H), 3.81 (s, 3H), 3.80 (s, 3H), 2.98-2.86 (m, 2H), 2.87-2.80 (m, 1H), 2.79 (d, J = 4.8 Hz, 3H), 2.37-2.19 (m, 2H), 2.00-1.92 (m, 2H), 1.68-1.53 (m, 2H), 1.02 (d, J = 6.6 Hz, 6H). MS (ESI) m/z: 360[M + H]$^+$. |
| X | 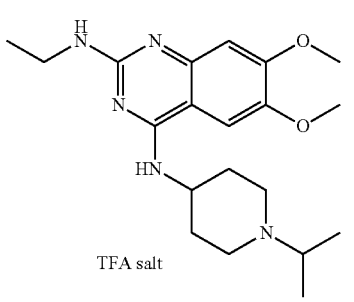 [SMILES: CCNc1nc(NC2CCN(C(C)C)CC2)c2cc(OC)c(OC)cc2n1]<br>TFA salt | $^1$H NMR (600 MHz, Methanol-$d_4$) δ 7.71 (s, 1H), 6.98 (s, 1H), 4.60-4.48 (m, 1H), 3.97 (s, 3H), 3.93 (s, 3H), 3.65-3.49 (m, 5H), 3.23 (t, J = 12.8 Hz, 2H), 2.48-2.36 (m, 2H), 2.20-1.99 (m, 2H), 1.41 (d, J = 6.6 Hz, 6H), 1.30 (t, J = 7.2 Hz, 3H). MS (ESI) m/z: 374[M + H]$^+$. |

-continued

| Formula number | Chemical Structure | H NMR and MS |
|---|---|---|
| XI | 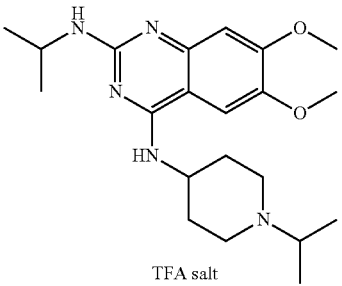 [SMILES: COc1cc2nc(NC(C)C)nc(NC3CCN(C(C)C)CC3)c2cc1OC] TFA salt | ¹H NMR (600 MHz, Chloroform-d) δ 8.64 (s, 1H), 8.31 (s, 1H), 7.40 (s, 1H), 6.86 (s, 1H), 4.55-4.44 (m, 1H), 4.22-4.05 (m, 1H), 3.97 (s, 3H), 3.88 (s, 3H), 3.60-3.42 (m, 3H), 3.01-2.84 (m, 2H), 2.57-2.36 (m, 2H), 2.36-2.22 (m, 2H), 1.39 (d, J = 6.0 Hz, 6H), 1.27 (d, J = 6.4 Hz, 6H). MS (ESI) m/z: 388[M + H]⁺. |
| XII | 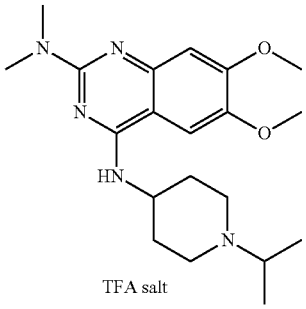 [SMILES: COc1cc2nc(N(C)C)nc(NC3CCN(C(C)C)CC3)c2cc1OC] TFA salt | ¹H NMR (600 MHz, DMSO-d₆) δ 7.79 (s, 1H), 7.30 (s, 1H), 4.47-4.29 (m, 1H), 3.89 (s, 3H), 3.86 (s, 3H), 3.56-3.45 (m, 3H), 3.27 (s, 6H), 3.23-3.10 (m, 2H), 2.32-2.21 (m, 2H), 2.02-1.87 (m, 2H), 1.29 (d, J = 6.6 Hz, 6H). MS (ESI) m/z: 374[M + H]⁺. |
| XIII | 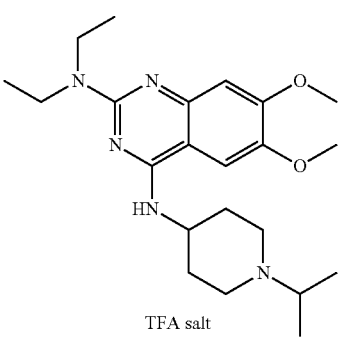 [SMILES: CCN(CC)c1nc(NC2CCN(C(C)C)CC2)c2cc(OC)c(OC)cc2n1] TFA salt | ¹H NMR (600 MHz, Chloroform-d) δ 7.15 (s, 1H), 7.12 (s, 1H), 4.13 (tt, J = 9.7, 4.9 Hz, 1H), 3.90 (s, 3H), 3.89 (s, 3H), 3.65 (q, J = 7.1 Hz, 4H), 3.13-3.04 (m, 2H), 3.03-2.93 (m, 1H), 2.56-2.41 (m, 2H), 2.25-2.12 (m, 2H), 1.93-1.82 (m, 2H), 1.21 (t, J = 7.1 Hz, 6H), 1.14 (d, J = 6.6 Hz, 6H). MS (ESI) m/z: 402[M + H]⁺. |
| XIV | 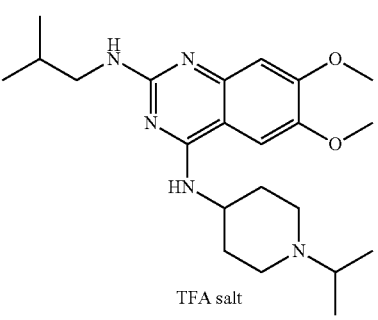 [SMILES: COc1cc2nc(NCC(C)C)nc(NC3CCN(C(C)C)CC3)c2cc1OC] TFA salt | ¹H NMR (600 MHz, Chloroform-d) δ 8.73 (s, 1H), 8.14 (s, 1H), 7.34 (s, 1H), 6.86 (s, 1H), 4.59-4.44 (m, 1H), 3.97 (s, 3H), 3.89 (s, 3H), 3.63-3.53 (m, 3H), 3.31-3.19 (m, 2H), 3.02-2.85 (m, 2H), 2.51-2.37 (m, 2H), 2.39-2.24 (m, 2H), 1.99-1.79 (m, 1H), 1.45-1.34 (m, 6H), 0.94 (d, J = 6.5 Hz, 6H). MS (ESI) m/z: 402 [M + H]⁺. |
| XV | 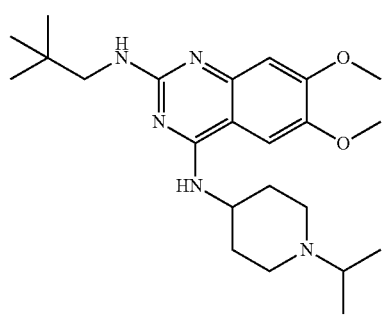 [SMILES: COc1cc2nc(NCC(C)(C)C)nc(NC3CCN(C(C)C)CC3)c2cc1OC] | ¹H NMR (600 MHz, Chloroform-d) δ 6.91 (s, 1H), 6.85 (s, 1H), 4.21-4.11 (m, 1H), 3.93 (s, 3H), 3.91 (s, 3H), 3.33-3.25 (m, 2H), 3.00-2.87 (m, 2H), 2.84-2.71 (m, 1H), 2.38-2.28 (m, 2H), 2.18-2.07 (m, 2H), 1.75-1.60 (m, 2H), 1.07 (d, J = 6.6 Hz, 6H), 0.96 (s, 9H). MS (ESI) m/z: 416[M + H]⁺. |

| Formula number | Chemical Structure | H NMR and MS |
|---|---|---|
| XVI | 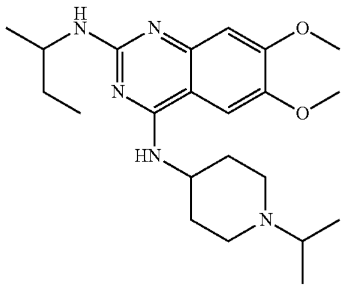 [SMILES: CCC(C)Nc1nc(NC2CCN(C(C)C)CC2)c2cc(OC)c(OC)cc2n1] | ¹H NMR (600 MHz, Chloroform-d) δ 7.09 (s, 1H), 6.90 (s, 1H), 4.35-4.18 (m, 1H), 3.97 (s, 3H), 3.93 (s, 3H), 3.72-3.58 (m, 1H), 3.25-3.10 (m, 2H), 3.10-2.94 (m, 1H), 2.60-2.47 (m, 2H), 2.28-2.13 (m, 2H), 2.09-1.91 (m, 3H), 1.75-1.47 (m, 2H), 1.26-1.24 (m, 2H), 1.18 (d, J = 6.7 Hz, 6H), 0.99-0.90 (m, 3H). MS (ESI) m/z: 402[M + H]⁺. |
| XVII | 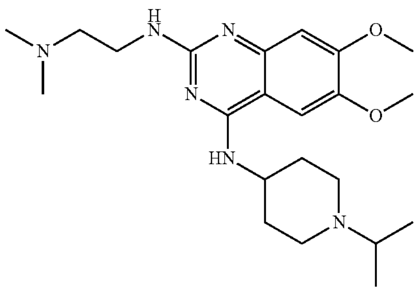 [SMILES: COc1cc2nc(NCCN(C)C)nc(NC3CCN(C(C)C)CC3)c2cc1OC] | ¹H NMR (600 MHz, Chloroform-d) δ 7.05 (s, 1H), 6.83 (s, 1H), 4.24-4.09 (m, 1H), 3.91 (s, 3H), 3.89 (s, 3H), 3.63-3.44 (m, 2H), 2.98-2.88 (m, 2H), 2.88-2.73 (m, 1H), 2.55-2.47 (m, 2H), 2.40-2.30 (m, 2H), 2.26 (s, 6H), 2.15-2.07 (m, 2H), 1.79-1.65 (m, 2H), 1.07 (d, J = 6.6 Hz, 6H). MS (ESI) m/z: 417[M + H]⁺. |
| XVIII | 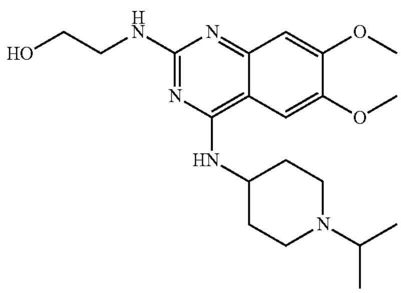 [SMILES: COc1cc2nc(NCCO)nc(NC3CCN(C(C)C)CC3)c2cc1OC] | ¹H NMR (600 MHz, Chloroform-d) δ 6.83 (s, 1H), 6.78 (s, 1H), 5.38 (s, 1H), 4.21-4.06 (m, 1H), 3.93 (s, 3H), 3.92 (s, 3H), 3.87-3.82 (m, 2H), 3.62-3.55 (m, 2H), 2.98-2.89 (m, 2H), 2.87-2.72 (m, 1H), 2.42-2.30 (m, 2H), 2.20-2.07 (m, 2H), 1.72-1.61 (m, 2H), 1.09 (d, J = 6.5 Hz, 6H). MS (ESI) m/z: 390[M + H]⁺. |
| XIX | TFA salt | ¹H NMR (600 MHz, Methanol-d₄) δ 7.75 (s, 1H), 7.19(s, 1H), 4.69-4.51 (m, 1H), 4.10-4.03 (m, 4H), 3.99 (s, 3H), 3.96 (s, 3H), 3.65-3.54 (m, 3H), 3.36-3.29 (m, 2H), 2.44-2.37 (m, 2H), 2.25-2.14 (m, 4H), 2.16-2.05 (m, 2H), 1.43 (d, J = 6.7 Hz, 6H).MS (ESI) m/z: 450[M + H]⁺. |
| XX | TFA salt | ¹H NMR (600 MHz, Methanol-d₄) δ 7.44 (s, 1H), 6.89 (s, 1H), 4.66 (s, 1H), 4.31-4.13 (m, 1H), 3.90 (d, J = 5.0 Hz, 6H), 3.86-3.79 (m, 4H), 3.23-3.14 (m, 2H), 2.70-2.59 (m, 2H), 2.57-2.49 (m, 4H), 2.35 (s, 3H),2.26-2.16 (m, 2H), 1.87-1.71 (m, 2H), 1.21 (d, J = 6.6 Hz, 6H). MS (ESI) m/z: 429[M + H]⁺. |

-continued

| Formula number | Chemical Structure | H NMR and MS |
|---|---|---|
| XXI | 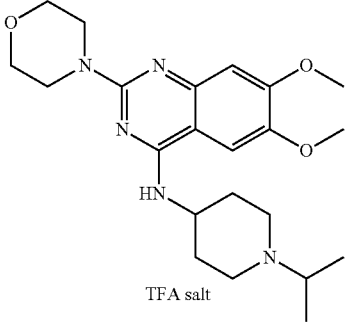 [SMILES: COc1cc2nc(N3CCOCC3)nc(NC3CCN(C(C)C)CC3)c2cc1OC] TFA salt | $^1$H NMR (600 MHz, Chloroform-d) δ 6.98-6.86 (m, 2H), 4.37-4.25 (m, 1H), 3.97-3.93 (m, 6H), 3.82-3.76 (m, 8H), 3.44-3.17 (m, 3H), 2.78-2.65 (m, 2H), 2.34-2.23 (m, 2H), 2.14-1.97 (m, 2H), 1.28 (d, J = 6.7 Hz, 6H). MS (ESI) m/z: 416[M + H]$^+$. |
| XXII | 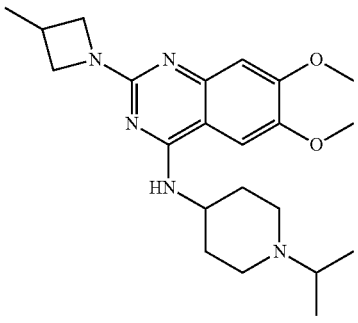 [SMILES: COc1cc2nc(N3CC(C)C3)nc(NC3CCN(C(C)C)CC3)c2cc1OC] | $^1$H NMR (600 MHz, Chloroform-d) δ 6.98 (s, 1H), 6.78 (s, 1H), 5.34 (s, 1H), 4.27 (t, J = 8.1 Hz, 2H), 4.21-4.12 (m, 1H), 3.95-3.88 (m, 6H), 3.78-3.68 (m, 2H), 3.03-2.92 (m, 2H), 2.89-2.81 (m, 1H), 2.80-2.69 (m, 1H), 2.44-2.34 (m, 2H), 2.24-2.15 (m, 2H), 1.73-1.61 (m, 2H), 1.31-1.27 (m, 3H), 1.13-1.06 (m, 6H). MS (ESI) m/z: 400[M + H]$^+$. |
| XXIII | 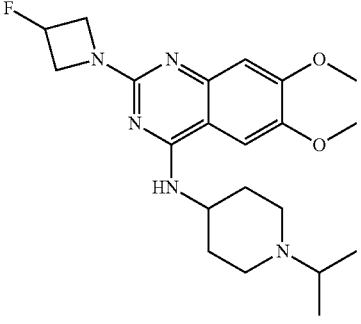 [SMILES: COc1cc2nc(N3CC(F)C3)nc(NC3CCN(C(C)C)CC3)c2cc1OC] | $^1$H NMR (600 MHz, Chloroform-d) δ 6.94 (s, 1H), 6.80 (s, 1H), 5.39-5.25 (m, 1H), 4.48-4.35 (m, 2H), 4.33-4.18 (m, 2H), 4.19-4.09 (m, 1H), 3.94-3.89 (m, 6H), 2.96-2.91 (m, 2H), 2.87-2.66 (m, 1H), 2.41-2.29 (m, 2H), 2.22-2.11 (m, 2H), 1.71-1.50 (m, 2H), 1.08 (d, J = 6.5 Hz, 6H). MS (ESI) m/z: 404[M + H]$^+$. |
| XXIV | 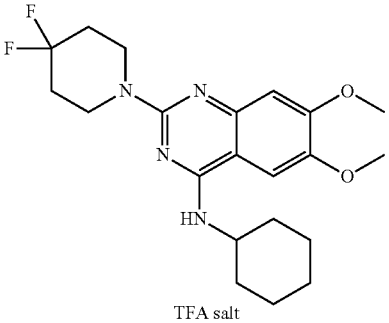 [SMILES: COc1cc2nc(N3CCC(F)(F)CC3)nc(NC3CCCCC3)c2cc1OC] TFA salt | $^1$H NMR (600 MHz, DMSO-d$_6$) δ 8.90 (s, 1H), 7.77 (s, 1H), 7.21 (s, 1H), 4.21-4.03 (m, 1H), 3.96-3.90 (m, 3H), 3.88 (s, 2H), 3.86 (s, 2H), 3.61-3.28 (m, 2H), 2.22-2.05 (m, 4H), 2.01-1.93 (m, 2H), 1.85-1.76 (m, 2H), 1.51-1.28 (m, 4H). MS (ESI) m/z: 407[M + H]$^+$. |

| Formula number | Chemical Structure | H NMR and MS |
|---|---|---|
| XXV | 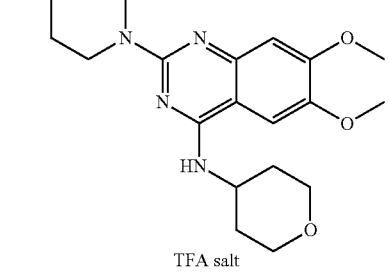<br>TFA salt | $^1$H NMR (600 MHz, Methanol-d$_4$) δ 7.72 (s, 1H), 7.14 (s, 1H), 4.57-4.43 (m, 1H), 4.05-3.99 (m, 4H), 3.97 (s, 3H), 3.94 (s, 3H), 3.66-3.54 (m, 2H), 3.38-3.23 (m, 2H), 2.25-2.10 (m, 4H), 2.07-1.94 (m, 2H), 1.91-1.74 (m, 2H). MS (ESI) m/z: 409[M + H]$^+$. |
| XXVI | 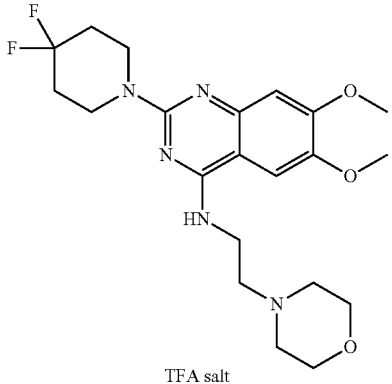 [SMILES: COc1cc2nc(N3CCC(F)(F)CC3)nc(NCCN3CCOCC3)c2cc1OC]<br>TFA salt | $^1$H NMR (600 MHz, Chloroform-d) δ 9.85 (s, 1H), 7.42 (s, 1H), 7.14 (s, 1H), 4.11-4.03 (m, 2H), 4.01-3.98 (m, 4H), 3.97-3.94 (m, 4H), 3.92 (s, 3H), 3.91 (s, 3H), 3.63-3.48 (m, 2H), 3.47-3.33 (m, 2H), 3.13-2.85 (m, 2H), 2.18-1.99 (m, 4H). MS (ESI) m/z: 438[M + H]$^+$. |
| XXVII | 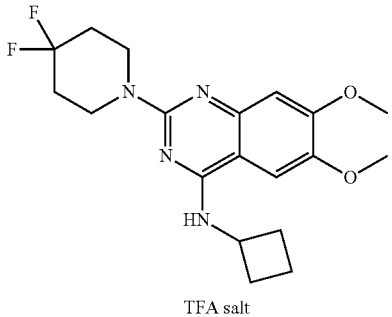 [SMILES: COc1cc2nc(N3CCC(F)(F)CC3)nc(NC3CCC3)c2cc1OC]<br>TFA salt | $^1$H NMR (600 MHz, Chloroform-d) δ 9.21 (s, 1H), 7.56 (s, 1H), 6.80 (s, 1H), 4.39-4.24 (m, 1H), 3.97-3.90 (m, 4H), 3.87 (s, 3H), 3.86 (s, 3H), 2.36 (s, 2H), 2.21 (t, J = 10.1 Hz, 2H), 2.11-2.00 (m, 4H), 1.95-1.76 (m, 2H). MS (ESI) m/z: 379[M + H]$^+$. |
| XXVIII | 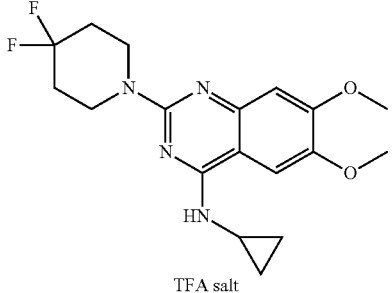 [SMILES: COc1cc2nc(N3CCC(F)(F)CC3)nc(NC3CC3)c2cc1OC]<br>TFA salt | $^1$H NMR (600 MHz, Chloroform-d) δ 9.19 (s, 1H), 7.44 (s, 1H), 6.83 (s, 1H), 4.03-3.93 (m, 4H), 3.88 (s, 3H), 3.85 (s, 3H), 3.08-2.77 (m, 1H), 2.21-1.91 (m, 4H), 0.96-0.66 (m, 4H). MS (ESI) m/z: 365[M + H]$^+$. |

| Formula number | Chemical Structure | H NMR and MS |
|---|---|---|
| XXIX | (structure) | ¹H NMR (600 MHz, Chloroform-d) δ 6.92 (s, 1H), 6.77 (s, 1H), 4.03 (t, J = 5.9 Hz, 4H), 3.96 (s, 3H), 3.93 (s, 3H), 3.13 (d, J = 4.7 Hz, 3H), 2.03 (tt, J = 13.5, 5.8 Hz, 4H). MS (ESI) m/z: 339[M + H]⁺. |
| XXX | (structure) | ¹H NMR (600 MHz, Chloroform-d) δ 6.93-6.81 (m, 2H), 6.07 (s, 1H), 4.03-3.99 (m, 4H), 3.96 (s, 3H), 3.94 (s, 3H), 3.65 (d, J = 5.3 Hz, 2H), 2.63 (p, J = 5.3, 4.5 Hz, 2H), 2.39-2.23 (m, 6H), 2.08-1.92 (m, 4H). MS (ESI) m/z: 396[M + H]⁺. |
| XXXI | (structure) TFA salt | ¹H NMR (600 MHz, Chloroform-d) δ 8.88 (s, 1H), 7.38 (s, 1H), 6.86 (s, 1H), 3.98-3.91 (m, 4H), 3.88 (s, 3H), 3.87 (s, 3H), 3.49-3.30 (m, 2H), 2.33 (s, 2H), 2.15-1.96 (m, 4H), 1.65 (p, J = 7.2 Hz, 2H), 1.32-1.27 (m, 4H), 0.88 (t, 3H). MS (ESI) m/z: 409[M + H]⁺. |
| XXXII | (structure) TFA salt | ¹H NMR (600 MHz, Methanol-d₄) δ 7.45 (s, 1H), 7.21 (s, 1H), 4.08-4.00 (m, 7H), 3.96 (s, 3H), 3.75-3.67 (m, 2H), 3.48 (s, 3H), 3.34-3.30 (m, 2H), 2.96 (s, 3H), 2.32-2.25 (m, 4H), 2.25-2.16 (m, 4H), 1.45-1.36 (m, 1H). MS (ESI) m/z: 436[M + H]⁺. |
| XXXIII | (structure) TFA salt | ¹H NMR (600 MHz, Chloroform-d) δ 10.71 (s, 1H), 7.85 (d, J = 7.9 Hz, 2H), 7.69 (s, 1H), 7.41 (t, J = 7.8 Hz, 2H), 7.25-7.20 (m, 1H), 6.75 (s, 1H), 3.93 (s, 3H), 3.74-3.68 (m, 4H), 3.65 (s, 3H), 2.19-1.83 (m, 4H). MS (ESI) m/z: 401[M + H]⁺. |

-continued
| Formula number | Chemical Structure | H NMR and MS |
|---|---|---|
| XXXIV | 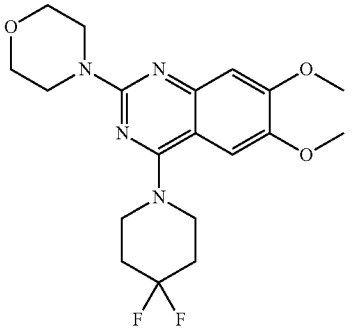<br>TFA salt | ¹H NMR (600 MHz, DMSO-d₆) δ 7.28 (s, 1H), 7.22 (s, 1H), 4.06-3.98 (m, 4H), 3.93 (s, 3H), 3.90 (s, 3H), 3.84-3.78 (m, 4H), 3.78-3.72 (m, 4H), 2.30-2.08 (m, 4H). MS (ESI) m/z: 395[M + H]⁺. |
| XXXV | 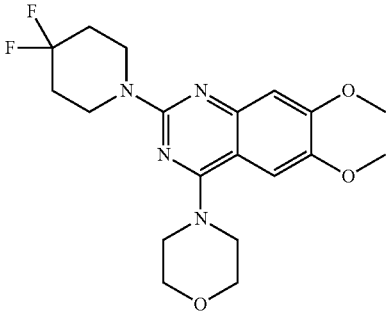<br>TFA salt | ¹H NMR (600 MHz, DMSO-d₆) δ 7.28-7.15 (m, 2H), 4.00-3.95 (m, 4H), 3.95-3.92 (m, 4H), 3.91 (s, 3H), 3.87 (s, 3H), 3.78-3.71 (m, 4H), 2.24-1.98 (m, 4H). MS (ESI) m/z: 395[M + H]⁺. |
| XXXVI | 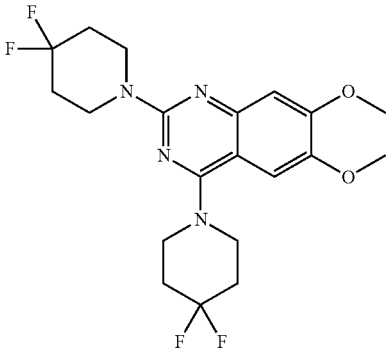<br>TFA salt | ¹H NMR (600 MHz, DMSO-d₆) δ 7.69-6.70 (m, 2H), 4.02-3.93 (m, 8H), 3.92 (s, 3H), 3.88 (s, 3H), 2.27-2.17 (m, 4H), 2.17-2.08 (m, 4H). MS (ESI) m/z: 429[M + H]⁺. |
| XXXVII | 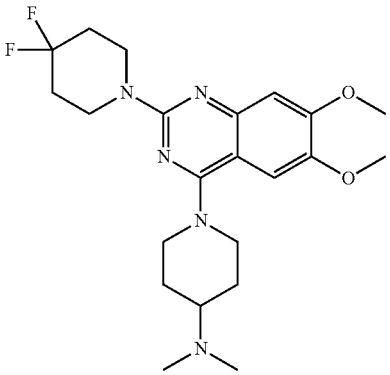 [SMILES: COc1cc2nc(N3CCC(F)(F)CC3)nc(N3CCC(N(C)C)CC3)c2cc1OC] | ¹H NMR (600 MHz, Chloroform-d) δ 6.98 (s, 1H), 6.92 (s, 1H), 4.22-4.12 (m, 2H), 4.03-3.98 (m, 4H), 3.97 (s, 3H), 3.92 (s, 3H), 3.05-2.94 (m, 2H), 2.52-2.42 (m, 1H), 2.38 (s, 6H), 2.08-1.91 (m, 6H), 1.78-1.62 (m, 2H). MS (ESI) m/z: 436[M + H]⁺. |

-continued

| Formula number | Chemical Structure | H NMR and MS |
|---|---|---|
| XXXVIII | 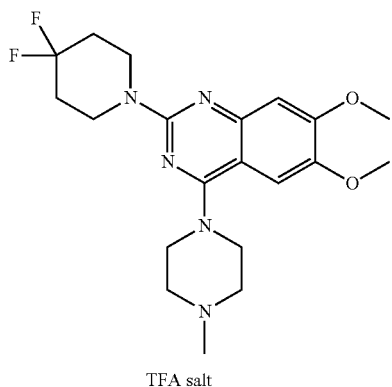 [SMILES: COc1cc2nc(N3CCC(F)(F)CC3)nc(N3CCN(C)CC3)c2cc1OC]<br>TFA salt | $^1$H NMR (600 MHz, DMSO-$d_6$) δ 7.22 (s, 1H), 7.15 (s, 1H), 4.66-4.40 (m, 2H), 3.96 (t, J = 5.7 Hz, 4H), 3.91 (s, 3H), 3.89 (s, 3H), 3.72-3.42 (m, 4H), 3.34-3.15 (m, 2H), 2.86 (s, 3H), 2.17-2.04 (m, 4H). MS (ESI) m/z: 408[M + H]$^+$. |
| XXXIX | 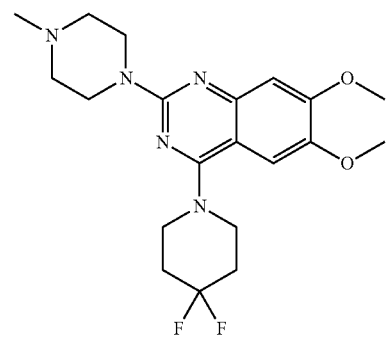 | $^1$H NMR (600 MHz, Chloroform-d) δ 6.92-6.90 (m, 2H), 3.94 (s, 3H), 3.88 (s, 3H), 3.87-3.81 (m, 4H), 3.68 (t, J = 5.7 Hz, 4H), 2.47 (t, J = 5.1 Hz, 4H), 2.32 (s, 3H), 2.21-2.06 (m, 4H). MS (ESI) m/z: 408[M + H]$^+$. |
| XL | 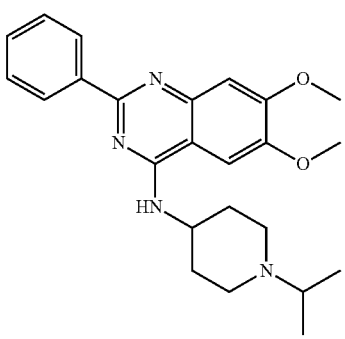 [SMILES: COc1cc2nc(-c3ccccc3)nc(NC3CCN(C(C)C)CC3)c2cc1OC] | $^1$H NMR (600 MHz, Methanol-$d_4$) δ 8.25 (d, J = 7.0 Hz, 2H), 7.46 (s, 1H), 7.43-7.33 (m, 3H), 7.11 (s, 1H), 4.37-4.23 (m, 1H), 3.88 (s, 3H), 3.87 (s, 3H), 3.11-2.94 (m, 2H), 2.89-2.76 (m, 1H), 2.59-2.37 (m, 2H), 2.19-2.07 (m, 2H), 1.79-1.56 (m, 2H), 1.08 (d, J = 6.6 Hz, 6H). MS (ESI) m/z: 407[M + H]$^+$. |
| XLI | 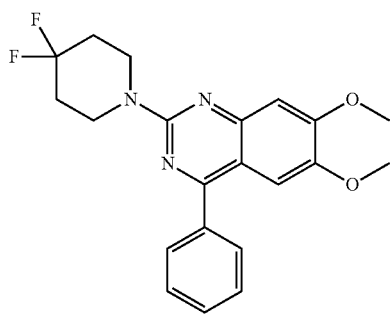 | $^1$H NMR (600 MHz, Chloroform-d) δ 7.81-7.69 (m, 2H), 7.61-7.47 (m, 3H), 7.15 (s, 1H), 7.03 (s, 1H), 4.14-4.09 (m, 4H), 4.03 (s, 3H), 3.83 (s, 3H), 2.16-1.95 (m, 4H). MS (ESI) m/z: 386[M + H]$^+$. |

-continued

| Formula number | Chemical Structure | H NMR and MS |
|---|---|---|
| XLII | 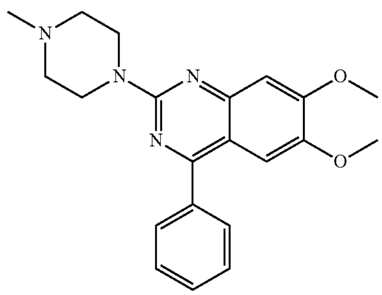 | $^1$H NMR (600 MHz, Methanol-d$_4$) δ 7.76-7.71 (m, 2H), 7.63-7.53 (m, 3H), 7.16 (s, 1H), 7.10 (s, 1H), 3.96 (s, 3H), 3.74 (s, 3H), 3.70-3.39 (m, 4H), 3.42-3.10 (m, 4H), 2.97 (s, 3H). MS (ESI) m/z: 365[M + H]$^+$. |
| XLIII | TFA salt | $^1$H NMR (600 MHz, Chloroform-d) δ 10.26 (s, 1H), 7.86-7.80 (m, 2H), 7.69-7.55 (m, 3H), 7.23 (s, 1H), 7.16 (s, 1H), 4.09 (s, 3H), 3.85 (s, 3H), 3.15-3.06 (m, 1H), 0.92-0.84 (m, 2H), 0.82-0.75 (m, 2H). MS (ESI) m/z: 322[M + H]$^+$. |
| XLIV | TFA salt | $^1$H NMR (600 MHz, Methanol-d$_4$) δ 7.87-7.79 (m, 2H), 7.71-7.67 (m, 1H), 7.66-7.61 (m, 3H), 7.29 (s, 1H), 4.43-4.30 (m, 1H), 4.07 (s, 3H), 3.82 (s, 3H), 1.38 (d, J = 6.5 Hz, 6H). MS (ESI) m/z: 324[M + H]$^+$. |
| XLV | 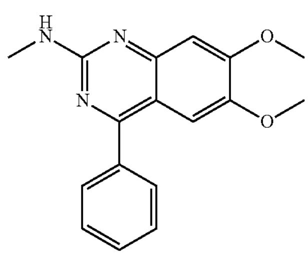 | $^1$H NMR (600 MHz, Chloroform-d) δ 7.74-7.66 (m, 2H), 7.57-7.49 (m, 3H), 7.11-7.06 (m, 2H), 5.29 (s, 1H), 4.03 (s, 3H), 3.81 (s, 3H), 3.11 (d, J = 5.1 Hz, 3H). MS (ESI) m/z: 296[M + H]$^+$. |
| XLVI | 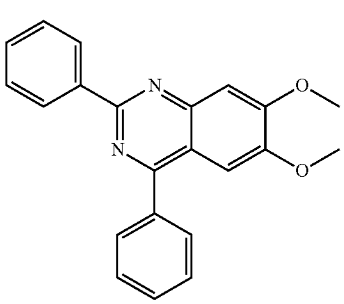 [SMILES: COc1cc2nc(-c3ccccc3)nc(-c3ccccc3)c2cc1OC] | $^1$H NMR (600 MHz, Chloroform-d) δ 8.65-8.61 (m, 2H), 7.91-7.87 (m, 2H), 7.65-7.54 (m, 4H), 7.56-7.42 (m, 4H), 4.10 (s, 3H), 3.91 (s, 3H). MS (ESI) m/z: 343[M + H]$^+$. |

-continued

| Formula number | Chemical Structure | H NMR and MS |
|---|---|---|
| XLVII | 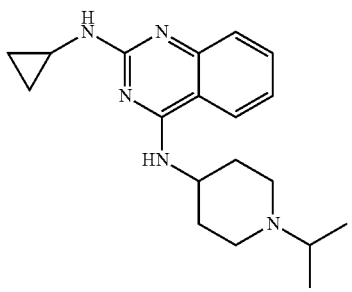 | $^1$H NMR (600 MHz, Chloroform-d) δ 8.30 (dd, J = 4.2, 1.5 Hz, 1H), 7.75 (d, J = 8.4 Hz, 1H), 7.41 (dd, J = 8.5, 4.2 Hz, 1H), 6.91 (d, J = 7.9 Hz, 1H), 5.37 (s, 1H), 4.25-3.78 (m, 1H), 2.94-2.82 (m, 2H), 2.80-2.68 (m, 1H), 2.39-2.26 (m, 2H), 2.18-2.06 (m, 2H), 1.72-1.59 (m, 2H), 1.06 (d, J = 6.6 Hz, 6H), 0.82-0.75 (m, 2H), 0.59-0.52 (m, 2H). MS (ESI) m/z: 326[M + H]$^+$. |
| XLVIII | 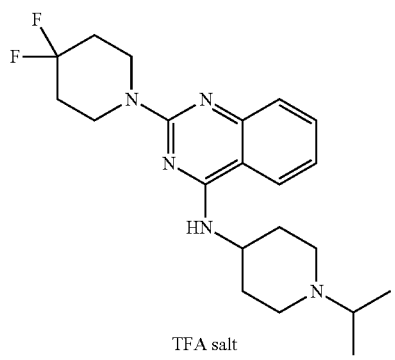 [SMILES: CC(C)N1CCC(Nc2nc(N3CCC(F)(F)CC3)nc3ccccc23)CC1]<br>TFA salt | $^1$H NMR (600 MHz, Methanol-d$_4$) δ 8.28 (dd, J = 8.3, 1.2 Hz, 1H), 7.83 (ddd, J = 8.3, 7.2, 1.3 Hz, 1H), 7.68 (d, J = 8.3 Hz, 1H), 7.51-7.45 (m, 1H), 4.71-4.56 (m, 1H), 4.17-4.01 (m, 4H), 3.64-3.54 (m, 3H), 3.36-3.32 (m, 2H), 2.45-2.33 (m, 2H), 2.25-2.15 (m, 4H), 2.15-2.07 (m, 2H), 1.41 (d, J = 6.6 Hz, 6H). MS (ESI) m/z: 390[M + H]$^+$. |
| XLIX | 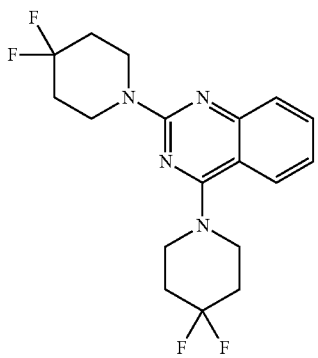<br>TFA salt | $^1$H NMR (600 MHz, DMSO-d$_6$) δ 8.05-7.98 (m, 1H), 7.90-7.83 (m, 1H), 7.75 (d, J = 8.3 Hz, 1H), 7.44 (t, J = 7.6 Hz, 1H), 4.13-3.94 (m, 8H), 2.37-2.07 (m, 8H). MS (ESI) m/z: 369[M + H]$^+$. |
| L | 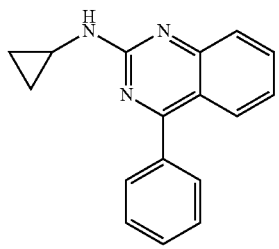 [SMILES: c1ccc(-c2nc(NC3CC3)nc3ccccc23)cc1] | $^1$H NMR (600 MHz, Chloroform-d) δ 10.68 (s, 1H), 8.00 (d, J = 8.2 Hz, 1H), 7.90-7.78 (m, 4H), 7.69 (t, J = 7.4 Hz, 1H), 7.63 (t, J = 7.4 Hz, 2H), 7.41 (t, J = 7.5 Hz, 1H), 3.35-3.06 (m, 1H), 1.02-0.69 (m, 4H). MS (ESI) m/z: 262[M + H]$^+$. |

| Formula number | Chemical Structure | H NMR and MS |
|---|---|---|
| LI | 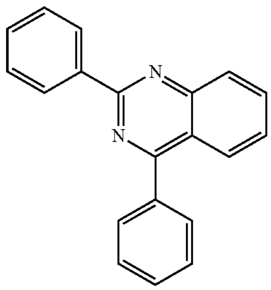 [SMILES: c1ccc(-c2nc(-c3ccccc3)c3ccccc3n2)cc1] | $^1$H NMR (600 MHz, Chloroform-d) δ 8.74-8.67 (m, 2H), 8.21-8.10 (m, 2H), 7.92-7.85 (m, 3H), 7.66-7.57 (m, 3H), 7.58-7.47 (m, 4H). MS (ESI) m/z: 283[M + H]$^+$. |

Example 2: Evaluation of STK19 Kinase Inhibitory Activity

The optimal conditions of the STK19 enzyme and the ATP concentrations in the 96-well format kinase assay were first determined using Promega ADP-Glo® kinase assay according to the manufacture's protocol. For the enzyme concentration and reaction time optimization, Flag-tagged STK19 at various concentrations (ranging from 0.2 to 400 nM), ATP (100 μM) and the substrate HA-tagged GTP-preloaded NRAS (1 μM) were added to 96-well white solid plates (15 μL volume) for 0 to 40 min in the kinase buffer. The kinase reaction was stopped by ADP-Glo™ Reagent and the ADP generated in the kinase reaction was converted to ATP for luciferase assay. Phosphorylation of HA-tagged NRAS was quantified based on the luminescence readout measured with Tecan Infinite® M1000 Microplate Reader.

The optimal amount of STK19 is the minimal amount that produces luminescence within the linear portion of the kinase titration curve and generates an adequate signal-to-background ratio. The optimal kinase reaction time was defined as the point at which the EC$_{50}$ from the enzyme titration no longer changes. The inventors finally chose 12.5 nM STK19 and 15 min as the optimal kinase concentration and reaction time for the kinase assay.

The ATP titration was conducted with STK19 kinase using the enzyme concentration previously determined, and the kinase assays were performed at ATP concentrations ranging from 0.5 μM to 200 μM. The apparent ATP K$_{m(app)}$ was calculated by fitting data using the Michaelis-Menten equation. The ATP concentrations of 6.36 μM K$_{m(app)}$ for STK19 was required to show a 50% change between the maximum and minimum phosphorylated NRAS levels.

Assay quality was determined using the Z-factor, indicating the quality of an assay. Z-factors of 0.5 or greater indicate an excellent assay. The assay optimization procedure uses the wells in the row that contain no kinase as the 100% inhibition control wells and each of the wells in the row containing STK19 as the 0% inhibition control wells. The Z-factor value was calculated using the following equation: Z-factor=$1-3\times(\sigma_{0\% \, Inhibition}+\sigma_{100\% \, Inhibition})/(\mu_{0\% \, Inhibition}-\mu_{100\% \, Inhibition})$, where σ represents standard deviation and μ represents the mean value of the luminescence. The Z-factor was 0.703 for Flag-tagged STK19, confirming the optimization of the enzyme concentration, the reaction time and the ATP concentration.

Table 4 lists the formula numbers of the compounds, their corresponding STK19 kinase inhibitory activity and IC50 values.

| Formula number | Chemical Structure | Inhibition of STK19 kinase activity at 10 μM | IC$_{50}$ (nm) |
|---|---|---|---|
| IV |  TFA salt | 83.96% | 24.04 |

-continued

| Formula number | Chemical Structure | Inhibition of STK19 kinase activity at 10 μM | IC$_{50}$ (nm) |
|---|---|---|---|
| V | 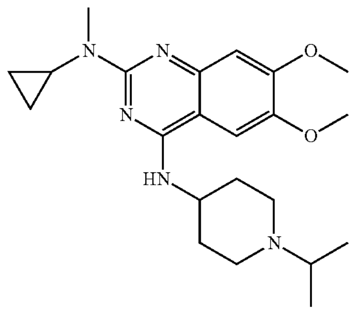 [SMILES: COc1cc2nc(N(C)C3CC3)nc(NC3CCN(C(C)C)CC3)c2cc1OC] | 47.93% | 251.9 |
| VI | TFA salt | 43.92% | |
| VII | TFA salt | 40.61% | |
| VIII | TFA salt | 78.43% | |

-continued

| Formula number | Chemical Structure | Inhibition of STK19 kinase activity at 10 μM | IC$_{50}$ (nm) |
|---|---|---|---|
| IX | 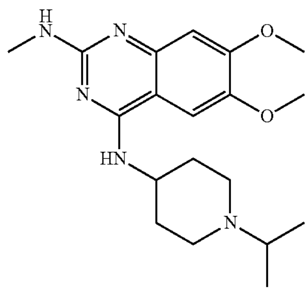 [SMILES: CNc1nc(NC2CCN(C(C)C)CC2)c2cc(OC)c(OC)cc2n1] | 59.75% | |
| X | TFA salt | 64.60% | |
| XI | TFA salt | 14.29% | |
| XII | TFA salt | 25.89% | |

-continued
| Formula number | Chemical Structure | Inhibition of STK19 kinase activity at 10 μM | IC$_{50}$ (nm) |
|---|---|---|---|
| XIII | 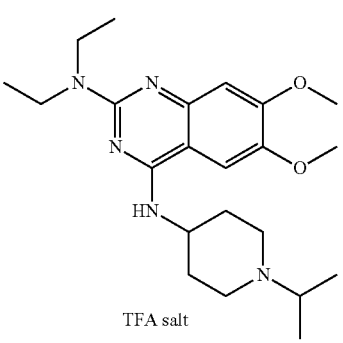 [SMILES: CCN(CC)c1nc(NC2CCN(C(C)C)CC2)c2cc(OC)c(OC)cc2n1] TFA salt | 34.57% | |
| XIV | 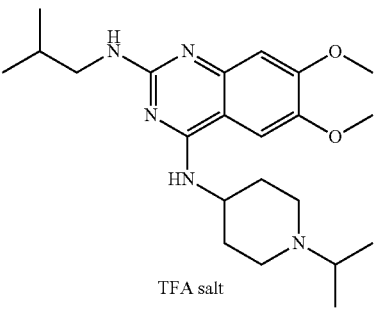 [SMILES: COc1cc2nc(NCC(C)C)nc(NC3CCN(C(C)C)CC3)c2cc1OC] TFA salt | 11.06% | |
| XV | 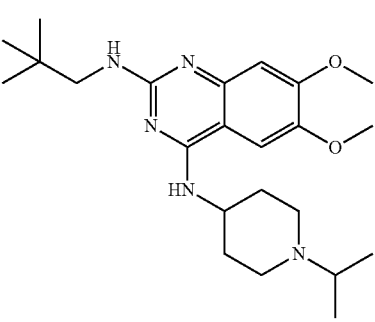 [SMILES: COc1cc2nc(NCC(C)(C)C)nc(NC3CCN(C(C)C)CC3)c2cc1OC] | 15.41% | |
| XVI | 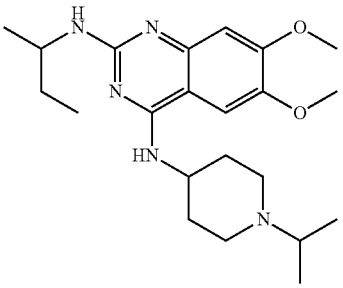 [SMILES: CCC(C)Nc1nc(NC2CCN(C(C)C)CC2)c2cc(OC)c(OC)cc2n1] | 61.01% | 178.2 |

| Formula number | Chemical Structure | Inhibition of STK19 kinase activity at 10 μM | IC$_{50}$ (nm) |
|---|---|---|---|
| XVII | [structure: 2-((2-(dimethylamino)ethyl)amino)-6,7-dimethoxy-N-(1-isopropylpiperidin-4-yl)quinazolin-4-amine] | 66.17% | 127.2 |
| XVIII | [structure: 2-((2-hydroxyethyl)amino)-6,7-dimethoxy-N-(1-isopropylpiperidin-4-yl)quinazolin-4-amine] | 9.58% | |
| XIX | [structure: 2-(4,4-difluoropiperidin-1-yl)-6,7-dimethoxy-N-(1-isopropylpiperidin-4-yl)quinazolin-4-amine, TFA salt] | 60.64% | 148.3 |
| XX | [structure: 6,7-dimethoxy-N-(1-isopropylpiperidin-4-yl)-2-(4-methylpiperazin-1-yl)quinazolin-4-amine, TFA salt] | 70.70% | 90.91 |

-continued
| Formula number | Chemical Structure | Inhibition of STK19 kinase activity at 10 μM | IC$_{50}$ (nm) |
|---|---|---|---|
| XXI | 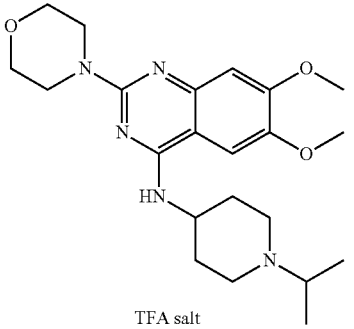 [SMILES: COc1cc2nc(N3CCOCC3)nc(NC3CCN(C(C)C)CC3)c2cc1OC] TFA salt | 59.05% | |
| XXII | 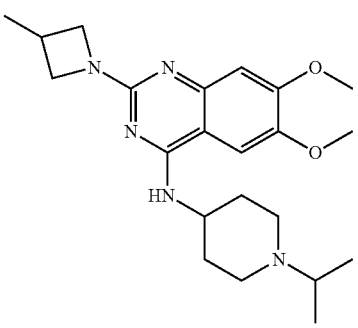 [SMILES: COc1cc2nc(N3CC(C)C3)nc(NC3CCN(C(C)C)CC3)c2cc1OC] | | |
| XXIII | 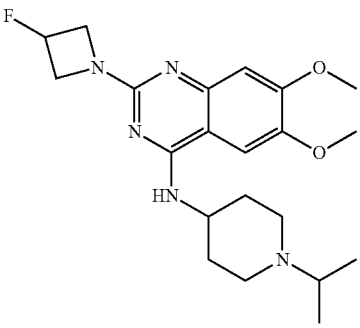 [SMILES: COc1cc2nc(N3CC(F)C3)nc(NC3CCN(C(C)C)CC3)c2cc1OC] | | |
| XXIV | 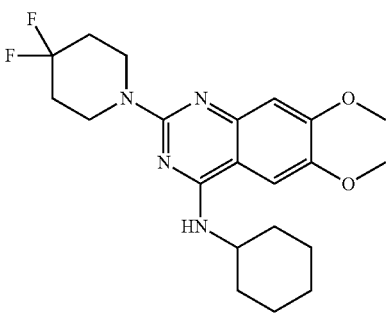 TFA salt | 53.38% | |

-continued
| Formula number | Chemical Structure | Inhibition of STK19 kinase activity at 10 μM | IC$_{50}$ (nm) |
|---|---|---|---|
| XXV | 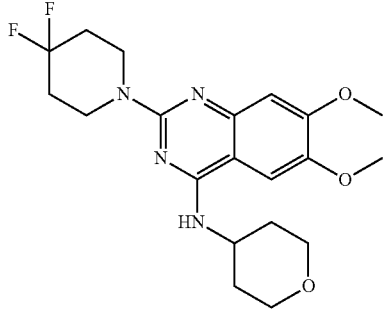<br>TFA salt | 36.37% | |
| XXVI | 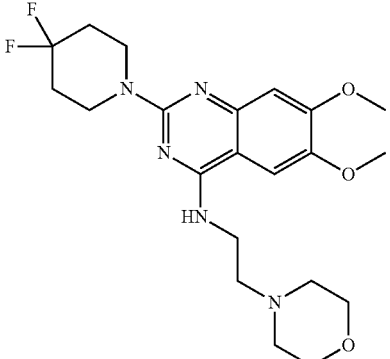<br>TFA salt | 57.88% | |
| XXVII | 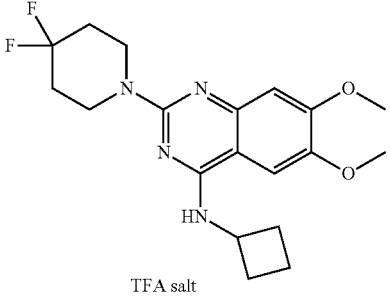 [SMILES: COc1cc2nc(N3CCC(F)(F)CC3)nc(NC3CCC3)c2cc1OC]<br>TFA salt | 70.42% | 98.77 |
| XXVIII | 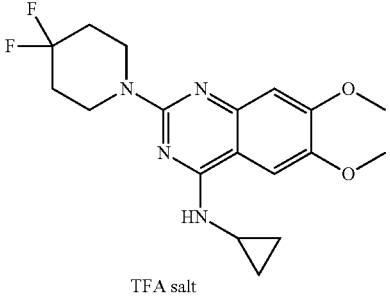 [SMILES: COc1cc2nc(N3CCC(F)(F)CC3)nc(NC3CC3)c2cc1OC]<br>TFA salt | 55.00% | |

-continued

| Formula number | Chemical Structure | Inhibition of STK19 kinase activity at 10 μM | IC$_{50}$ (nm) |
|---|---|---|---|
| XXDC | 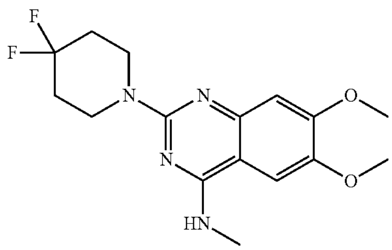 [SMILES: CNc1nc(N2CCC(F)(F)CC2)nc2cc(OC)c(OC)cc12] | 74.61% | |
| XXX | 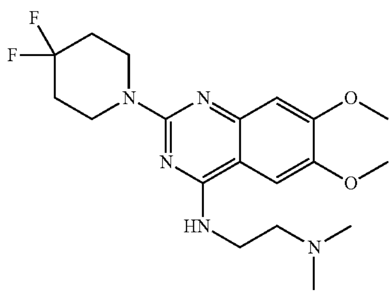 [SMILES: COc1cc2nc(N3CCC(F)(F)CC3)nc(NCCN(C)C)c2cc1OC] | 68.92% | 70.01 |
| XXXI | TFA salt | 22.68% | |
| XXXII | TFA salt | 51.95% | |

-continued

| Formula number | Chemical Structure | Inhibition of STK19 kinase activity at 10 μM | IC$_{50}$ (nm) |
|---|---|---|---|
| XXXIII | 4,4-difluoropiperidin-1-yl at 2-position, 6,7-dimethoxy, 4-phenylamino quinazoline (TFA salt) | 67.48% | 137 |
| XXXIV | 2-morpholino, 6,7-dimethoxy, 4-(4,4-difluoropiperidin-1-yl) quinazoline (TFA salt) | 48.06% | |
| XXXV | 2-(4,4-difluoropiperidin-1-yl), 6,7-dimethoxy, 4-morpholino quinazoline (TFA salt) | 58.18% | |
| XXXVI | 2,4-bis(4,4-difluoropiperidin-1-yl), 6,7-dimethoxy quinazoline (TFA salt) | 69.75% | 101.7 |

-continued

| Formula number | Chemical Structure | Inhibition of STK19 kinase activity at 10 μM | IC$_{50}$ (nm) |
|---|---|---|---|
| XXXVII | (4,4-difluoropiperidin-1-yl)-6,7-dimethoxy-quinazoline with 4-(dimethylamino)piperidine | 53.79% | |
| XXXVIII | (4,4-difluoropiperidin-1-yl)-6,7-dimethoxy-quinazoline with 4-methylpiperazine, TFA salt | 68.63% | 79.88 |
| XXXIX | 2-(4-methylpiperazin-1-yl)-6,7-dimethoxy-quinazoline with 4,4-difluoropiperidine | 79.54% | 57.12 |
| XL | 2-phenyl-6,7-dimethoxy-quinazoline with N-(1-isopropylpiperidin-4-yl)amine | 67.28% | 96.67 |

-continued

| Formula number | Chemical Structure | Inhibition of STK19 kinase activity at 10 μM | IC$_{50}$ (nm) |
|---|---|---|---|
| XLI | 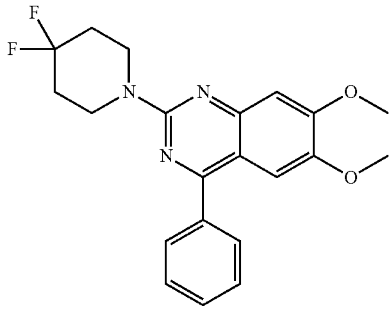 [SMILES: COc1cc2nc(N3CCC(F)(F)CC3)nc(-c3ccccc3)c2cc1OC] | 75.33% | 64.55 |
| XLII | 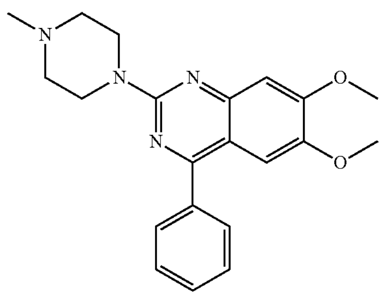 | 50.97% | |
| XLIII | TFA salt | 34.44% | |
| XLIV | TFA salt | 47.32% | |
| XLV | 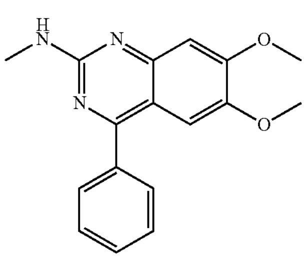 | 56.92% | |

-continued

| Formula number | Chemical Structure | Inhibition of STK19 kinase activity at 10 μM | IC$_{50}$ (nm) |
| --- | --- | --- | --- |
| XLVI | 2,4-diphenyl-6,7-dimethoxyquinazoline | 81.26% | 29.33 |
| XLVII | N2-cyclopropyl-N4-(1-isopropylpiperidin-4-yl)quinazoline-2,4-diamine | 46.10% | 79.04 |
| XLVIII | 2-(4,4-difluoropiperidin-1-yl)-N-(1-isopropylpiperidin-4-yl)quinazolin-4-amine, TFA salt | 80.36% | 48.32 |
| XLIX | 2,4-bis(4,4-difluoropiperidin-1-yl)quinazoline, TFA salt | 47.74% | |

| Formula number | Chemical Structure | Inhibition of STK19 kinase activity at 10 μM | IC$_{50}$ (nm) |
|---|---|---|---|
| L | (structure: N-cyclopropyl-4-phenylquinazolin-2-amine) | 15.54% | |
| LI | (structure: 2,4-diphenylquinazoline) | 38.73% | |

Table 5 lists blood chemistry data (including but not limited to serum transaminase levels).

| Blood chemistry in tolerability studies | | |
|---|---|---|
| | Vehicle | IV |
| Alanine aminotransferase (ALT), U/L | 28.2 ± 8.4 | 27.6 ± 5.6 |
| Aspartate aminotransferase (AST), U/L | 54.6 ± 8.8 | 54.4 ± 9.4 |
| Total bilirubin (T-Bil), μmol/L | 2.90 ± 0.29 | 2.68 ± 0.44 |
| Alkaline phosphatase (ALP), U/L | 3.2 ± 1.4 | 3.9 ± 1.7 |
| Total protein (TP), g/L | 49.5 ± 2.9 | 50.9 ± 2.5 |
| Albumin (ALB), g/L | 27.9 ± 1.7 | 28.3 ± 2.7 |
| Creatinine (CRE), μmol/L | 17.4 ± 4.8 | 17.7 ± 4.2 |
| Lactic dehydrogenase (LDH), U/L | 249.7 ± 54.8 | 247.3 ± 41.0 |
| Phosphorus (P), μmol/L | 1.72 ± 0.22 | 1.67 ± 0.39 |

Table 6 lists KINOMEscan data. The data show that compound IV has high kinase selectivity using a KINOMEscan, which profiled the inhibitor at a concentration of 1 μM against a panel of 468 diverse kinases using an in vitro ATP-site competition binding assay.

| Compound Name | DiscoveRx Gene Symbol | Percent Control | Concentration (nM) |
|---|---|---|---|
| IV | AAK1 | 91 | 1000 |
| IV | ABL1(E255K)-phosphorylated | 89 | 1000 |
| IV | ABL1(F317I)-nonphosphorylated | 85 | 1000 |
| IV | ABL1(F317I)-phosphorylated | 90 | 1000 |
| IV | ABL1(F317L)-nonphosphorylated | 82 | 1000 |
| IV | ABL1(F317L)-phosphorylated | 40 | 1000 |
| IV | ABL1(H396P)-nonphosphorylated | 69 | 1000 |
| IV | ABL1(H396P)-phosphorylated | 68 | 1000 |
| IV | ABL1(M351T)-phosphorylated | 59 | 1000 |
| IV | ABL1(Q252H)-nonphosphorylated | 84 | 1000 |
| IV | ABL1(Q252H)-phosphorylated | 69 | 1000 |
| IV | ABL1(T315I)-nonphosphorylated | 100 | 1000 |
| IV | ABL1(T315I)-phosphorylated | 49 | 1000 |
| IV | ABL1(Y253F)-phosphorylated | 100 | 1000 |
| IV | ABL1-nonphosphorylated | 91 | 1000 |
| IV | ABL1-phosphorylated | 88 | 1000 |
| IV | ABL2 | 98 | 1000 |
| IV | ACVR1 | 100 | 1000 |
| IV | ACVR1B | 94 | 1000 |
| IV | ACVR2A | 100 | 1000 |
| IV | ACVR2B | 76 | 1000 |
| IV | ACVRL1 | 99 | 1000 |
| IV | ADCK3 | 100 | 1000 |
| IV | ADCK4 | 100 | 1000 |
| IV | AKT1 | 95 | 1000 |
| IV | AKT2 | 89 | 1000 |
| IV | AKT3 | 91 | 1000 |
| IV | ALK | 61 | 1000 |
| IV | ALK(C1156Y) | 92 | 1000 |
| IV | ALK(L1196M) | 78 | 1000 |
| IV | AMPK-alpha1 | 92 | 1000 |
| IV | AMPK-alpha2 | 93 | 1000 |
| IV | ANKK1 | 50 | 1000 |
| IV | ARK5 | 98 | 1000 |
| IV | ASK1 | 75 | 1000 |
| IV | ASK2 | 93 | 1000 |
| IV | AURKA | 56 | 1000 |
| IV | AURKB | 84 | 1000 |
| IV | AURKC | 100 | 1000 |
| IV | AXL | 94 | 1000 |
| IV | BIKE | 100 | 1000 |
| IV | BLK | 100 | 1000 |
| IV | BMPR1V | 100 | 1000 |
| IV | BMPR1B | 55 | 1000 |
| IV | BMPR2 | 40 | 1000 |
| IV | BMX | 100 | 1000 |
| IV | BRAF | 88 | 1000 |
| IV | BRAF(V600E) | 89 | 1000 |
| IV | BRK | 100 | 1000 |

| Compound Name | DiscoveRx Gene Symbol | Percent Control | Concentration (nM) |
|---|---|---|---|
| IV | BRSK1 | 92 | 1000 |
| IV | BRSK2 | 100 | 1000 |
| IV | BTK | 89 | 1000 |
| IV | BUB1 | 63 | 1000 |
| IV | CAMK1 | 91 | 1000 |
| IV | CAMK1B | 59 | 1000 |
| IV | CAMK1D | 100 | 1000 |
| IV | CAMK1G | 99 | 1000 |
| IV | CAMK2A | 87 | 1000 |
| IV | CAMK2B | 91 | 1000 |
| IV | CAMK2D | 89 | 1000 |
| IV | CAMK2G | 100 | 1000 |
| IV | CAMK4 | 98 | 1000 |
| IV | CAMKK1 | 97 | 1000 |
| IV | CAMKK2 | 100 | 1000 |
| IV | CASK | 60 | 1000 |
| IV | CDC2L1 | 100 | 1000 |
| IV | CDC2L2 | 99 | 1000 |
| IV | CDC2L5 | 55 | 1000 |
| IV | CDK11 | 82 | 1000 |
| IV | CDK2 | 91 | 1000 |
| IV | CDK3 | 100 | 1000 |
| IV | CDK4 | 62 | 1000 |
| IV | CDK4-cyclinD1 | 67 | 1000 |
| IV | CDK4-cyclinD3 | 54 | 1000 |
| IV | CDK5 | 93 | 1000 |
| IV | CDK7 | 69 | 1000 |
| IV | CDK8 | 96 | 1000 |
| IV | CDK9 | 100 | 1000 |
| IV | CDKL1 | 53 | 1000 |
| IV | CDKL2 | 100 | 1000 |
| IV | CDKL3 | 66 | 1000 |
| IV | CDKL5 | 52 | 1000 |
| IV | CHEK1 | 93 | 1000 |
| IV | CHEK2 | 100 | 1000 |
| IV | CIT | 100 | 1000 |
| IV | CLK1 | 96 | 1000 |
| IV | CLK2 | 90 | 1000 |
| IV | CLK3 | 91 | 1000 |
| IV | CLK4 | 69 | 1000 |
| IV | CSF1R | 91 | 1000 |
| IV | CSF1R-autoinhibited | 54 | 1000 |
| IV | CSK | 98 | 1000 |
| IV | CSNK1V1 | 74 | 1000 |
| IV | CSNK1V1L | 99 | 1000 |
| IV | CSNK1D | 98 | 1000 |
| IV | CSNK1E | 100 | 1000 |
| IV | CSNK1G1 | 100 | 1000 |
| IV | CSNK1G2 | 86 | 1000 |
| IV | CSNK1G3 | 100 | 1000 |
| IV | CSNK2A1 | 61 | 1000 |
| IV | CSNK2A2 | 63 | 1000 |
| IV | CTK | 32 | 1000 |
| IV | DAPK1 | 99 | 1000 |
| IV | DAPK2 | 93 | 1000 |
| IV | DAPK3 | 89 | 1000 |
| IV | DCAMKL1 | 53 | 1000 |
| IV | DCAMKL2 | 90 | 1000 |
| IV | DCAMKL3 | 92 | 1000 |
| IV | DDR1 | 88 | 1000 |
| IV | DDR2 | 66 | 1000 |
| IV | DLK | 62 | 1000 |
| IV | DMPK | 99 | 1000 |
| IV | DMPK2 | 99 | 1000 |
| IV | DRAK1 | 96 | 1000 |
| IV | DRAK2 | 79 | 1000 |
| IV | DYRKIV | 60 | 1000 |
| IV | DYRK1B | 86 | 1000 |
| IV | DYRK2 | 84 | 1000 |
| IV | EGFR | 97 | 1000 |
| IV | EGFR(E746-A750del) | 63 | 1000 |
| IV | EGFR(G719C) | 91 | 1000 |
| IV | EGFR(G719S) | 91 | 1000 |
| IV | EGFR(L747-E749del, A750P) | 98 | 1000 |
| IV | EGFR(L747-S752del, P753S) | 49 | 1000 |
| IV | EGFR(L747-T751del, Sins) | 80 | 1000 |
| IV | EGFR(L858R) | 99 | 1000 |
| IV | EGFR(L858R, T790M) | 35 | 1000 |
| IV | EGFR(L861Q) | 75 | 1000 |
| IV | EGFR(S752-I759del) | 100 | 1000 |
| IV | EGFR(T790M) | 44 | 1000 |
| IV | EIF2AK1 | 73 | 1000 |
| IV | EPHA1 | 100 | 1000 |
| IV | EPHA2 | 100 | 1000 |
| IV | EPHA3 | 93 | 1000 |
| IV | EPHA4 | 100 | 1000 |
| IV | EPHA5 | 86 | 1000 |
| IV | EPHA6 | 100 | 1000 |
| IV | EPHA7 | 93 | 1000 |
| IV | EPHA8 | 93 | 1000 |
| IV | EPHB1 | 89 | 1000 |
| IV | EPHB2 | 70 | 1000 |
| IV | EPHB3 | 100 | 1000 |
| IV | EPHB4 | 100 | 1000 |
| IV | EPHB6 | 81 | 1000 |
| IV | ERBB2 | 100 | 1000 |
| IV | ERBB3 | 100 | 1000 |
| IV | ERBB4 | 96 | 1000 |
| IV | ERK1 | 98 | 1000 |
| IV | ERK2 | 81 | 1000 |
| IV | ERK3 | 90 | 1000 |
| IV | ERK4 | 91 | 1000 |
| IV | ERK5 | 86 | 1000 |
| IV | ERK8 | 83 | 1000 |
| IV | ERN1 | 33 | 1000 |
| IV | FAK | 88 | 1000 |
| IV | FER | 90 | 1000 |
| IV | FES | 100 | 1000 |
| IV | FGFR1 | 100 | 1000 |
| IV | FGFR2 | 100 | 1000 |
| IV | FGFR3 | 100 | 1000 |
| IV | FGFR3(G697C) | 100 | 1000 |
| IV | FGFR4 | 100 | 1000 |
| IV | FGR | 100 | 1000 |
| IV | FLT1 | 95 | 1000 |
| IV | FLT3 | 100 | 1000 |
| IV | FLT3(D835H) | 81 | 1000 |
| IV | FLT3(D835V) | 44 | 1000 |
| IV | FLT3(D835Y) | 88 | 1000 |
| IV | FLT3(ITD) | 92 | 1000 |
| IV | FLT3(ITD, D835V) | 56 | 1000 |
| IV | FLT3(ITD, F691L) | 57 | 1000 |
| IV | FLT3(K663Q) | 98 | 1000 |
| IV | FLT3(N841I) | 63 | 1000 |
| IV | FLT3(R834Q) | 40 | 1000 |
| IV | FLT3-autoinhibited | 51 | 1000 |
| IV | FLT4 | 80 | 1000 |
| IV | FRK | 100 | 1000 |
| IV | FYN | 100 | 1000 |
| IV | GAK | 92 | 1000 |
| IV | GCN2(Kin.Dom.2, S808G) | 94 | 1000 |
| IV | GRK1 | 67 | 1000 |
| IV | GRK2 | 83 | 1000 |
| IV | GRK3 | 53 | 1000 |
| IV | GRK4 | 100 | 1000 |
| IV | GRK7 | 90 | 1000 |
| IV | GSK3A | 95 | 1000 |
| IV | GSK3B | 72 | 1000 |
| IV | HASPIN | 71 | 1000 |
| IV | HCK | 95 | 1000 |
| IV | HIPK1 | 100 | 1000 |
| IV | HIPK2 | 64 | 1000 |
| IV | HIPK3 | 61 | 1000 |
| IV | HIPK4 | 91 | 1000 |
| IV | HPK1 | 86 | 1000 |
| IV | HUNK | 74 | 1000 |
| IV | ICK | 100 | 1000 |
| IV | IGF1R | 97 | 1000 |
| IV | IKK-alpha | 80 | 1000 |
| IV | IKK-beta | 66 | 1000 |
| IV | IKK-epsilon | 84 | 1000 |
| IV | INSR | 57 | 1000 |

-continued

| Compound Name | DiscoveRx Gene Symbol | Percent Control | Concentration (nM) |
|---|---|---|---|
| IV | INSRR | 86 | 1000 |
| IV | IRAK1 | 80 | 1000 |
| IV | IRAK3 | 99 | 1000 |
| IV | IRAK4 | 78 | 1000 |
| IV | ITK | 96 | 1000 |
| IV | JAK1(JH1domain-catalytic) | 96 | 1000 |
| IV | JAK1(JH2domain-pseudokinase) | 51 | 1000 |
| IV | JAK2(JH1domain-catalytic) | 74 | 1000 |
| IV | JAK3(JH1domain-catalytic) | 70 | 1000 |
| IV | JNK1 | 52 | 1000 |
| IV | JNK2 | 45 | 1000 |
| IV | JNK3 | 100 | 1000 |
| IV | KIT | 95 | 1000 |
| IV | KIT(A829P) | 78 | 1000 |
| IV | KIT(D816H) | 78 | 1000 |
| IV | KIT(D816V) | 100 | 1000 |
| IV | KIT(L576P) | 100 | 1000 |
| IV | KIT(V559D) | 100 | 1000 |
| IV | KIT(V559D,T670I) | 86 | 1000 |
| IV | KIT(V559D,V654A) | 76 | 1000 |
| IV | KIT-autoinhibited | 57 | 1000 |
| IV | LATS1 | 100 | 1000 |
| IV | LATS2 | 95 | 1000 |
| IV | LCK | 100 | 1000 |
| IV | LIMK1 | 100 | 1000 |
| IV | LIMK2 | 96 | 1000 |
| IV | LKB1 | 97 | 1000 |
| IV | LOK | 90 | 1000 |
| IV | LRRK2 | 71 | 1000 |
| IV | LRRK2(G2019S) | 54 | 1000 |
| IV | LTK | 82 | 1000 |
| IV | LYN | 77 | 1000 |
| IV | LZK | 45 | 1000 |
| IV | MAK | 88 | 1000 |
| IV | MAP3K1 | 54 | 1000 |
| IV | MAP3K15 | 52 | 1000 |
| IV | MAP3K2 | 65 | 1000 |
| IV | MAP3K3 | 55 | 1000 |
| IV | MAP3K4 | 100 | 1000 |
| IV | MAP4K2 | 87 | 1000 |
| IV | MAP4K3 | 91 | 1000 |
| IV | MAP4K4 | 100 | 1000 |
| IV | MAP4K5 | 100 | 1000 |
| IV | MAPKAPK2 | 100 | 1000 |
| IV | MAPKAPK5 | 63 | 1000 |
| IV | MARK1 | 92 | 1000 |
| IV | MARK2 | 100 | 1000 |
| IV | MARK3 | 100 | 1000 |
| IV | MARK4 | 95 | 1000 |
| IV | MAST1 | 72 | 1000 |
| IV | MEK1 | 63 | 1000 |
| IV | MEK2 | 58 | 1000 |
| IV | MEK3 | 66 | 1000 |
| IV | MEK4 | 84 | 1000 |
| IV | MEK5 | 60 | 1000 |
| IV | MEK6 | 99 | 1000 |
| IV | MELK | 85 | 1000 |
| IV | MERTK | 70 | 1000 |
| IV | MET | 96 | 1000 |
| IV | MET(M1250T) | 88 | 1000 |
| IV | MET(Y1235D) | 93 | 1000 |
| IV | MINK | 69 | 1000 |
| IV | MKK7 | 72 | 1000 |
| IV | MKNK1 | 100 | 1000 |
| IV | MKNK2 | 82 | 1000 |
| IV | MLCK | 91 | 1000 |
| IV | MLK1 | 98 | 1000 |
| IV | MLK2 | 95 | 1000 |
| IV | MLK3 | 93 | 1000 |
| IV | MRCKA | 100 | 1000 |
| IV | MRCKB | 92 | 1000 |
| IV | MST1 | 84 | 1000 |
| IV | MST1R | 100 | 1000 |
| IV | MST2 | 100 | 1000 |
| IV | MST3 | 96 | 1000 |
| IV | MST4 | 82 | 1000 |
| IV | MTOR | 87 | 1000 |
| IV | MUSK | 83 | 1000 |
| IV | MYLK | 49 | 1000 |
| IV | MYLK2 | 96 | 1000 |
| IV | MYLK4 | 93 | 1000 |
| IV | MYO3A | 100 | 1000 |
| IV | MYO3B | 91 | 1000 |
| IV | NDR1 | 81 | 1000 |
| IV | NDR2 | 100 | 1000 |
| IV | NEK1 | 100 | 1000 |
| IV | NEK10 | 50 | 1000 |
| IV | NEK11 | 42 | 1000 |
| IV | NEK2 | 100 | 1000 |
| IV | NEK3 | 50 | 1000 |
| IV | NEK4 | 69 | 1000 |
| IV | NEK5 | 90 | 1000 |
| IV | NEK6 | 83 | 1000 |
| IV | NEK7 | 89 | 1000 |
| IV | NEK9 | 83 | 1000 |
| IV | NIK | 46 | 1000 |
| IV | NIM1 | 72 | 1000 |
| IV | NLK | 100 | 1000 |
| IV | OSR1 | 73 | 1000 |
| IV | p38-alpha | 100 | 1000 |
| IV | p38-beta | 87 | 1000 |
| IV | p38-delta | 98 | 1000 |
| IV | p38-gamma | 78 | 1000 |
| IV | PAK1 | 87 | 1000 |
| IV | PAK2 | 63 | 1000 |
| IV | PAK3 | 71 | 1000 |
| IV | PAK4 | 96 | 1000 |
| IV | PAK6 | 91 | 1000 |
| IV | PAK7 | 92 | 1000 |
| IV | PCTK1 | 43 | 1000 |
| IV | PCTK2 | 94 | 1000 |
| IV | PCTK3 | 86 | 1000 |
| IV | PDGFRA | 75 | 1000 |
| IV | PDGFRB | 93 | 1000 |
| IV | PDPK1 | 97 | 1000 |
| IV | PFCDPK1(P.falciparum) | 56 | 1000 |
| IV | PFPK5(P.falciparum) | 48 | 1000 |
| IV | PFTAIRE2 | 90 | 1000 |
| IV | PFTK1 | 98 | 1000 |
| IV | PHKG1 | 90 | 1000 |
| IV | PHKG2 | 83 | 1000 |
| IV | PIK3C2B | 87 | 1000 |
| IV | PIK3C2G | 100 | 1000 |
| IV | PIK3CA | 97 | 1000 |
| IV | PIK3CA(C420R) | 91 | 1000 |
| IV | PIK3CA(E542K) | 70 | 1000 |
| IV | PIK3CA(E545A) | 89 | 1000 |
| IV | PIK3CA(E545K) | 48 | 1000 |
| IV | PIK3CA(H1047L) | 90 | 1000 |
| IV | PIK3CA(H1047Y) | 91 | 1000 |
| IV | PIK3CA(I800L) | 94 | 1000 |
| IV | PIK3CA(M1043I) | 83 | 1000 |
| IV | PIK3CA(Q546K) | 54 | 1000 |
| IV | PIK3CB | 71 | 1000 |
| IV | PIK3CD | 74 | 1000 |
| IV | PIK3CG | 83 | 1000 |
| IV | PIK4CB | 100 | 1000 |
| IV | PIKFYVE | 96 | 1000 |
| IV | PIM1 | 90 | 1000 |
| IV | PIM2 | 91 | 1000 |
| IV | PIM3 | 85 | 1000 |
| IV | PIP5KIV | 96 | 1000 |
| IV | PIP5K1C | 100 | 1000 |
| IV | PIP5K2B | 100 | 1000 |
| IV | PIP5K2C | 80 | 1000 |
| IV | PKAC-alpha | 85 | 1000 |
| IV | PKAC-beta | 96 | 1000 |
| IV | PKMYT1 | 93 | 1000 |
| IV | PKN1 | 99 | 1000 |
| IV | PKN2 | 98 | 1000 |
| IV | PKNB(M.tuberculosis) | 62 | 1000 |
| IV | PLK1 | 70 | 1000 |

| Compound Name | DiscoveRx Gene Symbol | Percent Control | Concentration (nM) |
|---|---|---|---|
| IV | PLK2 | 55 | 1000 |
| IV | PLK3 | 68 | 1000 |
| IV | PLK4 | 58 | 1000 |
| IV | PRKCD | 97 | 1000 |
| IV | PRKCE | 100 | 1000 |
| IV | PRKCH | 81 | 1000 |
| IV | PRKCI | 71 | 1000 |
| IV | PRKCQ | 86 | 1000 |
| IV | PRKD1 | 100 | 1000 |
| IV | PRKD2 | 64 | 1000 |
| IV | PRKD3 | 91 | 1000 |
| IV | PRKG1 | 64 | 1000 |
| IV | PRKG2 | 88 | 1000 |
| IV | PRKR | 99 | 1000 |
| IV | PRKX | 100 | 1000 |
| IV | PRP4 | 84 | 1000 |
| IV | PYK2 | 93 | 1000 |
| IV | QSK | 44 | 1000 |
| IV | RAF1 | 83 | 1000 |
| IV | RET | 100 | 1000 |
| IV | RET(M918T) | 85 | 1000 |
| IV | RET(V804L) | 75 | 1000 |
| IV | RET(V804M) | 100 | 1000 |
| IV | RIOK1 | 100 | 1000 |
| IV | RIOK2 | 80 | 1000 |
| IV | RIOK3 | 100 | 1000 |
| IV | RIPK1 | 87 | 1000 |
| IV | RIPK2 | 94 | 1000 |
| IV | RIPK4 | 99 | 1000 |
| IV | RIPK5 | 54 | 1000 |
| IV | ROCK1 | 45 | 1000 |
| IV | ROCK2 | 49 | 1000 |
| IV | ROS1 | 90 | 1000 |
| IV | RPS6KA4(Kin.Dom.1-N-terminal) | 90 | 1000 |
| IV | RPS6KA4(Kin.Dom.2-C-terminal) | 46 | 1000 |
| IV | RPS6KA5(Kin.Dom.1-N-terminal) | 75 | 1000 |
| IV | RPS6KA5(Kin.Dom.2-C-terminal) | 100 | 1000 |
| IV | RSK1(Kin.Dom.1-N-terminal) | 93 | 1000 |
| IV | RSK1(Kin.Dom.2-C-terminal) | 98 | 1000 |
| IV | RSK2(Kin.Dom.1-N-terminal) | 67 | 1000 |
| IV | RSK2(Kin.Dom.2-C-terminal) | 53 | 1000 |
| IV | RSK3(Kin.Dom.1-N-terminal) | 93 | 1000 |
| IV | RSK3(Kin.Dom.2-C-terminal) | 81 | 1000 |
| IV | RSK4(Kin.Dom.1-N-terminal) | 92 | 1000 |
| IV | RSK4(Kin.Dom.2-C-terminal) | 82 | 1000 |
| IV | S6K1 | 50 | 1000 |
| IV | SBK1 | 64 | 1000 |
| IV | SGK | 68 | 1000 |
| IV | SgK110 | 97 | 1000 |
| IV | SGK2 | 64 | 1000 |
| IV | SGK3 | 60 | 1000 |
| IV | SIK | 81 | 1000 |
| IV | SIK2 | 81 | 1000 |
| IV | SLK | 100 | 1000 |
| IV | SNARK | 57 | 1000 |
| IV | SNRK | 78 | 1000 |
| IV | SRC | 97 | 1000 |
| IV | SRMS | 89 | 1000 |
| IV | SRPK1 | 97 | 1000 |
| IV | SRPK2 | 80 | 1000 |
| IV | SRPK3 | 100 | 1000 |
| IV | STK16 | 83 | 1000 |
| IV | STK33 | 92 | 1000 |
| IV | STK35 | 94 | 1000 |
| IV | STK36 | 77 | 1000 |
| IV | STK39 | 58 | 1000 |
| IV | SYK | 99 | 1000 |
| IV | TAK1 | 84 | 1000 |
| IV | TAOK1 | 100 | 1000 |
| IV | TAOK2 | 87 | 1000 |
| IV | TAOK3 | 54 | 1000 |
| IV | TBK1 | 98 | 1000 |
| IV | TEC | 100 | 1000 |
| IV | TESK1 | 100 | 1000 |
| IV | TGFBR1 | 82 | 1000 |
| IV | TGFBR2 | 94 | 1000 |
| IV | TIE1 | 97 | 1000 |
| IV | TIE2 | 100 | 1000 |
| IV | TLK1 | 90 | 1000 |
| IV | TLK2 | 100 | 1000 |
| IV | TNIK | 98 | 1000 |
| IV | TNK1 | 67 | 1000 |
| IV | TNK2 | 100 | 1000 |
| IV | TNNI3K | 96 | 1000 |
| IV | TRKA | 67 | 1000 |
| IV | TRKB | 48 | 1000 |
| IV | TRKC | 53 | 1000 |
| IV | TRPM6 | 90 | 1000 |
| IV | TSSK1B | 85 | 1000 |
| IV | TSSK3 | 96 | 1000 |
| IV | TTK | 85 | 1000 |
| IV | TXK | 98 | 1000 |
| IV | TYK2(JH1domain-catalytic) | 37 | 1000 |
| IV | TYK2(JH2domain-pseudokinase) | 79 | 1000 |
| IV | TYRO3 | 100 | 1000 |
| IV | ULK1 | 51 | 1000 |
| IV | ULK2 | 59 | 1000 |
| IV | ULK3 | 71 | 1000 |
| IV | VEGFR2 | 45 | 1000 |
| IV | VPS34 | 51 | 1000 |
| IV | VRK2 | 56 | 1000 |
| IV | WEE1 | 100 | 1000 |
| IV | WEE2 | 96 | 1000 |
| IV | WNK1 | 59 | 1000 |
| IV | WNK2 | 58 | 1000 |
| IV | WNK3 | 69 | 1000 |
| IV | WNK4 | 70 | 1000 |
| IV | YANK1 | 95 | 1000 |
| IV | YANK2 | 56 | 1000 |
| IV | YANK3 | 94 | 1000 |
| IV | YES | 100 | 1000 |
| IV | YSK1 | 98 | 1000 |
| IV | YSK4 | 78 | 1000 |
| IV | ZAK | 100 | 1000 |
| IV | ZAP70 | 91 | 1000 |

What is claimed herein is:

1. A compound of Formula I:

FORMULA I

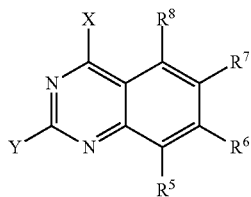

wherein:

X is

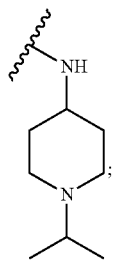 [SMILES: *NC1CCN(C(C)C)CC1]

Y is N(R³R⁴), aryl,

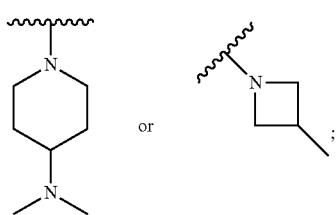

R³ and R⁴ are independently hydrogen, alkyl, cycloalkyl, heterocyclyl, aryl or heteroaryl, each of cycloalkyl, heterocyclyl, aryl and heteroaryl can be substituted or unsubstituted, and wherein the alkyl is methyl, ethyl, i-propyl, n-butyl, t-butyl, n-pentyl, heptyl, octyl, decyl, dodecyl, tridecyl, tetradecyl, pentadecyl or hexadecyl and can be unsubstituted or substituted with one or more substituents independently selected from the group consisting halogen, hydroxy, caboxy, oxo, nitro, haloalkyl, alkyl, alkenyl, alkynyl, alkaryl, cycloalkyl, heterocyclyl, aryl, heteroaryl, aralkyl, alkoxy, aryloxy, alkylamino, dialkylamino, alkoxycarbonyl, carboxy, hydroxyalkyl, alkanesulfonyl, arenesulfonyl, alkane- sulfonamido, arenesulfonamido, aralkylsulfonamido, alkylcarbonyl, acyloxy, cyano and ureido;

R⁵, R⁷ and R⁸ are independently selected from the group consisting of: hydrogen, alkyl, halogen, nitro, cyano, hydroxyl, amino, mercapto, formyl, carboxy, alkanoyl, carbamoyl, alkoxy, alkylthio, alkylamino, dialkylamino, alkylsulfinyl, alkylsulfonyl, arylsulfonyl, cycloalkyl, heterocyclyl, aryl, or heteroaryl, each of which can be substituted or unsubstituted;

R⁶ is hydrogen, alkyl, halogen, nitro, cyano, hydroxyl, amino, mercapto, formyl, carboxy, alkanoyl, carbamoyl, unsubstituted alkoxy, alkylthio, alkylamino, dialkylamino, alkylsulfinyl, alkylsulfonyl, arylsulfonyl, cycloalkyl, heterocyclyl, aryl, or heteroaryl; and tautomers or a pharmaceutically acceptable salt thereof.

2. The compound of claim 1, wherein the compound is of Formula (II):

FORMULA (II)

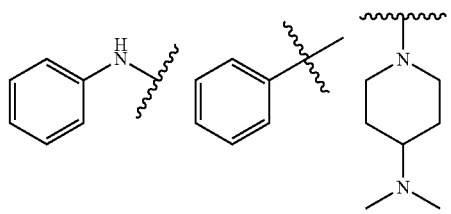

3. The compound of claim 1, wherein Y is selected from the group consisting of:

-continued

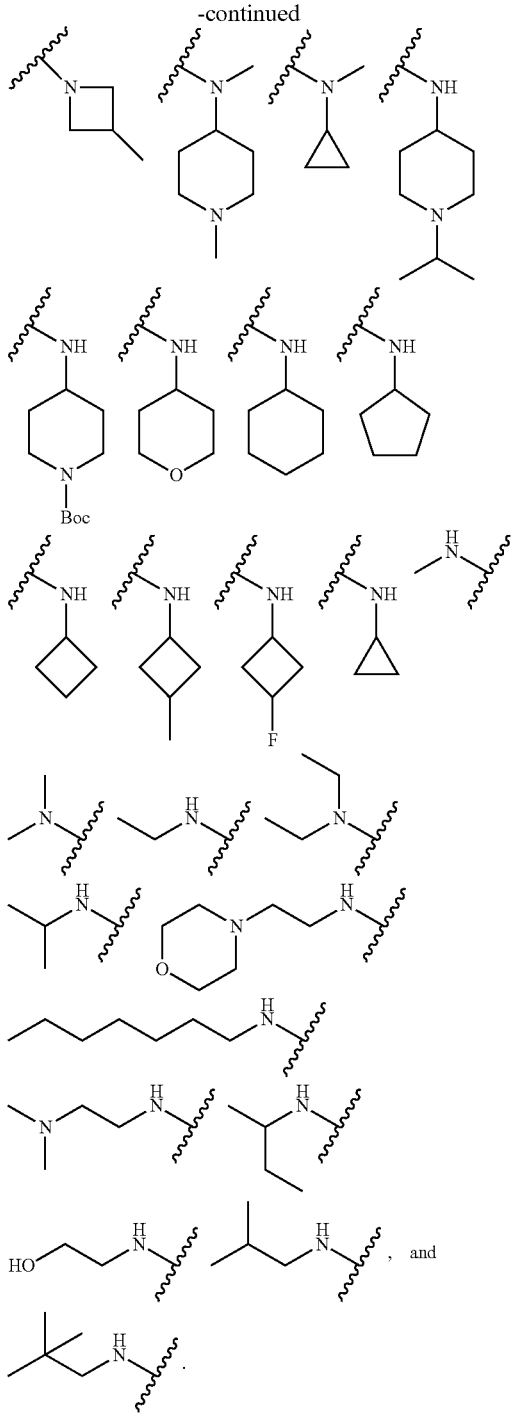

4. The compound of claim 3, wherein Y is selected from the group consisting of:

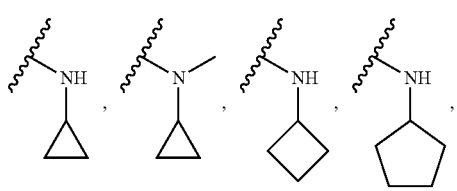

-continued

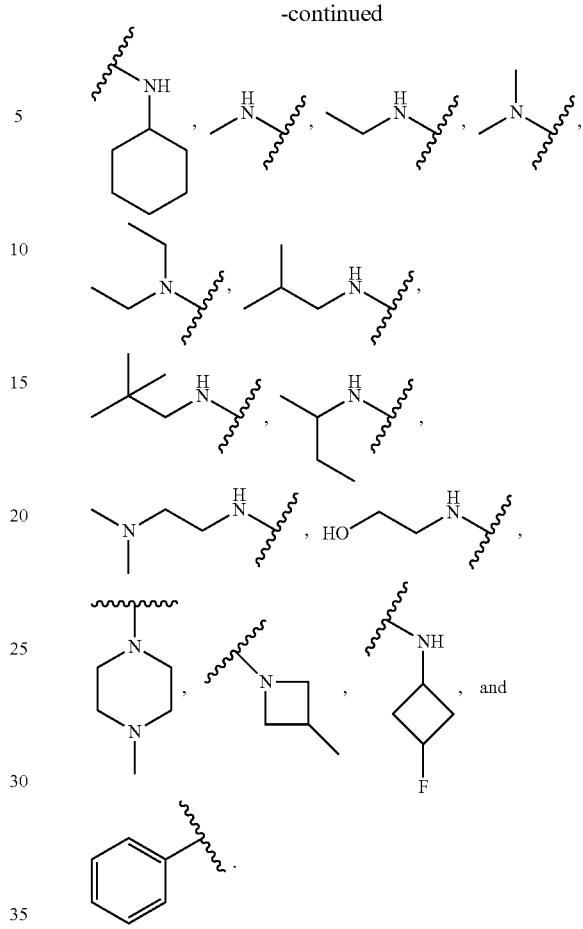

5. The compound of claim 1, wherein $R^6$ is H or unsubstituted alkoxy or $R^7$ is H or a substituted or unsubstituted alkoxy.

6. The compound of claim 1, wherein $R^6$ is H or —$OR^9$, where $R^9$ is unsubstituted alkyl; substituted or unsubstituted cycloalkyl; substituted or unsubstituted heterocyclyl; substituted or unsubstituted aryl; substituted or unsubstituted heteroaryl.

7. The compound of claim 1, wherein $R^6$ is H or —$OR^9$, where $R^9$ is unsubstituted $C_1$-$C_6$ alkyl.

8. The compound of claim 1, wherein $R^6$ is H or —$OR^9$, where $R^9$ is methyl, ethyl, propyl, isopropyl, 1-mthylpropy, 2-methylpropyl, butyl, t-butyl, pentyl or hexyl.

9. The compound of claim 1, wherein $R^7$ is H or —$OR^{10}$, where $R^{10}$ is substituted or unsubstituted alkyl; substituted or unsubstituted cycloalkyl; substituted or unsubstituted hetrocyclyl; substituted or unsubstituted aryl; or substituted or unsubstituted heteroaryl.

10. The compound of claim 1, wherein $R^7$ is H or —$OR^{10}$, where $R^{10}$ is substituted or unsubstituted $C_1$-$C_6$ alkyl.

11. The compound of claim 1, wherein $R^7$ is H or —$OR^{10}$, where $R^{10}$ is methyl, ethyl, propyl, isopropyl, 1-methylpropy, 2-methylpropyl, butyl, t-butyl, pentyl or hexyl.

12. The compound of claim 1, wherein $R^6$ and $R^7$ are H or —$OCH_3$.

13. The compound of claim 1, wherein $R^5$ or $R^8$ are each independently hydrogen, alkyl, halogen, nitro, cyano, hydroxyl, alkoxy, carboxy, amino, alkylamino or dialkylamino.

14. The compound of claim 1, wherein $R^5$ and $R^8$ are hydrogen, and $R^6$ and $R^7$ are H or —$OCH_3$.
15. The compound of claim 1, wherein the compound is of Formula (IV):
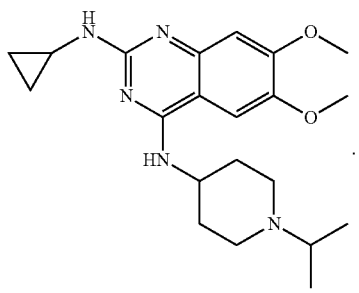 [SMILES: COc1cc2nc(NC3CC3)nc(NC3CCN(C(C)C)CC3)c2cc1OC]
16. A compound selected from the group consisting of:
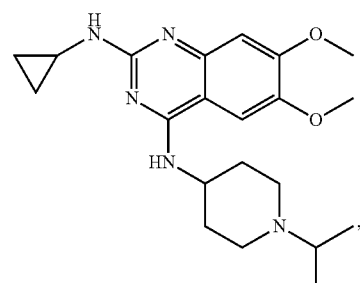
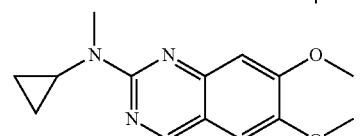
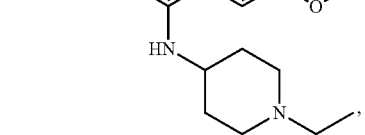
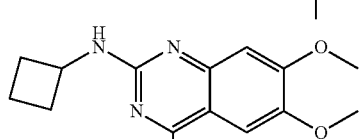
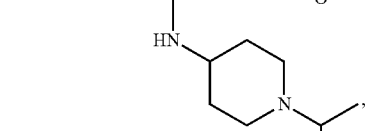
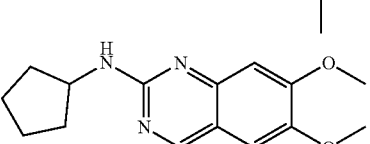
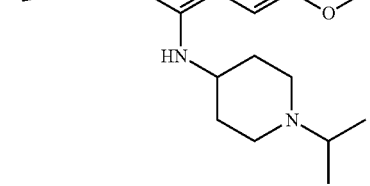
-continued
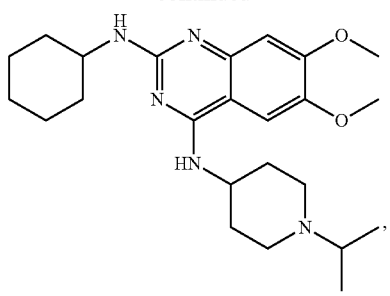
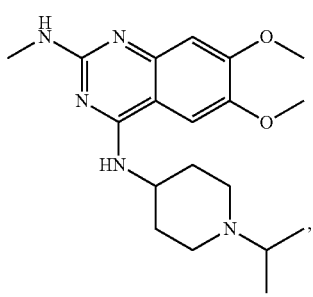
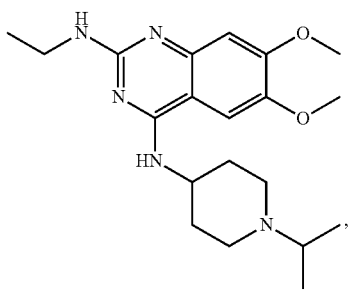
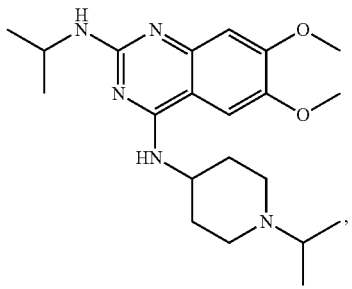
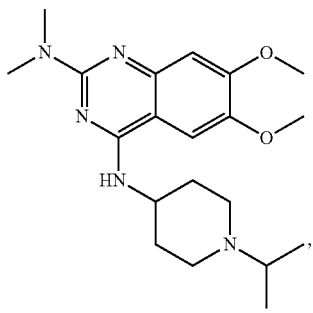

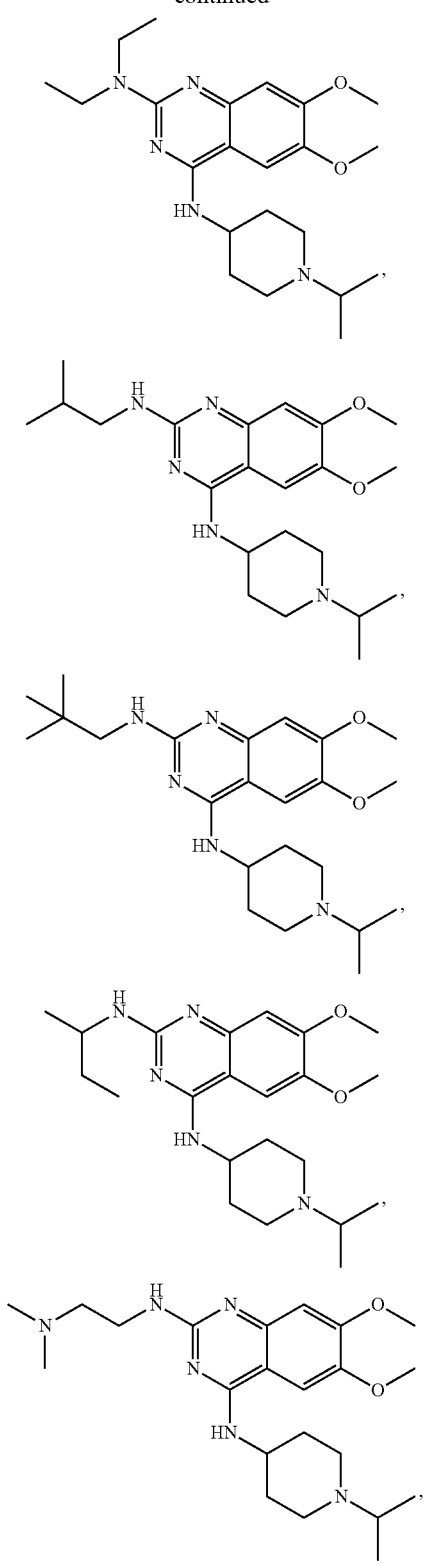
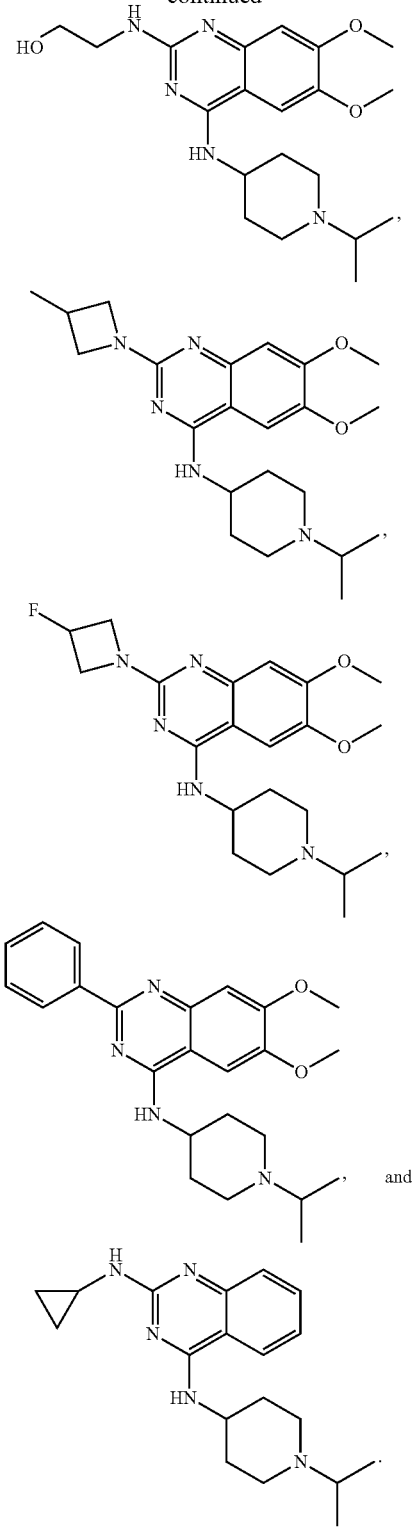
17. A pharmaceutical composition comprising a compound of claim 1 and a pharmaceutically acceptable carrier or excipient.
18. A method of treating cancer, the method comprising administering a therapeutically effective dose of a compound of claim 1 to a subject in need of treatment for cancer, and wherein the cancer is melanoma.

19. The method of claim 18, wherein the method further comprises a first step of measuring the level of activity or expression of a cancer marker in one or more cell types relative to a reference level and the administering step is performed if the level is increased.

20. The method of claim 19, wherein the subject is determined to have an increased level of activity or expression of an oncogene in one or more cell types relative to a reference level occurring in a cell selected from the group consisting of: a squamous cell; basal cell; and melanocyte.

21. The method of claim 20, wherein the oncogene is selected from the group consisting of:
NRAS; BRAF; KIT; MAPK1/2; ERBB4; GRIN2A; GRM3; RAC1; PREX2; IDH1; PPP6C; and CDK4.

22. A method of treating melanoma comprising:
isolating one or more cells selected from the group consisting of a squamous cell, basal cell and melanocyte from a subject in need thereof;
measuring the expression of one or more cancer genes, oncogenes or tumor suppressor genes products in the one or more cells;
administering a therapeutically effective dose of an inhibitor of an immune checkpoint polypeptide to the subject if the expression of one or more cancer genes, oncogenes or tumor suppressor gene is not altered or decreased in the one or more cells as compared to a reference level; or
administering a therapeutically effective dose of a compound of claim 1 to the subject if the expression of one or more cancer genes, oncogenes or tumor suppressor gene products is elevated in the one or more cells as compared to a reference level.

23. The method of claim 22, wherein the marker gene is selected from the group consisting of:
NRAS; BRAF; KIT; MAPK1/2; ERBB4; GRIN2A; GRM3; RAC1; PREX2; IDH1; PPP6C; and CDK4.

24. The method of claim 22, wherein the immune checkpoint polypeptide is selected from: CTLA4A; CTLA4; Ki-67; CD-28; PD-1; TIM-3; and LAG-3.

* * * * *